US008173659B2

(12) United States Patent
Bandiera et al.

(10) Patent No.: US 8,173,659 B2
(45) Date of Patent: May 8, 2012

(54) SUBSTITUTED PYRAZOLO[4,3-C]PYRIDINE DERIVATIVES ACTIVE AS KINASE INHIBITORS

(75) Inventors: Tiziano Bandiera, Gambolo' (IT); Andrea Lombardi Borgia, Paullo (IT); Paolo Polucci, Parabiago (IT); Manuela Villa, Lurago D'erba (IT); Marcella Nesi, Saronno (IT); Mauro Angiolini, Gavirate (IT); Mario Varasi, Milan (IT)

(73) Assignee: Nerviano Medical Sciences S.R.L., Nerviano (MI) (IT)

( * ) Notice: Subject to any disclaimer, the term of this patent is extended or adjusted under 35 U.S.C. 154(b) by 0 days.

(21) Appl. No.: 13/085,889

(22) Filed: Apr. 13, 2011

(65) Prior Publication Data
US 2011/0230470 A1    Sep. 22, 2011

Related U.S. Application Data

(62) Division of application No. 12/096,979, filed as application No. PCT/EP2006/069285 on Dec. 6, 2006, now Pat. No. 7,947,686.

(30) Foreign Application Priority Data

Dec. 12, 2005   (EP) ..................... 05111959

(51) Int. Cl.
    *A61K 31/496*    (2006.01)
    *A61K 31/437*    (2006.01)
(52) U.S. Cl. .................. 514/253.04; 514/303
(58) Field of Classification Search ............ 514/253.04, 514/303
    See application file for complete search history.

(56) References Cited

FOREIGN PATENT DOCUMENTS
WO    WO 02/12242 A2    2/2002

OTHER PUBLICATIONS

Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Cancer [online], [retrieved on Jul. 6, 2007], Retrieved from the Internet, URL: http://www.nlm.nih.gov/medlineplus/cancer.html.*
Cancer [online], [retrieved on Jul. 6, 2007], Retrieved from the Internet, URL: http://en.wikipedia.org/wiki/Cancer.*
Search Report dated Apr. 13, 2007 received from the European Patent Office.
Office Action dated Aug. 24, 2010 received in U.S. Appl. No. 12/096,979.
Wolff et al., Burger's Medicinal Chemistry and Drug Discovery, 1994, Wiley-Interscience, Fifth Edition, vol. I: Principles and Practice, pp. 975-977.
Kwon et al., Handbook of Essential Pharmacokinetics, Pharmacodynamics and Drug Metabolism for Industrial Scientists, 2001, http://www.myilibrary.com/Browse/open.asp?ID=4284&loc=1, Retrieved from the Internet Jun. 16, 2008, p. 213.
Metabolomics [Online], Retrieved from the Internet Jun. 16, 2008, URL: http://www.en.wikipedia.org/wiki/Metabolomics, p. 1.

* cited by examiner

*Primary Examiner* — Kamal Saeed
*Assistant Examiner* — Kristin Bianchi
(74) *Attorney, Agent, or Firm* — Scully, Scott, Murphy & Presser, P.C.

(57) ABSTRACT

Substituted pyrazolo[4,3-c]pyridine derivatives of formula (I) and pharmaceutically acceptable salts thereof, as defined in the specification, process for their preparation and pharmaceutical compositions comprising them are disclosed; the compounds of the invention may be useful in therapy in the treatment of diseases associated with a dysregulated protein kinase activity, like cancer.

5 Claims, 1 Drawing Sheet

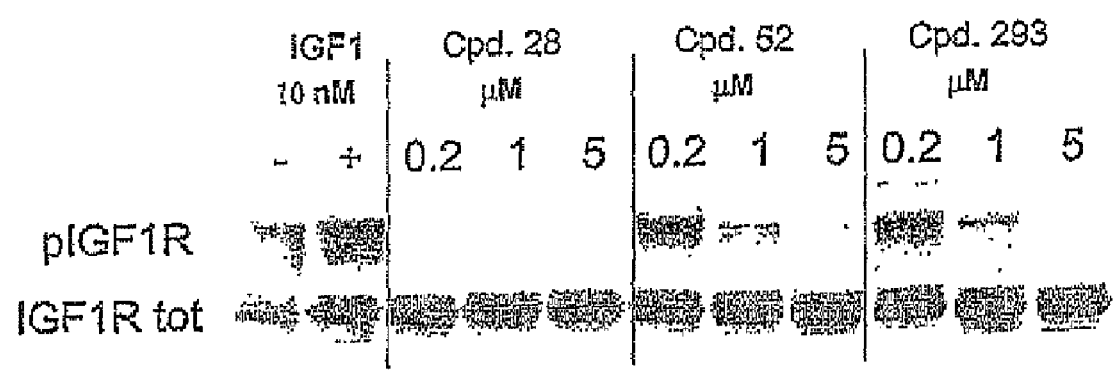

SUBSTITUTED PYRAZOLO[4,3-C]PYRIDINE DERIVATIVES ACTIVE AS KINASE INHIBITORS

CROSS REFERENCE TO RELATED APPLICATIONS

The present application is a divisional of application Ser. No. 12/096,979 filed Jun. 17, 2008, which is a national stage application under 35 U.S.C. §371 of International Application Serial No. PCT/EP2006/069285 filed Dec. 6, 2006, which claims benefit of European Patent Application No. 05111959.2 filed Dec. 12, 2005, the entire contents of which are incorporated herein by reference.

BACKGROUND OF THE INVENTION

1. Field of the Invention

The present invention relates to certain pyrazolo[4,3-c]pyridine compounds, which modulate the activity of protein kinases. The compounds of this invention are therefore useful in treating diseases caused by dysregulated protein kinase activity. The present invention also provides methods for preparing these compounds, pharmaceutical compositions comprising these compounds, and methods of treating diseases utilizing pharmaceutical compositions comprising these compounds.

2. Discussion of the Background

The insulin-like growth factor 1 receptor (IGF-1R, IGF1R) is a member of the insulin receptor subfamily of receptor tyrosine kinases (RTKs). IGF-1R mature protein consists of two alpha chains, which are extracellular and contain ligand-binding function, and two beta chains, which span the cell membrane and contain the intracellular kinase domains. This disulphide-linked (alpha/beta) 2 heterodimer complex is able to bind and be activated by the ligands insulin-like growth factor-1 and -2 (IGF-1 and IGF-2), two circulating growth factors which are believed to mediate many of the effects of Growth Hormone (GH), and which have important physiological roles in foetal and post-natal growth and metabolism. Extracellular ligand binding to IGF-1R results in intracellular tyrosine kinase activation, and like several other RTKs such as the EGF and PDGF receptors, the activated receptor has potent mitogenic, motogenic and anti-apoptotic activity in a wide range of cell types: notably, it directly activates at least two major cell signalling pathways, the ras/MAPK pathway, through recruitment of SHC, and the PI-3 kinase/AKT(PKB) pathway, through recruitment and phosphorylation of the IRS adapter proteins. There is much evidence, both at preclinical and clinical levels, linking increased IGF-1R signalling to development and progression of cancer. This evidence includes observation that IGF-1R is able to induce cellular transformation, that fibroblasts from animals lacking IGF-1R through genetic ablation are extremely resistant to the transforming activity of a wide range of oncogenes, and that IGFs are potent anti-apoptotic agents. Studies of interference with receptor activity through various approaches have demonstrated that inhibition of IGF-1R dependent signalling can result in single agent antitumor activity, and in the enhancement of the activity of a wide range of chemotherapeutic agents and radiotherapy in human tumor cells cultured in vitro, as well as in animal models of disease, including human tumor xenograft models. Such IGF-1R inhibition strategies have included cellular transfection with dominant negative IGF-1R constructs or antisense oligonucleotides, use of IGF binding antagonists and blocking monoclonal antibodies directed against the extracellular receptor, and, significantly, selective small molecule inhibitors of IGF-1R kinase activity.

Additional indication that IGF-1R signalling contributes to development of cancer, and thus that inhibition of this receptor may represent a valuable therapeutic option, is provided by the observation that high circulating levels of IGF-1 in human are associated with increased lifetime risk of developing several tumor types, including breast, colorectal, prostate and ovarian cancers, and with poor outcome in multiple myeloma. Importantly, gene and protein expression studies performed on clinical samples have revealed that IGF-1R and its ligands are frequently expressed in a wide range of human tumors. For an overview of IGFs and IGF-1R signalling, physiological function, and detailed description of the evidence supporting involvement of this system in human cancer that is summarised above, as well as in other pathologies, the reader is directed to the many reviews on the subject and references contained therein, for example Baserga R., Bongo A., Rubini M., Prisco M. and Valentinis B. Biochim Biophys Acta vol. 1332 pages F105-F126, 1997; Khandwala H. M., McCutcheon I. E., Flyvbjerg A. and Friend K. E. Endocr Rev vol. 21, pages 215-44, 2000; Le Roith D., Bondy C., Yakar S., Liu J. L. and Butler A. Endocr Rev vol. 22, pages 53-74, 2001; Valentinis B., and Baserga R. Mol Pathol vol. 54, pages 133-7, 2001; Wang Y. and Sun Y., Curr Cancer Drug Targets vol. 2 pages 191-207, 2002, Laron, Z. J Clin Endocrinol Metab vol. 89, pages 1031-1044, 2004; Hofmann F and Garcia-Echeverria C. Drug Discov Today vol. 10, pages 1041-7, 2005.

SUMMARY OF THE INVENTION

It has been found that compounds of formula (I), described below, are inhibitors of the tyrosine kinase activity of the IGF-1 Receptor.

Accordingly, a first object of the present invention is to provide a substituted pyrazolo pyridine compound represented by formula (I),

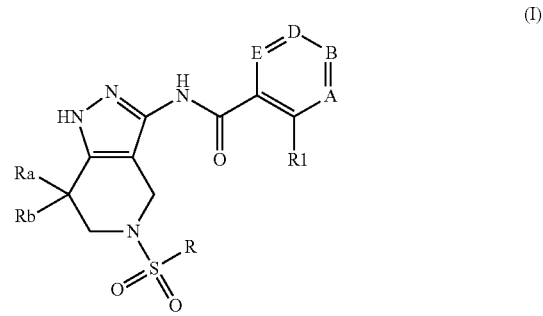

wherein:

R is an optionally further substituted straight or branched $C_1$-$C_6$ alkyl, $C_3$-$C_6$ cycloalkyl, heterocycloalkyl or aryl;

R1 is selected from hydrogen, halogen, nitro, NHCOR4, $NHSO_2R10$, NR5R6, OR7, R8R9N—$C_1$-$C_6$ alkyl, R7O—$C_1$-$C_6$ alkyl and an optionally further substituted straight or branched $C_1$-$C_6$ alkyl, wherein:

R4 is selected from hydrogen, an optionally further substituted straight or branched $C_1$-$C_6$ alkyl, $C_3$-$C_6$ cycloalkyl, heterocycloalkyl, aryl, NR8R9, R8R9N—$C_1$-$C_6$ alkyl and R7O—$C_1$-$C_6$ alkyl;

R5 and R6, being the same or different, are independently selected from hydrogen, an optionally further substituted straight or branched $C_1$-$C_6$ alkyl, $C_3$-$C_6$ cycloalkyl, heterocycloalkyl, aryl, R8R9N—$C_2$-$C_6$ alkyl and R7O—$C_2$-$C_6$ alkyl;

R7 is selected from hydrogen, an optionally further substituted straight or branched $C_1$-$C_6$ alkyl, $C_3$-$C_6$ cycloalkyl, heterocycloalkyl, aryl and R8R9N—$C_2$-$C_6$ alkyl;

R8 and R9, being the same or different, are independently selected from hydrogen, an optionally further substituted straight or branched $C_1$-$C_6$ alkyl, $C_3$-$C_6$ cycloalkyl, heterocycloalkyl and aryl, and R8 and R9, taken together with the nitrogen atom to which they are bonded, form an optionally substituted heterocycloalkyl group;

R10 is an optionally further substituted straight or branched $C_1$-$C_6$ alkyl, $C_3$-$C_6$ cycloalkyl, heterocycloalkyl or aryl;

A, B, D and E represent a nitrogen atom, CH, CR2 or CR3, with a maximum of two of A, B, D and E representing a nitrogen atom, CR2 or CR3, wherein:

R2 and R3 are independently selected from halogen, trifluoromethyl, nitro, OR7, NR8R9, an optionally further substituted straight or branched $C_1$-$C_6$ alkyl, R8R9N—$C_1$-$C_6$ alkyl and R7O—$C_1$-$C_6$ alkyl, wherein R7, R8 and R9 are as defined above;

Ra and Rb are independently hydrogen or methyl, with the proviso that when Ra, Rb, and R1 are hydrogen atoms, then at least one of A, B, D and E is nitrogen;

or isomers, tautomers, carriers, metabolites, prodrugs or pharmaceutically acceptable salt thereof.

The present invention also provides a method for treating diseases caused by and/or associated with dysregulated protein kinase activity, particularly IGF-1R or Aurora kinases activity, and more particularly IGF-1R kinase activity, which comprises administering to a mammal in need thereof an effective amount of a substituted pyrazolo pyridine compound represented by formula (I) as above defined.

A preferred method of the present invention is to treat a disease caused by and/or associated with dysregulated protein kinase activity selected from the group consisting of cancer, cell proliferative disorders, viral infections, retinopathies including diabetic and neonatal retinopathies and age related macular degeneration, atherosclerosis and conditions involving vascular smooth muscle proliferation or neointimal formation such as restenosis following angioplasty or surgery, graft vessel disease, such as can occur following vessel or organ transplantation, acromegaly and disorders secondary to acromegaly as well as other hypertrophic conditions in which IGF/IGF-1R signalling is implicated, such as benign prostatic hyperplasia, psoriasis, fibrotic lung disease, pulmonary fibrosis, pathologies related to chronic or acute oxidative stress or hyperoxia induced tissue damage, and metabolic disorders in which elevated IGF levels or IGF-1R activity are implicated, such as obesity.

Another preferred method of the present invention, is to treat specific types of cancer including carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratocanthomas, thyroid follicular cancer and Kaposi's sarcoma.

Another preferred method of the present invention, is to treat specific types of cancer such as, but not restricted to, breast cancer, lung cancer, colorectal cancer, prostate cancer, ovarian cancer, endometrial cancer, gastric cancer, clear cell renal cell carcinoma, uveal melanoma, multiple myeloma, rhabdomyosarcoma, Ewing's sarcoma, Kaposi's sarcoma, and medulloblastoma.

Another preferred method of the present invention, is to treat cell proliferative disorders such as, but not restricted to, benign prostate hyperplasia, familial adenomatosis polyposis, neuro-fibromatosis, psoriasis, vascular smooth cell proliferation associated with atherosclerosis, pulmonary fibrosis, arthritis, glomerulonephritis and post-surgical stenosis and restenosis.

In addition, the method of the present invention also provides tumor angiogenesis and metastasis inhibition.

The present invention also provides methods of synthetizing the substituted pyrazolo[4,3-c]pyridine derivatives of formula (I) prepared through a process consisting of standard synthetic transformations.

The present invention also provides a pharmaceutical composition comprising one or more compounds of formula (I) or a pharmaceutically acceptable salt thereof and a pharmaceutically acceptable excipient, carrier or diluent.

The present invention further provides a pharmaceutical composition comprising a compound of formula (I) in combination with one or more chemotherapeutic agents or radiotherapy. Such agents can include, but are not limited to, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

DETAILED DESCRIPTION OF THE INVENTION

Several fused bicyclic compounds comprising pyrazole moieties and possessing kinase inhibitory activity have been disclosed in WO 00/69846, WO 02/12242, WO 03/028720, WO 03/097610, WO 04/007504, WO 04/013146, US2005/0026984 and WO 2005030776.

We have now found that pyrazolo[4,3-c]pyridine compounds of the present invention possess a better anti-tumor activity.

The compounds of formula (I) may have one or more asymmetric centres, and may therefore exist as individual optical isomers or racemic mixtures. Accordingly, all the possible isomers, and their mixtures, of the compounds of formula (I) are within the scope of the present invention.

Derivatives of compounds of formula (I) originating from metabolism in a mammal, and the pharmaceutically acceptable bio-precursors (otherwise referred to as pro-drugs) of the compounds of formula (I) are also within the scope of the present invention.

In addition to the above, as known to those skilled in the art, the unsubstituted nitrogen on the pyrazole ring of the compounds of formula (I) rapidly equilibrates in solution to form a mixture of tautomers, as depicted below:

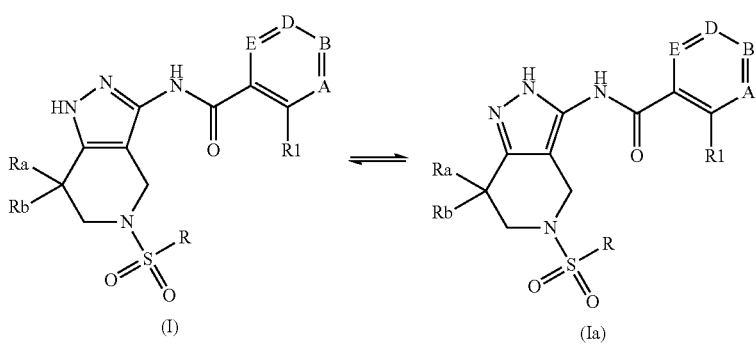

(I)     (Ia)

wherein R, R1, Ra and Rb, and A, B, D, E are as defined above.

Accordingly, in the present invention, where only one tautomer is indicated for the compounds of formula (I), the other tautomer (Ia) is also within the scope of the present invention, unless specifically noted otherwise.

In compounds of formula (I), the skilled person will recognize that the meaning of A, B, D, and E is such that the resulting six-membered ring linked to the aminopyrazole group through an amidic bond is an aromatic ring, optionally substituted by up to three substituents. Representative and not limiting examples of ring systems are the following:

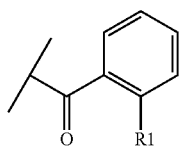

(G1)

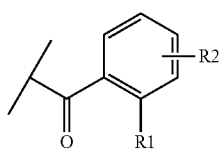

(G2)

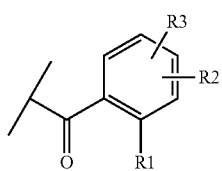

(G3)

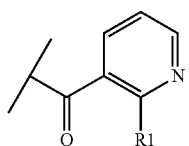

(G4)

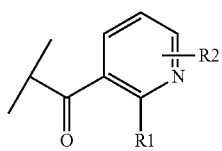

(G5)

-continued

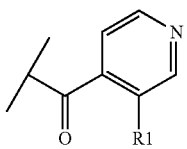

(G6)

The general terms as used herein, unless otherwise specified, have the meaning reported below.

The term "straight or branched $C_1$-$C_6$ alkyl" refers to a saturated aliphatic hydrocarbon radical, including straight chain and branched chain groups of from 1 to 6 carbon atoms, e.g. methyl, ethyl, propyl, 2-propyl, n-butyl, iso-butyl, tert-butyl, pentyl and the like. The alkyl group may be substituted or unsubstituted. When substituted, the substituent groups are preferably one to three, independently selected from the group consisting of halogen, trifluoromethyl, alkylthio, cyano, nitro, formyl, alkylcarbonyl, alkylsulfonyl, carboxy, carboxamido, monoalkylcarboxamido, dialkylcarboxamido, hydroxyalkyl, OR7, NR8R9, aryl or arylalkyl, wherein R7, R8 and R9 are as defined above.

The term "$C_3$-$C_6$ cycloalkyl" refers to a 3- to 6-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene and cyclohexadiene. A cycloalkyl group may be substituted or unsubstituted. When substituted, the substituent groups are preferably one or two substituents, independently selected from the group consisting of halogen, trifluoromethyl, alkylthio, cyano, nitro, formyl, alkylcarbonyl, alkylsulfonyl, carboxy, carboxamido, monoalkylcarboxamido, dialkylcarboxamido, hydroxyalkyl, OR7, NR8R9, aryl and arylalkyl, wherein R7, R8 and R9 are as defined above.

The term "heterocycloalkyl" refers to a 3- to 7-membered, saturated or partially unsaturated carbocyclic ring where one or more carbon atoms are replaced by heteroatoms such as nitrogen, oxygen and sulfur. Not limiting examples of heterocycloalkyl groups are, for instance, oxirane, aziridine, oxetane, azetidine, tetrahydrofuran, dihydrofuran, tetrahydrothiophene, dihydrothiophene, pyrrolidine, dihydropyrrole, pyran, dihydropyran, tetrahydropyran, tetrahydrothiopyran, piperidine, pyrazoline, isoxazolidine, isoxazoline, thiazolidine, thiazoline, isothiazoline, dioxane, piperazine, morpholine, thiomorpholine, examethyleneimine, homopiperazine and the like. An heterocycloalkyl group may be substituted or unsubstituted. When substituted, the substituent groups are preferably one or two substituents, independently selected from the group consisting of halogen, trifluoromethyl, alkylthio, cyano, nitro, formyl, alkylcarbonyl, alkylsulfonyl, carboxy, carboxamido, monoalkylcarboxamido, dialkylcarboxamido, hydroxyalkyl, OR7, NR8R9, aryl and arylalkyl, wherein R7, R8 and R9 are as defined above.

The term "aryl" refers to a mono-, bi- or poly-carbocyclic as well as heterocyclic hydrocarbon with from 1 to 4 ring systems, either fused or linked to each other by single bonds, wherein at least one of the carbocyclic or heterocyclic rings is aromatic. Not limiting examples of aryl groups are, for instance, phenyl, α- or β-naphthyl, 9,10-dihydroanthracenyl, indanyl, fluorenyl, biphenyl, pyrrolyl, furoyl, thiophenyl, imidazolyl, pyrazolyl, oxazolyl, isoxazolyl, thiazolyl, isothiazolyl, indolyl, benzofuranyl, benzothiophenyl, benzimidazolyl, benzopyrazolyl, benzoxazolyl, benzoisoxazolyl, benzothiazolyl, benzoisothiazolyl, triazolyl, oxadiazolyl, tetrazolyl, pyridyl, pyrazinyl, pyrimidinyl, pyridazinyl, quinolinyl, isoquinolinyl, quinazolinyl, quinoxalinyl and the like.

The term "aryl" may also refer to aromatic carbocyclic or heterocyclic rings further fused or linked to non-aromatic heterocyclic rings, typically 5- to 7-membered heterocycles. Not limiting examples of such aryl groups are, for instance, 2,3-dihydroindolyl, 2,3-dihydrobenzofuranyl, 2,3-dihydrobenzothiophenyl; benzopyranyl, 2,3-dihydrobenzoxazinyl, 2,3-dihydroquinoxalinyl and the like.

The aryl group can be optionally substituted by one to three, preferably one or two, substituents selected from $C_1$-$C_6$ alkyl, halogen, trifluoromethyl, alkylthio, cyano, nitro, formyl, alkylcarbonyl, alkylsulfonyl, carboxy, carboxamido, monoalkylcarboxamido, dialkylcarboxamido, hydroxyalkyl, OR7 and NR8R9, wherein R7, R8 and R9 are as defined above.

The term "halogen" indicates fluorine, chlorine, bromine or iodine.

The term "trifluoromethyl" indicates a —$CF_3$ group.

The term "hydroxyalkyl" indicates a hydroxy group linked to an alkyl group. Examples of hydroxyalkyl groups are hydroxymethyl (—$CH_2OH$), hydroxyethyl (—$CH_2CH_2OH$) and the like.

The term "alkylthio" indicates an alkyl group linked to a sulphur atom (—S-alkyl). Examples of alkylthio groups are methylthio (—$SCH_3$), ethylthio (—$SCH_2CH_3$), isopropylthio [—$SCH(CH_3)_2$] and the like.

The term "alkylcarbonyl" indicates an alkyl residue linked to a CO group [—C(=O)alkyl]. Examples of alkylcarbonyl are methylcarbonyl [—C(=O)$CH_3$], ethylcarbonyl [—C(=O)$CH_2CH_3$] and the like.

The term "alkylsulfonyl" indicates a —$SO_2$alkyl group. Examples of alkylsulfonyl groups are methylsulfonyl (—$SO_2CH_3$), ethylsulfonyl (—$SO_2CH_2CH_3$) and the like.

The term "arylalkyl" indicates an aryl group linked to a $C_1$-$C_4$ alkyl chain. Examples of aryalkyl are benzyl (—$CH_2Ph$), phenetyl (—$CH_2CH_2Ph$) and the like.

The terms "monoalkylcarboxamido" or "dialkylcarboxamido" indicate a carboxamido group where one or both hydrogens are substituted by an alkyl group. Examples of monoalkylcarboxamido are methylcarboxamido (—$CONHCH_3$), ethylcarboxamido (—$CONHCH_2CH_3$), and the like. Examples of dialkylcarboxamido are dimethylcarboxamido [—$CON(CH_3)_2$], diethylcarboxamido [—$CON(CH_2CH_3)_2$] and the like.

The term "pharmaceutically acceptable salt" of compounds of formula (I) refers to those salts that retain the biological effectiveness and properties of the parent compounds. Such salts include:

acid addition salts with inorganic acids such as hydrochloric, hydrobromic, nitric, phosphoric, sulfuric, perchloric acid and the like, or with organic acids such as acetic, trifluoroacetic, propionic, glycolic, lactic, (D) or (L) malic, maleic, methanesulfonic, ethanesulfonic, benzoic, p-toluenesulfonic, salicylic, cinnamic, mandelic, tartaric, citric, succinic, malonic acid and the like;

salts formed when an acidic proton present in a compound of formula (I) is either replaced by a metal ion, e.g., an alkali metal ion such as sodium or potassium, or an alkaline earth ion such as calcium or magnesium, or coordinates with an organic base such as ethanolamine, diethanolamine, triethanolamine, tromethamine, N-methylglucamine, and the like.

Preferred compounds of formula (I) are the compounds wherein:

R is selected from $C_3$-$C_6$ cycloalkyl, heterocycloalkyl and aryl;

R1 is selected from hydrogen, halogen, NHCOR4, NHSO2R10, NR5R6, R8R9N—$C_1$-$C_6$ alkyl, R7O—$C_1$-$C_6$ alkyl and an optionally further substituted straight or branched $C_1$-$C_6$ alkyl;

A and D are CH or nitrogen, B is nitrogen, CH or CR2, and E is CH or CR3;

R2 and R3 are independently selected from halogen, trifluoromethyl, OR7, NR8R9, R8R9N—$C_1$-$C_6$ alkyl and R7O—$C_1$-$C_6$ alkyl.

Other preferred compounds of formula (I) are the compounds wherein:

R is selected from $C_3$-$C_6$ cycloalkyl, heterocycloalkyl and aryl;

R1 is selected from NHCOR4, NR5R6, R8R9N—$C_1$-$C_6$ alkyl, R7O—$C_1$-$C_6$ alkyl and an optionally further substituted straight or branched $C_1$-$C_6$ alkyl;

A is CH or nitrogen, B is nitrogen, CH or CR2, E is CH or CR3, and D is CH;

R2 and R3 are independently selected from halogen, OR7, NR8R9, R8R9N—$C_1$-$C_6$ alkyl and R7O—$C_1$-$C_6$ alkyl.

Further preferred compounds of formula (I) are the compounds wherein:

R is heterocycloalkyl or aryl;

R1 is selected from NHCOR4, NR5R6, R8R9N—$C_1$-$C_6$ alkyl and an optionally further substituted straight or branched $C_1$-$C_6$ alkyl;

B is nitrogen, CH or CR2, E is CH or CR3, and A and D is CH;

R2 and R3 are independently selected from halogen, OR7, NR8R9, R8R9N—$C_1$-$C_6$ alkyl and R7O—$C_1$-$C_6$ alkyl.

Particularly preferred compounds of formula (I) are the compounds wherein:

R is aryl;

R1 is selected from NHCOR4, NR5R6, R8R9N—$C_1$-$C_6$ alkyl and an optionally further substituted straight or branched $C_1$-$C_6$ alkyl;

B and E are CH, CR2 or CR3, and A and D are CH;

R2 and R3 are independently selected from halogen, OR7, NR8R9, R8R9N—$C_1$-$C_6$ alkyl and R7O—$C_1$-$C_6$ alkyl.

Most preferred compounds of formula (I) are the compounds wherein:

R is aryl;

R1 is selected from NHCOR4, NR5R6, R8R9N—$C_1$-$C_6$ alkyl and an optionally further substituted straight or branched $C_1$-$C_6$ alkyl;

B is CR2, and A, D and E are CH;

R2 is selected from OR7, NR8R9, R8R9N—$C_1$-$C_6$ alkyl and R7O—$C_1$-$C_6$ alkyl.

Specific compounds (cpd.) of the invention are listed below:

1. N-[5-(3,5-Difluoro-benzenesulfonyl)-4,5,6,7-tetrahydro-1H-pyrazolo[4,3-c]pyridin-3-yl]-2-fluoro-4-(4-methyl-piperazin-1-yl)-benzamide;
2. N-[5-(3,5-Difluoro-benzenesulfonyl)-7,7-dimethyl-4,5,6,7-tetrahydro-1H-pyrazolo[4,3-c]pyridin-3-yl]-4-(4-methyl-piperazin-1-yl)-benzamide;
3. 2-Acetylamino-N-[5-(3,5-difluoro-benzenesulfonyl)-4,5,6,7-tetrahydro-1H-pyrazolo[4,3-c]pyridin-3-yl]-4-(4-methyl-piperazin-1-yl)-benzamide;
4. N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-propionylamino-benzamide;
5. N-[5-(3,5-Difluoro-benzenesulfonyl)-4,5,6,7-tetrahydro-1H-pyrazolo[4,3-c]pyridin-3-yl]-2-isobutyrylamino-4-(4-methyl-piperazin-1-yl)-benzamide;
6. 2-(Cyclopropanecarbonyl-amino)-N-[5-(3,5-difluoro-benzenesulfonyl)-4,5,6,7-tetrahydro-1H-pyrazolo[4,3-c]pyridin-3-yl]-4-(4-methyl-piperazin-1-yl)-benzamide;
7. 2-(Cyclobutanecarbonyl-amino)-N-[5-(3,5-difluoro-benzenesulfonyl)-4,5,6,7-tetrahydro-1H-pyrazolo[4,3-c]pyridin-3-yl]-4-(4-methyl-piperazin-1-yl)-benzamide;
8. 2-(Cyclopentanecarbonyl-amino)-N-[5-(3,5-difluoro-benzenesulfonyl)-4,5,6,7-tetrahydro-1H-pyrazolo[4,3-c]pyridin-3-yl]-4-(4-methyl-piperazin-1-yl)-benzamide;
9. 2-(Cyclohexanecarbonyl-amino)-N-[5-(3,5-difluoro-benzenesulfonyl)-4,5,6,7-tetrahydro-1H-pyrazolo[4,3-c]pyridin-3-yl]-4-(4-methyl-piperazin-1-yl)-benzamide;
10. 2-(2-Amino-acetylamino)-N-[5-(3,5-difluoro-benzenesulfonyl)-4,5,6,7-tetrahydro-1H-pyrazolo[4,3-c]pyridin-3-yl]-4-(4-methyl-piperazin-1-yl)-benzamide;
11. N-[5-(3,5-Difluoro-benzenesulfonyl)-4,5,6,7-tetrahydro-1H-pyrazolo[4,3-c]pyridin-3-yl]-2-(2-methylamino-acetylamino)-4-(4-methyl-piperazin-1-yl)-benzamide;
12. N-[5-(3,5-Difluoro-benzenesulfonyl)-4,5,6,7-tetrahydro-1H-pyrazolo[4,3-c]pyridin-3-yl]-2-(2-dimethylamino-acetylamino)-4-(4-methyl-piperazin-1-yl)-benzamide;
13. 2-((R)-2-Amino-propionylamino)-N-[5-(3,5-difluoro-benzenesulfonyl)-4,5,6,7-tetrahydro-1H-pyrazolo[4,3-c]pyridin-3-yl]-4-(4-methyl-piperazin-1-yl)-benzamide;
14. 2-((S)-2-Amino-propionylamino)-N-[5-(3,5-difluoro-benzenesulfonyl)-4,5,6,7-tetrahydro-1H-pyrazolo[4,3-c]pyridin-3-yl]-4-(4-methyl-piperazin-1-yl)-benzamide;
15. (S)-Pyrrolidine-2-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;
16. (R)-Pyrrolidine-2-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;
17. (S)-1-Methyl-pyrrolidine-2-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;
18. (R)-1-Methyl-pyrrolidine-2-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;
19. 2-(3-Amino-propionylamino)-N-[5-(3,5-difluoro-benzenesulfonyl)-4,5,6,7-tetrahydro-1H-pyrazolo[4,3-c]pyridin-3-yl]-4-(4-methyl-piperazin-1-yl)-benzamide;
20. N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-(2-piperidin-1-yl-acetylamino)-benzamide;
21. Piperidine-2-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;
22. Piperidine-3-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;
23. Piperidine-4-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;
24. (S)-Tetrahydro-furan-2-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;
25. (R)-Tetrahydro-furan-2-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;
26. Tetrahydro-furan-3-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;
27. Tetrahydro-pyran-4-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;
28. 1H-Pyrrole-2-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;
29. 1-Methyl-1H-pyrrole-2-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;
30. 1H-Pyrrole-3-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;
31. Furan-2-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;
32. Thiophene-2-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;
33. 2H-Pyrazole-3-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;
34. 5-Methyl-2H-pyrazole-3-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;
35. 2-Ethyl-5-methyl-2H-pyrazole-3-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;
36. 1H-Pyrazole-4-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;

37. 1,3,5-Trimethyl-1H-pyrazole-4-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;

38. 3H-Imidazole-4-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;

39. 3-Methyl-3H-imidazole-4-carboxylic acid [2-[5-(3,5-difluoro-benzenesulfonyl)-4,5,6,7-tetrahydro-1H-pyrazolo[4,3-c]pyridin-3-ylcarbamoyl]-5-(4-ethyl-piperazin-1-yl)-phenyl]-amide;

40. 1H-Imidazole-2-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;

41. 1-Methyl-1H-imidazole-2-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;

42. Isoxazole-5-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;

43. 5-Methyl-isoxazole-4-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;

44. 4-Methyl-oxazole-5-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;

45. Pyridine-2-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;

46. N-[2-[5-(3,5-Difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-nicotinamide;

47. N-[2-[5-(3,5-Difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-isonicotinamide;

48. N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-(2-pyridin-4-yl-acetylamino)-benzamide;

49. N-[5-(3,5-Difluoro-benzenesulfonyl)-4,5,6,7-tetrahydro-1H-pyrazolo[4,3-c]pyridin-3-yl]-2-methylamino-4-(4-methyl-piperazin-1-yl)-benzamide;

50. N-[5-(3,5-Difluoro-benzenesulfonyl)-4,5,6,7-tetrahydro-1H-pyrazolo[4,3-c]pyridin-3-yl]-2-ethylamino-4-(4-methyl-piperazin-1-yl)-benzamide;

51. N-[5-(3,5-Difluoro-benzenesulfonyl)-4,5,6,7-tetrahydro-1H-pyrazolo[4,3-c]pyridin-3-yl]-2-isobutylamino-4-(4-methyl-piperazin-1-yl)-benzamide;

52. N-[5-(3,5-Difluoro-benzenesulfonyl)-4,5,6,7-tetrahydro-1H-pyrazolo[4,3-c]pyridin-3-yl]-2-[(furan-2-ylmethyl)-amino]-4-(4-methyl-piperazin-1-yl)-benzamide;

53. N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-[(1H-pyrrol-2-ylmethyl)-amino]-benzamide;

54. N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-[(1-methyl-1H-pyrrol-2-ylmethyl)-amino]-benzamide;

55. N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-[((S)-1-pyrrolidin-2-ylmethyl)-amino]-benzamide;

56. N-[5-(3,5-Difluoro-benzenesulfonyl)-4,5,6,7-tetrahydro-1H-pyrazolo[4,3-c]pyridin-3-yl]-2-[(1H-imidazol-2-ylmethyl)-amino]-4-(4-methyl-piperazin-1-yl)-benzamide;

57. 2-Cyclohexylamino-N-[5-(3,5-difluoro-benzenesulfonyl)-4,5,6,7-tetrahydro-1H-pyrazolo[4,3-c]pyridin-3-yl]-4-(4-methyl-piperazin-1-yl)-benzamide;

58. N-[5-(3,5-Difluoro-benzenesulfonyl)-4,5,6,7-tetrahydro-1H-pyrazolo[4,3-c]pyridin-3-yl]-2-(4-hydroxy-cyclohexylamino)-4-(4-methyl-piperazin-1-yl)-benzamide;

59. N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-(piperidin-2-ylamino)-benzamide;

60. N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-(piperidin-3-ylamino)-benzamide;

61. N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-(piperidin-4-ylamino)-benzamide;

62. N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-(1-methyl-piperidin-4-ylamino)-benzamide;

63. N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-(tetrahydro-pyran-4-ylamino)-benzamide;

64. N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-[methyl-(tetrahydro-pyran-4-yl)-amino]-benzamide;

65. 1H-Pyrrole-2-carboxylic acid [2-[5-(3-fluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;

66. 1H-Pyrrole-2-carboxylic acid [2-(5-benzenesulfonyl-4,5,6,7-tetrahydro-1H-pyrazolo[4,3-c]pyridin-3-ylcarbamoyl)-5-(4-methyl-piperazin-1-yl)-phenyl]-amide;

67. 1H-Pyrrole-2-carboxylic acid [2-[5-(3-fluoro-5-methoxy-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;

68. N-[5-(3-Fluoro-benzenesulfonyl)-4,5,6,7-tetrahydro-1H-pyrazolo[4,3-c]pyridin-3-yl]-4-(4-methyl-piperazin-1-yl)-2-(tetrahydro-pyran-4-ylamino)-benzamide;

69. N-[5-(2-Chloro-benzenesulfonyl)-4,5,6,7-tetrahydro-1H-pyrazolo[4,3-c]pyridin-3-yl]-4-(4-methyl-piperazin-1-yl)-2-(tetrahydro-pyran-4-ylamino)-benzamide;

70. N-[5-(3-Methoxy-benzenesulfonyl)-4,5,6,7-tetrahydro-1H-pyrazolo[4,3-c]pyridin-3-yl]-4-(4-methyl-piperazin-1-yl)-2-(tetrahydro-pyran-4-ylamino)-benzamide;

71. N-[5-(3-Chloro-benzenesulfonyl)-4,5,6,7-tetrahydro-1H-pyrazolo[4,3-c]pyridin-3-yl]-4-(4-methyl-piperazin-1-yl)-2-(tetrahydro-pyran-4-ylamino)-benzamide;

72. N-[5-(3,5-Dichloro-benzenesulfonyl)-4,5,6,7-tetrahydro-1H-pyrazolo[4,3-c]pyridin-3-yl]-4-(4-methyl-piperazin-1-yl)-2-(tetrahydro-pyran-4-ylamino)-benzamide;

73. 4-(4-Methyl-piperazin-1-yl)-N-[5-(pyridine-3-sulfonyl)-4,5,6,7-tetrahydro-1H-pyrazolo[4,3-c]pyridin-3-yl]-2-(tetrahydro-pyran-4-ylamino)-benzamide;

74. N-(5-Benzenesulfonyl-4,5,6,7-tetrahydro-1H-pyrazolo[4,3-c]pyridin-3-yl)-4-(4-methyl-piperazin-1-yl)-2-(tetrahydro-pyran-4-ylamino)-benzamide;

75. N-[5-(3,5-Difluoro-benzenesulfonyl)-4,5,6,7-tetrahydro-1H-pyrazolo[4,3-c]pyridin-3-yl]-4-piperazin-1-yl-2-(tetrahydro-pyran-4-ylamino)-benzamide;
76. N-[5-(3,5-Difluoro-benzenesulfonyl)-4,5,6,7-tetrahydro-1H-pyrazolo[4,3-c]pyridin-3-yl]-4-(4-ethyl-piperazin-1-yl)-2-(tetrahydro-pyran-4-ylamino)-benzamide;
77. N-[5-(3,5-Difluoro-benzenesulfonyl)-4,5,6,7-tetrahydro-1H-pyrazolo[4,3-c]pyridin-3-yl]-4-(4-propyl-piperazin-1-yl)-2-(tetrahydro-pyran-4-ylamino)-benzamide;
78. N-[5-(3,5-Difluoro-benzenesulfonyl)-4,5,6,7-tetrahydro-1H-pyrazolo[4,3-c]pyridin-3-yl]-4-(4-isopropyl-piperazin-1-yl)-2-(tetrahydro-pyran-4-ylamino)-benzamide;
79. N-[5-(3,5-Difluoro-benzenesulfonyl)-4,5,6,7-tetrahydro-1H-pyrazolo[4,3-c]pyridin-3-yl]-2-fluoro-4-(4-methyl-piperazin-1-yl)-6-(tetrahydro-pyran-4-ylamino)-benzamide;
80. 2-Fluoro-N-[5-(3-fluoro-benzenesulfonyl)-4,5,6,7-tetrahydro-1H-pyrazolo[4,3-c]pyridin-3-yl]-4-(4-methyl-piperazin-1-yl)-6-(tetrahydro-pyran-4-ylamino)-benzamide;
81. N-[5-(3,5-Difluoro-benzenesulfonyl)-4,5,6,7-tetrahydro-1H-pyrazolo[4,3-c]pyridin-3-yl]-4-(4-methyl-4-oxy-piperazin-1-yl)-2-(tetrahydro-pyran-4-ylamino)-benzamide;
82. N-[5-(3,5-Difluoro-benzenesulfonyl)-4,5,6,7-tetrahydro-1H-pyrazolo[4,3-c]pyridin-3-yl]-2-(isopropylaminomethyl)-4-(4-methyl-piperazin-1-yl)-benzamide;
83. 2-Cyclopentylaminomethyl-N-[5-(3,5-difluoro-benzenesulfonyl)-4,5,6,7-tetrahydro-1H-pyrazolo[4,3-c]pyridin-3-yl]-4-(4-methyl-piperazin-1-yl)-benzamide;
84. 2-Cyclohexylaminomethyl-N-[5-(3,5-difluoro-benzenesulfonyl)-4,5,6,7-tetrahydro-1H-pyrazolo[4,3-c]pyridin-3-yl]-4-(4-methyl-piperazin-1-yl)-benzamide;
85. N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-[(tetrahydro-pyran-4-ylamino)-methyl]-benzamide;
86. N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-pyrrolidin-1-ylmethyl-benzamide;
87. N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-piperidin-1-ylmethyl-benzamide;
88. N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-morpholin-4-ylmethyl-benzamide;
89. 1H-Pyrrole-2-carboxylic acid [2-(5-methanesulfonyl-4,5,6,7-tetrahydro-1H-pyrazolo[4,3-c]pyridin-3-ylcarbamoyl)-5-(4-methyl-piperazin-1-yl)-phenyl]-amide;
90. 1H-Pyrrole-2-carboxylic acid [5-(4-methyl-piperazin-1-yl)-2-(5-phenylmethanesulfonyl-4,5,6,7-tetrahydro-1H-pyrazolo[4,3-c]pyridin-3-ylcarbamoyl)-phenyl]-amide;
91. 1H-Pyrrole-2-carboxylic acid [2-(5-cyclopropanesulfonyl-4,5,6,7-tetrahydro-1H-pyrazolo[4,3-c]pyridin-3-ylcarbamoyl)-5-(4-methyl-piperazin-1-yl)-phenyl]-amide;
92. N-[5-(3,5-Difluoro-benzenesulfonyl)-4,5,6,7-tetrahydro-1H-pyrazolo[4,3-c]pyridin-3-yl]-2-(3-ethyl-ureido)-4-(4-methyl-piperazin-1-yl)-benzamide;
93. N-[5-(3,5-Difluoro-benzenesulfonyl)-4,5,6,7-tetrahydro-1H-pyrazolo[4,3-c]pyridin-3-yl]-2-(3,3-dimethyl-ureido)-4-(4-methyl-piperazin-1-yl)-benzamide;
94. Pyrrolidine-1-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;
95. Morpholine-4-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;
96. 4-Methyl-piperazine-1-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;
97. 1H-Pyrrole-2-carboxylic acid {2-[5-(3,5-difluoro-benzenesulfonyl)-4,5,6,7-tetrahydro-1H-pyrazolo[4,3-c]pyridin-3-ylcarbamoyl]-5-morpholin-4-yl-phenyl}-amide;
98. 1H-Pyrrole-2-carboxylic acid {5-morpholin-4-yl-2-[5-(pyridine-3-sulfonyl)-4,5,6,7-tetrahydro-1H-pyrazolo[4,3-c]pyridin-3-ylcarbamoyl]-phenyl}-amide;
99. 1H-Pyrrole-3-carboxylic acid {2-[5-(3,5-difluoro-benzenesulfonyl)-4,5,6,7-tetrahydro-1H-pyrazolo[4,3-c]pyridin-3-ylcarbamoyl]-5-morpholin-4-yl-phenyl}-amide;
100. (S)-Pyrrolidine-2-carboxylic acid {2-[5-(3,5-difluoro-benzenesulfonyl)-4,5,6,7-tetrahydro-1H-pyrazolo[4,3-c]pyridin-3-ylcarbamoyl]-5-morpholin-4-yl-phenyl}-amide;
101. (R)-Pyrrolidine-2-carboxylic acid {2-[5-(3,5-difluoro-benzenesulfonyl)-4,5,6,7-tetrahydro-1H-pyrazolo[4,3-c]pyridin-3-ylcarbamoyl]-5-morpholin-4-yl-phenyl}-amide;
102. (S)-1-Methyl-pyrrolidine-2-carboxylic acid {2-[5-(3,5-difluoro-benzenesulfonyl)-4,5,6,7-tetrahydro-1H-pyrazolo[4,3-c]pyridin-3-ylcarbamoyl]-5-morpholin-4-yl-phenyl}-amide;
103. (R)-1-Methyl-pyrrolidine-2-carboxylic acid {2-[5-(3,5-difluoro-benzenesulfonyl)-4,5,6,7-tetrahydro-1H-pyrazolo[4,3-c]pyridin-3-ylcarbamoyl]-5-morpholin-4-yl-phenyl}-amide;
104. Piperidine-2-carboxylic acid {2-[5-(3,5-difluoro-benzenesulfonyl)-4,5,6,7-tetrahydro-1H-pyrazolo[4,3-c]pyridin-3-ylcarbamoyl]-5-morpholin-4-yl-phenyl}-amide;
105. Piperidine-3-carboxylic acid {2-[5-(3,5-difluoro-benzenesulfonyl)-4,5,6,7-tetrahydro-1H-pyrazolo[4,3-c]pyridin-3-ylcarbamoyl]-5-morpholin-4-yl-phenyl}-amide;
106. Piperidine-4-carboxylic acid {2-[5-(3,5-difluoro-benzenesulfonyl)-4,5,6,7-tetrahydro-1H-pyrazolo[4,3-c]pyridin-3-ylcarbamoyl]-5-morpholin-4-yl-phenyl}-amide;
107. (S)-Tetrahydro-furan-2-carboxylic acid {2-[5-(3,5-difluoro-benzenesulfonyl)-4,5,6,7-tetrahydro-1H-pyrazolo[4,3-c]pyridin-3-ylcarbamoyl]-5-morpholin-4-yl-phenyl}-amide;
108. (R)-Tetrahydro-furan-2-carboxylic acid {2-[5-(3,5-difluoro-benzenesulfonyl)-4,5,6,7-tetrahydro-1H-pyrazolo[4,3-c]pyridin-3-ylcarbamoyl]-5-morpholin-4-yl-phenyl}-amide;
109. Tetrahydro-furan-3-carboxylic acid {2-[5-(3,5-difluoro-benzenesulfonyl)-4,5,6,7-tetrahydro-1H-pyrazolo[4,3-c]pyridin-3-ylcarbamoyl]-5-morpholin-4-yl-phenyl}-amide;
110. Tetrahydro-pyran-4-carboxylic acid {2-[5-(3,5-difluoro-benzenesulfonyl)-4,5,6,7-tetrahydro-1H-pyrazolo[4,3-c]pyridin-3-ylcarbamoyl]-5-morpholin-4-yl-phenyl}-amide;
111. N-[5-(3,5-Difluoro-benzenesulfonyl)-4,5,6,7-tetrahydro-1H-pyrazolo[4,3-c]pyridin-3-yl]-4-morpholin-4-yl-2-[((R)-1-pyrrolidin-2-ylmethyl)-amino]-benzamide;
112. N-[5-(3,5-Difluoro-benzenesulfonyl)-4,5,6,7-tetrahydro-1H-pyrazolo[4,3-c]pyridin-3-yl]-4-morpholin-4-yl-2-[((S)-1-pyrrolidin-2-ylmethyl)-amino]-benzamide;

113. N-[5-(3,5-Difluoro-benzenesulfonyl)-4,5,6,7-tetrahydro-1H-pyrazolo[4,3-c]pyridin-3-yl]-2-[((R)-1-methyl-pyrrolidin-2-ylmethyl)-amino]-4-morpholin-4-yl-benzamide;
114. N-[5-(3,5-Difluoro-benzenesulfonyl)-4,5,6,7-tetrahydro-1H-pyrazolo[4,3-c]pyridin-3-yl]-2-[((S)-1-methyl-pyrrolidin-2-ylmethyl)-amino]-4-morpholin-4-yl-benzamide;
115. N-[5-(3,5-Difluoro-benzenesulfonyl)-4,5,6,7-tetrahydro-1H-pyrazolo[4,3-c]pyridin-3-yl]-4-morpholin-4-yl-2-(2-piperidin-1-yl-acetylamino)-benzamide;
116. N-[5-(3,5-Difluoro-benzenesulfonyl)-4,5,6,7-tetrahydro-1H-pyrazolo[4,3-c]pyridin-3-yl]-4-morpholin-4-yl-2-(piperidin-4-ylamino)-benzamide;
117. N-[5-(3,5-Difluoro-benzenesulfonyl)-4,5,6,7-tetrahydro-1H-pyrazolo[4,3-c]pyridin-3-yl]-2-(1-methyl-piperidin-4-ylamino)-4-morpholin-4-yl-benzamide;
118. N-[5-(3,5-Difluoro-benzenesulfonyl)-4,5,6,7-tetrahydro-1H-pyrazolo[4,3-c]pyridin-3-yl]-4-morpholin-4-yl-2-(tetrahydro-pyran-4-ylamino)-benzamide;
119. N-[5-(3,5-Difluoro-benzenesulfonyl)-4,5,6,7-tetrahydro-1H-pyrazolo[4,3-c]pyridin-3-yl]-4-(2-hydroxymethyl-pyrrolidin-1-yl)-2-(tetrahydro-pyran-4-ylamino)-benzamide;
120. N-[5-(3,5-Difluoro-benzenesulfonyl)-4,5,6,7-tetrahydro-1H-pyrazolo[4,3-c]pyridin-3-yl]-4-(3-hydroxy-pyrrolidin-1-yl)-2-(tetrahydro-pyran-4-ylamino)-benzamide;
121. 4-(3-Amino-pyrrolidin-1-yl)-N-[5-(3,5-difluoro-benzenesulfonyl)-4,5,6,7-tetrahydro-1H-pyrazolo[4,3-c]pyridin-3-yl]-2-(tetrahydro-pyran-4-ylamino)-benzamide;
122. N-[5-(3,5-Difluoro-benzenesulfonyl)-4,5,6,7-tetrahydro-1H-pyrazolo[4,3-c]pyridin-3-yl]-4-(3-hydroxy-azetidin-1-yl)-2-(tetrahydro-pyran-4-ylamino)-benzamide;
123. 1H-Pyrrole-2-carboxylic acid {2-[5-(3,5-difluoro-benzenesulfonyl)-4,5,6,7-tetrahydro-1H-pyrazolo[4,3-c]pyridin-3-ylcarbamoyl]-5-dimethylamino-phenyl}-amide;
124. 1H-Pyrrole-2-carboxylic acid {5-dimethylamino-2-[5-(pyridine-3-sulfonyl)-4,5,6,7-tetrahydro-1H-pyrazolo[4,3-c]pyridin-3-ylcarbamoyl]-phenyl}-amide;
125. 1H-Pyrrole-3-carboxylic acid {2-[5-(3,5-difluoro-benzenesulfonyl)-4,5,6,7-tetrahydro-1H-pyrazolo[4,3-c]pyridin-3-ylcarbamoyl]-5-dimethylamino-phenyl}-amide;
126. (S)-Pyrrolidine-2-carboxylic acid {2-[5-(3,5-difluoro-benzenesulfonyl)-4,5,6,7-tetrahydro-1H-pyrazolo[4,3-c]pyridin-3-ylcarbamoyl]-5-dimethylamino-phenyl}-amide;
127. (R)-Pyrrolidine-2-carboxylic acid {2-[5-(3,5-difluoro-benzenesulfonyl)-4,5,6,7-tetrahydro-1H-pyrazolo[4,3-c]pyridin-3-ylcarbamoyl]-5-dimethylamino-phenyl}-amide;
128. (S)-1-Methyl-pyrrolidine-2-carboxylic acid {2-[5-(3,5-difluoro-benzenesulfonyl)-4,5,6,7-tetrahydro-1H-pyrazolo[4,3-c]pyridin-3-ylcarbamoyl]-5-dimethylamino-phenyl}-amide;
129. (R)-1-Methyl-pyrrolidine-2-carboxylic acid {2-[5-(3,5-difluoro-benzenesulfonyl)-4,5,6,7-tetrahydro-1H-pyrazolo[4,3-c]pyridin-3-ylcarbamoyl]-5-dimethylamino-phenyl}-amide;
130. Piperidine-2-carboxylic acid {2-[5-(3,5-difluoro-benzenesulfonyl)-4,5,6,7-tetrahydro-1H-pyrazolo[4,3-c]pyridin-3-ylcarbamoyl]-5-dimethylamino-phenyl}-amide;
131. Piperidine-3-carboxylic acid {2-[5-(3,5-difluoro-benzenesulfonyl)-4,5,6,7-tetrahydro-1H-pyrazolo[4,3-c]pyridin-3-ylcarbamoyl]-5-dimethylamino-phenyl}-amide;
132. Piperidine-4-carboxylic acid {2-[5-(3,5-difluoro-benzenesulfonyl)-4,5,6,7-tetrahydro-1H-pyrazolo[4,3-c]pyridin-3-ylcarbamoyl]-5-dimethylamino-phenyl}-amide;
133. (S)-Tetrahydro-furan-2-carboxylic acid {2-[5-(3,5-difluoro-benzenesulfonyl)-4,5,6,7-tetrahydro-1H-pyrazolo[4,3-c]pyridin-3-ylcarbamoyl]-5-dimethylamino-phenyl}-amide;
134. (R)-Tetrahydro-furan-2-carboxylic acid {2-[5-(3,5-difluoro-benzenesulfonyl)-4,5,6,7-tetrahydro-1H-pyrazolo[4,3-c]pyridin-3-ylcarbamoyl]-5-dimethylamino-phenyl}-amide;
135. Tetrahydro-furan-3-carboxylic acid {2-[5-(3,5-difluoro-benzenesulfonyl)-4,5,6,7-tetrahydro-1H-pyrazolo[4,3-c]pyridin-3-ylcarbamoyl]-5-dimethylamino-phenyl}-amide;
136. Tetrahydro-pyran-4-carboxylic acid {2-[5-(3,5-difluoro-benzenesulfonyl)-4,5,6,7-tetrahydro-1H-pyrazolo[4,3-c]pyridin-3-ylcarbamoyl]-5-dimethylamino-phenyl}-amide;
137. N-[5-(3,5-Difluoro-benzenesulfonyl)-4,5,6,7-tetrahydro-1H-pyrazolo[4,3-c]pyridin-3-yl]-4-dimethylamino-2-[(pyrrolidin-2-ylmethyl)-amino]-benzamide;
138. N-[5-(3,5-Difluoro-benzenesulfonyl)-4,5,6,7-tetrahydro-1H-pyrazolo[4,3-c]pyridin-3-yl]-4-dimethylamino-2-[(1-methyl-pyrrolidin-2-ylmethyl)-amino]-benzamide;
139. N-[5-(3,5-Difluoro-benzenesulfonyl)-4,5,6,7-tetrahydro-1H-pyrazolo[4,3-c]pyridin-3-yl]-4-dimethylamino-2-(piperidin-4-ylamino)-benzamide;
140. N-[5-(3,5-Difluoro-benzenesulfonyl)-4,5,6,7-tetrahydro-1H-pyrazolo[4,3-c]pyridin-3-yl]-4-dimethylamino-2-(1-methyl-piperidin-4-ylamino)-benzamide;
141. N-[5-(3,5-Difluoro-benzenesulfonyl)-4,5,6,7-tetrahydro-1H-pyrazolo[4,3-c]pyridin-3-yl]-4-dimethylamino-2-(tetrahydro-pyran-4-ylamino)-benzamide;
142. 1H-Pyrrole-2-carboxylic acid {2-[5-(3,5-difluoro-benzenesulfonyl)-4,5,6,7-tetrahydro-1H-pyrazolo[4,3-c]pyridin-3-ylcarbamoyl]-5-[(2-dimethylamino-ethyl)-methyl-amino]-phenyl}-amide;
143. 1H-Pyrrole-3-carboxylic acid {2-[5-(3,5-difluoro-benzenesulfonyl)-4,5,6,7-tetrahydro-1H-pyrazolo[4,3-c]pyridin-3-ylcarbamoyl]-5-[(2-dimethylamino-ethyl)-methyl-amino]-phenyl}-amide;
144. (S)-Tetrahydro-furan-2-carboxylic acid {2-[5-(3,5-difluoro-benzenesulfonyl)-4,5,6,7-tetrahydro-1H-pyrazolo[4,3-c]pyridin-3-ylcarbamoyl]-5-[(2-dimethylamino-ethyl)-methyl-amino]-phenyl}-amide;
145. (R)-Tetrahydro-furan-2-carboxylic acid {2-[5-(3,5-difluoro-benzenesulfonyl)-4,5,6,7-tetrahydro-1H-pyrazolo[4,3-c]pyridin-3-ylcarbamoyl]-5-[(2-dimethylamino-ethyl)-methyl-amino]-phenyl}-amide;
146. Tetrahydro-furan-3-carboxylic acid {2-[5-(3,5-difluoro-benzenesulfonyl)-4,5,6,7-tetrahydro-1H-pyrazolo[4,3-c]pyridin-3-ylcarbamoyl]-5-[(2-dimethylamino-ethyl)-methyl-amino]-phenyl}-amide;
147. Tetrahydro-pyran-4-carboxylic acid {2-[5-(3,5-difluoro-benzenesulfonyl)-4,5,6,7-tetrahydro-1H-pyrazolo[4,3-c]pyridin-3-ylcarbamoyl]-5-[(2-dimethylamino-ethyl)-methyl-amino]-phenyl}-amide;
148. N-[5-(3,5-Difluoro-benzenesulfonyl)-4,5,6,7-tetrahydro-1H-pyrazolo[4,3-c]pyridin-3-yl]-4-[(2-dimethylamino-ethyl)-methyl-amino]-2-(tetrahydro-pyran-4-ylamino)-benzamide;
149. N-[5-(3,5-Difluoro-benzenesulfonyl)-4,5,6,7-tetrahydro-1H-pyrazolo[4,3-c]pyridin-3-yl]-4-[(3-dimethylamino-propyl)-methyl-amino]-2-(tetrahydro-pyran-4-ylamino)-benzamide;
150. N-[5-(3,5-Difluoro-benzenesulfonyl)-4,5,6,7-tetrahydro-1H-pyrazolo[4,3-c]pyridin-3-yl]-4-(2-hydroxy-ethylamino)-2-(tetrahydro-pyran-4-ylamino)-benzamide;

151. N-[5-(3,5-Difluoro-benzenesulfonyl)-4,5,6,7-tetrahydro-1H-pyrazolo[4,3-c]pyridin-3-yl]-4-[(2-hydroxy-ethyl)-methyl-amino]-2-(tetrahydro-pyran-4-ylamino)-benzamide;

152. 4-[Bis-(2-hydroxy-ethyl)-amino]-N-[5-(3,5-difluoro-benz enesulfonyl)-4,5,6,7-tetrahydro-1H-pyrazolo[4,3-c]pyridin-3-yl]-2-(tetrahydro-pyran-4-ylamino)-benzamide;

153. N-[5-(3,5-Difluoro-benzenesulfonyl)-4,5,6,7-tetrahydro-1H-pyrazolo[4,3-c]pyridin-3-yl]-4-(1-methyl-azetidin-3-ylamino)-2-(tetrahydro-pyran-4-ylamino)-benzamide;

154. N-[5-(3,5-Difluoro-benzenesulfonyl)-4,5,6,7-tetrahydro-1H-pyrazolo[4,3-c]pyridin-3-yl]-4-[methyl-(1-methyl-azetidin-3-yl)-amino]-2-(tetrahydro-pyran-4-ylamino)-benzamide;

155. N-[5-(3,5-Difluoro-benzenesulfonyl)-4,5,6,7-tetrahydro-1H-pyrazolo[4,3-c]pyridin-3-yl]-2,4-bis-(tetrahydro-pyran-4-ylamino)-benzamide;

156. N-[5-(3,5-Difluoro-benzenesulfonyl)-4,5,6,7-tetrahydro-1H-pyrazolo[4,3-c]pyridin-3-yl]-4-[methyl-(tetrahydro-pyran-4-yl)-amino]-2-(tetrahydro-pyran-4-ylamino)-benzamide;

157. N-[5-(3,5-Difluoro-benzenesulfonyl)-4,5,6,7-tetrahydro-1H-pyrazolo[4,3-c]pyridin-3-yl]-4-(1-methyl-piperidin-4-ylamino)-2-(tetrahydro-pyran-4-ylamino)-benzamide;

158. N-[5-(3,5-Difluoro-benzenesulfonyl)-4,5,6,7-tetrahydro-1H-pyrazolo[4,3-c]pyridin-3-yl]-4-[methyl-(1-methyl-piperidin-4-yl)-amino]-2-(tetrahydro-pyran-4-ylamino)-benzamide;

159. 1H-Pyrrole-2-carboxylic acid [2-[5-(3,5-difluoro-benzenesulfonyl)-4,5,6,7-tetrahydro-1H-pyrazolo[4,3-c]pyridin-3-ylcarbamoyl]-5-(2-dimethylamino-ethylamino)-phenyl]-amide;

160. 1H-Pyrrole-3-carboxylic acid [2-[5-(3,5-difluoro-benzenesulfonyl)-4,5,6,7-tetrahydro-1H-pyrazolo[4,3-c]pyridin-3-ylcarbamoyl]-5-(2-dimethylamino-ethylamino)-phenyl]-amide;

161. (S)-Tetrahydro-furan-2-carboxylic acid [2-[5-(3,5-difluoro-benzenesulfonyl)-4,5,6,7-tetrahydro-1H-pyrazolo[4,3-c]pyridin-3-ylcarbamoyl]-5-(2-dimethylamino-ethylamino)-phenyl]-amide;

162. (R)-Tetrahydro-furan-2-carboxylic acid [2-[5-(3,5-difluoro-benzenesulfonyl)-4,5,6,7-tetrahydro-1H-pyrazolo[4,3-c]pyridin-3-ylcarbamoyl]-5-(2-dimethylamino-ethylamino)-phenyl]-amide;

163. Tetrahydro-furan-3-carboxylic acid [2-[5-(3,5-difluoro-benzenesulfonyl)-4,5,6,7-tetrahydro-1H-pyrazolo[4,3-c]pyridin-3-ylcarbamoyl]-5-(2-dimethylamino-ethylamino)-phenyl]-amide;

164. Tetrahydro-pyran-4-carboxylic acid [2-[5-(3,5-difluoro-benzenesulfonyl)-4,5,6,7-tetrahydro-1H-pyrazolo[4,3-c]pyridin-3-ylcarbamoyl]-5-(2-dimethylamino-ethylamino)-phenyl]-amide;

165. N-[5-(3,5-Difluoro-benzenesulfonyl)-4,5,6,7-tetrahydro-1H-pyrazolo[4,3-c]pyridin-3-yl]-4-(2-dimethylamino-ethylamino)-2-(tetrahydro-pyran-4-ylamino)-benzamide;

166. N-[5-(3,5-Difluoro-benzenesulfonyl)-4,5,6,7-tetrahydro-1H-pyrazolo[4,3-c]pyridin-3-yl]-4-(3-dimethylamino-propylamino)-2-(tetrahydro-pyran-4-ylamino)-benzamide;

167. 1H-Pyrrole-2-carboxylic acid [2-[5-(3,5-difluoro-benzenesulfonyl)-4,5,6,7-tetrahydro-1H-pyrazolo[4,3-c]pyridin-3-ylcarbamoyl]-5-(2-dimethylamino-ethoxy)-phenyl]-amide;

168. 1H-Pyrrole-3-carboxylic acid [2-[5-(3,5-difluoro-benzenesulfonyl)-4,5,6,7-tetrahydro-1H-pyrazolo[4,3-c]pyridin-3-ylcarbamoyl]-5-(2-dimethylamino-ethoxy)-phenyl]-amide;

169. (S)-Tetrahydro-furan-2-carboxylic acid [2-[5-(3,5-difluoro-benzenesulfonyl)-4,5,6,7-tetrahydro-1H-pyrazolo[4,3-c]pyridin-3-ylcarbamoyl]-5-(2-dimethylamino-ethoxy)-phenyl]-amide;

170. (R)-Tetrahydro-furan-2-carboxylic acid [2-[5-(3,5-difluoro-benzenesulfonyl)-4,5,6,7-tetrahydro-1H-pyrazolo[4,3-c]pyridin-3-ylcarbamoyl]-5-(2-dimethylamino-ethoxy)-phenyl]-amide;

171. Tetrahydro-furan-3-carboxylic acid [2-[5-(3,5-difluoro-benzenesulfonyl)-4,5,6,7-tetrahydro-1H-pyrazolo[4,3-c]pyridin-3-ylcarbamoyl]-5-(2-dimethylamino-ethoxy)-phenyl]-amide;

172. Tetrahydro-pyran-4-carboxylic acid [2-[5-(3,5-difluoro-benzenesulfonyl)-4,5,6,7-tetrahydro-1H-pyrazolo[4,3-c]pyridin-3-ylcarbamoyl]-5-(2-dimethylamino-ethoxy)-phenyl]-amide;

173. N-[5-(3,5-Difluoro-benzenesulfonyl)-4,5,6,7-tetrahydro-1H-pyrazolo[4,3-c]pyridin-3-yl]-4-(2-dimethylamino-ethoxy)-2-(tetrahydro-pyran-4-ylamino)-benzamide;

174. N-[5-(3,5-Difluoro-benzenesulfonyl)-4,5,6,7-tetrahydro-1H-pyrazolo[4,3-c]pyridin-3-yl]-4-(2-pyrrolidin-1-yl-ethoxy)-2-(tetrahydro-pyran-4-ylamino)-benzamide;

175. 1H-Pyrrole-2-carboxylic acid [2-[5-(3,5-difluoro-benzenesulfonyl)-4,5,6,7-tetrahydro-1H-pyrazolo[4,3-c]pyridin-3-ylcarbamoyl]-5-(1-methyl-azetidin-3-yloxy)-phenyl]-amide;

176. 1H-Pyrrole-3-carboxylic acid [2-[5-(3,5-difluoro-benzenesulfonyl)-4,5,6,7-tetrahydro-1H-pyrazolo[4,3-c]pyridin-3-ylcarbamoyl]-5-(1-methyl-azetidin-3-yloxy)-phenyl]-amide;

177. (S)-Tetrahydro-furan-2-carboxylic acid [2-[5-(3,5-difluoro-benzenesulfonyl)-4,5,6,7-tetrahydro-1H-pyrazolo[4,3-c]pyridin-3-ylcarbamoyl]-5-(1-methyl-azetidin-3-yloxy)-phenyl]-amide;

178. (R)-Tetrahydro-furan-2-carboxylic acid [2-[5-(3,5-difluoro-benzenesulfonyl)-4,5,6,7-tetrahydro-1H-pyrazolo[4,3-c]pyridin-3-ylcarbamoyl]-5-(1-methyl-azetidin-3-yloxy)-phenyl]-amide;

179. Tetrahydro-furan-3-carboxylic acid [2-[5-(3,5-difluoro-benzenesulfonyl)-4,5,6,7-tetrahydro-1H-pyrazolo[4,3-c]pyridin-3-ylcarbamoyl]-5-(1-methyl-azetidin-3-yloxy)-phenyl]-amide;

180. Tetrahydro-pyran-4-carboxylic acid [2-[5-(3,5-difluoro-benzenesulfonyl)-4,5,6,7-tetrahydro-1H-pyrazolo[4,3-c]pyridin-3-ylcarbamoyl]-5-(1-methyl-azetidin-3-yloxy)-phenyl]-amide;

181. N-[5-(3,5-Difluoro-benzenesulfonyl)-4,5,6,7-tetrahydro-1H-pyrazolo[4,3-c]pyridin-3-yl]-4-(1-methyl-azetidin-3-yloxy)-2-(tetrahydro-pyran-4-ylamino)-benzamide;

182. 1H-Pyrrole-2-carboxylic acid [2-[5-(3,5-difluoro-benzenesulfonyl)-4,5,6,7-tetrahydro-1H-pyrazolo[4,3-c]pyridin-3-ylcarbamoyl]-5-(1-methyl-piperidin-4-yloxy)-phenyl]-amide;

183. 1H-Pyrrole-3-carboxylic acid [2-[5-(3,5-difluoro-benzenesulfonyl)-4,5,6,7-tetrahydro-1H-pyrazolo[4,3-c]pyridin-3-ylcarbamoyl]-5-(1-methyl-piperidin-4-yloxy)-phenyl]-amide;

184. (S)-Tetrahydro-furan-2-carboxylic acid [2-[5-(3,5-difluoro-benzenesulfonyl)-4,5,6,7-tetrahydro-1H-pyrazolo[4,3-c]pyridin-3-ylcarbamoyl]-5-(1-methyl-piperidin-4-yloxy)-phenyl]-amide;

185. (R)-Tetrahydro-furan-2-carboxylic acid [2-[5-(3,5-difluoro-benzenesulfonyl)-4,5,6,7-tetrahydro-1H-pyrazolo[4,3-c]pyridin-3-ylcarbamoyl]-5-(1-methyl-piperidin-4-yloxy)-phenyl]-amide;

186. Tetrahydro-furan-3-carboxylic acid [2-[5-(3,5-difluoro-benzenesulfonyl)-4,5,6,7-tetrahydro-1H-pyrazolo[4,3-c]pyridin-3-ylcarbamoyl]-5-(1-methyl-piperidin-4-yloxy)-phenyl]-amide;

187. Tetrahydro-pyran-4-carboxylic acid [2-[5-(3,5-difluoro-benzenesulfonyl)-4,5,6,7-tetrahydro-1H-pyrazolo[4,3-c]pyridin-3-ylcarbamoyl]-5-(1-methyl-piperidin-4-yloxy)-phenyl]-amide;

188. N-[5-(3,5-Difluoro-benzenesulfonyl)-4,5,6,7-tetrahydro-1H-pyrazolo[4,3-c]pyridin-3-yl]-4-(1-methyl-piperidin-4-yloxy)-2-(tetrahydro-pyran-4-ylamino)-benzamide;

189. 1H-Pyrrole-2-carboxylic acid {2-[5-(3,5-difluoro-benzenesulfonyl)-4,5,6,7-tetrahydro-1H-pyrazolo[4,3-c]pyridin-3-ylcarbamoyl]-5-methoxy-phenyl}-amide;

190. 1H-Pyrrole-2-carboxylic acid {5-methoxy-2-[5-(pyridine-3-sulfonyl)-4,5,6,7-tetrahydro-1H-pyrazolo[4,3-c]pyridin-3-ylcarbamoyl]-phenyl}-amide;

191. 1H-Pyrrole-3-carboxylic acid {2-[5-(3,5-difluoro-benzenesulfonyl)-4,5,6,7-tetrahydro-1H-pyrazolo[4,3-c]pyridin-3-ylcarbamoyl]-5-methoxy-phenyl}-amide;

192. (S)-Tetrahydro-furan-2-carboxylic acid {2-[5-(3,5-difluoro-benzenesulfonyl)-4,5,6,7-tetrahydro-1H-pyrazolo[4,3-c]pyridin-3-ylcarbamoyl]-5-methoxy-phenyl}-amide;

193. (R)-Tetrahydro-furan-2-carboxylic acid {2-[5-(3,5-difluoro-benzenesulfonyl)-4,5,6,7-tetrahydro-1H-pyrazolo[4,3-c]pyridin-3-ylcarbamoyl]-5-methoxy-phenyl}-amide;

194. Tetrahydro-furan-3-carboxylic acid {2-[5-(3,5-difluoro-benzenesulfonyl)-4,5,6,7-tetrahydro-1H-pyrazolo[4,3-c]pyridin-3-ylcarbamoyl]-5-methoxy-phenyl}-amide;

195. Tetrahydro-pyran-4-carboxylic acid {2-[5-(3,5-difluoro-benzenesulfonyl)-4,5,6,7-tetrahydro-1H-pyrazolo[4,3-c]pyridin-3-ylcarbamoyl]-5-methoxy-phenyl}-amide;

196. N-[5-(3,5-Difluoro-benzenesulfonyl)-4,5,6,7-tetrahydro-1H-pyrazolo[4,3-c]pyridin-3-yl]-4-methoxy-2-(tetrahydro-pyran-4-ylamino)-benzamide;

197. 1H-Pyrrole-2-carboxylic acid {2-[5-(3,5-difluoro-benzenesulfonyl)-4,5,6,7-tetrahydro-1H-pyrazolo[4,3-c]pyridin-3-ylcarbamoyl]-3-fluoro-phenyl}-amide;

198. 1H-Pyrrole-2-carboxylic acid {3-fluoro-2-[5-(pyridine-3-sulfonyl)-4,5,6,7-tetrahydro-1H-pyrazolo[4,3-c]pyridin-3-ylcarbamoyl]-phenyl}-amide;

199. 1H-Pyrrole-3-carboxylic acid {2-[5-(3,5-difluoro-benzenesulfonyl)-4,5,6,7-tetrahydro-1H-pyrazolo[4,3-c]pyridin-3-ylcarbamoyl]-3-fluoro-phenyl}-amide;

200. (S)-Tetrahydro-furan-2-carboxylic acid {2-[5-(3,5-difluoro-benzenesulfonyl)-4,5,6,7-tetrahydro-1H-pyrazolo[4,3-c]pyridin-3-ylcarbamoyl]-3-fluoro-phenyl}-amide;

201. (R)-Tetrahydro-furan-2-carboxylic acid {2-[5-(3,5-difluoro-benzenesulfonyl)-4,5,6,7-tetrahydro-1H-pyrazolo[4,3-c]pyridin-3-ylcarbamoyl]-3-fluoro-phenyl}-amide;

202. Tetrahydro-furan-3-carboxylic acid {2-[5-(3,5-difluoro-benzenesulfonyl)-4,5,6,7-tetrahydro-1H-pyrazolo[4,3-c]pyridin-3-ylcarbamoyl]-3-fluoro-phenyl}-amide;

203. Tetrahydro-pyran-4-carboxylic acid {2-[5-(3,5-difluoro-benzenesulfonyl)-4,5,6,7-tetrahydro-1H-pyrazolo[4,3-c]pyridin-3-ylcarbamoyl]-3-fluoro-phenyl}-amide;

204. N-[5-(3,5-Difluoro-benzenesulfonyl)-4,5,6,7-tetrahydro-1H-pyrazolo[4,3-c]pyridin-3-yl]-2-fluoro-6-(tetrahydro-pyran-4-ylamino)-benzamide;

205. 1H-Pyrrole-2-carboxylic acid {2-[5-(3,5-difluoro-benzenesulfonyl)-4,5,6,7-tetrahydro-1H-pyrazolo[4,3-c]pyridin-3-ylcarbamoyl]-5-pyrrolidin-1-ylmethyl-phenyl}-amide;

206. 1H-Pyrrole-3-carboxylic acid {2-[5-(3,5-difluoro-benzenesulfonyl)-4,5,6,7-tetrahydro-1H-pyrazolo[4,3-c]pyridin-3-ylcarbamoyl]-5-pyrrolidin-1-ylmethyl-phenyl}-amide;

207. (S)-Tetrahydro-furan-2-carboxylic acid {2-[5-(3,5-difluoro-benzenesulfonyl)-4,5,6,7-tetrahydro-1H-pyrazolo[4,3-c]pyridin-3-ylcarbamoyl]-5-pyrrolidin-1-ylmethyl-phenyl}-amide;

208. (R)-Tetrahydro-furan-2-carboxylic acid {2-[5-(3,5-difluoro-benzenesulfonyl)-4,5,6,7-tetrahydro-1H-pyrazolo[4,3-c]pyridin-3-ylcarbamoyl]-5-pyrrolidin-1-ylmethyl-phenyl}-amide;

209. Tetrahydro-furan-3-carboxylic acid {2-[5-(3,5-difluoro-benzenesulfonyl)-4,5,6,7-tetrahydro-1H-pyrazolo[4,3-c]pyridin-3-ylcarbamoyl]-5-pyrrolidin-1-ylmethyl-phenyl}-amide;

210. Tetrahydro-pyran-4-carboxylic acid {2-[5-(3,5-difluoro-benzenesulfonyl)-4,5,6,7-tetrahydro-1H-pyrazolo[4,3-c]pyridin-3-ylcarbamoyl]-5-pyrrolidin-1-ylmethyl-phenyl}-amide;

211. N-[5-(3,5-Difluoro-benzenesulfonyl)-4,5,6,7-tetrahydro-1H-pyrazolo[4,3-c]pyridin-3-yl]-4-pyrrolidin-1-ylmethyl-2-(tetrahydro-pyran-4-ylamino)-benzamide;

212. N-[5-(3,5-Difluoro-benzenesulfonyl)-4,5,6,7-tetrahydro-1H-pyrazolo[4,3-c]pyridin-3-yl]-4-piperidin-1-ylmethyl-2-(tetrahydro-pyran-4-ylamino)-benzamide;

213. 1H-Pyrrole-2-carboxylic acid {2-[5-(3,5-difluoro-benzenesulfonyl)-4,5,6,7-tetrahydro-1H-pyrazolo[4,3-c]pyridin-3-ylcarbamoyl]-5-morpholin-4-ylmethyl-phenyl}-amide;

214. 1H-Pyrrole-3-carboxylic acid {2-[5-(3,5-difluoro-benzenesulfonyl)-4,5,6,7-tetrahydro-1H-pyrazolo[4,3-c]pyridin-3-ylcarbamoyl]-5-morpholin-4-ylmethyl-phenyl}-amide;

215. (S)-Tetrahydro-furan-2-carboxylic acid {2-[5-(3,5-difluoro-benzenesulfonyl)-4,5,6,7-tetrahydro-1H-pyrazolo[4,3-c]pyridin-3-ylcarbamoyl]-5-morpholin-4-ylmethyl-phenyl}-amide;

216. (R)-Tetrahydro-furan-2-carboxylic acid {2-[5-(3,5-difluoro-benzenesulfonyl)-4,5,6,7-tetrahydro-1H-pyrazolo[4,3-c]pyridin-3-ylcarbamoyl]-5-morpholin-4-ylmethyl-phenyl}-amide;

217. Tetrahydro-furan-3-carboxylic acid {2-[5-(3,5-difluoro-benzenesulfonyl)-4,5,6,7-tetrahydro-1H-pyrazolo[4,3-c]pyridin-3-ylcarbamoyl]-5-morpholin-4-ylmethyl-phenyl}-amide;

218. Tetrahydro-pyran-4-carboxylic acid {2-[5-(3,5-difluoro-benzenesulfonyl)-4,5,6,7-tetrahydro-1H-pyrazolo[4,3-c]pyridin-3-ylcarbamoyl]-5-morpholin-4-ylmethyl-phenyl}-amide;

219. N-[5-(3,5-Difluoro-benzenesulfonyl)-4,5,6,7-tetrahydro-1H-pyrazolo[4,3-c]pyridin-3-yl]-4-morpholin-4-ylmethyl-2-(tetrahydro-pyran-4-ylamino)-benzamide;

220. N-[5-(3,5-Difluoro-benzenesulfonyl)-4,5,6,7-tetrahydro-1H-pyrazolo[4,3-c]pyridin-3-yl]-4-(4-methyl-piperazin-1-ylmethyl)-2-(tetrahydro-pyran-4-ylamino)-benzamide;

221. N-[5-(3,5-Difluoro-benzenesulfonyl)-4,5,6,7-tetrahydro-1H-pyrazolo[4,3-c]pyridin-3-yl]-4-[(2-hydroxy-ethylamino)-methyl]-2-(tetrahydro-pyran-4-ylamino)-benzamide;

222. N-[5-(3,5-Difluoro-benzenesulfonyl)-4,5,6,7-tetrahydro-1H-pyrazolo[4,3-c]pyridin-3-yl]-4-{[(2-hydroxy-ethyl)-methyl-amino]-methyl}-2-(tetrahydro-pyran-4-ylamino)-benzamide;

223. 1H-Pyrrole-2-carboxylic acid {2-[5-(3,5-difluoro-benzenesulfonyl)-4,5,6,7-tetrahydro-1H-pyrazolo[4,3-c]pyridin-3-ylcarbamoyl]-phenyl}-amide;

224. 1H-Pyrrole-3-carboxylic acid {2-[5-(3,5-difluoro-benzenesulfonyl)-4,5,6,7-tetrahydro-1H-pyrazolo[4,3-c]pyridin-3-ylcarbamoyl]-phenyl}-amide;

225. 3H-Imidazole-4-carboxylic acid {2-[5-(3,5-difluoro-benzenesulfonyl)-4,5,6,7-tetrahydro-1H-pyrazolo[4,3-c]pyridin-3-ylcarbamoyl]-phenyl}-amide;

226. 1H-Pyrrole-2-carboxylic acid {2-[5-(pyridine-3-sulfonyl)-4,5,6,7-tetrahydro-1H-pyrazolo[4,3-c]pyridin-3-ylcarbamoyl]-phenyl}-amide;

227. (S)-Tetrahydro-furan-2-carboxylic acid {2-[5-(3,5-difluoro-benzenesulfonyl)-4,5,6,7-tetrahydro-1H-pyrazolo[4,3-c]pyridin-3-ylcarbamoyl]-phenyl}-amide;

228. (R)-Tetrahydro-furan-2-carboxylic acid {2-[5-(3,5-difluoro-benzenesulfonyl)-4,5,6,7-tetrahydro-1H-pyrazolo[4,3-c]pyridin-3-ylcarbamoyl]-phenyl}-amide;

229. Tetrahydro-furan-3-carboxylic acid {2-[5-(3,5-difluoro-benzenesulfonyl)-4,5,6,7-tetrahydro-1H-pyrazolo[4,3-c]pyridin-3-ylcarbamoyl]-phenyl}-amide;

230. Tetrahydro-pyran-4-carboxylic acid {2-[5-(3,5-difluoro-benzenesulfonyl)-4,5,6,7-tetrahydro-1H-pyrazolo[4,3-c]pyridin-3-ylcarbamoyl]-phenyl}-amide;

231. Piperidine-4-carboxylic acid {2-[5-(3,5-difluoro-benzenesulfonyl)-4,5,6,7-tetrahydro-1H-pyrazolo[4,3-c]pyridin-3-ylcarbamoyl]-phenyl}-amide;

232. 1-Methyl-piperidine-4-carboxylic acid {2-[5-(3,5-difluoro-benzenesulfonyl)-4,5,6,7-tetrahydro-1H-pyrazolo[4,3-c]pyridin-3-ylcarbamoyl]-phenyl}-amide;

233. N-[5-(3,5-Difluoro-benzenesulfonyl)-4,5,6,7-tetrahydro-1H-pyrazolo[4,3-c]pyridin-3-yl]-2-(2-piperidin-1-yl-acetylamino)-benzamide;

234. N-[5-(3,5-Difluoro-benzenesulfonyl)-4,5,6,7-tetrahydro-1H-pyrazolo[4,3-c]pyridin-3-yl]-2-(2-pyridin-4-yl-acetylamino)-benzamide;

235. N-[5-(3,5-Difluoro-benzenesulfonyl)-4,5,6,7-tetrahydro-1H-pyrazolo[4,3-c]pyridin-3-yl]-2-(tetrahydro-pyran-4-ylamino)-benzamide;

236. (R)-Pyrrolidine-2-carboxylic acid {2-[5-(3,5-difluoro-benzenesulfonyl)-4,5,6,7-tetrahydro-1H-pyrazolo[4,3-c]pyridin-3-ylcarbamoyl]-phenyl}-amide;

237. N-[5-(3,5-Difluoro-benzenesulfonyl)-4,5,6,7-tetrahydro-1H-pyrazolo[4,3-c]pyridin-3-yl]-2-[(pyrrolidin-2-yl-methyl)-amino]-benzamide;

238. N-[5-(3,5-Difluoro-benzenesulfonyl)-4,5,6,7-tetrahydro-1H-pyrazolo[4,3-c]pyridin-3-yl]-3-[(1H-pyrrole-2-carbonyl)-amino]-isonicotinamide;

239. N-[5-(3,5-Difluoro-benzenesulfonyl)-4,5,6,7-tetrahydro-1H-pyrazolo[4,3-c]pyridin-3-yl]-3-[(1H-pyrrole-3-carbonyl)-amino]-isonicotinamide;

240. N-[5-(3,5-Difluoro-benzenesulfonyl)-4,5,6,7-tetrahydro-1H-pyrazolo[4,3-c]pyridin-3-yl]-3-[((S)-tetrahydrofuran-2-carbonyl)-amino]-isonicotinamide;

241. N-[5-(3,5-Difluoro-benzenesulfonyl)-4,5,6,7-tetrahydro-1H-pyrazolo[4,3-c]pyridin-3-yl]-3-[((R)-tetrahydrofuran-2-carbonyl)-amino]-isonicotinamide;

242. N-[5-(3,5-Difluoro-benzenesulfonyl)-4,5,6,7-tetrahydro-1H-pyrazolo[4,3-c]pyridin-3-yl]-3-[(tetrahydro-furan-3-carbonyl)-amino]-isonicotinamide;

243. N-[5-(3,5-Difluoro-benzenesulfonyl)-4,5,6,7-tetrahydro-1H-pyrazolo[4,3-c]pyridin-3-yl]-3-[(tetrahydro-pyran-4-carbonyl)-amino]-isonicotinamide;

244. N-[5-(3,5-Difluoro-benzenesulfonyl)-4,5,6,7-tetrahydro-1H-pyrazolo[4,3-c]pyridin-3-yl]-3-(tetrahydro-pyran-4-ylamino)-isonicotinamide;

245. 3-[(1H-Pyrrole-2-carbonyl)-amino]-pyridine-2-carboxylic acid [5-(3,5-difluoro-benzenesulfonyl)-4,5,6,7-tetrahydro-1H-pyrazolo[4,3-c]pyridin-3-yl]-amide;

246. 3-[(1H-Pyrrole-3-carbonyl)-amino]-pyridine-2-carboxylic acid [5-(3,5-difluoro-benzenesulfonyl)-4,5,6,7-tetrahydro-1H-pyrazolo[4,3-c]pyridin-3-yl]-amide;

247. 3-[((S)-Tetrahydro-furan-2-carbonyl)-amino]-pyridine-2-carboxylic acid [5-(3,5-difluoro-benzenesulfonyl)-4,5,6,7-tetrahydro-1H-pyrazolo[4,3-c]pyridin-3-yl]-amide;

248. 3-[((R)-Tetrahydro-furan-2-carbonyl)-amino]-pyridine-2-carboxylic acid [5-(3,5-difluoro-benzenesulfonyl)-4,5,6,7-tetrahydro-1H-pyrazolo[4,3-c]pyridin-3-yl]-amide;

249. 3-[(Tetrahydro-furan-3-carbonyl)-amino]-pyridine-2-carboxylic acid [5-(3,5-difluoro-benzenesulfonyl)-4,5,6,7-tetrahydro-1H-pyrazolo[4,3-c]pyridin-3-yl]-amide;

250. 3-[(Tetrahydro-pyran-4-carbonyl)-amino]-pyridine-2-carboxylic acid [5-(3,5-difluoro-benzenesulfonyl)-4,5,6,7-tetrahydro-1H-pyrazolo[4,3-c]pyridin-3-yl]-amide;

251. 3-(Tetrahydro-pyran-4-ylamino)-pyridine-2-carboxylic acid [5-(3,5-difluoro-benzenesulfonyl)-4,5,6,7-tetrahydro-1H-pyrazolo[4,3-c]pyridin-3-yl]-amide;

252. N-[5-(3,5-Difluoro-benzenesulfonyl)-4,5,6,7-tetrahydro-1H-pyrazolo[4,3-c]pyridin-3-yl]-2-[(1H-pyrrole-2-carbonyl)-amino]-nicotinamide;

253. N-[5-(3,5-Difluoro-benzenesulfonyl)-4,5,6,7-tetrahydro-1H-pyrazolo[4,3-c]pyridin-3-yl]-2-[(1H-pyrrole-3-carbonyl)-amino]-nicotinamide;

254. N-[5-(3,5-Difluoro-benzenesulfonyl)-4,5,6,7-tetrahydro-1H-pyrazolo[4,3-c]pyridin-3-yl]-2-[((S)-tetrahydrofuran-2-carbonyl)-amino]-nicotinamide;

255. N-[5-(3,5-Difluoro-benzenesulfonyl)-4,5,6,7-tetrahydro-1H-pyrazolo[4,3-c]pyridin-3-yl]-2-[((R)-tetrahydrofuran-2-carbonyl)-amino]-nicotinamide;

256. N-[5-(3,5-Difluoro-benzenesulfonyl)-4,5,6,7-tetrahydro-1H-pyrazolo[4,3-c]pyridin-3-yl]-2-[(tetrahydro-pyran-4-carbonyl)-amino]-nicotinamide;

257. N-[5-(3,5-Difluoro-benzenesulfonyl)-4,5,6,7-tetrahydro-1H-pyrazolo[4,3-c]pyridin-3-yl]-2-(tetrahydro-pyran-4-ylamino)-nicotinamide;

258. N-[5-(3,5-Difluoro-benzenesulfonyl)-4,5,6,7-tetrahydro-1H-pyrazolo[4,3-c]pyridin-3-yl]-2-methylaminomethyl-6-fluoro-benzamide;

259. N-[5-(3,5-Difluoro-benzenesulfonyl)-4,5,6,7-tetrahydro-1H-pyrazolo[4,3-c]pyridin-3-yl]-2-ethylaminomethyl-6-fluoro-benzamide;

260. N-[5-(3,5-Difluoro-benzenesulfonyl)-4,5,6,7-tetrahydro-1H-pyrazolo[4,3-c]pyridin-3-yl]-2-fluoro-6-(isopropylamino-methyl)-benzamide;

261. 2-Cyclopentylaminomethyl-N-[5-(3,5-difluoro-benzenesulfonyl)-4,5,6,7-tetrahydro-1H-pyrazolo[4,3-c]pyridin-3-yl]-6-fluoro-benzamide;

262. 2-Cyclohexylaminomethyl-N-[5-(3,5-difluoro-benzenesulfonyl)-4,5,6,7-tetrahydro-1H-pyrazolo[4,3-c]pyridin-3-yl]-6-fluoro-benzamide 263. N-[5-(3,5-Difluoro-benzenesulfonyl)-4,5,6,7-tetrahydro-1H-pyrazolo[4,3-c]pyridin-3-yl]-2-fluoro-6-[(tetrahydro-pyran-4-ylamino)-methyl]-benzamide;

264. N-[5-(3,5-Difluoro-benzenesulfonyl)-4,5,6,7-tetrahydro-1H-pyrazolo[4,3-c]pyridin-3-yl]-2-fluoro-6-pyrrolidin-1-ylmethyl-benzamide;

265. N-[5-(3,5-Difluoro-benzenesulfonyl)-4,5,6,7-tetrahydro-1H-pyrazolo[4,3-c]pyridin-3-yl]-2-fluoro-6-piperidin-1-ylmethyl-benzamide;

266. N-[5-(3,5-Difluoro-benzenesulfonyl)-4,5,6,7-tetrahydro-1H-pyrazolo[4,3-c]pyridin-3-yl]-2-fluoro-6-morpholin-4-ylmethyl-benzamide;
267. N-[5-(3,5-Difluoro-benzenesulfonyl)-4,5,6,7-tetrahydro-1H-pyrazolo[4,3-c]pyridin-3-yl]-2-fluoro-6-(4-methyl-piperazin-1-ylmethyl)-benzamide;
268. N-[5-(3,5-Difluoro-benzenesulfonyl)-7,7-dimethyl-4,5,6,7-tetrahydro-1H-pyrazolo[4,3-c]pyridin-3-yl]-2-fluoro-4-(4-methyl-piperazin-1-yl)-benzamide;
269. 2-Acetylamino-N-[5-(3,5-difluoro-benzenesulfonyl)-7,7-dimethyl-4,5,6,7-tetrahydro-1H-pyrazolo[4,3-c]pyridin-3-yl]-4-(4-methyl-piperazin-1-yl)-benzamide;
270. N-[5-(3,5-Difluoro-benzenesulfonyl)-7,7-dimethyl-4,5,6,7-tetrahydro-1H-pyrazolo[4,3-c]pyridin-3-yl]-4-(4-methyl-piperazin-1-yl)-2-propionylamino-benzamide;
271. N-[5-(3,5-Difluoro-benzenesulfonyl)-7,7-dimethyl-4,5,6,7-tetrahydro-1H-pyrazolo[4,3-c]pyridin-3-yl]-2-isobutyrylamino-4-(4-methyl-piperazin-1-yl)-benzamide;
272. 2-(Cyclopropanecarbonyl-amino)-N-[5-(3,5-difluoro-benzenesulfonyl)-7,7-dimethyl-4,5,6,7-tetrahydro-1H-pyrazolo[4,3-c]pyridin-3-yl]-4-(4-methyl-piperazin-1-yl)-benzamide;
273. 2-(Cyclobutanecarbonyl-amino)-N-[5-(3,5-difluoro-benzenesulfonyl)-7,7-dimethyl-4,5,6,7-tetrahydro-1H-pyrazolo[4,3-c]pyridin-3-yl]-4-(4-methyl-piperazin-1-yl)-benzamide;
274. 2-(Cyclopentanecarbonyl-amino)-N-[5-(3,5-difluoro-benzenesulfonyl)-7,7-dimethyl-4,5,6,7-tetrahydro-1H-pyrazolo[4,3-c]pyridin-3-yl]-4-(4-methyl-piperazin-1-yl)-benzamide;
275. 2-(Cyclohexanecarbonyl-amino)-N-[5-(3,5-difluoro-benzenesulfonyl)-7,7-dimethyl-4,5,6,7-tetrahydro-1H-pyrazolo[4,3-c]pyridin-3-yl]-4-(4-methyl-piperazin-1-yl)-benzamide;
276. 2-(2-Amino-acetylamino)-N-[5-(3,5-difluoro-benzenesulfonyl)-7,7-dimethyl-4,5,6,7-tetrahydro-1H-pyrazolo[4,3-c]pyridin-3-yl]-4-(4-methyl-piperazin-1-yl)-benzamide;
277. N-[5-(3,5-Difluoro-benzenesulfonyl)-7,7-dimethyl-4,5,6,7-tetrahydro-1H-pyrazolo[4,3-c]pyridin-3-yl]-2-(2-methylamino-acetylamino)-4-(4-methyl-piperazin-1-yl)-benzamide;
278. N-[5-(3,5-Difluoro-benzenesulfonyl)-7,7-dimethyl-4,5,6,7-tetrahydro-1H-pyrazolo[4,3-c]pyridin-3-yl]-2-(2-dimethylamino-acetylamino)-4-(4-methyl-piperazin-1-yl)-benzamide;
279. 2-((R)-2-Amino-propionylamino)-N-[5-(3,5-difluoro-benzenesulfonyl)-7,7-dimethyl-4,5,6,7-tetrahydro-1H-pyrazolo[4,3-c]pyridin-3-yl]-4-(4-methyl-piperazin-1-yl)-benzamide;
280. 2-((S)-2-Amino-propionylamino)-N-[5-(3,5-difluoro-benzenesulfonyl)-7,7-dimethyl-4,5,6,7-tetrahydro-1H-pyrazolo[4,3-c]pyridin-3-yl]-4-(4-methyl-piperazin-1-yl)-benzamide;
281. (S)-Pyrrolidine-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
282. (R)-Pyrrolidine-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
283. (S)-1-Methyl-pyrrolidine-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
284. (R)-1-Methyl-pyrrolidine-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
285. 2-(3-Amino-propionylamino)-N-[5-(3,5-difluoro-benzenesulfonyl)-7,7-dimethyl-4,5,6,7-tetrahydro-1H-pyrazolo[4,3-c]pyridin-3-yl]-4-(4-methyl-piperazin-1-yl)-benzamide;
286. N-[5-(3,5-Difluoro-benzenesulfonyl)-7,7-dimethyl-4,5,6,7-tetrahydro-1H-pyrazolo[4,3-c]pyridin-3-yl]-4-(4-methyl-piperazin-1-yl)-2-(2-piperidin-1-yl-acetylamino)-benzamide;
287. Piperidine-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
288. Piperidine-3-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
289. Piperidine-4-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
290. (S)-Tetrahydro-furan-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
291. (R)-Tetrahydro-furan-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
292. Tetrahydro-furan-3-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
293. Tetrahydro-pyran-4-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
294. 1H-Pyrrole-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
295. 1-Methyl-1H-pyrrole-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
296. 1H-Pyrrole-3-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
297. Furan-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
298. Thiophene-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
299. 2H-Pyrazole-3-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
300. 5-Methyl-2H-pyrazole-3-carboxylic acid [2-[5-(3,5-difluoro-benzenesulfonyl)-7,7-dimethyl-4,5,6,7-tetrahydro- 300. ...1H-pyrazolo[4,3-c]pyridin-3-ylcarbamoyl]-5-(4-methyl-piperazin-1-yl)-phenyl]-amide;
301. 2-Ethyl-5-methyl-2H-pyrazole-3-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
302. 1H-Pyrazole-4-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
303. 1,3,5-Trimethyl-1H-pyrazole-4-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
304. 3H-Imidazole-4-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
305. 3-Methyl-3H-imidazole-4-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-ethyl-piperazin-1-yl)-phenyl]-amide;
306. 1H-Imidazole-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
307. 1-Methyl-1H-imidazole-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
308. Isoxazole-5-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
309. 5-Methyl-isoxazole-4-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
310. 4-Methyl-oxazole-5-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
311. Pyridine-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
312. N-[2-[5-(3,5-Difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-nicotinamide;
313. N-[2-[5-(3,5-Difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-isonicotinamide;
314. N-[5-(3,5-Difluoro-benzenesulfonyl)-7,7-dimethyl-4,5,6,7-tetrahydro-1H-pyrazolo[4,3-c]pyridin-3-yl]-4-(4-methyl-piperazin-1-yl)-2-(2-pyridin-4-yl-acetylamino)-benzamide;
315. N-[5-(3,5-Difluoro-benzenesulfonyl)-7,7-dimethyl-4,5,6,7-tetrahydro-1H-pyrazolo[4,3-c]pyridin-3-yl]-2-methylamino-4-(4-methyl-piperazin-1-yl)-benzamide;
316. N-[5-(3,5-Difluoro-benzenesulfonyl)-7,7-dimethyl-4,5,6,7-tetrahydro-1H-pyrazolo[4,3-c]pyridin-3-yl]-2-ethylamino-4-(4-methyl-piperazin-1-yl)-benzamide;
317. N-[5-(3,5-Difluoro-benzenesulfonyl)-7,7-dimethyl-4,5,6,7-tetrahydro-1H-pyrazolo[4,3-c]pyridin-3-yl]-2-isobutylamino-4-(4-methyl-piperazin-1-yl)-benzamide;
318. N-[5-(3,5-Difluoro-benzenesulfonyl)-7,7-dimethyl-4,5,6,7-tetrahydro-1H-pyrazolo[4,3-c]pyridin-3-yl]-2-[(furan-2-ylmethyl)-amino]-4-(4-methyl-piperazin-1-yl)-benzamide;
319. N-[5-(3,5-Difluoro-benzenesulfonyl)-7,7-dimethyl-4,5,6,7-tetrahydro-1H-pyrazolo[4,3-c]pyridin-3-yl]-4-(4-methyl-piperazin-1-yl)-2-[(1H-pyrrol-2-ylmethyl)-amino]-benzamide;
320. N-[5-(3,5-Difluoro-benzenesulfonyl)-7,7-dimethyl-4,5,6,7-tetrahydro-1H-pyrazolo[4,3-c]pyridin-3-yl]-4-(4-methyl-piperazin-1-yl)-2-[(1-methyl-1H-pyrrol-2-ylmethyl)-amino]-benzamide;
321. N-[5-(3,5-Difluoro-benzenesulfonyl)-7,7-dimethyl-4,5,6,7-tetrahydro-1H-pyrazolo[4,3-c]pyridin-3-yl]-4-(4-methyl-piperazin-1-yl)-2-[((S)-1-pyrrolidin-2-ylmethyl)-amino]-benzamide;
322. N-[5-(3,5-Difluoro-benzenesulfonyl)-7,7-dimethyl-4,5,6,7-tetrahydro-1H-pyrazolo[4,3-c]pyridin-3-yl]-2-[(1H-imidazol-2-ylmethyl)-amino]-4-(4-methyl-piperazin-1-yl)-benzamide;
323. 2-Cyclohexylamino-N-[5-(3,5-difluoro-benzenesulfonyl)-7,7-dimethyl-4,5,6,7-tetrahydro-1H-pyrazolo[4,3-c]pyridin-3-yl]-4-(4-methyl-piperazin-1-yl)-benzamide;
324. N-[5-(3,5-Difluoro-benzenesulfonyl)-7,7-dimethyl-4,5,6,7-tetrahydro-1H-pyrazolo[4,3-c]pyridin-3-yl]-2-(4-hydroxy-cyclohexylamino)-4-(4-methyl-piperazin-1-yl)-benzamide;
325. N-[5-(3,5-Difluoro-benzenesulfonyl)-7,7-dimethyl-4,5,6,7-tetrahydro-1H-pyrazolo[4,3-c]pyridin-3-yl]-4-(4-methyl-piperazin-1-yl)-2-(piperidin-2-ylamino)-benzamide;
326. N-[5-(3,5-Difluoro-benzenesulfonyl)-7,7-dimethyl-4,5,6,7-tetrahydro-1H-pyrazolo[4,3-c]pyridin-3-yl]-4-(4-methyl-piperazin-1-yl)-2-(piperidin-3-ylamino)-benzamide;
327. N-[5-(3,5-Difluoro-benzenesulfonyl)-7,7-dimethyl-4,5,6,7-tetrahydro-1H-pyrazolo[4,3-c]pyridin-3-yl]-4-(4-methyl-piperazin-1-yl)-2-(piperidin-4-ylamino)-benzamide;
328. N-[5-(3,5-Difluoro-benzenesulfonyl)-7,7-dimethyl-4,5,6,7-tetrahydro-1H-pyrazolo[4,3-c]pyridin-3-yl]-4-(4-methyl-piperazin-1-yl)-2-(1-methyl-piperidin-4-ylamino)-benzamide;
329. N-[5-(3,5-Difluoro-benzenesulfonyl)-7,7-dimethyl-4,5,6,7-tetrahydro-1H-pyrazolo[4,3-c]pyridin-3-yl]-4-(4-methyl-piperazin-1-yl)-2-(tetrahydro-pyran-4-ylamino)-benzamide;
330. N-[5-(3,5-Difluoro-benzenesulfonyl)-7,7-dimethyl-4,5,6,7-tetrahydro-1H-pyrazolo[4,3-c]pyridin-3-yl]-4-(4-methyl-piperazin-1-yl)-2-[methyl-(tetrahydro-pyran-4-yl)-amino]-benzamide;
331. 1H-Pyrrole-2-carboxylic acid [2-[5-(3-fluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
332. 1H-Pyrrole-2-carboxylic acid [2-(5-benzenesulfonyl-7,7-dimethyl-4,5,6,7-tetrahydro-1H-pyrazolo[4,3-c]pyridin-3-ylcarbamoyl)-5-(4-methyl-piperazin-1-yl)-phenyl]-amide;
333. 1H-Pyrrole-2-carboxylic acid [2-[5-(3-fluoro-5-methoxy-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
334. N-[5-(3-Fluoro-benzenesulfonyl)-7,7-dimethyl-4,5,6,7-tetrahydro-1H-pyrazolo[4,3-c]pyridin-3-yl]-4-(4-methyl-piperazin-1-yl)-2-(tetrahydro-pyran-4-ylamino)-benzamide;

335. N-[5-(2-Chloro-benzenesulfonyl)-7,7-dimethyl-4,5,6,7-tetrahydro-1H-pyrazolo[4,3-c]pyridin-3-yl]-4-(4-methyl-piperazin-1-yl)-2-(tetrahydro-pyran-4-ylamino)-benzamide;
336. N-[5-(3-Methoxy-benzenesulfonyl)-7,7-dimethyl-4,5,6,7-tetrahydro-1H-pyrazolo[4,3-c]pyridin-3-yl]-4-(4-methyl-piperazin-1-yl)-2-(tetrahydro-pyran-4-ylamino)-benzamide;
337. N-[5-(3-Chloro-benzenesulfonyl)-7,7-dimethyl-4,5,6,7-tetrahydro-1H-pyrazolo[4,3-c]pyridin-3-yl]-4-(4-methyl-piperazin-1-yl)-2-(tetrahydro-pyran-4-ylamino)-benzamide;
338. N-[5-(3,5-Dichloro-benzenesulfonyl)-7,7-dimethyl-4,5,6,7-tetrahydro-1H-pyrazolo[4,3-c]pyridin-3-yl]-4-(4-methyl-piperazin-1-yl)-2-(tetrahydro-pyran-4-ylamino)-benzamide;
339. 4-(4-Methyl-piperazin-1-yl)-N-[5-(pyridine-3-sulfonyl)-7,7-dimethyl-4,5,6,7-tetrahydro-1H-pyrazolo[4,3-c]pyridin-3-yl]-2-(tetrahydro-pyran-4-ylamino)-benzamide;
340. N-(5-Benzenesulfonyl-7,7-dimethyl-4,5,6,7-tetrahydro-1H-pyrazolo[4,3-c]pyridin-3-yl)-4-(4-methyl-piperazin-1-yl)-2-(tetrahydro-pyran-4-ylamino)-benzamide;
341. N-[5-(3,5-Difluoro-benzenesulfonyl)-7,7-dimethyl-4,5,6,7-tetrahydro-1H-pyrazolo[4,3-c]pyridin-3-yl]-4-piperazin-1-yl-2-(tetrahydro-pyran-4-ylamino)-benzamide;
342. N-[5-(3,5-Difluoro-benzenesulfonyl)-7,7-dimethyl-4,5,6,7-tetrahydro-1H-pyrazolo[4,3-c]pyridin-3-yl]-4-(4-ethyl-piperazin-1-yl)-2-(tetrahydro-pyran-4-ylamino)-benzamide;
343. N-[5-(3,5-Difluoro-benzenesulfonyl)-7,7-dimethyl-4,5,6,7-tetrahydro-1H-pyrazolo[4,3-c]pyridin-3-yl]-4-(4-propyl-piperazin-1-yl)-2-(tetrahydro-pyran-4-ylamino)-benzamide;
344. N-[5-(3,5-Difluoro-benzenesulfonyl)-7,7-dimethyl-4,5,6,7-tetrahydro-1H-pyrazolo[4,3-c]pyridin-3-yl]-4-(4-isopropyl-piperazin-1-yl)-2-(tetrahydro-pyran-4-ylamino)-benzamide;
345. N-[5-(3,5-Difluoro-benzenesulfonyl)-7,7-dimethyl-4,5,6,7-tetrahydro-1H-pyrazolo[4,3-c]pyridin-3-yl]-2-fluoro-4-(4-methyl-piperazin-1-yl)-6-(tetrahydro-pyran-4-ylamino)-benzamide;
346. 2-Fluoro-N-[5-(3-fluoro-benzenesulfonyl)-7,7-dimethyl-4,5,6,7-tetrahydro-1H-pyrazolo[4,3-c]pyridin-3-yl]-4-(4-methyl-piperazin-1-yl)-6-(tetrahydro-pyran-4-ylamino)-benzamide;
347. N-[5-(3,5-Difluoro-benzenesulfonyl)-7,7-dimethyl-4,5,6,7-tetrahydro-1H-pyrazolo[4,3-c]pyridin-3-yl]-4-(4-methyl-4-oxy-piperazin-1-yl)-2-(tetrahydro-pyran-4-ylamino)-benzamide;
348. N-[5-(3,5-Difluoro-benzenesulfonyl)-7,7-dimethyl-4,5,6,7-tetrahydro-1H-pyrazolo[4,3-c]pyridin-3-yl]-2-(isopropylamino-methyl)-4-(4-methyl-piperazin-1-yl)-benzamide;
349. 2-Cyclopentylaminomethyl-N-[5-(3,5-difluoro-benzenesulfonyl)-7,7-dimethyl-4,5,6,7-tetrahydro-1H-pyrazolo[4,3-c]pyridin-3-yl]-4-(4-methyl-piperazin-1-yl)-benzamide;
350. 2-Cyclohexylaminomethyl-N-[5-(3,5-difluoro-benzenesulfonyl)-7,7-dimethyl-4,5,6,7-tetrahydro-1H-pyrazolo[4,3-c]pyridin-3-yl]-4-(4-methyl-piperazin-1-yl)-benzamide;
351. N-[5-(3,5-Difluoro-benzenesulfonyl)-7,7-dimethyl-4,5,6,7-tetrahydro-1H-pyrazolo[4,3-c]pyridin-3-yl]-4-(4-methyl-piperazin-1-yl)-2-[(tetrahydro-pyran-4-ylamino)-methyl]-benzamide;
352. N-[5-(3,5-Difluoro-benzenesulfonyl)-7,7-dimethyl-4,5,6,7-tetrahydro-1H-pyrazolo[4,3-c]pyridin-3-yl]-4-(4-methyl-piperazin-1-yl)-2-pyrrolidin-1-ylmethyl-benzamide;
353. N-[5-(3,5-Difluoro-benzenesulfonyl)-7,7-dimethyl-4,5,6,7-tetrahydro-1H-pyrazolo[4,3-c]pyridin-3-yl]-4-(4-methyl-piperazin-1-yl)-2-piperidin-1-ylmethyl-benzamide;
354. N-[5-(3,5-Difluoro-benzenesulfonyl)-7,7-dimethyl-4,5,6,7-tetrahydro-1H-pyrazolo[4,3-c]pyridin-3-yl]-4-(4-methyl-piperazin-1-yl)-2-morpholin-4-ylmethyl-benzamide;
355. 1H-Pyrrole-2-carboxylic acid [2-(5-methanesulfonyl-7,7-dimethyl-4,5,6,7-tetrahydro-1H-pyrazolo[4,3-c]pyridin-3-ylcarbamoyl)-5-(4-methyl-piperazin-1-yl)-phenyl]-amide;
356. 1H-Pyrrole-2-carboxylic acid [5-(4-methyl-piperazin-1-yl)-2-(5-phenylmethanesulfonyl-7,7-dimethyl-4,5,6,7-tetrahydro-1H-pyrazolo[4,3-c]pyridin-3-ylcarbamoyl)-phenyl]-amide;
357. 1H-Pyrrole-2-carboxylic acid [2-(5-cyclopropanesulfonyl-7,7-dimethyl-4,5,6,7-tetrahydro-1H-pyrazolo[4,3-c]pyridin-3-ylcarbamoyl)-5-(4-methyl-piperazin-1-yl)-phenyl]-amide;
358. N-[5-(3,5-Difluoro-benzenesulfonyl)-7,7-dimethyl-4,5,6,7-tetrahydro-1H-pyrazolo[4,3-c]pyridin-3-yl]-2-(3-ethyl-ureido)-4-(4-methyl-piperazin-1-yl)-benzamide;
359. N-[5-(3,5-Difluoro-benzenesulfonyl)-7,7-dimethyl-4,5,6,7-tetrahydro-1H-pyrazolo[4,3-c]pyridin-3-yl]-2-(3,3-dimethyl-ureido)-4-(4-methyl-piperazin-1-yl)-benzamide;
360. Pyrrolidine-1-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
361. Morpholine-4-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
362. 4-Methyl-piperazine-1-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;
363. 1H-Pyrrole-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-morpholin-4-yl-phenyl}-amide;
364. 1H-Pyrrole-2-carboxylic acid {5-morpholin-4-yl-2-[5-(pyridine-3-sulfonyl)-7,7-dimethyl-4,5,6,7-tetrahydro-1H-pyrazolo[4,3-c]pyridin-3-ylcarbamoyl]-phenyl}-amide;
365. 1H-Pyrrole-3-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-morpholin-4-yl-phenyl}-amide;
366. (S)-Pyrrolidine-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-morpholin-4-yl-phenyl}-amide;
367. (R)-Pyrrolidine-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-morpholin-4-yl-phenyl}-amide;
368. (S)-1-Methyl-pyrrolidine-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-morpholin-4-yl-phenyl}-amide;

369. (R)-1-Methyl-pyrrolidine-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-morpholin-4-yl-phenyl}-amide;
370. Piperidine-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-morpholin-4-yl-phenyl}-amide;
371. Piperidine-3-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-morpholin-4-yl-phenyl}-amide;
372. Piperidine-4-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-morpholin-4-yl-phenyl}-amide;
373. (S)-Tetrahydro-furan-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-morpholin-4-yl-phenyl}-amide;
374. (R)-Tetrahydro-furan-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-morpholin-4-yl-phenyl}-amide;
375. Tetrahydro-furan-3-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-morpholin-4-yl-phenyl}-amide;
376. Tetrahydro-pyran-4-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-morpholin-4-yl-phenyl}-amide;
377. N-[5-(3,5-Difluoro-benzenesulfonyl)-7,7-dimethyl-4,5,6,7-tetrahydro-1H-pyrazolo[4,3-c]pyridin-3-yl]-4-morpholin-4-yl-2-[((R)-1-pyrrolidin-2-ylmethyl)-amino]-benzamide;
378. N-[5-(3,5-Difluoro-benzenesulfonyl)-7,7-dimethyl-4,5,6,7-tetrahydro-1H-pyrazolo[4,3-c]pyridin-3-yl]-4-morpholin-4-yl-2-[((S)-1-pyrrolidin-2-ylmethyl)-amino]-benzamide;
379. N-[5-(3,5-Difluoro-benzenesulfonyl)-7,7-dimethyl-4,5,6,7-tetrahydro-1H-pyrazolo[4,3-c]pyridin-3-yl]-2-[((R)-1-methyl-pyrrolidin-2-ylmethyl)-amino]-4-morpholin-4-yl-benzamide;
380. N-[5-(3,5-Difluoro-benzenesulfonyl)-7,7-dimethyl-4,5,6,7-tetrahydro-1H-pyrazolo[4,3-c]pyridin-3-yl]-2-[((S)-1-methyl-pyrrolidin-2-ylmethyl)-amino]-4-morpholin-4-yl-benzamide;
381. N-[5-(3,5-Difluoro-benzenesulfonyl)-7,7-dimethyl-4,5,6,7-tetrahydro-1H-pyrazolo[4,3-c]pyridin-3-yl]-4-morpholin-4-yl-2-(2-piperidin-1-yl-acetylamino)-benzamide;
382. N-[5-(3,5-Difluoro-benzenesulfonyl)-7,7-dimethyl-4,5,6,7-tetrahydro-1H-pyrazolo[4,3-c]pyridin-3-yl]-4-morpholin-4-yl-2-(piperidin-4-ylamino)-benzamide;
383. N-[5-(3,5-Difluoro-benzenesulfonyl)-7,7-dimethyl-4,5,6,7-tetrahydro-1H-pyrazolo[4,3-c]pyridin-3-yl]-2-(1-methyl-piperidin-4-ylamino)-4-morpholin-4-yl-benzamide;
384. N-[5-(3,5-Difluoro-benzenesulfonyl)-7,7-dimethyl-4,5,6,7-tetrahydro-1H-pyrazolo[4,3-c]pyridin-3-yl]-4-morpholin-4-yl-2-(tetrahydro-pyran-4-ylamino)-benzamide;
385. N-[5-(3,5-Difluoro-benzenesulfonyl)-7,7-dimethyl-4,5,6,7-tetrahydro-1H-pyrazolo[4,3-c]pyridin-3-yl]-4-(2-hydroxymethyl-pyrrolidin-1-yl)-2-(tetrahydro-pyran-4-ylamino)-benzamide;
386. N-[5-(3,5-Difluoro-benzenesulfonyl)-7,7-dimethyl-4,5,6,7-tetrahydro-1H-pyrazolo[4,3-c]pyridin-3-yl]-4-(3-hydroxy-pyrrolidin-1-yl)-2-(tetrahydro-pyran-4-ylamino)-benzamide;
387. 4-(3-Amino-pyrrolidin-1-yl)-N-[5-(3,5-difluoro-benzenesulfonyl)-7,7-dimethyl-4,5,6,7-tetrahydro-1H-pyrazolo[4,3-c]pyridin-3-yl]-2-(tetrahydro-pyran-4-ylamino)-benzamide;
388. N-[5-(3,5-Difluoro-benzenesulfonyl)-7,7-dimethyl-4,5,6,7-tetrahydro-1H-pyrazolo[4,3-c]pyridin-3-yl]-4-(3-hydroxy-azetidin-1-yl)-2-(tetrahydro-pyran-4-ylamino)-benzamide;
389. 1H-Pyrrole-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-dimethylamino-phenyl}-amide;
390. 1H-Pyrrole-2-carboxylic acid {5-dimethylamino-2-[(pyridine-3-sulfonyl)-7,7-dimethyl-4,5,6,7-tetrahydro-1H-pyrazolo[4,3-c]pyridin-3-ylcarbamoyl]-phenyl}-amide;
391. 1H-Pyrrole-3-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-dimethylamino-phenyl}-amide;
392. (S)-Pyrrolidine-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-dimethylamino-phenyl}-amide;
393. (R)-Pyrrolidine-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-dimethylamino-phenyl}-amide;
394. (S)-1-Methyl-pyrrolidine-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-dimethylamino-phenyl}-amide;
395. (R)-1-Methyl-pyrrolidine-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-dimethylamino-phenyl}-amide;
396. Piperidine-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-dimethylamino-phenyl}-amide;
397. Piperidine-3-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-dimethylamino-phenyl}-amide;
398. Piperidine-4-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-dimethylamino-phenyl}-amide;
399. (S)-Tetrahydro-furan-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-dimethylamino-phenyl}-amide;
400. (R)-Tetrahydro-furan-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-dimethylamino-phenyl}-amide;
401. Tetrahydro-furan-3-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-dimethylamino-phenyl}-amide;

402. Tetrahydro-pyran-4-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-dimethylamino-phenyl}-amide;
403. N-[5-(3,5-Difluoro-benzenesulfonyl)-7,7-dimethyl-4,5,6,7-tetrahydro-1H-pyrazolo[4,3-c]pyridin-3-yl]-4-dimethylamino-2-[(pyrrolidin-2-ylmethyl)-amino]-benzamide;
404. N-[5-(3,5-Difluoro-benzenesulfonyl)-7,7-dimethyl-4,5,6,7-tetrahydro-1H-pyrazolo[4,3-c]pyridin-3-yl]-4-dimethylamino-2[(1-methyl-pyrrolidin-2-ylmethyl)-amino]-benzamide;
405. N-[5-(3,5-Difluoro-benzenesulfonyl)-7,7-dimethyl-4,5,6,7-tetrahydro-1H-pyrazolo[4,3-c]pyridin-3-yl]-4-dimethylamino-2-(piperidin-4-ylamino)-benzamide;
406. N-[5-(3,5-Difluoro-benzenesulfonyl)-7,7-dimethyl-4,5,6,7-tetrahydro-1H-pyrazolo[4,3-c]pyridin-3-yl]-4-dimethylamino-2-(1-methyl-piperidin-4-ylamino)-benzamide;
407. N-[5-(3,5-Difluoro-benzenesulfonyl)-7,7-dimethyl-4,5,6,7-tetrahydro-1H-pyrazolo[4,3-c]pyridin-3-yl]-4-dimethylamino-2-(tetrahydro-pyran-4-ylamino)-benzamide;
408. 1H-Pyrrole-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-[(2-dimethylamino-ethyl)-methyl-amino]-phenyl}-amide;
409. 1H-Pyrrole-3-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-[(2-dimethylamino-ethyl)-methyl-amino]-phenyl}-amide;
410. (S)-Tetrahydro-furan-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-[(2-dimethylamino-ethyl)-methyl-amino]-phenyl}-amide;
411. (R)-Tetrahydro-furan-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-[(2-dimethylamino-ethyl)-methyl-amino]-phenyl}-amide;
412. Tetrahydro-furan-3-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-[(2-dimethylamino-ethyl)-methyl-amino]-phenyl}-amide;
413. Tetrahydro-pyran-4-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-[(2-dimethylamino-ethyl)-methyl-amino]-phenyl}-amide;
414. N-[5-(3,5-Difluoro-benzenesulfonyl)-7,7-dimethyl-4,5,6,7-tetrahydro-1H-pyrazolo[4,3-c]pyridin-3-yl]-4-[(2-dimethylamino-ethyl)-methyl-amino]-2-(tetrahydro-pyran-4-ylamino)-benzamide;
415. N-[5-(3,5-Difluoro-benzenesulfonyl)-7,7-dimethyl-4,5,6,7-tetrahydro-1H-pyrazolo[4,3-c]pyridin-3-yl]-4-[(3-dimethylamino-propyl)-methyl-amino]-2-(tetrahydro-pyran-4-ylamino)-benzamide;
416. N-[5-(3,5-Difluoro-benzenesulfonyl)-7,7-dimethyl-4,5,6,7-tetrahydro-1H-pyrazolo[4,3-c]pyridin-3-yl]-4-(2-hydroxy-ethylamino)-2-(tetrahydro-pyran-4-ylamino)-benzamide;
417. N-[5-(3,5-Difluoro-benzenesulfonyl)-7,7-dimethyl-4,5,6,7-tetrahydro-1H-pyrazolo[4,3-c]pyridin-3-yl]-4-[2-hydroxy-ethyl)-methyl-amino]-2-(tetrahydro-pyran-4-ylamino)-benzamide;
418. 4-[Bis-(2-hydroxy-ethyl)-amino]-N-[5-(3,5-difluoro-benzenesulfonyl)-7,7-dimethyl-4,5,6,7-tetrahydro-1H-pyrazolo[4,3-c]pyridin-3-yl]-2-(tetrahydro-pyran-4-ylamino)-benzamide;
419. N-[5-(3,5-Difluoro-benzenesulfonyl)-7,7-dimethyl-4,5,6,7-tetrahydro-1H-pyrazolo[4,3-c]pyridin-3-yl]-4-(1-methyl-azetidin-3-ylamino)-2-(tetrahydro-pyran-4-ylamino)-benzamide;
420. N-[5-(3,5-Difluoro-benzenesulfonyl)-7,7-dimethyl-4,5,6,7-tetrahydro-1H-pyrazolo[4,3-c]pyridin-3-yl]-4-[methyl-(1-methyl-azetidin-3-yl)-amino]-2-(tetrahydro-pyran-4-ylamino)-benzamide;
421. N-[5-(3,5-Difluoro-benzenesulfonyl)-7,7-dimethyl-4,5,6,7-tetrahydro-1H-pyrazolo[4,3-c]pyridin-3-yl]-2,4-bis-(tetrahydro-pyran-4-ylamino)-benzamide;
422. N-[5-(3,5-Difluoro-benzenesulfonyl)-7,7-dimethyl-4,5,6,7-tetrahydro-1H-pyrazolo[4,3-c]pyridin-3-yl]-4-[methyl-(tetrahydro-pyran-4-yl)-amino]-2-(tetrahydro-pyran-4-ylamino)-benzamide;
423. N-[5-(3,5-Difluoro-benzenesulfonyl)-7,7-dimethyl-4,5,6,7-tetrahydro-1H-pyrazolo[4,3-c]pyridin-3-yl]-4-(1-methyl-piperidin-4-ylamino)-2-(tetrahydro-pyran-4-ylamino)-benzamide;
424. N-[5-(3,5-Difluoro-benzenesulfonyl)-7,7-dimethyl-4,5,6,7-tetrahydro-1H-pyrazolo[4,3-c]pyridin-3-yl]-4-[methyl-(1-methyl-piperidin-4-yl)-amino]-2-(tetrahydro-pyran-4-ylamino)-benzamide;
425. 1H-Pyrrole-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(2-dimethylamino-ethylamino)-phenyl]-amide;
426. 1H-Pyrrole-3-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(2-dimethylamino-ethylamino)-phenyl]-amide;
427. (S)-Tetrahydro-furan-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(2-dimethylamino-ethylamino)-phenyl]-amide;
428. (R)-Tetrahydro-furan-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(2-dimethylamino-ethylamino)-phenyl]-amide;
429. Tetrahydro-furan-3-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(2-dimethylamino-ethylamino)-phenyl]-amide;
430. Tetrahydro-pyran-4-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(2-dimethylamino-ethylamino)-phenyl]-amide;
431. N-[5-(3,5-Difluoro-benzenesulfonyl)-7,7-dimethyl-4,5,6,7-tetrahydro-1H-pyrazolo[4,3-c]pyridin-3-yl]-4-(2-dimethylamino-ethylamino)-2-(tetrahydro-pyran-4-ylamino)-benzamide;
432. N-[5-(3,5-Difluoro-benzenesulfonyl)-7,7-dimethyl-4,5,6,7-tetrahydro-1H-pyrazolo[4,3-c]pyridin-3-yl]-4-(3-dimethylamino-propylamino)-2-(tetrahydro-pyran-4-ylamino)-benzamide;
433. 1H-Pyrrole-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(2-dimethylamino-ethoxy)-phenyl]-amide;
434. 1H-Pyrrole-3-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(2-dimethylamino-ethoxy)-phenyl]-amide;
435. (S)-Tetrahydro-furan-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(2-dimethylamino-ethoxy)-phenyl]-amide;

436. (R)-Tetrahydro-furan-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(2-dimethylamino-ethoxy)-phenyl]-amide;
437. Tetrahydro-furan-3-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(2-dimethylamino-ethoxy)-phenyl]-amide;
438. Tetrahydro-pyran-4-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(2-dimethylamino-ethoxy)-phenyl]-amide;
439. N-[5-(3,5-Difluoro-benzenesulfonyl)-7,7-dimethyl-4,5,6,7-tetrahydro-1H-pyrazolo[4,3-c]pyridin-3-yl]-4-(2-dimethylamino-ethoxy)-2-(tetrahydro-pyran-4-ylamino)-benzamide;
440. N-[5-(3,5-Difluoro-benzenesulfonyl)-7,7-dimethyl-4,5,6,7-tetrahydro-1H-pyrazolo[4,3-c]pyridin-3-yl]-4-(2-pyrrolidin-1-yl-ethoxy)-2-(tetrahydro-pyran-4-ylamino)-benzamide;
441. 1H-Pyrrole-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(1-methyl-azetidin-3-yloxy)-phenyl]-amide;
442. 1H-Pyrrole-3-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(1-methyl-azetidin-3-yloxy)-phenyl]-amide;
443. (S)-Tetrahydro-furan-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(1-methyl-azetidin-3-yloxy)-phenyl]-amide;
444. (R)-Tetrahydro-furan-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(1-methyl-azetidin-3-yloxy)-phenyl]-amide;
445. Tetrahydro-furan-3-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(1-methyl-azetidin-3-yloxy)-phenyl]-amide;
446. Tetrahydro-pyran-4-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(1-methyl-azetidin-3-yloxy)-phenyl]-amide;
447. N-[5-(3,5-Difluoro-benzenesulfonyl)-7,7-dimethyl-4,5,6,7-tetrahydro-1H-pyrazolo[4,3-c]pyridin-3-yl]-4-(1-methyl-azetidin-3-yloxy)-2-(tetrahydro-pyran-4-ylamino)-benzamide;
448. 1H-Pyrrole-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(1-methyl-piperidin-4-yloxy)-phenyl]-amide;
449. 1H-Pyrrole-3-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(1-methyl-piperidin-4-yloxy)-phenyl]-amide;
450. (S)-Tetrahydro-furan-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(1-methyl-piperidin-4-yloxy)-phenyl]-amide;
451. (R)-Tetrahydro-furan-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(1-methyl-piperidin-4-yloxy)-phenyl]-amide;
452. Tetrahydro-furan-3-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(1-methyl-piperidin-4-yloxy)-phenyl]-amide;
453. Tetrahydro-pyran-4-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(1-methyl-piperidin-4-yloxy)-phenyl]-amide;
454. N-[5-(3,5-Difluoro-benzenesulfonyl)-7,7-dimethyl-4,5,6,7-tetrahydro-1H-pyrazolo[4,3-c]pyridin-3-yl]-4-(1-methyl-piperidin-4-yloxy)-2-(tetrahydro-pyran-4-ylamino)-benzamide;
455. 1H-Pyrrole-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-methoxy-phenyl}-amide;
456. 1H-Pyrrole-2-carboxylic acid {5-methoxy-2-[5-(pyridine-3-sulfonyl)-7,7-dimethyl-4,5,6,7-tetrahydro-1H-pyrazolo[4,3-c]pyridin-3-ylcarbamoyl]-phenyl}-amide;
457. 1H-Pyrrole-3-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-methoxy-phenyl}-amide;
458. (S)-Tetrahydro-furan-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-methoxy-phenyl}-amide;
459. (R)-Tetrahydro-furan-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-methoxy-phenyl}-amide;
460. Tetrahydro-furan-3-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-methoxy-phenyl}-amide;
461. Tetrahydro-pyran-4-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-methoxy-phenyl}-amide;
462. N-[5-(3,5-Difluoro-benzenesulfonyl)-7,7-dimethyl-4,5,6,7-tetrahydro-1H-pyrazolo[4,3-c]pyridin-3-yl]-4-methoxy-2-(tetrahydro-pyran-4-ylamino)-benzamide;
463. 1H-Pyrrole-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-3-fluoro-phenyl}-amide;
464. 1H-Pyrrole-2-carboxylic acid {3-fluoro-2-[5-(pyridine-3-sulfonyl)-7,7-dimethyl-4,5,6,7-tetrahydro-1H-pyrazolo[4,3-c]pyridin-3-ylcarbamoyl]-phenyl}-amide;
465. 1H-Pyrrole-3-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-3-fluoro-phenyl}-amide;
466. (S)-Tetrahydro-furan-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-3-fluoro-phenyl}-amide;
467. (R)-Tetrahydro-furan-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-3-fluoro-phenyl}-amide;
468. Tetrahydro-furan-3-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-3-fluoro-phenyl}-amide;
469. Tetrahydro-pyran-4-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-3-fluoro-phenyl}-amide;

470. N-[5-(3,5-Difluoro-benzenesulfonyl)-7,7-dimethyl-4,5,6,7-tetrahydro-1H-pyrazolo[4,3-c]pyridin-3-yl]-2-fluoro-6-(tetrahydro-pyran-4-ylamino)-benzamide;
471. 1H-Pyrrole-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-pyrrolidin-1-ylmethyl-phenyl}-amide;
472. 1H-Pyrrole-3-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-pyrrolidin-1-ylmethyl-phenyl}-amide;
473. (S)-Tetrahydro-furan-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-pyrrolidin-1-ylmethyl-phenyl}-amide;
474. (R)-Tetrahydro-furan-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-pyrrolidin-1-ylmethyl-phenyl}-amide;
475. Tetrahydro-furan-3-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-pyrrolidin-1-ylmethyl-phenyl}-amide;
476. Tetrahydro-pyran-4-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-pyrrolidin-1-ylmethyl-phenyl}-amide;
477. N-[5-(3,5-Difluoro-benzenesulfonyl)-7,7-dimethyl-4,5,6,7-tetrahydro-1H-pyrazolo[4,3-c]pyridin-3-yl]-4-pyrrolidin-1-ylmethyl-2-(tetrahydro-pyran-4-ylamino)-benzamide;
478. N-[5-(3,5-Difluoro-benzenesulfonyl)-7,7-dimethyl-4,5,6,7-tetrahydro-1H-pyrazolo[4,3-c]pyridin-3-yl]-4-piperidin-1-ylmethyl-2-(tetrahydro-pyran-4-ylamino)-benzamide;
479. 1H-Pyrrole-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-morpholin-4-ylmethyl-phenyl}-amide;
480. 1H-Pyrrole-3-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-morpholin-4-ylmethyl-phenyl}-amide;
481. (S)-Tetrahydro-furan-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-morpholin-4-ylmethyl-phenyl}-amide;
482. (R)-Tetrahydro-furan-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-morpholin-4-ylmethyl-phenyl}-amide;
483. Tetrahydro-furan-3-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-morpholin-4-ylmethyl-phenyl}-amide;
484. Tetrahydro-pyran-4-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-morpholin-4-ylmethyl-phenyl}-amide;
485. N-[5-(3,5-Difluoro-benzenesulfonyl)-7,7-dimethyl-4,5,6,7-tetrahydro-1H-pyrazolo[4,3-c]pyridin-3-yl]-4-morpholin-4-ylmethyl-2-(tetrahydro-pyran-4-ylamino)-benzamide;
486. N-[5-(3,5-Difluoro-benzenesulfonyl)-7,7-dimethyl-4,5,6,7-tetrahydro-1H-pyrazolo[4,3-c]pyridin-3-yl]-4-(4-methyl-piperazin-1-ylmethyl)-2-(tetrahydro-pyran-4-ylamino)-benzamide;
487. N-[5-(3,5-Difluoro-benzenesulfonyl)-7,7-dimethyl-4,5,6,7-tetrahydro-1H-pyrazolo[4,3-c]pyridin-3-yl]-4-[(2-hydroxy-ethylamino)-methyl]-2-(tetrahydro-pyran-4-ylamino)-benzamide;
488. N-[5-(3,5-Difluoro-benzenesulfonyl)-7,7-dimethyl-4,5,6,7-tetrahydro-1H-pyrazolo[4,3-c]pyridin-3-yl]-4-{[(2-hydroxy-ethyl)-methyl-amino]-methyl}-2-(tetrahydro-pyran-4-ylamino)-benzamide;
489. 1H-Pyrrole-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-phenyl}-amide;
490. 1H-Pyrrole-3-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-phenyl}-amide;
491. 3H-Imidazole-4-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-phenyl}-amide;
492. 1H-Pyrrole-2-carboxylic acid {2-[5-(pyridine-3-sulfonyl)-7,7-dimethyl-4,5,6,7-tetrahydro-1H-pyrazolo[4,3-c]pyridin-3-ylcarbamoyl]-phenyl}-amide;
493. (S)-Tetrahydro-furan-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-phenyl}-amide;
494. (R)-Tetrahydro-furan-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-phenyl}-amide;
495. Tetrahydro-furan-3-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-phenyl}-amide;
496. Tetrahydro-pyran-4-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-phenyl}-amide;
497. Piperidine-4-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-phenyl}-amide;
498. 1-Methyl-piperidine-4-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-phenyl}-amide;
499. N-[5-(3,5-Difluoro-benzenesulfonyl)-7,7-dimethyl-4,5,6,7-tetrahydro-1H-pyrazolo[4,3-c]pyridin-3-yl]-2-(2-piperidin-1-yl-acetylamino)-benzamide;
500. N-[5-(3,5-Difluoro-benzenesulfonyl)-7,7-dimethyl-4,5,6,7-tetrahydro-1H-pyrazolo[4,3-c]pyridin-3-yl]-2-(2-pyridin-4-yl-acetylamino)-benzamide;
501. N-[5-(3,5-Difluoro-benzenesulfonyl)-7,7-dimethyl-4,5,6,7-tetrahydro-1H-pyrazolo[4,3-c]pyridin-3-yl]-2-(tetrahydro-pyran-4-ylamino)-benzamide;
502. (R)-Pyrrolidine-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-phenyl}-amide;
503. N-[5-(3,5-Difluoro-benzenesulfonyl)-7,7-dimethyl-4,5,6,7-tetrahydro-1H-pyrazolo[4,3-c]pyridin-3-yl]-2-[(pyrrolidin-2-ylmethyl)-amino]-benzamide;
504. N-[5-(3,5-Difluoro-benzenesulfonyl)-7,7-dimethyl-4,5,6,7-tetrahydro-1H-pyrazolo[4,3-c]pyridin-3-yl]-3-[(1H-pyrrole-2-carbonyl)-amino]-isonicotinamide;
505. N-[5-(3,5-Difluoro-benzenesulfonyl)-7,7-dimethyl-4,5,6,7-tetrahydro-1H-pyrazolo[4,3-c]pyridin-3-yl]-3-[(1H-pyrrole-3-carbonyl)-amino]-isonicotinamide;
506. N-[5-(3,5-Difluoro-benzenesulfonyl)-7,7-dimethyl-4,5,6,7-tetrahydro-1H-pyrazolo[4,3-c]pyridin-3-yl]-3-[((S)-tetrahydro-furan-2-carbonyl)-amino]-isonicotinamide;

507. N-[5-(3,5-Difluoro-benzenesulfonyl)-7,7-dimethyl-4,5,6,7-tetrahydro-1H-pyrazolo[4,3-c]pyridin-3-yl]-3-[((R)-tetrahydro-furan-2-carbonyl)-amino]-isonicotinamide;
508. N-[5-(3,5-Difluoro-benzenesulfonyl)-7,7-dimethyl-4,5,6,7-tetrahydro-1H-pyrazolo[4,3-c]pyridin-3-yl]-3-[(tetrahydro-furan-3-carbonyl)-amino]-isonicotinamide;
509. N-[5-(3,5-Difluoro-benzenesulfonyl)-7,7-dimethyl-4,5,6,7-tetrahydro-1H-pyrazolo[4,3-c]pyridin-3-yl]-3-[(tetrahydro-pyran-4-carbonyl)-amino]-isonicotinamide;
510. N-[5-(3,5-Difluoro-benzenesulfonyl)-7,7-dimethyl-4,5,6,7-tetrahydro-1H-pyrazolo[4,3-c]pyridin-3-yl]-3-(tetrahydro-pyran-4-ylamino)-isonicotinamide;
511. 3-[(1H-Pyrrole-2-carbonyl)-amino]-pyridine-2-carboxylic acid [5-(3,5-difluoro-benzenesulfonyl)-7,7-dimethyl-4,5,6,7-tetrahydro-1H-pyrazolo[4,3-c]pyridin-3-yl]-amide;
512. 3-[(1H-Pyrrole-3-carbonyl)-amino]-pyridine-2-carboxylic acid [5-(3,5-difluoro-benzenesulfonyl)-7,7-dimethyl-4,5,6,7-tetrahydro-1H-pyrazolo[4,3-c]pyridin-3-yl]-amide;
513. 3-[((S)-Tetrahydro-furan-2-carbonyl)-amino]-pyridine-2-carboxylic acid [5-(3,5-difluoro-benzenesulfonyl)-7,7-dimethyl-4,5,6,7-tetrahydro-1H-pyrazolo[4,3-c]pyridin-3-yl]-amide;
514. 3-[((R)-Tetrahydro-furan-2-carbonyl)-amino]-pyridine-2-carboxylic acid [5-(3,5-difluoro-benzenesulfonyl)-7,7-dimethyl-4,5,6,7-tetrahydro-1H-pyrazolo[4,3-c]pyridin-3-yl]-amide;
515. 3-[(Tetrahydro-furan-3-carbonyl)-amino]-pyridine-2-carboxylic acid [5-(3,5-difluoro-benzenesulfonyl)-7,7-dimethyl-4,5,6,7-tetrahydro-1H-pyrazolo[4,3-c]pyridin-3-yl]-amide;
516. 3-[(Tetrahydro-pyran-4-carbonyl)-amino]-pyridine-2-carboxylic acid [5-(3,5-difluoro-benzenesulfonyl)-7,7-dimethyl-4,5,6,7-tetrahydro-1H-pyrazolo[4,3-c]pyridin-3-yl]-amide;
517. 3-(Tetrahydro-pyran-4-ylamino)-pyridine-2-carboxylic acid [5-(3,5-difluoro-benzenesulfonyl)-7,7-dimethyl-4,5,6,7-tetrahydro-1H-pyrazolo[4,3-c]pyridin-3-yl]-amide;
518. N-[5-(3,5-Difluoro-benzenesulfonyl)-7,7-dimethyl-4,5,6,7-tetrahydro-1H-pyrazolo[4,3-c]pyridin-3-yl]-2-[(1H-pyrrole-2-carbonyl)-amino]-nicotinamide;
519. N-[5-(3,5-Difluoro-benzenesulfonyl)-7,7-dimethyl-4,5,6,7-tetrahydro-1H-pyrazolo[4,3-c]pyridin-3-yl]-2-[(1H-pyrrole-3-carbonyl)-amino]-nicotinamide;
520. N-[5-(3,5-Difluoro-benzenesulfonyl)-7,7-dimethyl-4,5,6,7-tetrahydro-1H-pyrazolo[4,3-c]pyridin-3-yl]-2-[((S)-tetrahydro-furan-2-carbonyl)-amino]-nicotinamide;
521. N-[5-(3,5-Difluoro-benzenesulfonyl)-7,7-dimethyl-4,5,6,7-tetrahydro-1H-pyrazolo[4,3-c]pyridin-3-yl]-2-[((R)-tetrahydro-furan-2-carbonyl)-amino]-nicotinamide;
522. N-[5-(3,5-Difluoro-benzenesulfonyl)-7,7-dimethyl-4,5,6,7-tetrahydro-1H-pyrazolo[4,3-c]pyridin-3-yl]-2-[(tetrahydro-pyran-4-carbonyl)-amino]-nicotinamide;
523. N-[5-(3,5-Difluoro-benzenesulfonyl)-7,7-dimethyl-4,5,6,7-tetrahydro-1H-pyrazolo[4,3-c]pyridin-3-yl]-2-(tetrahydro-pyran-4-ylamino)-nicotinamide;
524. N-[5-(3,5-Difluoro-benzenesulfonyl)-7,7-dimethyl-4,5,6,7-tetrahydro-1H-pyrazolo[4,3-c]pyridin-3-yl]-2-methylaminomethyl-6-fluoro-benzamide;
525. N-[5-(3,5-Difluoro-benzenesulfonyl)-7,7-dimethyl-4,5,6,7-tetrahydro-1H-pyrazolo[4,3-c]pyridin-3-yl]-2-ethylaminomethyl-6-fluoro-benzamide;
526. N-[5-(3,5-Difluoro-benzenesulfonyl)-7,7-dimethyl-4,5,6,7-tetrahydro-1H-pyrazolo[4,3-c]pyridin-3-yl]-2-fluoro-6-(isopropylamino-methyl)-benzamide;
527. 2-Cyclopentylaminomethyl-N-[5-(3,5-difluoro-benzenesulfonyl)-7,7-dimethyl-4,5,6,7-tetrahydro-1H-pyrazolo[4,3-c]pyridin-3-yl]-6-fluoro-benzamide;
528. 2-Cyclohexylaminomethyl-N-[5-(3,5-difluoro-benzenesulfonyl)-7,7-dimethyl-4,5,6,7-tetrahydro-1H-pyrazolo[4,3-c]pyridin-3-yl]-6-fluoro-benzamide;
529. N-[5-(3,5-Difluoro-benzenesulfonyl)-7,7-dimethyl-4,5,6,7-tetrahydro-1H-pyrazolo[4,3-c]pyridin-3-yl]-2-fluoro-6-[(tetrahydro-pyran-4-ylamino)-methyl]-benzamide;
530. N-[5-(3,5-Difluoro-benzenesulfonyl)-7,7-dimethyl-4,5,6,7-tetrahydro-1H-pyrazolo[4,3-c]pyridin-3-yl]-2-fluoro-6-pyrrolidin-1-ylmethyl-benzamide;
531. N-[5-(3,5-Difluoro-benzenesulfonyl)-7,7-dimethyl-4,5,6,7-tetrahydro-1H-pyrazolo[4,3-c]pyridin-3-yl]-2-fluoro-6-piperidin-1-ylmethyl-benzamide;
532. N-[5-(3,5-Difluoro-benzenesulfonyl)-7,7-dimethyl-4,5,6,7-tetrahydro-1H-pyrazolo[4,3-c]pyridin-3-yl]-2-fluoro-6-morpholin-4-ylmethyl-benzamide;
533. N-[5-(3,5-Difluoro-benzenesulfonyl)-7,7-dimethyl-4,5,6,7-tetrahydro-1H-pyrazolo[4,3-c]pyridin-3-yl]-2-fluoro-6-(4-methyl-piperazin-1-ylmethyl)-benzamide;
534. N-[5-(3,5-Difluoro-benzenesulfonyl)-4,5,6,7-tetrahydro-1H-pyrazolo[4,3-c]pyridin-3-yl]-2-(isopropylaminomethyl)-benzamide hydrochloride;
535. N-[5-(3,5-Difluoro-benzenesulfonyl)-4,5,6,7-tetrahydro-1H-pyrazolo[4,3-c]pyridin-3-yl]-2-[(tetrahydro-pyran-4-ylamino)-methyl]-benzamide hydrochloride;
536. N-[5-(3,5-Difluoro-benzenesulfonyl)-4,5,6,7-tetrahydro-1H-pyrazolo[4,3-c]pyridin-3-yl]-4-(2-methoxy-ethylamino)-2-(tetrahydro-pyran-4-ylamino)-benzamide;
537. 4-Amino-N-[5-(3,5-difluoro-benzenesulfonyl)-4,5,6,7-tetrahydro-1H-pyrazolo[4,3-c]pyridin-3-yl]-2-(tetrahydro-pyran-4-ylamino)-benzamide;
538. N-[5-(3,5-Difluoro-benzenesulfonyl)-4,5,6,7-tetrahydro-1H-pyrazolo[4,3-c]pyridin-3-yl]-4-(2-dimethylamino-1-methyl-ethylamino)-2-(tetrahydro-pyran-4-ylamino)-benzamide;
539. 3-Amino-N-[5-(3,5-difluoro-benzenesulfonyl)-4,5,6,7-tetrahydro-1H-pyrazolo[4,3-c]pyridin-3-yl]-isonicotinamide;
540. 1H-Pyrrole-2-carboxylic acid {2-[7,7-dimethyl-5-(pyridine-3-sulfonyl)-4,5,6,7-tetrahydro-1H-pyrazolo[4,3-c]pyridin-3-ylcarbamoyl]-phenyl}-amide;
541. 2-Amino-N-[5-(3,5-difluoro-benzenesulfonyl)-7,7-dimethyl-4,5,6,7-tetrahydro-1H-pyrazolo[4,3-c]pyridin-3-yl]-benzamide;
542. 1H-Pyrrole-2-carboxylic acid {2-[5-(3,5-dimethyl-isoxazole-4-sulfonyl)-7,7-dimethyl-4,5,6,7-tetrahydro-1H-pyrazolo[4,3-c]pyridin-3-ylcarbamoyl]-phenyl}-amide;
543. 2-Amino-N-[5-(3-fluoro-benzenesulfonyl)-7,7-dimethyl-4,5,6,7-tetrahydro-1H-pyrazolo[4,3-c]pyridin-3-yl]-benzamide;
544. N-[5-(3,5-Difluoro-benzenesulfonyl)-4,5,6,7-tetrahydro-1H-pyrazolo[4,3-c]pyridin-3-yl]-3-[(1-methyl-1H-pyrrole-2-carbonyl)-amino]-isonicotinamide;
545. 1-Methyl-1H-pyrrole-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-dimethylamino-phenyl}-amide;
546. 2-Amino-N-[5-(3,5-difluoro-benzenesulfonyl)-4,5,6,7-tetrahydro-1H-pyrazolo[4,3-c]pyridin-3-yl]-benzamide;
547. (R)-Pyrrolidine-2-carboxylic acid {2-[5-(3,5-difluoro-benzenesulfonyl)-4,5,6,7-tetrahydro-1H-pyrazolo[4,3-c]pyridin-3-ylcarbamoyl]-3-fluoro-phenyl}-amide;

548. N-[5-(3,5-Difluoro-benzenesulfonyl)-4,5,6,7-tetrahydro-1H-pyrazolo[4,3-c]pyridin-3-yl]-2-methanesulfonylamino-4-(4-methyl-piperazin-1-yl)-benzamide;
549. N-(5-Cyclopropanesulfonyl-4,5,6,7-tetrahydro-1H-pyrazolo[4,3-c]pyridin-3-yl)-4-(4-methyl-piperazin-1-yl)-2-(tetrahydro-pyran-4-ylamino)-benzamide;
550. 2-Amino-N-[5-(3,5-difluoro-benzenesulfonyl)-4,5,6,7-tetrahydro-1H-pyrazolo[4,3-c]pyridin-3-yl]-4-[(3-dimethylamino-propyl)-methyl-amino]-benzamide;
551. N-[5-(3,5-Difluoro-benzenesulfonyl)-4,5,6,7-tetrahydro-1H-pyrazolo[4,3-c]pyridin-3-yl]-4-[4-(2-fluoro-ethyl)-piperazin-1-yl]-2-(tetrahydro-pyran-4-ylamino)-benzamide;
552. N-[5-(3,5-Difluoro-benzenesulfonyl)-4,5,6,7-tetrahydro-1H-pyrazolo[4,3-c]pyridin-3-yl]-2-(tetrahydro-pyran-4-ylamino)-4-((3R,5S)-3,4,5-trimethyl-piperazin-1-yl)-benzamide;
553. Acetic acid 2-{[4-[5-(3,5-difluoro-benzenesulfonyl)-4,5,6,7-tetrahydro-1H-pyrazolo[4,3-c]pyridin-3-ylcarbamoyl]-3-(tetrahydro-pyran-4-ylamino)-phenyl]-methyl-amino}-ethyl ester;
554. N-[5-(3,5-Difluoro-benzenesulfonyl)-4,5,6,7-tetrahydro-1H-pyrazolo[4,3-c]pyridin-3-yl]-4-[(2-hydroxy-ethyl)-methyl-amino]-2-(tetrahydro-pyran-4-ylamino)-benzamide;
555. N-[5-(3,5-Difluoro-benzenesulfonyl)-4,5,6,7-tetrahydro-1H-pyrazolo[4,3-c]pyridin-3-yl]-4-(4-methyl-[1,4]diazepan-1-yl)-2-(tetrahydro-pyran-4-ylamino)-benzamide;
556. 4-[(2-Diethylamino-ethyl)-methyl-amino]-N-[5-(3,5-difluoro-benzenesulfonyl)-4,5,6,7-tetrahydro-1H-pyrazolo[4,3-c]pyridin-3-yl]-2-(tetrahydro-pyran-4-ylamino)-benzamide;
557. N-[5-(3,5-Difluoro-benzenesulfonyl)-4,5,6,7-tetrahydro-1H-pyrazolo[4,3-c]pyridin-3-yl]-4-(2-methoxy-ethoxy)-2-(tetrahydro-pyran-4-ylamino)-benzamide;
558. N-[5-(3,5-Difluoro-benzenesulfonyl)-4,5,6,7-tetrahydro-1H-pyrazolo[4,3-c]pyridin-3-yl]-2-(2,2-dimethyl-tetrahydro-pyran-4-ylamino)-4-(4-methyl-piperazin-1-yl)-benzamide;
559. N-[5-(3,5-Difluoro-benzenesulfonyl)-4,5,6,7-tetrahydro-1H-pyrazolo[4,3-c]pyridin-3-yl]-4-[(2-dimethylamino-ethyl)-ethyl-amino]-2-(tetrahydro-pyran-4-ylamino)-benzamide;
560. N-[5-(3,5-Difluoro-benzenesulfonyl)-4,5,6,7-tetrahydro-1H-pyrazolo[4,3-c]pyridin-3-yl]-4-[(2-methoxy-ethyl)-methyl-amino]-2-(tetrahydro-pyran-4-ylamino)-benzamide;
561. Acetic acid (S)-1-[4-[5-(3,5-difluoro-benzenesulfonyl)-4,5,6,7-tetrahydro-1H-pyrazolo[4,3-c]pyridin-3-ylcarbamoyl]-3-(tetrahydro-pyran-4-ylamino)-phenyl]-pyrrolidin-2-ylmethyl ester;
562. N-[5-(3,5-Difluoro-benzenesulfonyl)-4,5,6,7-tetrahydro-1H-pyrazolo[4,3-c]pyridin-3-yl]-4-((S)-2-hydroxymethyl-pyrrolidin-1-yl)-2-(tetrahydro-pyran-4-ylamino)-benzamide;
563. N-[5-(3,5-Difluoro-benzenesulfonyl)-4,5,6,7-tetrahydro-1H-pyrazolo[4,3-c]pyridin-3-yl]-4-[4-(2-methoxy-ethyl)-piperazin-1-yl]-2-[(tetrahydro-furan-3-ylmethyl)-amino]-benzamide;
564. N-[5-(3,5-Difluoro-benzenesulfonyl)-4,5,6,7-tetrahydro-1H-pyrazolo[4,3-c]pyridin-3-yl]-4-[4-(2-methoxy-ethyl)-piperazin-1-yl]-2-(tetrahydro-pyran-4-ylamino)-benzamide;
565. N-[5-(3,5-Difluoro-benzenesulfonyl)-4,5,6,7-tetrahydro-1H-pyrazolo[4,3-c]pyridin-3-yl]-4-(4-pyrrolidin-1-yl-piperidin-1-yl)-2-(tetrahydro-pyran-4-ylamino)-benzamide;
566. N-[5-(3,5-Difluoro-benzenesulfonyl)-4,5,6,7-tetrahydro-1H-pyrazolo[4,3-c]pyridin-3-yl]-2-((3R,4S)-3,4,5-trihydroxy-pentylamino)-benzamide;
567. N-[5-(3,5-Difluoro-benzenesulfonyl)-4,5,6,7-tetrahydro-1H-pyrazolo[4,3-c]pyridin-3-yl]-2-(2,3-dihydroxy-propylamino)-benzamide;
568. N-[5-(3,5-Difluoro-benzenesulfonyl)-4,5,6,7-tetrahydro-1H-pyrazolo[4,3-c]pyridin-3-yl]-4-(4-dimethylamino-piperidin-1-yl)-2-(tetrahydro-pyran-4-ylamino)-benzamide;
569. N-[5-(3,5-Difluoro-benzenesulfonyl)-4,5,6,7-tetrahydro-1H-pyrazolo[4,3-c]pyridin-3-yl]-2-(3-hydroxy-1-methyl-propylamino)-benzamide;
570. N-[5-(3,5-Difluoro-benzenesulfonyl)-4,5,6,7-tetrahydro-1H-pyrazolo[4,3-c]pyridin-3-yl]-4-[methyl-(2-pyrrolidin-1-yl-ethyl)-amino]-2-nitro-benzamide hydrochloride;
571. N-[5-(3,5-Difluoro-benzenesulfonyl)-4,5,6,7-tetrahydro-1H-pyrazolo[4,3-c]pyridin-3-yl]-4-(2-diisopropylamino-ethoxy)-2-nitro-benzamide hydrochloride;
572. 2-Amino-N-[5-(3,5-difluoro-benzenesulfonyl)-4,5,6,7-tetrahydro-1H-pyrazolo[4,3-c]pyridin-3-yl]-4-[methyl-(2-pyrrolidin-1-yl-ethyl)-amino]-benzamide;
573. 2-Amino-N-[5-(3,5-difluoro-benzenesulfonyl)-4,5,6,7-tetrahydro-1H-pyrazolo[4,3-c]pyridin-3-yl]-4-(2-diisopropylamino-ethoxy)-benzamide;
574. N-[5-(3,5-Difluoro-benzenesulfonyl)-4,5,6,7-tetrahydro-1H-pyrazolo[4,3-c]pyridin-3-yl]-4-(2-diisopropylamino-ethoxy)-2-(tetrahydro-pyran-4-ylamino)-benzamide;
575. N-[5-(3,5-Difluoro-benzenesulfonyl)-4,5,6,7-tetrahydro-1H-pyrazolo[4,3-c]pyridin-3-yl]-4-[methyl-(2-pyrrolidin-1-yl-ethyl)-amino]-2-(tetrahydro-pyran-4-ylamino)-benzamide;
576. N-[5-(3,5-Difluoro-benzenesulfonyl)-4,5,6,7-tetrahydro-1H-pyrazolo[4,3-c]pyridin-3-yl]-4-{[2-(isopropyl-methyl-amino)-ethyl]-methyl-amino}-2-nitro-benzamide hydrochloride;
577. N-[5-(3,5-Difluoro-benzenesulfonyl)-4,5,6,7-tetrahydro-1H-pyrazolo[4,3-c]pyridin-3-yl]-2-(2-methoxy-1-methyl-ethylamino)-4-(4-methyl-piperazin-1-yl)-benzamide;
578. N-[5-(3,5-Difluoro-benzenesulfonyl)-4,5,6,7-tetrahydro-1H-pyrazolo[4,3-c]pyridin-3-yl]-2-((S)-2-methoxy-1-methyl-ethylamino)-4-(4-methyl-piperazin-1-yl)-benzamide;
579. N-[5-(3,5-Difluoro-benzenesulfonyl)-4,5,6,7-tetrahydro-1H-pyrazolo[4,3-c]pyridin-3-yl]-2-((R)-2-methoxy-1-methyl-ethylamino)-4-(4-methyl-piperazin-1-yl)-benzamide;
580. N-[5-(3,5-Difluoro-benzenesulfonyl)-4,5,6,7-tetrahydro-1H-pyrazolo[4,3-c]pyridin-3-yl]-2-(2-methoxy-ethylamino)-4-(4-methyl-piperazin-1-yl)-benzamide;
581. N-[5-(3,5-Difluoro-benzenesulfonyl)-4,5,6,7-tetrahydro-1H-pyrazolo[4,3-c]pyridin-3-yl]-4-[methyl-(2-morpholin-4-yl-ethyl)-amino]-2-(tetrahydro-pyran-4-ylamino)-benzamide;
582. 2-Amino-N-[5-(3,5-difluoro-benzenesulfonyl)-4,5,6,7-tetrahydro-1H-pyrazolo[4,3-c]pyridin-3-yl]-4-[methyl-(2-morpholin-4-yl-ethyl)-amino]-benzamide;

583. N-[5-(3,5-Difluoro-benzenesulfonyl)-4,5,6,7-tetrahydro-1H-pyrazolo[4,3-c]pyridin-3-yl]-4-[methyl-(2-piperidin-1-yl-ethyl)-amino]-2-(tetrahydro-pyran-4-ylamino)-benzamide;
584. 2-Amino-N-[5-(3,5-difluoro-benzenesulfonyl)-4,5,6,7-tetrahydro-1H-pyrazolo[4,3-c]pyridin-3-yl]-4-[methyl-(2-piperidin-1-yl-ethyl)-amino]-benzamide;
585. N-[5-(3,5-Difluoro-benzenesulfonyl)-4,5,6,7-tetrahydro-1H-pyrazolo[4,3-c]pyridin-3-yl]-4-[methyl-(2-piperidin-1-yl-ethyl)-amino]-2-nitro-benzamide hydrochloride;
586. 2-Amino-N-[5-(3,5-difluoro-benzenesulfonyl)-4,5,6,7-tetrahydro-1H-pyrazolo[4,3-c]pyridin-3-yl]-4-{[2-(isopropyl-methyl-amino)-ethyl]-methyl-amino}-benzamide;
587. N-[5-(3,5-Difluoro-benzenesulfonyl)-4,5,6,7-tetrahydro-1H-pyrazolo[4,3-c]pyridin-3-yl]-4-{[2-(isopropyl-methyl-amino)-ethyl]-methyl-amino}-2-(tetrahydro-pyran-4-ylamino)-benzamide;
588. N-[5-(3,5-Difluoro-benzenesulfonyl)-4,5,6,7-tetrahydro-1H-pyrazolo[4,3-c]pyridin-3-yl]-2-(2-methoxy-1-methoxymethyl-ethylamino)-4-(4-methyl-piperazin-1-yl)-benzamide;
589. N-[5-(3,5-Difluoro-benzenesulfonyl)-4,5,6,7-tetrahydro-1H-pyrazolo[4,3-c]pyridin-3-yl]-4-[(2-methoxy-ethyl)-methyl-amino]-2-(2-methoxy-1-methyl-ethylamino)-benzamide;
590. N-[5-(3,5-Difluoro-benzenesulfonyl)-4,5,6,7-tetrahydro-1H-pyrazolo[4,3-c]pyridin-3-yl]-4-(4-fluoro-piperidin-1-ylmethyl)-2-(tetrahydro-pyran-4-ylamino)-benzamide;
591. N-[5-(3,5-Difluoro-benzenesulfonyl)-4,5,6,7-tetrahydro-1H-pyrazolo[4,3-c]pyridin-3-yl]-4-(1-propyl-piperidin-4-ylamino)-2-(tetrahydro-pyran-4-ylamino)-benzamide;
592. N-[5-(3,5-Difluoro-benzenesulfonyl)-4,5,6,7-tetrahydro-1H-pyrazolo[4,3-c]pyridin-3-yl]-4-(1-ethyl-3-methyl-piperidin-4-ylamino)-2-(tetrahydro-pyran-4-ylamino)-benzamide;
593. 4-(2-Diethylamino-1-methyl-ethylamino)-N-[5-(3,5-difluoro-benzenesulfonyl)-4,5,6,7-tetrahydro-1H-pyrazolo[4,3-c]pyridin-3-yl]-2-(tetrahydro-pyran-4-ylamino)-benzamide;
594. 4-Acetylamino-N-[5-(3,5-difluoro-benzenesulfonyl)-4,5,6,7-tetrahydro-1H-pyrazolo[4,3-c]pyridin-3-yl]-2-(tetrahydro-pyran-4-ylamino)-benzamide;
595. N-[5-(3,5-Difluoro-benzenesulfonyl)-4,5,6,7-tetrahydro-1H-pyrazolo[4,3-c]pyridin-3-yl]-4-(1-isopropyl-piperidin-4-ylamino)-2-(tetrahydro-pyran-4-ylamino)-benzamide;
596. N-[5-(3,5-Difluoro-benzenesulfonyl)-4,5,6,7-tetrahydro-1H-pyrazolo[4,3-c]pyridin-3-yl]-2-((2R,6S)-2,6-dimethyl-tetrahydro-pyran-4-ylamino)-4-(4-methyl-piperazin-1-yl)-benzamide;
597. N-[5-(3,5-Difluoro-benzenesulfonyl)-4,5,6,7-tetrahydro-1H-pyrazolo[4,3-c]pyridin-3-yl]-2-((S)-3-methoxy-1-methyl-propylamino)-4-(4-methyl-piperazin-1-yl)-benzamide;
598. N-[5-(3,5-Difluoro-benzenesulfonyl)-4,5,6,7-tetrahydro-1H-pyrazolo[4,3-c]pyridin-3-yl]-2-((R)-3-methoxy-1-methyl-propylamino)-4-(4-methyl-piperazin-1-yl)-benzamide;
599. N-[5-(3,5-Difluoro-benzenesulfonyl)-4,5,6,7-tetrahydro-1H-pyrazolo[4,3-c]pyridin-3-yl]-2-(3-methoxy-propylamino)-4-(4-methyl-piperazin-1-yl)-benzamide;
600. N-[5-(3,5-Difluoro-benzenesulfonyl)-4,5,6,7-tetrahydro-1H-pyrazolo[4,3-c]pyridin-3-yl]-2-(2-methoxy-1,1-dimethyl-ethylamino)-4-(4-methyl-piperazin-1-yl)-benzamide;
601. N-[5-(3,5-Difluoro-benzenesulfonyl)-4,5,6,7-tetrahydro-1H-pyrazolo[4,3-c]pyridin-3-yl]-2-((S)-2-methoxy-propylamino)-4-(4-methyl-piperazin-1-yl)-benzamide and
602. N-[5-(3,5-Difluoro-benzenesulfonyl)-4,5,6,7-tetrahydro-1H-pyrazolo[4,3-c]pyridin-3-yl]-2-((R)-2-methoxy-propylamino)-4-(4-methyl-piperazin-1-yl)-benzamide.

Preferred specific compounds (cpd.) of the invention are listed below:

1H-Pyrrole-2-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;

1H-Pyrrole-3-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;

1-Methyl-1H-pyrrole-2-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;

Tetrahydro-pyran-4-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;

Furan-2-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide;

N-[5-(3,5-Difluoro-benzenesulfonyl)-4,5,6,7-tetrahydro-1H-pyrazolo[4,3-c]pyridin-3-yl]-2-isobutylamino-4-(4-methyl-piperazin-1-yl)-benzamide;

N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-(tetrahydro-pyran-4-ylamino)-benzamide;

N-[5-(3,5-Difluoro-benzenesulfonyl)-4,5,6,7-tetrahydro-1H-pyrazolo[4,3-c]pyridin-3-yl]-4-(4-ethyl-piperazin-1-yl)-2-(tetrahydro-pyran-4-ylamino)-benzamide;

N-[5-(3,5-Difluoro-benzenesulfonyl)-4,5,6,7-tetrahydro-1H-pyrazolo[4,3-c]pyridin-3-yl]-4-morpholin-4-yl-2-(tetrahydro-pyran-4-ylamino)-benzamide;

1H-Pyrrole-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;

1H-Pyrrole-3-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;

1-Methyl-1H-pyrrole-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide;

1H-Pyrrole-2-carboxylic acid {5-dimethylamino-2-[5-(pyridine-3-sulfonyl)-7,7-dimethyl-4,5,6,7-tetrahydro-1H-pyrazolo[4,3-c]pyridin-3-ylcarbamoyl]-phenyl}-amide;

1H-Pyrrole-2-carboxylic acid {2-[5-(3,5-difluoro-benzenesulfonyl)-4,5,6,7-tetrahydro-1H-pyrazolo[4,3-c]pyridin-3-ylcarbamoyl]-phenyl}-amide;

1H-Pyrrole-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-phenyl}-amide;

1H-Pyrrole-2-carboxylic acid {2-[5-(3,5-difluoro-benzenesulfonyl)-4,5,6,7-tetrahydro-1H-pyrazolo[4,3-c]pyridin-3-ylcarbamoyl]-5-[(2-dimethylamino-ethyl)-methyl-amino]-phenyl}-amide;

1H-Pyrrole-2-carboxylic acid [2-[5-(3,5-difluoro-benzenesulfonyl)-4,5,6,7-tetrahydro-1H-pyrazolo[4,3-c]pyridin-3-ylcarbamoyl]-5-(2-dimethylamino-ethoxy)-phenyl]-amide; N-[5-(3,5-Difluoro-benzenesulfonyl)-4,5,6,7-tetrahydro-1H-pyrazolo[4,3-c]pyridin-3-yl]-2-((S)-2-methoxy-1-methyl-ethylamino)-4-(4-methyl-piperazin-1-yl)-benzamide;

N-[5-(3,5-Difluoro-benzenesulfonyl)-4,5,6,7-tetrahydro-1H-pyrazolo[4,3-c]pyridin-3-yl]-2-((R)-2-methoxy-1-methyl-ethylamino)-4-(4-methyl-piperazin-1-yl)-benzamide;

N-[5-(3,5-Difluoro-benzenesulfonyl)-4,5,6,7-tetrahydro-1H-pyrazolo[4,3-c]pyridin-3-yl]-2-(2-methoxy-ethylamino)-4-(4-methyl-piperazin-1-yl)-benzamide;

1H-Pyrrole-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-dimethylamino-phenyl}-amide;

1-Methyl-1H-pyrrole-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-dimethylamino-phenyl}-amide;

N-[5-(3,5-Difluoro-benzenesulfonyl)-4,5,6,7-tetrahydro-1H-pyrazolo[4,3-c]pyridin-3-yl]-4-(2-dimethylamino-1-methyl-ethylamino)-2-(tetrahydro-pyran-4-ylamino)-benzamide;

N-[5-(3,5-Difluoro-benzenesulfonyl)-4,5,6,7-tetrahydro-1H-pyrazolo[4,3-c]pyridin-3-yl]-4-(4-isopropyl-piperazin-1-yl)-2-(tetrahydro-pyran-4-ylamino)-benzamide;

N-[5-(3,5-Difluoro-benzenesulfonyl)-4,5,6,7-tetrahydro-1H-pyrazolo[4,3-c]pyridin-3-yl]-4-(2-pyrrolidin-1-yl-ethoxy)-2-(tetrahydro-pyran-4-ylamino)-benzamide;

N-[5-(3,5-Difluoro-benzenesulfonyl)-4,5,6,7-tetrahydro-1H-pyrazolo[4,3-c]pyridin-3-yl]-4-(4-propyl-piperazin-1-yl)-2-(tetrahydro-pyran-4-ylamino)-benzamide;

N-[5-(3,5-Difluoro-benzenesulfonyl)-4,5,6,7-tetrahydro-1H-pyrazolo[4,3-c]pyridin-3-yl]-4-[(3-dimethylamino-propyl)-methyl-amino]-2-(tetrahydro-pyran-4-ylamino)-benzamide;

4-[(2-Diethylamino-ethyl)-methyl-amino]-N-[5-(3,5-difluoro-benzenesulfonyl)-4,5,6,7-tetrahydro-1H-pyrazolo[4,3-c]pyridin-3-yl]-2-(tetrahydro-pyran-4-ylamino)-benzamide;

N-[5-(3,5-Difluoro-benzenesulfonyl)-4,5,6,7-tetrahydro-1H-pyrazolo[4,3-c]pyridin-3-yl]-2-((2R,6S)-2,6-dimethyl-tetrahydro-pyran-4-ylamino)-4-(4-methyl-piperazin-1-yl)-benzamide;

N-[5-(3,5-Difluoro-benzenesulfonyl)-4,5,6,7-tetrahydro-1H-pyrazolo[4,3-c]pyridin-3-yl]-4-[(2-dimethylamino-ethyl)-ethyl-amino]-2-(tetrahydro-pyran-4-ylamino)-benzamide;

N-[5-(3,5-Difluoro-benzenesulfonyl)-4,5,6,7-tetrahydro-1H-pyrazolo[4,3-c]pyridin-3-yl]-4-(2-diisopropylamino-ethoxy)-2-(tetrahydro-pyran-4-ylamino)-benzamide;

N-[5-(3,5-Difluoro-benzenesulfonyl)-4,5,6,7-tetrahydro-1H-pyrazolo[4,3-c]pyridin-3-yl]-4-[methyl-(2-pyrrolidin-1-yl-ethyl)-amino]-2-(tetrahydro-pyran-4-ylamino)-benzamide;

N-[5-(3,5-Difluoro-benzenesulfonyl)-4,5,6,7-tetrahydro-1H-pyrazolo[4,3-c]pyridin-3-yl]-4-[methyl-(2-piperidin-1-yl-ethyl)-amino]-2-(tetrahydro-pyran-4-ylamino)-benzamide;

N-[5-(3,5-Difluoro-benzenesulfonyl)-4,5,6,7-tetrahydro-1H-pyrazolo[4,3-c]pyridin-3-yl]-4-{[2-(isopropyl-methyl-amino)-ethyl]-methyl-amino}-2-(tetrahydro-pyran-4-ylamino)-benzamide;

4-(2-Diethylamino-1-methyl-ethylamino)-N-[5-(3,5-difluoro-benzenesulfonyl)-4,5,6,7-tetrahydro-1H-pyrazolo[4,3-c]pyridin-3-yl]-2-(tetrahydro-pyran-4-ylamino)-benzamide;

N-[5-(3,5-Difluoro-benzenesulfonyl)-4,5,6,7-tetrahydro-1H-pyrazolo[4,3-c]pyridin-3-yl]-2-(2-methoxy-1-methyl-ethylamino)-4-(4-methyl-piperazin-1-yl)-benzamide;

N-[5-(3,5-Difluoro-benzenesulfonyl)-4,5,6,7-tetrahydro-1H-pyrazolo[4,3-c]pyridin-3-yl]-2-(2-methoxy-1-methoxymethyl-ethylamino)-4-(4-methyl-piperazin-1-yl)-benzamide;

N-[5-(3,5-Difluoro-benzenesulfonyl)-4,5,6,7-tetrahydro-1H-pyrazolo[4,3-c]pyridin-3-yl]-4-[methyl-(2-morpholin-4-yl-ethyl)-amino]-2-(tetrahydro-pyran-4-ylamino)-benzamide;

N-[5-(3,5-Difluoro-benzenesulfonyl)-4,5,6,7-tetrahydro-1H-pyrazolo[4,3-c]pyridin-3-yl]-4-(4-fluoro-piperidin-1-ylmethyl)-2-(tetrahydro-pyran-4-ylamino)-benzamide and N-[5-(3,5-Difluoro-benzenesulfonyl)-4,5,6,7-tetrahydro-1H-pyrazolo[4,3-c]pyridin-3-yl]-4-[4-(2-methoxy-ethyl)-piperazin-1-yl]-2-(tetrahydro-pyran-4-ylamino)-benzamide.

The present inventions also provides a process for the preparation of compounds of formula (I). Compounds of formula (I) and the pharmaceutically acceptable salts may be obtained by two independent ways: pathway A or pathway B.

Pathway A comprises:

a) reacting a compound of formula (II)

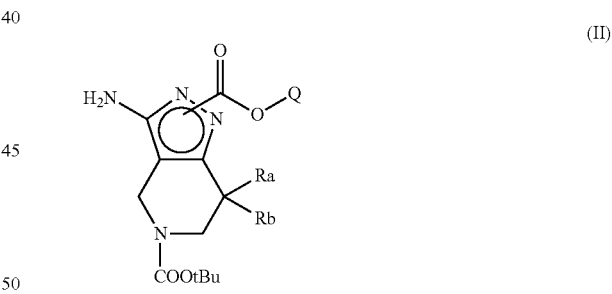

wherein Ra and Rb are as defined above, Q is a lower alkyl group, for instance a $C_1$-$C_4$ alkyl group, more preferably methyl or ethyl, tBu is tert-butyl, with a compound of formula (III)

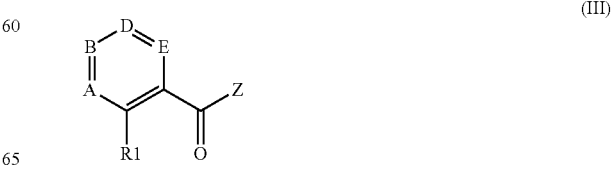

wherein R1 and A, B, D, E are as defined above and Z is hydroxy, halogen or a suitable leaving group;

b) deprotecting the resulting compound of formula (IV),

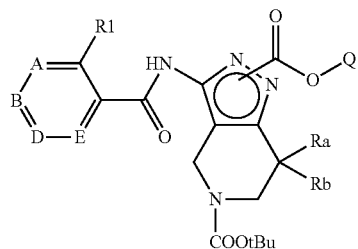

(IV)

wherein R1, A, B, D, E, Ra, Rb, and Q are as defined above, under acidic conditions;

c) reacting the resulting compound of formula (V),

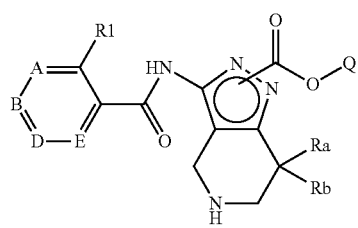

(V)

wherein R1, A, B, D, E, Ra, Rb, and Q are as defined above, with a compound of formula (VI),

(VI)

wherein Z and R are as defined above so as to obtain a compound of formula (VII),

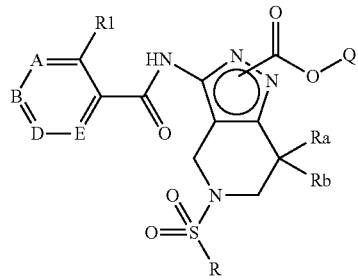

(VII)

wherein R, R1, A, B, D, E, Ra, Rb, and Q are as defined above and optionally converting it into another compound of formula (VII);

d) deprotecting the compound of formula (VII) as defined above under basic conditions so as to obtain the corresponding compound of formula (I), which can be further separated into the single isomers when it contains one or more asymmetric centers, and optionally converted into another compound of formula (I) and/or into a pharmaceutically acceptable salt if desired.

Pathway B comprises:

e) deprotecting a compound of formula (II) as defined above, under acidic conditions;

f) reacting the resulting compound of formula (XI)

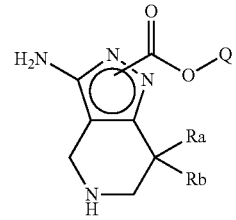

(XI)

wherein Ra, Rb and Q are as defined above, with a compound of formula (VI) as defined above;

g) deprotecting the resulting compound of formula (XII)

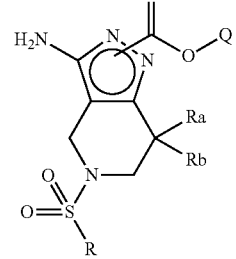

(XII)

wherein R, Ra, Rb and Q are as defined above, under basic conditions;

h) trifluoroacetylating the resulting compound of formula (XIII)

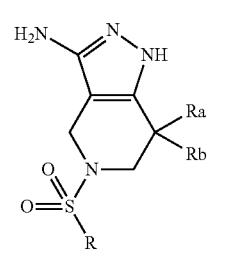

(XIII)

wherein R, Ra and Rb are as defined above;

i) reacting the resulting compound of formula (XIV)

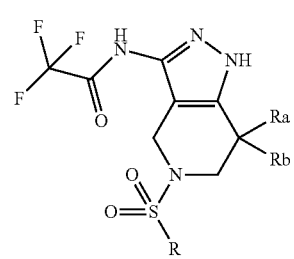

(XIV)

wherein R, Ra and Rb are as defined above, with trityl chloride;

j) deprotecting the resulting compound of formula (XV)

(XV)

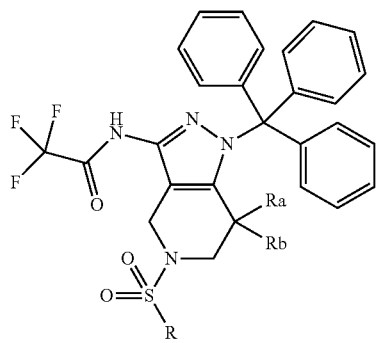

wherein R, Ra and Rb are as defined above, under basic conditions;

k) reacting the resulting compound of formula (XVI), (XVI)

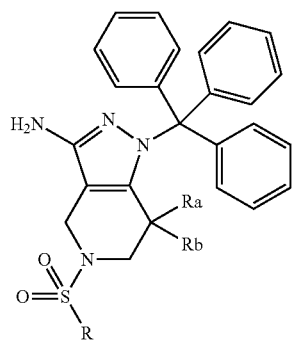

wherein R, Ra and Rb are as defined above, with a compound of formula (III) as defined above so as to obtain a compound of formula (XVII)

(XVII)

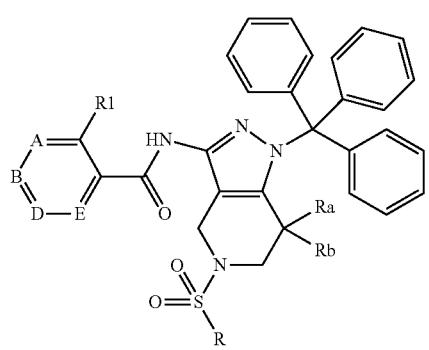

wherein R, R1, Ra, Rb, A, B, D and E are as defined above and optionally converting it into another compound of formula (XVII);

1) deprotecting the compound of formula (XVII) as defined above under acidic conditions so as to obtain the corresponding compound of formula (I), which can be further separated into the single isomers when it contains one or more asymmetric centers, and optionally converted into another compound of formula (I) and/or into a pharmaceutically acceptable salt if desired.

It is to be noted that a compound of formula (II), (IV), (V), (VII), (XI) and (XII) as defined above can be in any one of its isomeric forms a or b:

a

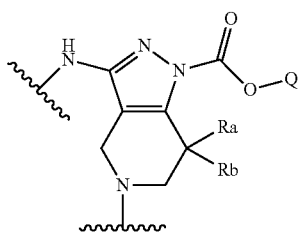

b

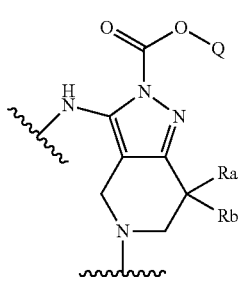

As said above, a compound of formula (VII) or (XVII) can be converted into another compound of formula (VII) or (XVII), the following being examples of possible conversions:

1) preparation of a compound of formula (VII) or (XVII), wherein R1 is amino by reducing a compound of formula (VII) or (XVII), wherein R1 is nitro;

2) preparation of a compound of formula (VII) or (XVII), wherein R1 is NHCOR4 by reacting a compound of formula (VII) or (XVII), wherein R1 is amino with a compound of formula (VIII), (VIII)

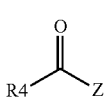

wherein R4 and Z are as defined above;

3) preparation of a compound of formula (VII) or (XVII), wherein R1 is NHCONHR8 by reacting a compound of formula (VII) or (XVII), wherein R1 is amino with an isocyanate of formula (IX),

R8—N=C=O          (IX)

wherein R8 is as defined above;

4) preparation of a compound of formula (VII) or (XVII), wherein R1 is NHSO$_2$R10, and R, A, B, D, E, Ra, Rb, R10 and Q are as defined above, by reacting a compound of formula (VII) or (XVII), wherein R1 is amino and R, A, B, D, E, Ra, Rb and Q are as defined above, with a compound of formula (X),

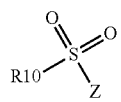

wherein R10 and Z are as defined above;

5) preparation of a compound of formula (VII) or (XVII), wherein R1 is a NR5R6 group, wherein one of the R5 or R6 is hydrogen and the other is an optionally further substituted straight or branched $C_1$-$C_6$ alkyl, $C_3$-$C_6$ cycloalkyl, heterocycloalkyl, R8R9N—$C_2$-$C_6$ alkyl, R7O—$C_2$-$C_6$ alkyl, wherein R7, R8 and R9 are as defined above, by reacting a compound of formula (VII) or (XVII), wherein R1 is amino with a suitable aldehyde or ketone in presence of a reducing agent.

As said above, a compound of formula (I) may be converted into another compound of formula (I), the following being an example of possible conversions:

a compound of formula (I), wherein R1 is amino may be converted into a compound of formula (I) wherein R1 is NR5R6, wherein R5 and R6 are defined as in conversion 5), by reacting it with a suitable aldeyde or ketone in presence of a reducing agent.

The synthesis of a compound of formula (I), according to the synthetic process described above, can be conducted in a stepwise manner, whereby each intermediate is isolated and purified by standard purification techniques, like, for example, column chromatography, before carrying out the subsequent reaction. Alternatively, two or more steps of the synthetic sequence can be carried out in a so-called "one-pot" procedure, as known in the art, whereby only the compound resulting from the two or more steps is isolated and purified.

According to step a) of the process, the reaction between a compound of formula (II) and a compound of formula (III) can be carried out in a variety of ways, according to conventional methods for acylating amino derivatives. As an example, a compound of formula (II) may be reacted with an acyl chloride of formula (III), in which case Z represents a chlorine atom. Preferably, this reaction is carried out in a suitable solvent such as, for instance, tetrahydrofuran, dichloromethane, toluene, 1,4-dioxane, acetonitrile and in presence of a proton scavenger such as, for example, triethylamine, N,N-diisopropylethylamine, pyridine, at a temperature ranging from room temperature to reflux, for a time ranging from about 30 min. to about 96 hours.

It is known to the skilled person that when a compound of formula (III) carries functional groups that may interfere with the above reaction, such groups have to be protected before carrying out the reaction. In particular, when a compound of formula (III) is substituted by residues of general formula NR5R6, OR7, or R8R9N—$C_1$-$C_6$ alkyl, wherein R7 or one or both of R5 and R6, or R8 and R9 represent hydrogen, such groups are protected as known in the art. Introduction of a nitrogen protecting group may also be required for a compound of formula (III), wherein R1 is NHCOR7 or NHSO$_2$R10.

It is also known to the skilled person that such protecting group may be removed just after the reaction of a compound of formula (III) with a compound of formula (II) or at a later stage in the synthetic process. Removal of some protective groups may also affect the pyrazole protecting group (—COOQ) of a compound of formula (IV) or (VII). If needed, such pyrazole protecting group can be reinstalled at a later stage in the synthetic process.

According to step b) or e) of the process, a compound of formula (IV) or (II) is easily deprotected at the tetrahydropyridine nitrogen atom by acidic treatment. This reaction can be conveniently carried out in presence of an inorganic or organic acid such as, for instance, hydrochloric, trifluoroacetic or methanesulfonic acid, in a suitable solvent such as dichloromethane, 1,4-dioxane, a lower alcohol, such as methanol or ethanol, at a temperature ranging from room temperature to about 40° C. and for a period of time varying from about 1 hour to about 48 hours.

The compound of formula (V) or (XI) thus obtained is further reacted, according to step c) or f) of the process, with a compound of formula (VI). From the above it is clear to the skilled person that this sulfonylation reaction may be accomplished in a variety of ways and experimental conditions, which are widely known in the art for the preparation of sulfonamides. As an example, the reaction between a compound of formula (V) and a sulfonyl chloride of formula (VI), in which case Z is a chlorine atom, can be carried out in a suitable solvent such as, for instance, diethyl ether, tetrahydrofuran, dichloromethane, chloroform, toluene, 1,4-dioxane, acetonitrile and in presence of a proton scavenger such as, for example, triethylamine, N,N-diisopropylethylamine, pyridine, at a temperature ranging from about −10° C. to reflux, and for a period of time ranging, for instance, from about 30 min to about 96 hours.

According to step d) or g) of the process, a compound of formula (VII) or (XII) is transformed into a compound of formula (I) or (XIII) by deprotection of the pyrazole nitrogen atom by working according to conventional methods enabling the selective hydrolysis of a carbamate protecting group. As an example, this reaction may be carried out under basic conditions, for instance in presence of sodium hydroxide, potassium hydroxide, lithium hydroxide or barium hydroxyde, or of a tertiary amine such as triethylamine, or of hydrazine, and in a suitable solvent such as methanol, ethanol, tetrahydrofuran, N,N-dimethylformamide, water and mixtures thereof. Typically, the reaction is carried out at a temperature ranging from room temperature to about 60° C. and for a time varying from about 30 minutes to about 96 hours.

According to step h) of the process, a compound of formula (XIII) can be converted into a compound of formula (XIV) by selective trifluoroacetylation of the amino group on the pyrazole ring. Such transformation may be conducted in a two-step fashion. For instance, a compound of formula (XIII) can be reacted with an excess of trifluoroacetyl chloride or trifluoroacetic anhydride in a suitable solvent such as dichloromethane, chloroform, acetonitrile, tetrahydrofuran, diethylether or toluene at a temperature ranging from −10° C. to 50° C. and for a period of time varying from about 30 minutes to about 12 hours so as to obtain a compound of formula (XVIII)

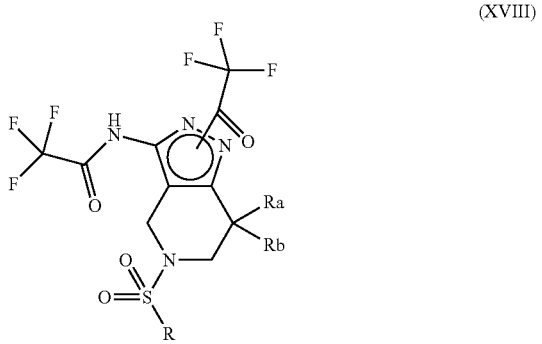

(XVIII)

wherein R, Ra and Rb are as defined above. This reaction may also be conducted in presence of an organic base such as triethylamine, N,N-diisopropylethylamine or pyridine. The compound of formula (XVIII) as defined above is then transformed into a compound of formula (XIV) by selective hydrolysis of the trifluoroacetyl group bound to one of the pyrazole nitrogen atoms. This hydrolysis may be carried out, for instance, in presence of water, methanol, ethanol or mixtures thereof at a temperature ranging from room temperature to 50° C. and for a period of time varying from approximately 10 minutes to 6 hours.

According to the step i) of the process a compound of formula (XIV) can be reacted with trityl chloride in presence of an organic base, such as triethylamine, N,N-diisopropylethylamine or pyridine in a suitable solvent such as dichloromethane, chloroform, acetonitrile, tetrahydrofuran, diethylether or toluene, at a temperature ranging from 0° C. to 50° C. and for a period of time varying from 1 hour to 24 hours so as to obtain a compound of formula (XV).

According to step j) of the process a compound of formula (XV) can be converted into a compound of formula (XVI) by cleavage of the trifluoroacetyl protecting group under basic conditions. For instance this reaction can be conducted in presence of sodium hydroxide, potassium hydroxide, lithium hydroxide or barium hydroxyde, or of a tertiary amine such as triethylamine, or N,N-diisopropylethylamine, in a suitable solvent such as methanol, ethanol, tetrahydrofuran, N,N-dimethylformamide, water or mixtures thereof. Typically, the reaction is carried out at a temperature ranging from room temperature to reflux and for a period of time varying from about 30 minutes to about 96 hours.

According to step k) the reaction between a compound of formula (XVI) and a compound of formula (III) can be carried out in a way analogous to that specified above under a) so as to obtain a compound of formula (XVII).

According to step l) of the process a compound of formula (XVII) is transformed into a compound of formula (I) by deprotection of the pyrazole nitrogen atom by working according to conventional methods enabling the selective hydrolysis of a trityl protecting group. As an example, this reaction may be carried out under acidic conditions for instance in the presence of hydrochloric acid or trifluoroacetic acid in a suitable solvent such as diethylether, 1,4-dioxane, methanol, ethanol, water or mixtures thereof, at a temperature ranging from room temperature to reflux and for a period of time varying from 1 hour to 2 days.

According to the conversion described in 1) the reduction of a compound of formula (VII) or (XVII), wherein R1 is nitro, to a compound of formula (VII) or (XVII) wherein R1 is amino can be carried out in a variety of ways, according to conventional methods for reducing a nitro to an amino group. Preferably, this reaction is carried out in a suitable solvent such as, for instance, methanol, ethanol, water, tetrahydrofuran, 1,4-dioxane, N,N-dimethylformamide, acetic acid, or a mixture thereof, in presence of a suitable reducing agent, such as, for instance, hydrogen and a hydrogenation catalyst, or by treatment with cyclohexene or cyclohexadiene, or formic acid or ammonium formate and a hydrogenation catalyst, or a metal such as iron or zinc in presence of an inorganic acid, such as hydrochloric acid, or by treatment with tin (II) chloride, at a temperature ranging from 0° C. to reflux and for a time varying from about 1 hour to about 96 hours. The hydrogenation catalyst is usually a metal, most often palladium, which can be used as such or supported on carbon.

According to the conversion described in 2) the acylation of a compound of formula (VII) or (XVII), wherein R1 is amino, can be accomplished in a variety of ways and experimental conditions, which are widely known in the art for the preparation of carboxamides. As an example, the reaction between a compound of formula (VII) or (XVII) and a carboxylic acid derivative of formula (VIII), wherein Z is as defined above, can be carried out in presence of a tertiary base, such as triethylamine, N,N-diisopropylethylamine or pyridine, in a suitable solvent, such as toluene, dichloromethane, chloroform, diethyl ether, tetrahydrofuran, 1,4-dioxane, acetonitrile, or N,N-dimethylformamide, at a temperature ranging from about −10° C. to reflux and for a period of time varying from about 1 hour to about 96 hours.

According to the conversion described in 3) the reaction of a compound of formula (VII) or (XVII), wherein R1 is amino with an isocyanate of formula (IX), may be carried out in a solvent such as toluene, dichloromethane, chloroform, diethyl ether, tetrahydrofuran, 1,4-dioxane, or acetonitrile at a temperature ranging from about −10° C. to reflux and for a period of time varying from about 1 hour to about 96 hours.

According to the conversion described in 4) the reaction of a compound of formula (VII) or (XVII), wherein R1 is amino with a compound of formula (X) may be accomplished in a variety of ways and experimental conditions which are widely known in the art for the preparation of sulfonamides. As an example, the reaction between a compound of formula (VII) or (XVII) and a sulfonyl chloride of formula (X), in which case Z is a chlorine atom, can be carried out in a suitable solvent such as, for instance, diethyl ether, tetrahydrofuran, dichloromethane, chloroform, toluene, 1,4-dioxane, acetonitrile and in presence of a proton scavenger such as triethylamine, N,N-diisopropylethylamine, pyridine, at a temperature ranging from about −10° C. to reflux, and for a period of time ranging, for instance, from about 30 min to about 96 hours.

According to the conversions described in 5) the reaction of a compound of formula (VII) or (XVII), wherein R1 is amino with an aldehyde or a ketone, can be conducted in a variety of ways, according to conventional methods for carrying out reductive alkylation. Preferably, this reaction is carried out in a suitable solvent such as, for instance, methanol, N,N-dimethylformamide, dichloromethane, tetrahydrofuran, or a mixture thereof, in presence of a suitable reducing agent such as, for instance, sodium borohydride, tetra-alkylammonium borohydride, sodium cyano borohydride, sodium triacetoxyborohydride, tetramethylammonium triacetoxy borohydride, hydrogen and a hydrogenation catalyst, such as for instance nickel or platinum or palladium, and in presence of an acid catalyst, such as, for instance, acetic acid or trifluoroacetic acid, at a temperature ranging from about 0° C. to reflux and for a time varying from about 1 hour to about 96 hours.

A compound of formula (I) can be converted into another compound of formula (I) in a way analogous to that specified above under 5.

The deprotection of a compound of formula (VII) or (XVII) wherein R1 is a protected amino group, can be made in a variety of ways according to conventional methods for deprotecting amino groups. Depending on the amino protecting group, this reaction can be conducted in different ways. In one aspect, such reaction can be carried out by treatment of a compound of formula (VII) or (XVII) with an inorganic acid, such as hydrochloric, sulphuric or perchloric acid, or an organic acid, such as trifluoroacetic or methanesulfonic acid, in a suitable solvent, such as water, methanol, ethanol, 1,4-dioxane, tetrahydrofuran, diethyl ether, diisopropyl ether, acetonitrile, N,N-dimethylformamide, dichloromethane or mixtures thereof, at a temperature ranging from −10° C. to 80° C., and for a period of time ranging from 30 minutes to 48 hours. In another aspect, such reaction can be carried out by treatment of a compound of formula (VII) or (XVII) with an inorganic base, such as lithium or sodium or potassium hydroxide, or sodium or potassium or caesium carbonate, or with an organic base, such as triethylamine or N,N-diisopropylethylamine, or with anhydrous hydrazine or hydrazine hydrate in a suitable solvent such as water, methanol, ethanol, 1,4-dioxane, tetrahydrofuran, diethyl ether, diisopropyl ether, acetonitrile, N,N-dimethylformamide, dichloromethane or mixtures thereof, at a temperature ranging from −10° C. to 80° C., and for a period of time ranging from 30 minutes to 72 hours. In still another option, such reaction can be carried out by treatment of a compound of formula (VII) or (XVII) with hydrogen or cyclohexene or cyclohexadiene and a hydrogenation catalyst, such as palladium on carbon, or with a metal, such as zinc, and an inorganic or organic acid, such as hydrochloric or acetic acid, in a suitable solvent such as water, methanol, ethanol, 1,4-dioxane, tetrahydrofuran or mixture thereof, at a temperature ranging from −10° C. to 80° C., and for a period of time ranging from 30 minutes to 72 hours.

Substituted pyrazolo[4,3-c]pyridine derivatives can be prepared using standard procedures in organic synthesis as reported, for instance, in Smith, Michael—*March's Advanced Organic Chemistry: reactions mechanisms and structure*—5$^{th}$ *Edition*, Michael B. Smith and Jerry March, John Wiley & Sons Inc., New York (NY), 2001. It is known to the skilled person that transformation of a chemical function into another may require that one or more reactive centers in the compound containing this function be protected in order to avoid undesired side reactions. Protection of such reactive centers, and subsequent deprotection at the end of the synthetic transformations, can be accomplished following standard procedures described, for instance, in: Green, Theodora W. and Wuts, Peter G. M.—*Protective Groups in Organic Synthesis, Third Edition*, John Wiley & Sons Inc., New York (NY), 1999.

In cases where a compound of formula (I) contains one or more asymmetric centers, said compound can be separated into the single isomers by procedures known to those skilled in the art. Such procedures comprise standard chromatographic techniques, including chromatography using a chiral stationary phase, or crystallization. General methods for separation of compounds containing one or more asymmetric centers are reported, for instance, in Jacques, Jean; Collet, André; Wilen, Samuel H.,—*Enantiomers, Racemates, and Resolutions*, John Wiley & Sons Inc., New York (NY), 1981.

A compound of formula (I) can also be transformed into a pharmaceutically acceptable salt according to standard procedures that are known to those skilled in the art. Alternatively, a compound of formula (I) that is obtained as a salt can be transformed into the free base or the free acid according to standard procedures that are known to the skilled person.

The starting materials of the process of the present invention are either known or can be prepared according to known methods. As an example, the preparation of a compound of formula (II), wherein Q represents ethyl, is disclosed in the international applications WO 2002/12242 and WO 2004/080457 (see, in particular, example 18 at page 47; this same compound is therein named as 3-amino-5-tert-butyloxycarbonyl-1-ethoxycarbonyl-pyrazolo[4,3-e]4,5,6,7-tetrahydropyridine). Additional compounds of formula (II), wherein Q represents a lower alkyl group other than ethyl, can be prepared by applying procedures similar to those disclosed in the above mentioned patent applications. The desired isomeric form of compounds of formula (II) may be obtained by separation of the mixture of isomers by methods known in the art.

The compounds of formula (III) and (VIII), for instance those wherein Z represents a halogen atom, e.g. a chlorine atom, are either known or can be easily obtained from the corresponding carboxylic acids, that are either known or can be prepared by working according to conventional synthetic methods. The compounds of formula (VI) and (X), for instance those wherein Z represents a halogen atom, e.g. a chlorine atom, are either known or can be prepared from sulfonic acids according to conventional synthetic methods. The compounds of formula (IX) are either known or can be synthesized according to conventional methods for the preparation of isocianates such as, for instance, treatment of an amine with trifosgene.

Pharmacology

The short forms and abbreviations used herein have the following meaning:

| | |
|---|---|
| Ci | Curie |
| DMSO | dimethylsulfoxide |
| KDa | kiloDalton |
| microCi | microCurie |
| mg | milligram |
| microg | microgram |
| mL | milliliter |
| microL | microliter |
| M | molar |
| mM | millimolar |
| microM | micromolar |
| nM | nanomolar |

Assays

Compounds of the present invention were tested in biochemical as well as in cell-based assays, as described below.

Preparation of IGF-1R for Use in Biochemical Assay

Cloning and Expression

Human cDNA was used as template for amplification by polymerase chain reaction (PCR) of the predicted cytoplasmic portion of IGF-1R (amino acid residues 960-1367 of precursor protein; see NCBI Entrez Protein Accession #P08069) which includes the entire kinase domain. PCR was conducted using the forward primer sequence 5'-CTCG-GATCCAGAAAGAGAAATAACAGCAGGCTG-3' (SEQ ID NO:1) and the reverse primer sequence 5'-CTCGGATC-CTCAGCAGGTCGAAGACTGGGGCAGCGG-3' (SEQ ID NO:2). In order to facilitate subsequent cloning steps, both primers comprise a BamHI restriction endonuclease site sequence. This PCR product was cloned in frame using BamHI sticky ends into a transfer vector for the baculovirus expression system, pVL1392 (Pharmingen), previously modified by insertion into the pVL1392 multiple cloning site of sequences encoding Glutathione 5-transferase (GST)

fusion protein, PreScission protease cleavage site and partial MCS cassette derived from the pGex-6P plasmid (Amersham BioSciences). Insertion of the IGF-1R PCR product described above into the pGex-6P derived BamHI site of the modified pVL1392 vector results in an open reading frame corresponding to the pGEX-6P GST protein and PreScission peptide fused with the human IGF-1R cytoplasmic domain. In order to obtain fusion protein, Sf21 insect cells (Invitrogen) are cotransfected with 2 microg of purified plasmid and 1 microg of virus DNA (BaculoGold™ Transfection Kit, Pharmingen), as described in the Baculovirus Instruction manual (Pharmingen). A first amplification of the virus is performed using 600 microL of cotransfected virus on $6 \times 10^6$ Sf21 in a monolayer culture, in 12 mL of medium (TNM-FH Grace's medium—Pharmingen). After 3 days the medium is collected, centrifuged and transferred to a sterile tube. A second amplification is prepared with the same method using 2 mL on $3 \times 10^7$ cells, diluted in 40 mL of medium. For the third amplification of virus, 1 mL of supernatant from the second round are used per $3 \times 10^7$ cells diluted in 40 mL of medium.

Protein expression is performed in H5 insect cells infected with 14 mL virus/$1 \times 10^9$ insect cells (MOI=1.5) for 65 h with shaking at 27° C. Cells are harvested by centrifugation at 1200×g for 10 minutes.

Protein Purification

Cells were resuspended in phosphate buffered saline solution (PBS), 20 mM dithiothreitol (DTT), 0.2% CHAPS, 20% glycerol, 1 mM OVA, "Complete" protease inhibitor cocktail (1 tablet/50 mL buffer; Roche Diagnostics, Milan, Italy) and lysed by liquid extrusion with a Gaulin homogenizer (Niro Soavi, Italy). The lysate was centrifuged at 14000×g for 45 minutes and the supernatant was loaded onto a column containing 10 mL Glutathione Sepharose (Amersham Biosciences). The column was first washed with PBS buffer for 5 column volumes, then with 100 mM Tris pH 8.0, 20% glycerol for 5 column volumes, and lastly eluted with 10 mM glutathione in 100 mM Tris pH 8.0, 20% glycerol. Fractions of 10 mL were collected, and protein-rich fractions were pooled. Typically, 20 mg of fusion protein were recovered from $1 \times 10^9$ cells, and this was typically >85% pure as judged by SDS-PAGE followed by Coomassie staining. Purified protein was stored at −80° C. prior to its use in biochemical assays.

Biochemical Assay for Inhibitors of IGF-1R Kinase Activity

The inhibitory activity of putative kinase inhibitors and the potency of selected compounds were determined using a trans-phosphorylation assay.

A specific substrate was incubated with the kinase in appropriate buffer conditions in presence of ATP traced with $^{33}P$-γ-ATP (gamma phosphate-labeled, Redivue™ Code Number AH9968, 1000-3000 Ci/mmole, Amersham Biosciences Piscataway, N.J., USA), optimal cofactors and test compound.

At the end of the phosphorylation reaction, more than 98% cold and radioactive ATP were captured by an excess of Dowex ion exchange resin. The resin was allowed to settle to the bottom of reaction wells by gravity. Supernatant, containing substrate peptide, was subsequently withdrawn and transferred into a counting plate, and radioactivity (corresponding to phosphate incorporated into peptide) was evaluated by β-counting.

Reagents/Assay Conditions i. Dowex Resin Preparation 500 g of wet resin (SIGMA, custom prepared DOWEX resin 1×8 200-400 mesh, 2.5 Kg) were weighed out and diluted to 2 L in 150 mM sodium formate, pH 3.00.

The resin was allowed to settle for several hours and then the supernatant was discarded. This washing procedure was repeated three times over two days. Finally, the resin was allowed to settle, supernatant was discarded and two volumes (with respect to the resin volume) of 150 mM sodium formate buffer were added. The final pH was circa 3.0. The washed resin was kept at 4° C. before use, and was stable for more than one week.

ii. Kinase Buffer (KB)

Kinase buffer was composed of 50 mM HEPES pH 7.9 containing 3 mM $MnCl_2$, 1 mM DTT, 3 microM $Na_3VO_4$, and 0.2 mg/mL BSA. 3×KB is buffer of the same composition and pH as KB, but with three times the concentration of each component.

iii. Enzyme Pre-Activation and Preparation of 3× Enzyme Mix.

Prior to starting the kinase inhibition assay, IGF-1R was pre-phosphorylated in order to linearize reaction kinetics. To achieve this, the desired total quantity of enzyme was prepared at an enzyme concentration of 360 nM in KB containing 100 microM ATP, and this preparation was incubated for 30 min at 28° C. 3×Enzyme Mix was obtained by diluting this preactivated enzyme 20-fold in 3×KB.

iv. Assay Conditions

The kinase assay was run with a final enzyme concentration of 6 nM, in presence of 6 microM ATP, 1 nM $^{33}P$-γ-ATP and 10 microM substrate, a carboxy-terminally biotinylated peptide of the following sequence: KKKSPGEYVNIEFGGGGGK-biotin (SEQ ID NO:3). The peptide was obtained in batches of >95% peptide purity from American Peptide Company, Inc. (Sunnyvale, Calif., USA).

Robotized Dowex Assay

Test reactions were performed in a total final volume of 21 microL consisting of:

a) 7 microL/well of 3× Enzyme Mix (18 nM preactivated enzyme in 3× kinase buffer), b) 7 microL/well of 3× substrate/ATP mix (30 microM substrate, 18 microM ATP, 3 nM $^{33}P$-γ-ATP in double-distilled water ($ddH_2O$)), c) 7 microL/well 3× test compounds diluted into $ddH_2O$-3% DMSO.

Compound Dilution and Assay Scheme is Reported Below.

i. Dilution of Compounds 10 mM stock solutions of test compounds in 100% DMSO were distributed into 96 well 12×8 format microtiter plates.

For % inhibition studies, dilution plates at 1 mM, 100 microM and 10 microM were prepared in 100% DMSO, then diluted to 3× final desired concentration (30, 3 and 0.3 microM) in $ddH_2O$, 3% DMSO. A Multimek 96 (Beckman Coulter, Inc. 4300 N. Harbor Boulevard, P.O. Box 3100 Fullerton, Calif. 92834-3100 USA) was used for compound pipetting into test plates.

For $IC_{50}$ determination, starting solutions of 30 microM compound in 3% DMSO were derived from 1 mM/100% DMSO stock solutions. These 30 microM starting solutions were used for generation of a further 9 serial 1/3 dilutions in $ddH_2O$, 3% DMSO, so as to generate a 10-point dilution curve at 3× the final assay concentration. Serial dilution was conducted in 96-well plates using a Biomek 2000 (Beckman Coulter) system. Dilution curves of 7 compounds/plate were prepared, and each plate also included a 10-point dilution curve of Staurosporine, as well as several negative and positive control wells.

ii. Assay Scheme 7 microL of each test compound dilution (or control) in $ddH_2O$, 3% DMSO were pipetted into each well of a 384-well, V-bottom assay plate, which was then transferred to a PlateTrak 12 robotized station (Perkin Elmer, 45 William Street Wellesley, Mass. 02481-4078, USA) equipped with one 384-tip pipetting head for starting the assay, plus one 96-tip head for dispensing the resin) prepared with reservoirs containing sufficient 3× Enzyme mix and 3×ATP mix (3×) to complete the assay run.

At the start of the assay the liquid handling system aspirates 7 microL of ATP mix, introduces an air gap inside the tips (5 microL) and then aspirates 7 microL of 3× Enzyme Mix. To start the reaction, tips contents were dispensed into the test wells already containing 7 microL test compound (at 3× desired final concentration), followed by 3 cycles of mixing, so as to restore desired final concentration for all reaction components.

Plates were incubated for 60 minutes at room temperature, and then the reaction was stopped by pipetting 70 microL of Dowex resin suspension into the reaction mix, followed by three cycles of mixing. After stopping the reaction, plates were allowed to rest for one hour in order to maximize ATP capture. At this point, 20 microL of supernatant were transferred from each well into wells of 384-Optiplates (Perkin Elmer) containing 70 microL/well of Microscint 40 (Perkin Elmer); after 5 min of orbital shaking the plates were read on a Perkin-Elmer Top Count radioactivity counter.

iii. Data Analysis

Data were analysed using a customized version of the "Assay Explorer" software package (Elsevier MDL, San Leandro, Calif. 94577). For single compound concentrations, inhibitory activity was typically expressed as % inhibition obtained in presence of compound, compared to total activity of enzyme obtained when inhibitor is omitted.

Compounds showing desired inhibition were further analysed in order to study the potency of the inhibitor through $IC_{50}$ calculation. In this case, inhibition data obtained using serial dilutions of the inhibitor were fitted by non-linear regression using the following equation:

$$v = v_0 + \frac{(v_0 - v_b)}{1 + 10^{n(\log IC_{50} - \log[I])}}$$

where $v_b$ is the baseline velocity, $v$ is the observed reaction velocity, $v_o$ is the velocity in the absence of inhibitors, and $[I]$ is the inhibitor concentration.

Cell-Based Assays for Inhibitors of IGF-1R Kinase Activity
Western Blot Analysis of Receptor Phosphorylation Following Stimulation with IGF-1 in MCF-7 Human Breast Cancer Cells MCF-7 cells (ATCC#HTB-22) were seeded in 12-well tissue culture plates at $2\times10^5$ cells/well in E-MEM medium (MEM+Earle's BSS+2 mM glutamine+0.1 mM non-essential amino acids)+10% FCS, and incubated overnight at 37° C., 5% CO2, 100% relative humidity. Cells were then starved by replacing E-MEM+10% FCS with E-MEM+0.1% BSA, and incubating overnight. After this incubation, wells were treated with desired concentrations of compound for 1 hour at 37° C., and were then stimulated with 10 nM recombinant human IGF-1 (Invitrogen, Carlsbad, Calif., USA) for 10 minutes at 37° C. Cells were then washed with PBS and lysed in 100 microL/well cell lysis buffer (M-PER Mammalian Protein Extraction Reagent [Product #78501, Pierce, Rockford, Ill., USA]+10 mM EDTA+Protease inhibitor cocktail [Sigma-Aldrich product #P8340]+phosphatase inhibitor cocktail [Sigma-Aldrich products #P2850+#P5726]). Cell lysates were cleared by centrifugation at 10,000×g for 5 minutes, and 10 microg/lane of cleared lysate protein were run on NuPAGE gels (NuPAGE 4-12% 10-lane Bis-Tris gels, Invitrogen) with MOPS running buffer, then transferred onto Hybond-ECL nitrocellulose filters (Amersham Biosciences, Little Chalfont, Buckinghamshire, UK) using Mini PROTEAN II chambers (Bio-Rad Laboratories, Hercules, Calif., USA). Filters bearing transferred protein were incubated for 1 hour in blocking buffer (TBS+5% BSA+0.15% Tween 20), and probed for 2 hours in the same buffer containing 1/1000 rabbit anti-phospho IGF-1R Tyr1131/InsR Tyr1146 antibody (product #3021, Cell Signaling Technology, Beverly, Mass., USA) for the detection of phosphorylated IGF-1R, or 1/1000 dilution of rabbit IGF-Irβ (H-60) antibody (product #sc-9038, Santa Cruz Biotechnology, Inc., Santa Cruz, Calif., USA) for detecting total IGF-1R B chain. In either case, filters were then washed for 30 minutes with several changes of TBS+0.15% Tween 20, and incubated for 1 hour in washing buffer containing 1/5000 dilution of horseradish peroxidase conjugated anti-rabbit IgG (Amersham, product #NA934), then were washed again and developed using the ECL chemiluminescence system (Amersham) according to manufacturer's recommendations. Unless otherwise stated, reagents used were from Sigma-Aldrich, St. Louis, Mo., USA.

Growth Factor Induced S6 Ribosomal Protein Phosphorylation in Primary Human Fibroblasts.

Phosphorylation of S6 ribosomal protein in response to growth factor stimulation of normal human dermal fibroblasts (NHDF) was used to assess compound potency in inhibiting IGF-1 induced signal transduction in cells, and selectivity towards EGF and PDGF stimulus. NHDF cells obtained from PromoCell (Heidelberg, Germany), were maintained at 37° C. in a humidified atmosphere with 5% $CO_2$ in complete Fibroblast Growth Medium (PromoCell). For assay, NHDF were seeded in 384-well tissue culture plates (clear- and flat-bottomed black plates; Matrix Technologies Inc., Hudson, N.H., USA) at a density of 5000 cells/well in serum-free medium containing 0.1% bovine serum albumin (BSA) and incubated for 5 days. Starved cells were treated for 1 hour with desired doses of compounds and then stimulated for a further 2 hours with either 10 nM IGF-1 (Invitrogen Corp., CA, USA), 10 nM EGF (Gibco BRL, USA) or 1 nM PDGF-B/B (Roche Diagnostics GmbH, Germany). Cells were then fixed in PBS/3.7% paraformaldehyde for 20 minutes at room temperature, washed ×2 with PBS, and permeabilized with PBS/0.3% Triton X-100 for 15 minutes. Wells were then saturated with PBS/1% non-fat dry milk (Bio-Rad Laboratories, Hercules, Calif., USA) for 1 hour, and then probed for 1 hour at 37° C. with anti-phospho-S6 (Ser 235/236) antibody (Cell Signaling Technology, Beverly, Mass., USA, cat. #2211) at 1/200 dilution in PBS/1% milk/0.3% Tween 20. Wells were then washed twice with PBS, and incubated for 1 hour at 37° C. with PBS/1% milk/0.3% Tween 20+1 microg/mL DAPI (4,6-diamidino-2-phenylindole)+1/500 Goat anti-rabbit Cy5™-conjugated secondary antibody (Amersham Biosciences, Little Chalfont, Buckinghamshire, UK). Wells were then washed ×2 with PBS, and 40 microL PBS are left in each well for immunofluorescence analysis. Fluorescence images in the DAPI and Cy5™ channels were automatically acquired, stored and analysed using a Cellomics ArrayScan™ IV instrument (Cellomics, Pittsburgh, USA); the Cellomics Cytotoxicity Algorithm was used to quantify cytoplasmic fluorescence associated with phospho-S6 (Cy5™ signal parameter: "Mean Lyso Mass-pH") for each cell in 10 fields/well, and eventually expressed as a mean population value. Unless otherwise stated, reagents were obtained from Sigma-Aldrich, St. Louis, Mo., USA.

Biochemical Assay for Inhibitors of Aurora-2 Kinase Activity

The in vitro kinase inhibition assay was conducted in the same way as described for IGF-1R. At variance with IGF-1R, Aurora-2 enzyme does not need pre-activation.

i. Kinase Buffer (KB) for Aurora-2

The kinase buffer was composed of 50 mM HEPES, pH 7.0, 10 mM $MnCl_2$, 1 mM DTT, 3 microM $Na_3VO_4$, and 0.2 mg/mL BSA.

ii. Assay Conditions for Aurora-2 (Final Concentrations)

The kinase assay was run with an enzyme concentration of 2.5 nM, 10 microM ATP, 1 nM $^{33}P$-γ-ATP, and 8 microM substrate, composed of 4 LRRWSLG repeats.

In Vitro Cell Proliferation Assay for Inhibitors of Aurora-2 Kinase Activity

The human colon cancer cell line HCT-116 was seeded at 5000 cells/$cm^2$ in 24 wells plate (Costar) using F12 medium (Gibco) supplemented with 10% FCS (EuroClone, Italy) 2 mM L-glutamine and 1% penicillin/streptomycin and maintained at 37° C., 5% $CO_2$ and 96% relative humidity. The following day, plates were treated in duplicates with 5 mL of an appropriate dilution of compounds starting from a 10 mM stock in DMSO. Two untreated control wells were included in each plate. After 72 hours of treatment, medium was withdrawn and cells detached from each well using 0.5 mL of 0.05% (w/v) Trypsin, 0.02% (w/v) EDTA (Gibco). Samples were diluted with 9.5 mL of Isoton (Coulter) and counted using a Multisizer 3 cell counter (Beckman Coulter). Data were evaluated as percent of the control wells:

% of CTR=(Treated−Blank)/(Control−Blank).

$IC_{50}$ values were calculated by LSW/Data Analysis using Microsoft Excel sigmoidal curve fitting.

Biochemical and cell-based assay data for representative compounds are reported in Table 1.

TABLE 1

| Compound | IGF1R $IC_{50}$ (μM) Biochemical assay | Inhibition of IGF1-induced S6 phosphorylation $IC_{50}$ (μM) |
| --- | --- | --- |
| 28 | 0.049 | 0.08 |
| 52 | 0.055 | 0.64 |
| 293 | 0.14 | 0.28 |

The same compounds were tested for inhibition of IGF1-induced IGF1R phosphorylation in MCF-7 cells and results are shown in FIG. 1.

The compounds of the present invention can be administered either as single agents or, alternatively, in combination with known anticancer treatments such as radiation therapy or chemotherapy regimen in combination with, for example, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, and conditions of the patient and administration route.

For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions.

As an example the syrups may contain, as a carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim to better illustrate the present invention, without posing any limitation to it, the following examples are now given.

BRIEF DESCRIPTION OF THE DRAWINGS

FIG. 1 shows the inhibition of IGF1R auto-phosphorylation in MCF-7 starved cells stimulated with 10 nM IGF1 by compounds of formula (I), exemplified by compound 28, 52, and 293.

Treatment of starved MCF-7 cells with 10 nM IGF1 induced receptor auto-phosphorylation as shown by the appearance of a more intense band of phosphorylated IGF1R (pIGF1R). Incubation of cells with increasing concentrations of compound 28, 52, and 293 prior to treatment with IGF1 resulted in inhibition of IGF1-induced IGF1R auto-phosphorylation as shown by the disappearance of the band of phosphorylated IGF1R (pIGF1R).

EXPERIMENTAL SECTION

General Purification and Analytical Methods

Flash Chromatography was performed on silica gel (Merck grade 9395, 60A). HPLC was performed on Waters X Terra RP 18 (4.6×50 mm, 3.5 µm) column using a Waters 2790 HPLC system equipped with a 996 Waters PDA detector and Micromass mod. ZQ single quadrupole mass spectrometer, equipped with an electrospray (ESI) ion source. Mobile phase A was ammonium acetate 5 mM buffer (pH 5.5 with acetic acid-acetonitrile 95:5), and Mobile phase B was water-acetonitrile (5:95). Gradient from 10 to 90% B in 8 minutes, hold 90% B 2 minutes. UV detection at 220 nm and 254 nm Flow rate 1 mL/min. Injection volume 10 microL. Full scan, mass range from 100 to 800 amu. Capillary voltage was 2.5 KV; source temperature was 120° C.; cone was 10 V. Retention times (HPLC r.t.) are given in minutes at 220 nm or at 254 nm. Mass are given as m/z ratio.

When necessary, compounds were purified by preparative HPLC on a Waters Symmetry C18 (19×50 mm, 5 µm) column or on a Waters X Terra RP 18 (30×150 mm, 5 µm) column using a Waters preparative HPLC 600 equipped with a 996 Waters PDA detector and a Micromass mod. ZMD single quadrupole mass spectrometer, electron spray ionization, positive mode. Mobile phase A was water-0.01% trifluoroacetic acid, and mobile phase B was acetonitrile. Gradient from 10 to 90% B in 8 min, hold 90% B 2 min. Flow rate 20 mL/min. In alternative, mobile phase A was water-0.1% $NH_3$, and mobile phase B was acetonitrile. Gradient from 10 to 100% B in 8 min, hold 100% B 2 min. Flow rate 20 mL/min.

1H-NMR spectrometry was performed on a Mercury VX 400 operating at 400.45 MHz equipped with a 5 mm double resonance probe [1H (15N-31P) ID_PFG Varian].

EXAMPLE 1

Preparation of 3-Amino-4,5,6,7-tetrahydro-1H-pyrazolo[4,3-c]pyridine-1,5-dicarboxylic acid 5-tert-butyl ester 1-ethyl ester [(II), Ra=Rb=H, Q=ethyl] and 3-amino-4,5,6,7-tetrahydro-2H-pyrazolo[4,3-c]pyridine-2,5-dicarboxylic acid 5-tert-butyl ester 2-ethyl ester [(II), Ra=Rb=H, Q=ethyl]

Step 1. 3-Cyano-4-hydroxy-1,2,5,6-tetrahydro-pyridine-1-carboxylic acid tert-butyl ester To a refluxing solution of 206 g potassium tert-butoxide in 2 L of toluene, 200 mL of 3,3'-iminodipropionitrile was dropped in 40 min under nitrogen stream. The suspension was refluxed for 30 min while stirring. Then, 400 mL of water was added, followed by 600 mL of 37% HCl. The two-phase solution was stirred at 80° C. for 30 min., cooled at room temperature, and finally ca. 1 L of toluene were added. The acidic two-phase solution was cooled on an ice bath and treated with 1 L of 28% NaOH. The basic two-phase solution thus obtained was cooled and treated with 388 g of di-tert-butyl dicarbonate [$(Boc)_2O$]. The mixture was kept under stirring for 2.5 h at room temperature, then the resulting suspension was cooled and brought to acidic pH by adding dropwise 660 mL of 37% HCl. The two phases were separated and the aqueous layer was extracted with ethyl acetate. The combined organic extracts were washed with brine, dried over sodium sulfate and evaporated to dryness to give 330.9 g of a light yellow solid.

Step 2. 3-Amino-4,5,6,7-tetrahydro-1H-pyrazolo[4,3-c]pyridine-5-carboxylic acid tert-butyl ester To a solution of 141.5 g of 3-cyano-4-hydroxy-1,2,5,6-tetrahydropyridine-1-carboxylic acid tert-butyl ester in 1.2 L of ethanol were added under stirring 57.8 mL of aqueous 35% hydrazine. The mixture was heated at 70° C. for 4 h. The solution was evaporated at under vacuum, the residue was diluted with 1 L of water and extracted with ethyl acetate. The combined organic extracts were washed with brine, dried over sodium sulfate and evaporated to dryness. The crude product was taken-up with 300 mL tert-butyl methyl ether and the crystallized compound was collected by filtration to give 115.6 g of the title compound.

1H-NMR (400 MHz), δ (ppm, DMSO-$d_6$): 11.06 (bs, 1H), 4.58 (bs, 2H), 4.14 (s, 2H), 3.51 (bt, J=5.5 Hz, 2H), 2.47 (bt, J=5.5 Hz, 2H), 1.41 (s, 9H).

Step 3. 3-Amino-4,5,6,7-tetrahydro-1H-pyrazolo[4,3-c]pyridine-1,5-dicarboxylic acid 5-tert-butyl ester 1-ethyl ester [(II), Ra=Rb=H, Q=ethyl] and 3-amino-4,5,6,7-tetrahydro-4H-pyrazolo[4,3-c]pyridine-2,5-dicarboxylic acid 5-tert-butyl ester 2-ethyl ester [(II), Ra=Rb=H, Q=ethyl]

To a solution of 94.1 g of 3-amino-4,5,6,7-tetrahydro-1H-pyrazolo[4,3-c]pyridine-5-carboxylic acid tert-butyl ester in 1.7 L of THF were added 135 mL of N,N-diisopropylethylamine. A solution of 37.6 mL of ethyl chloroformate in 300 mL of THF was added dropwise at 0° C. during 75 min. The mixture was stirred at 0° C. for 30 min. then evaporated under vacuum. The residue was taken-up with 1 L of water and extracted with ethyl acetate. The combined organic extracts were washed with 500 mL brine, dried over sodium sulfate, and evaporated to dryness. The crude mixture of isomers was purified by silica gel flash-chromatography, using a starting 87:13 mixture of dichloromethane-ethyl acetate as eluant, and increasing gradually the percentage of ethyl acetate up to 50%. The fractions containing the same isomer were evaporated to give 61.6 g of 3-amino-4,5,6,7-tetrahydro-2H-pyrazolo[4,3-c]pyridine-2,5-dicarboxylic acid 5-tert-butyl ester 2-ethyl ester.

1H-NMR (400 MHz), δ (ppm, DMSO-$d_6$): 6.37 (bs, 2H), 4.35 (q, J=7.1 Hz, 2H), 4.19 (bs, 2H), 3.55 (bt, J=5.8 Hz, 2H), 2.49 (bt, J=5.8 Hz, 2H), 1.43 (s, 9H), 1.32 (t, J=7.1 Hz, 3H).

From fractions containing the other isomer, 29 g of 3-amino-4,5,6,7-tetrahydro-1H-pyrazolo[4,3-c]pyridine-1,5-dicarboxylic acid 5-tert-butyl ester 1-ethyl ester were obtained.

1H-NMR (400 MHz), δ (ppm, DMSO-$d_6$): 5.52 (bs, 2H), 4.28 (q, J=7.1 Hz, 2H), 4.16 (bs, 2H), 3.56 (bt, J=5.8 Hz, 2H), 2.84 (bt, J=5.8 Hz, 2H), 1.44 (s, 9H), 1.29 (t, J=7.1 Hz, 3H).

EXAMPLE 2

Preparation of 5-tert-butyl 2-ethyl 3-amino-7,7-dimethyl-4,5,6,7-tetrahydro-2H-pyrazolo[4,3-c]pyridine 2,5-dicarboxylate [(II), Q=ethyl, Ra=Rb=methy]

Step 1. Preparation of methyl 3-(1,3-dioxo-1,3-dihydro-2H-isoindol-2-yl)-2,2-dimethylpropanoate The title compound was prepared as reported in the literature (see, for instance, Ducry L. et al. Helvetica Chimica Acta vol. 82, pages 2432-2447, 1999).

1H-NMR (400 MHz), δ (ppm, DMSO-$d_6$): 7.90 (m, 4H), 3.71 (s, 2H), 3.62 (s, 3H), 1.16 (s, 6H).

Step 2. Preparation of methyl 3-amino-2,2-dimethylpropanoate

Hydrazine (1.1 eq., 0.27 mL, 8.42 mmol) was added to the solution of methyl 3-(1,3-dioxo-1,3-dihydro-2H-isoindol-2-yl)-2,2-dimethylpropanoate (0.2 g, 7.66 mmol) in methanol (60 mL) maintained under magnetic stirring at 65° C. After 5 hours the reaction mixture was allowed to cool to room temperature, diluted with diethyl ether and filtered. The filtrate was washed thoroughly with diethyl ether. The title compound was obtained after evaporation of the solvents and it was used in the next step without any further purification. (0.8 g, 75% yield).

1H-NMR (400 MHz), δ (ppm, $CDCl_3$): 3.68 (s, 3H), 2.92 (s, 2H), 2.62 (bs, 2H), 1.21 (s, 6H).

Step 3. Preparation of methyl 3-(2-cyano-ethylamino)-2,2-dimethylpropanoate

A mixture of methyl 3-amino-2,2-dimethylpropanoate (1.0 g, 7.63 mmol) and acrylonitrile (2 eq., 1 mL, 15.26 mmol) in methanol (50 mL) was stirred at room temperature for about 18 hours. After evaporation of the solvent, the residue was purified by flash chromatography on silica gel, using cyclohexane-ethyl acetate 1:1 as eluant, to give the title compound as colourless oil (0.7 g, 70% yield).

1H-NMR (400 MHz), δ (ppm, $CDCl_3$): 3.64 (s, 3H), 2.97 (t, J=7 Hz, 2H), 2.73 (s, 2H), 2.57 (t, J=7 Hz, 2H), 1.21 (s, 6H).

Step 4. Preparation of methyl 3-[N-tert-butyloxycarbonyl-(2-cyano-ethyl)-amino]-2,2-dimethylpropanoate A solution of (Boc)$_2$O (1.15 eq., 0.95 g, 4.37 mmol) in dry THF (3 mL) was added to the solution of methyl 3-(2-cyano-ethylamino)-2,2-dimethylpropanoate (0.7 g, 3.80 mmol) in dry THF (30 mL) at room temperature. After about 24 and 48 hours, two additional portions of (Boc)$_2$O (0.5 eq., 0.4 g, 1.9 mmol) were added and stiffing was continued for 24 hours more. The solvent was evaporated and the crude material was purified by flash chromatography on silica gel, using cyclohexane-ethyl acetate 3:1 as eluant, to give the title compound as colourless oil (0.9 g, 80% yield).

1H-NMR (400 MHz), δ (ppm, $CDCl_3$): 3.67 (s, 3H), 3.56 (s, 2H), 3.52 (t, J=6 Hz, 2H), 2.60 (m, 2H), 1.43 (s, 9H), 1.21 (s, 6H).

Step 5. Preparation of 1-tert-butyl-3,3-dimethyl-4-oxo-5-cyano-piperidine

A solution of 3-[N-tert-butyloxycarbonyl-(2-cyano-ethyl)-amino]-2,2-dimethylpropanoate (0.3 g, 1.052 mmol) in dry THF (5 mL) was added to the suspension of 60% mineral oil sodium hydride (1.2 eq., 0.05 g, 1.26 mmol) in dry THF (10 mL) at room temperature. Stirring was continued at room temperature for 2.5 hours, then the reaction mixture was heated to 50° C. for 2 hours, added with $NH_4Cl$ and extracted with ethyl acetate (3×50 mL). The organic layers were combined, dried over sodium sulphate and evaporated to dryness. The crude material was purified by flash chromatography on silica gel, using cyclohexane-ethyl acetate 3:1 as eluant, to give the title compound as colourless solid (0.14 g, 60% yield).

1H-NMR (400 MHz), δ (ppm, DMSO-$d_6$): 10.42 (bs, 1H), 4.60 (m, 2H), 3.91 (bs, 2H), 1.43 (s, 9H), 1.03 (s, 6H).

Step 6. Preparation of 5-tert-butyl 3-amino-7,7-dimethyl-4,5,6,7-tetrahydro-1H-pyrazolo[4,3-c]pyridine-carboxylate Hydrazine (1.3 eq., 0.022 mL, 0.71 mmol) and acetic acid (1.5 eq., 0.050 mL, 0.825 mmol) were subsequently added to the solution of 1-tert-butyl-3,3-dimethyl-4-oxo-5-cyanopiperidine (0.14 g, 0.55 mmol) in ethanol (6 mL). The reaction mixture was maintained under magnetic stirring at 70° C. for about 4 hours. After evaporation of the solvent, the crude material was taken up in dichloromethane (15 mL), washed with saturated sodium hydrogenocarbonate (2×10 mL), brine (2×10 mL), dried over sodium sulphate and evaporated to yield the title compound as colourless solid (0.12 g, 82% yield).

1H-NMR (400 MHz), δ (ppm, DMSO-$d_6$): 4.55 (bs, 2H), 4.16 (s, 2H), 3.27 (s, 2H), 1.43 (s, 9H), 1.14 (s, 6H).

Step 7. Preparation of 5-tert-butyl 2-ethyl 3-amino-7,7-dimethyl-4,5,6,7-tetrahydro-2H-pyrazolo[4,3-c]pyridine-2,5(4H)-dicarboxylate [(II), Q=ethyl, Ra=Rb=methyl]

Ethyl chloroformate (1 eq., 1.13 mL, 1.31 mmol) was slowly added over 10 minutes to a solution of 5-tert-butyl 3-amino-7,7-dimethyl-4,5,6,7-tetrahydro-1H-pyrazolo[4,3-c]pyridine-carboxylate (0.35 g, 1.31 mmol) and N,N-diisopropylethylamine (1.5 eq., 0.74 mL, 1.96 mmol) in dry THF (11 mL), maintained under magnetic stiffing at −10° C. (ice bath). Stirring was continued for 20 minutes, then the reaction mixture was diluted with ethyl acetate (30 mL), washed with water (2×20 mL), dried over sodium sulphate and evaporated to dryness. The crude material was chromatographed on silica gel, using cyclohexane-ethyl acetate 1:1 as eluant, to give 0.325 g (72% yield) of the title compound as colourless solid.

1H-NMR (400 MHz), δ (ppm, DMSO-$d_6$): 6.32 (bs, 2H), 4.37 (q, J=7.07 Hz, 2H), 4.20 (s, 2H), 3.40-3.28 (bs, 2H), 1.43 (s, 9H), 1.33 (t, J=7.07 Hz, 3H), 1.15 (s, 6H).

EXAMPLE 3

Preparation of 4-(4-methylpiperazin-1-yl)-2-nitro benzoic acid [(III), A=D=E=CH, B=CR2, R1=nitro, R2=4-methylpiperazin-1-yl, Z=OH]

Step 1. Preparation of tert-butyl 4-fluoro-2-nitro benzoate

A solution of 4-fluoro-2-nitro benzoic acid (10 g, 54 mmol), (Boc)$_2$O (2 eq., 23.6 g, 108 mmol) and 4-(N,N-dimethylamino)pyridine (0.3 eq., 1.98 g, 16.2 mmol) in tert-butanol (100 mL) and dichloromethane (100 mL) was stirred at room temperature for 20 hours. The reaction mixture was then diluted with ethyl acetate (500 mL), washed with 1N HCl (500 mL), water (500 mL), brine (500 mL), dried over sodium sulphate and evaporated to dryness. The title compound was obtained as pale yellow oil (quantitative) and it was used in the next step without any further purification.

1H-NMR (400 MHz), δ (ppm, DMSO-$d_6$): 8.04 (dd, J=8.47, 2.50 Hz, 1H) 7.95 (dd, J=8.66, 5.37 Hz, 1H) 7.71 (ddd, J=8.66, 8.17, 2.56 Hz, 1H) 1.51 (s, 9H).

Step 2. Preparation of tert-butyl 4-(4-methyl-piperazin-1-yl)-2-nitro benzoate A solution of tert-butyl 4-fluoro-2-nitro benzoate (13 g, 54 mmol) and N-methylpiperazine (17 mL) was stirred at room temperature for 6 hours. The reaction mixture was then diluted with water (800 mL) and maintained under magnetic stirring for 20 hours. The resulting solid was filtered, washed thoroughly with water and dried under vacuum at 40° C. The title compound was obtained as yellow solid (16.4 g, 94% yield) and it was used in the next step without any further purification.

1H-NMR (400 MHz), δ (ppm, DMSO-$d_6$): 7.69 (d, J=8.90 Hz, 1H) 7.29 (d, J=2.56 Hz, 1H), 7.15 (dd, J1=8.90 Hz, J2=2.56 Hz, 1H), 3.37 (m, 4H), 2.44 (m, 4H), 1.46 (s, 9H).

Step 3. Preparation of 4-(4-methyl-piperazin-1-yl)-2-nitro benzoic acid hydrochloride A mixture of tert-butyl 4-(4-methylpiperazin-1-yl)-2-nitro benzoate (16.4 g, 51 mmol) and 37% HCl (100 mL) in 1,4-dioxane (200 mL) was stirred at room temperature for 4 hours. The resulting solid was filtered, washed thoroughly with 1,4-dioxane and dried under vacuum at 45° C. The title compound was obtained as a pale yellow solid (13.45 g, 87.5% yield), and it was used in the next step without any further purification.

1H-NMR (400 MHz), δ (ppm, DMSO-$d_6$): 10.27 (bs, 1H), 7.81 (d, J=8.90 Hz, 1H), 7.40 (d, J=2.69 Hz, 1H), 7.24 (dd, J1=8.90 Hz, J2=2.69 Hz, 1H), 4.13 (bs, 2H), 3.55-3.06 (bs, 6H), 2.83 (s, 3H).

EXAMPLE 4

Preparation of 2-nitro-4-[4-(2,2,2-trifluoro-acetyl)-piperazin-1-yl]-benzoic acid [(III), A=D=E=CH, B=CR2, R1=nitro, R2=4-(2,2,2-trifluoro-acetyl)-piperazin-1-yl, Z=OH]

Step 1. Preparation of 2-nitro-4-piperazin-1-yl-benzoic acid tert-butyl ester To a solution of piperazine (0.18 g, 2.07 mmol) in tetrahydrofuran (2 mL) 4-fluoro-2-nitro-benzoic acid tert-butyl ester (0.1 g, 0.41 mmol) was added. The mixture was stirred at room temperature for 15 h, then poured in water and extracted with dichloromethane. The organic phase was washed with water, brine, dried with sodium sulfate and evaporated to give the title compound as yellow oil (0.107 g, 85%).

1H-NMR (400 MHz), δ (ppm, DMSO-$d_6$): 7.67 (d, J=8.9 Hz, 1H), 7.25 (d, J=2.6 Hz, 1H), 7.14 (dd, J1=8.9 Hz, J2=2.6 Hz, 1H), 3.31 (m, 4H), 2.81 (m, 4H), 1.46 (s, 9H).

Step 2. 2-Nitro-4-[4-(2,2,2-trifluoro-acetyl)-piperazin-1-yl]-benzoic acid tert-butyl ester To a solution of 2-nitro-4-piperazin-1-yl-benzoic acid tert-butyl ester (1.4 g, 4.56 mmol) in dichloromethane (30 mL), triethylamine (2.49 mL, 18.24 mmol) and trifluoroacetic anhydride (1.27 mL, 9.12 mmol) were added. The mixture was stirred at room temperature for 1 h. The solvent was evaporated to give a residue, which was purified by flash chromatography using exane-ethyl acetate 7:3 as the eluant. The title compound (1.77 g, 96%) was obtained as yellow solid.

1H-NMR (400 MHz), δ(ppm, DMSO-$d_6$): 7.72 (d, J=8.9 Hz, 1H), 7.33 (d, J=2.6 Hz, 1H), 7.19 (dd, J1=8.9 Hz, J2=2.6 Hz, 1H), 3.73 (m, 4H), 3.55 (m, 4H), 2.81 (m, 4H), 1.47 (s, 9H).

Step 3. 2-Nitro-4-[4-(2,2,2-trifluoro-acetyl)-piperazin-1-yl]-benzoic acid

To a solution of 2-nitro-4-[4-(2,2,2-trifluoro-acetyl)-piperazin-1-yl]-benzoic acid tert-butyl ester (1.70 g, 4.22 mmol) in dichloromethane (25 mL) trifluoroacetic acid (5 mL) was added. The mixture was stirred at room temperature for 2 h, and then evaporated to give the title compound as yellow solid. 1H-NMR (400 MHz), δ (ppm, DMSO-$d_6$): 13.21 (bs, 1H), 7.78 (d, J=8.9 Hz, 1H), 7.31 (d, J=2.5 Hz, 1H), 7.17 (dd, J1=8.9 Hz, J2=2.5 Hz, 1H), 3.74 (m, 4H), 3.56 (m, 4H).

EXAMPLE 5

Applying a procedure analogous to that described in Example 3, the following compounds were obtained:

4-(4-morpholin-1-yl)-2-nitro benzoic acid [(III), A=D=E=CH, B=CR2, R1=nitro, R2=4-morpholin-1-yl, Z=OH]

Step 1. tert-butyl 4-(morpholin-4-yl)-2-nitro benzoate

1H-NMR (400 MHz), δ (ppm, DMSO-$d_6$): 7.71 (d, J=8.77 Hz, 1H), 7.31 (d, J=2.44 Hz, 1H), 7.17 (dd, J1=8.77 Hz, J2=2.44 Hz, 1H), 3.73 (m, 4H), 3.35 (m, 4H), 1.46 (s, 9H).

Step 2. 4-(morpholin-4-yl)-2-nitro benzoic acid hydrochloride

1H-NMR (400 MHz), δ (ppm, DMSO-$d_6$): 12.98 (bs, 1H), 7.78 (d, J=8.91 Hz, 1H), 7.30 (d, J=2.44 Hz, 1H), 7.15 (dd, J1=8.91 Hz, J2=2.44 Hz, 1H), 3.73 (m, 4H), 3.33 (m, 4H).

4-(N,N-dimethylamino)-2-nitro benzoic acid [(III), A=D=E=CH, B=CR2, R1=nitro, R2=N,N-dimethylamino, Z=OH]

Step 1. tert-butyl 4-(N,N-dimethylamino)-2-nitro benzoate

1H-NMR (400 MHz), δ (ppm, DMSO-$d_6$): 7.69 (d, J=8.90 Hz, 1H), 6.99 (d, J=2.68 Hz, 1H), 6.89 (dd, J1=8.90 Hz, J2=2.68 Hz, 1H), 3.04 (s, 6H), 1.46 (s, 9H).

Step 2. 4-(N,N-dimethylamino)-2-nitro benzoic acid hydrochloride

1H-NMR (400 MHz), δ (ppm, DMSO-$d_6$): 12.81 (bs, 1H), 7.72 (d, J=8.90 Hz, 1H), 6.96 (d, J=2.57 Hz, 1H), 6.84 (dd, J1=8.90 Hz, J2=2.58 Hz, 1H), 3.01 (s, 6H).

4-[(2-Dimethylamino-ethyl)-methyl-amino]-2-nitro-benzoic acid hydrochloride [(III), A=D=E=CH, B=CR2, R1=nitro, R2=(2-Dimethylamino-ethyl)-methyl-amino, Z=OH]

Step 1. 4-[(2-Dimethylamino-ethyl)-methyl-amino]-2-nitro-benzoic acid tert-butyl ester 1H-NMR (400 MHz), δ (ppm, DMSO-$d_6$): 7.67 (d, J=8.9 Hz, 1H), 6.98 (d, J=2.6 Hz, 1H), 6.89 (dd, J1=2.6 Hz, J2=8.9 Hz, 1H), 3.54 (m, 2H), 3.02 (s, 3H), 2.40 (m, 2H), 2.19 (s, 6H), 1.46 (s, 9H).

Step 2. 4-[(2-Dimethylamino-ethyl)-methyl-amino]-2-nitro-benzoic acid hydrochloride 1H-NMR (400 MHz), δ (ppm, DMSO-$d_6$): 10.14 (bs, 1H), 7.78 (d, J=8.9 Hz, 1H), 7.11 (d, J=2.6 Hz, 1H), 7.01 (dd, J1=2.6 Hz, J2=8.9 Hz, 1H), 3.83 (m, 2H), 3.24 (m, 2H), 3.05 (s, 3H), 2.82 (d, 6H).

EXAMPLE 6

Preparation of 4-(4-methylpiperazin-1-yl)-2-fluoro benzoic acid [(III), A=D=E=CH, B=CR2, R1=fluoro, R2=4-methylpiperazin-1-yl, Z=OH]

Step 1. Preparation of methyl 2,4-difluoro benzoate

To 100 mL of MeOH, 2,4-difluorobenzoyl chloride (10 mL, 79.3 mmol) was added and the mixture stiffed at room temperature for 2 hours. The solvent was then evaporated affording the title compound as pale yellow oil (quantitative).

1H-NMR (400 MHz), δ (ppm, DMSO-$d_6$): 8.0 (m, 1H), 7.44 (m, 1H), 7.25 (m, 1H), 3.87 (s, 3H).

Step 2. Preparation of methyl 4-(4-methylpiperazin-1-yl)-2-fluoro benzoate

A mixture of methyl 2,4-difluoro benzoate (4.5 g, 26.2 mmol), 1-methylpiperazine (4.36 mL, 39.2 mmol, 1.5 eq) and $K_2CO_3$ (3.62 g, 26.2 mmol, 1 eq.) in N,N-dimethylformamide (10 mL) was stirred at 100° C. for 4 hours. The mixture was then poured into 200 mL of water and extracted with 150 mL of ethyl acetate. The organic layer was separated, washed with water (100 mL), dried over sodium sulphate and evaporated to dryness. The crude was purified by flash chromatography on silica gel, using dichloromethane-MeOH-30% $NH_4OH$ 95:5:0.5 as eluant, affording 1.65 g of methyl 4-(4-methylpiperazin-1-yl)-2-fluoro benzoate as pale yellow solid.

1H-NMR (400 MHz), δ (ppm, DMSO-$d_6$): 7.72 (t, J=9.0 Hz, 1H), 6.84-6.74 (m, 2H), 3.78 (s, 3H), 3.4-3.3 (m, 4H), 2.46 (m, 4H), 2.25 (bs, 3H).

A second-eluting fraction contained 3.04 g of the isomer methyl 4-fluoro-2-(4-methylpiperazin-1-yl)benzoate (yellow oil).

1H-NMR (400 MHz), δ (ppm, DMSO-$d_6$): 7.68 (m, 1H), 6.88 (m, 1H), 6.80 (m, 1H), 3.80 (s, 3H), 3.01 (m, 4H), 2.49 (m, 4H), 2.27 (bs, 3H).

Step 3. Preparation of 4-(4-methylpiperazin-1-yl)-2-fluoro benzoic acid

A mixture of methyl 4-(4-methylpiperazin-1-yl)-2-fluoro benzoate (800 mg, 3.17 mmol), 1N NaOH (6 mL) and MeOH (10 mL) was stiffed at room temperature overnight, then 1N HCl (6 mL) was added. The mixture was evaporated to dryness affording a mixture of the crude title compound and NaCl. The mixture was used in the next step without any further purification.

EXAMPLE 7

Preparation of 2-nitro-4-pyrrolidin-1-ylmethyl-benzoic acid chloride hydrochloride [(III), A=D=E=CH, B=CR2, R1=nitro, R2=pyrrolidin-1-ylmethyl, Z=OH]

Step 1. Preparation of 2-nitro-4-pyrrolidin-1-ylmethyl-benzoic acid methyl ester To a solution of 4-hydroxymethyl-2-nitro-benzoic acid methyl ester (2.0 g, 9.47 mmol) in dry dichloromethane (80 mL) under argon, at room temperature, triethylamine (1.6 mL, 10.9 mmol, 1.15 eq.) and then p-toluenesulfonyl chloride (2.08 g, 10.9 mmol, 1.15 eq.) were added. The reaction mixture was stirred at room temperature for 1 h, then pyrrolidine (1.6 mL, 18.94 mmol, 2 eq.) was added and the mixture stirred for additional 24 hours. The solvent was evaporated and the residue purified by flash chromatography on silica gel, using dichloromethane-ethanol 95:5 as eluant, affording the title compound (1.12 g).

Step 2. Preparation of 2-nitro-4-pyrrolidin-1-ylmethyl-benzoic acid

A mixture of 2-nitro-4-pyrrolidin-1-ylmethyl-benzoic acid methyl ester (1.1 g, 4.16 mmol) in methanol (35 mL) and 2N sodium hydroxide (4.16 mL, 8.32 mmol, 2 eq.) was stirred at room temperature for 7 hours, then neutralized with 2N hydrochloric acid (4.16 mL, 8.32 mmol) and evaporated to dryness affording a mixture of the title compound and sodium chloride that was used as such for the next step.

1H-NMR (400 MHz), δ (ppm, DMSO-$d_6$): 7.96 (m, 1H), 7.88-7.75 (m, 2H), 4.04 (bs, 2H), 2.80 (m, 4H), 1.81 (m, 4H).

EXAMPLE 8

Preparation of 4-(2-dimethylamino-ethoxy)-2-nitro-benzoic acid hydrochloride [(III), A=D=E=CH, B=CR2, R1=nitro, R2=2-dimethylamino-ethoxy, Z=OH]

Step 1. Preparation of 4-(2-dimethylamino-ethoxy)-2-nitro-benzoic acid tert-butyl ester To a solution of 2-dimethylaminoethanol (6.67 mL, 64.8 mmol) in anhydrous THF (100 mL), at 0° C., potassium tert-butoxide (6.66 g, 59.4 mmol) was added. The mixture was stirred at 0° C. for 1 h, then 4-fluoro-2-nitro-benzoic acid tert-butyl ester (10 g, 41.5 mmol) in anhydrous THF (50 mL) was added dropwise. After 2 hours at 0° C., the mixture was poured into water (1 L) and extracted with ethyl acetate (4×200 mL). The organic phase was washed with water, brine, dried with anhydrous sodium sulfate, filtered and evaporated to dryness. The crude was purified by flash chromatography, using dichloromethane-EtOH-33% $NH_4OH$ 9:1:0.01 as eluant, to give the title compound (4.53 g) as yellow oil.

1H-NMR (400 MHz), δ (ppm, DMSO-d₆): 7.81 (d, 1H), 7.52 (d, 1H), 7.31 (dd, 1H), 4.21 (t, 2H), 2.65 (t, 2H), 2.22 (s, 6H), 1.49 (s, 9H).

Step 2. Preparation of 4-(2-dimethylamino-ethoxy)-2-nitro-benzoic acid hydrochloride To a solution of 4-(2-dimethylamino-ethoxy)-2-nitro-benzoic acid tert-butyl ester (4.53 g, 14.61 mmol) in dioxane (100 mL) was added 37% HCl (25 mL). The mixture was stirred at room temperature for 15 hours, then the suspension was evaporated and the solid dried under vacuum at 50° C. to give the title compound as yellowish solid.

1H-NMR (400 MHz), δ (ppm, DMSO-d₆): 9.92 (bs, 1H), 7.92 (d, 1H), 7.57 (d, 1H), 7.36 (dd, 1H), 4.50 (t, 2H), 3.55 (t, 2H), 2.87 (s, 6H).

Operating in a way analogous to that described above, the following compounds were obtained.

4-(1-Methyl-piperidin-4-yloxy)-2-nitro-benzoic acid tert-butyl ester

1H-NMR (400 MHz), δ (ppm, DMSO-d₆): 7.79 (d, J=8.78 Hz, 1H), 7.54 (d, J=2.56 Hz, 1H), 7.31 (dd, J1=2.56 Hz, J2=8.78 Hz, 1H), 4.60 (m, 1H), 2.62 (m, 2H), 2.22 (m, 2H), 2.20 (s, 3H), 1.96 (m, 2H), 1.67 (m, 2H), 1.48 (s, 9H).

4-(1-Methyl-piperidin-4-yloxy)-2-nitro benzoic acid hydrochloride

1H-NMR (400 MHz), δ (ppm, DMSO-d₆): 9.95 (bs, 1H), 7.90 (m, 1H), 7.58 (m, 1H), 7.36 (m, 1H), 4.95-4.74 (m, 1H), 3.6-3.0 (m, 4H), 2.80 (s, 3H), 2.35-1.8 (m, 4H).

EXAMPLE 9

Preparation of 3-[4-(4-Methyl-piperazin-1-yl)-2-nitro-benzoylamino]-6,7-dihydro-4H-pyrazolo[4,3-c]pyridine-1,5-dicarboxylic acid 5-tert-butyl ester 1-ethyl ester [(IV), Q=ethyl, Ra=Rb=H, A=D=E=CH, B=CR2, R1=nitro, R2=4-methylpiperazin-1-yl]

4-(4-methylpiperazin-1-yl)-2-nitrobenzoic acid (3.6 g, 11.94 mmol) in dry dichloromethane (30 mL) was treated with oxalyl chloride (1.52 mL, 17.91 mmol, 1.5 eq.) and a drop of dry N,N-dimethylformamide. The resulting suspension was stirred at reflux for about 12 hours and then cooled to room temperature. After removal of the solvent under vacuum, the crude material was diluted with dry tetrahydrofuran (100 mL) and added with N,N-diisopropylethylamine (11.34 mL, 65.1 mmol) and 5-tert-butyl 1-ethyl 3-amino-4,5,6,7-tetrahydro-1H-pyrazolo[4,3-c]pyridine-1,5-dicarboxylate (3.37 g, 10.85 mmol) at room temperature. The reaction mixture was stirred for about 20 hours. After removal of the solvent, the crude material was diluted with dichloromethane (300 mL), washed with water (2×200 mL), saturated sodium hydrogenocarbonate (2×200 mL), brine (2×200 mL), dried over sodium sulfate, evaporated to dryness and purified by flash chromatography on silica gel, using acetone-dichloromethane 60:40 as eluant. The title compound was obtained as a light yellow powder (4.5 g, 75% yield).

1H-NMR (400 MHz), δ (ppm, DMSO-d₆): 11.13 (s, 1H), 7.63 (d, J1=8.66 Hz, 1H), 7.43 (d, J2=2.44 Hz, 1H), 7.25 (dd, J1=8.66 Hz, J2=2.44 Hz, 1H), 4.39 (q, J=7.07 Hz, 2H), 4.31 (bs, 2H), 3.63 (m, 2H), 3.34 (m, 4H), 2.98 (m, 2H), 2.50 (m, 4H), 2.25 (s, 3H), 1.42 (s, 9H), 1.35 (t, J=7.07 Hz, 3H).

Operating in an analogous way, the following compounds were obtained:

3-{2-Nitro-4-[4-(2,2,2-trifluoro-acetyl)-piperazin-1-yl]-benzoylamino}-6,7-dihydro-4H-pyrazolo[4,3-c]pyridine-1,5-dicarboxylic acid 5-tert-butyl ester 1-ethyl ester [(IV), Q=ethyl, Ra=Rb=H, A=D=E=CH, B=CR2, R1=nitro, R2=4-(2,2,2-trifluoro-acetyl)-piperazin-1-yl]

1H-NMR (400 MHz), δ (ppm, DMSO-d₆): 11.17 (bs, 1H), 7.66 (d, J=8.7 Hz, 1H), 7.49 (d, J=2.5 Hz, 1H), 7.29 (dd, J1=8.9 Hz, J2=2.5 Hz, 1H), 4.39 (q, J=7.2 Hz, 2H), 4.32 (bs, 2H), 3.75 (m, 4H), 3.63 (m, 2H), 3.54 (m, 4H), 2.98 (m, 2H), 1.42 (s, 9H), 1.35 (t, J=7.2 Hz, 3H).

3-[2-Fluoro-4-(4-methyl-piperazin-1-yl)-benzoylamino]-6,7-dihydro-4H-pyrazolo[4,3-c]pyridine-1,5-dicarboxylic acid 5-tert-butyl ester 1-ethyl ester [(IV), Q=ethyl, Ra=Rb=H, A=D=E=CH, B=CR2, R1=fluoro, R2=4-methylpiperazin-1-yl]

1H-NMR (400 MHz), δ (ppm, DMSO-d₆): 10.44 (s, 1H), 7.72, 7.61 (m, 1H), 6.87-6.74 (m, 2H), 4.40 (q, J=7.07 Hz, 2H), 4.29 (s, 2H), 3.64 (m, 2H), 3.37-3.28 (m, 4H), 2.98 (m, 2H), 2.46 (m, bs, 4H), 2.25, 2.24 (s, 3H), 1.44, 1.42 (s, 9H), 1.35 (t, J=7.07 Hz, 3H), mixture of rotamers.

3-(4-Morpholin-4-yl-2-nitro-benzoylamino)-6,7-dihydro-4H-pyrazolo[4,3-c]pyridine-1,5-dicarboxylic acid 5-tert-butyl ester 1-ethyl ester [(IV), Q=ethyl, Ra=Rb=H, A=D=E=CH, B=CR2, R1=nitro, R2=4-morpholin-1-yl]

1H-NMR (400 MHz), δ (ppm, DMSO-d₆): 11.16 (s, 1H), 7.65 (d, J=8.8 Hz, 1H), 7.46 (d, J=2.3 Hz, 1H), 7.27 (dd, J1=2.3 Hz, J2=8.8 Hz, 1H), 4.40 (q, J=7.1 Hz, 2H), 4.31 (bs, 2H), 3.76 (m, 4H), 3.63 (m, 2H), 3.34 (m, 4H), 2.98 (m, 2H), 1.42 (s, 9H), 1.35 (t, J=7.1 Hz, 3H).

3-{4-[(2-Dimethylamino-ethyl)-methyl-amino]-2-nitro-benzoylamino}-6,7-dihydro-4H-pyrazolo[4,3-c]pyridine-1,5-dicarboxylic acid 5-tert-butyl ester 1-ethyl ester [(IV), Q=ethyl, Ra=Rb=H, A=D=E=CH, B=CR2, R1=nitro, R2=2-dimethylamino-ethyl)-methyl-amino]

1H-NMR (400 MHz), δ (ppm, DMSO-d₆): 11.04 (s, 1H), 7.60 (d, J=8.8 Hz, 1H), 7.12 (d, J=2.4 Hz, 1H), 6.94 (dd, J1=2.4 Hz, J2=8.8 Hz, 1H), 4.38 (q, J=7.1 Hz, 2H), 4.28 (bs, 2H), 3.61 (m, 2H), 3.54 (m, 2H), 3.02 (s, 3H), 2.96 (m, 2H), 2.40 (m, 2H), 2.19 (s, 6H), 1.40 (s, 9H), 1.33 (t, J=7.1 Hz, 3H).

3-[4-(2-Dimethylamino-ethoxy)-2-nitro-benzoylamino]-6,7-dihydro-4H-pyrazolo[4,3-c]pyridine-1,5-dicarboxylic acid 5-tert-butyl ester 1-ethyl ester [(IV), Q=ethyl, Ra=Rb=H, A=D=E=CH, B=CR2, R1=nitro, R2=2-dimethylamino-ethoxy]

1H-NMR (400 MHz), δ (ppm, DMSO-d₆): 11.26 (s, 1H), 7.71 (d, J=8.5 Hz, 1H), 7.62 (d, J=2.6 Hz, 1H), 7.39 (dd, J1=2.6 Hz, J2=8.5 Hz, 1H), 4.40 (q, J=7.1 Hz, 2H), 4.36 (bs, 2H), 4.24 (t, J=5.5 Hz, 2H), 3.64 (m, 2H), 2.98 (m, 2H), 2.68 (t, J=5.5 Hz, 2H), 2.25 (s, 6H), 1.43 (s, 9H), 1.34 (t, J=7.1 Hz, 3H).

3-[4-(1-Methyl-piperidin-4-yloxy)-2-nitro-benzoylamino]-6,7-dihydro-4H-pyrazolo[4,3-c]pyridine-1,5-dicarboxylic acid 5-tert-butyl ester 1-ethyl ester [(IV), Q=ethyl, Ra=Rb=H, A=D=E=CH, B=CR2, R1=nitro, R2=piperidin-4-yloxy]

1H-NMR (400 MHz), δ (ppm, DMSO-d$_6$): 11.25 (bs, 1H), 7.71 (d, J=8.5 Hz, 1H), 7.61 (d, J=2.5 Hz, 1H), 7.41 (dd, J1=8.5 Hz, J2=2.5 Hz, 1H), 4.64 (m, 1H), 4.40 (q, J=7.1 Hz, 2H), 4.35 (bs, 2H), 3.64 (m, 2H), 2.98 (m, 2H), 2.68 (m, 2H), 2.31 (m, 2H), 2.25 (bs, 3H), 1.99 (m, 2H), 1.71 (m, 2H), 1.43 (s, 9H), 1.34 (t, J=7.1 Hz, 3H).

3-(4-Methoxy-2-nitro-benzoylamino)-6,7-dihydro-4H-pyrazolo[4,3-c]pyridine-1,5-dicarboxylic acid 5-tert-butyl ester 1-ethyl ester [(IV), Q=ethyl, Ra=Rb=H, A=D=E=CH, B=CR2, R1=nitro, R2=methoxy]

1H-NMR (400 MHz), δ (ppm, DMSO-d$_6$): 11.27 (s, 1H), 7.73 (d, J=8.5 Hz, 1H), 7.62 (d, J=2.6 Hz, 1H), 7.40 (dd, J1=8.5 Hz, J2=2.6 Hz, 1H), 4.40 (q, J=7.1 Hz, 2H), 4.36 (bs, 2H), 3.93 (s, 3H), 3.64 (m, 2H), 2.98 (m, 2H), 1.43 (s, 9H), 1.35 (t, J=7.1 Hz, 3H).

3-(4-Dimethylamino-2-nitro-benzoylamino)-6,7-dihydro-4H-pyrazolo[4,3-c]pyridine-1,5-dicarboxylic acid 5-tert-butyl ester 1-ethyl ester [(IV), Q=ethyl, Ra=Rb=H, A=D=E=CH, B=CR2, R1=nitro, R2=N,N-dimethylamino]

1H-NMR (400 MHz), δ (ppm, DMSO-d$_6$): 11.08 (s, 1H), 7.63 (d, J=8.84 Hz, 1H), 7.14 (d, J=2.50 Hz, 1H), 6.97 (dd, J1=8.84 Hz, J2=2.50 Hz, 1H), 4.40 (q, J=7.07 Hz, 2H), 4.29 (s, 2H), 3.63 (m, 2H), 3.05 (s, 6H), 2.98 (m, 2H), 1.42 (s, 9H), 1.35 (t, J=7.07 Hz, 3H).

3-(2-Fluoro-6-nitro-benzoylamino)-6,7-dihydro-4H-pyrazolo[4,3-c]pyridine-1,5-dicarboxylic acid 5-tert-butyl ester 1-ethyl ester [(IV), Q=ethyl, Ra=Rb=H, A=B=D=CH, E=CR2, R1=nitro, R2=fluoro]

1H-NMR (400 MHz), δ (ppm, DMSO-d$_6$): 11.48 (s, 1H), 8.13 (d, J=7.9 Hz, 1H), 7.92-7.80 (m, 2H), 4.42 (bs, 2H), 4.40 (q, J=7.1 Hz, 2H), 3.66 (m, 2H), 2.99 (m, 2H), 1.43 (s, 9H), 1.35 (t, J=7.1 Hz, 3H).

3-(2-Nitro-benzoylamino)-6,7-dihydro-4H-pyrazolo[4,3-c]pyridine-1,5-dicarboxylic acid 5-tert-butyl ester 1-ethyl ester [(IV), Q=ethyl, Ra=Rb=H, A=B=D=E=CH, R1=nitro]

The title compound was obtained following the procedure described above, and starting from the commercially available 2-nitrobenzoic acid.

1H-NMR (400 MHz), δ (ppm, DMSO-d$_6$): 11.34 (s, 1H), 8.14 (d, J1=8.30 Hz, 1H), 7.88 (ddd, J1=8.54 Hz, J2=6.95 Hz, J3=0.73 Hz, 1H), 7.78 (m, 2H), 4.41 (m, 4H), 3.65 (m, 2H), 2.99 (m, 2H), 1.43 (s, 9H), 1.35 (t, J=7.07 Hz, 3H).

3-(2-Nitro-benzoylamino)-6,7-dihydro-4H-pyrazolo[4,3-c]pyridine-2,5-dicarboxylic acid 5-tert-butyl ester 2-ethyl ester [(IV) Q=ethyl, Ra=Rb=H, A=B=D=E=CH R1=nitro]

1H-NMR (400 MHz), δ (ppm, DMSO-d$_6$): 10.92 (s, 1H), 8.19 (d, J1=8.17 Hz, 1H), 7.94 (m, 1H), 7.81 (m, 1H), 7.75 (d, bs, J=7.31 Hz, 1H), 4.42-4.37 (m, 4H), 3.66 (m, 2H), 2.70 (m, 2H), 1.44 (s, 9H), 1.33 (t, J=7.07 Hz, 3H).

7,7-Dimethyl-3-[4-(4-methyl-piperazin-1-yl)-2-nitro-benzoylamino]-6,7-dihydro-4H-pyrazolo[4,3-c]pyridine-2,5-dicarboxylic acid 5-tert-butyl ester 2-ethyl ester [(IV), Q=ethyl, Ra=Rb=methyl, A=D=E=CH, B=CR2, R1=nitro, R2=4-methylpiperazin-1-yl]

1H-NMR (400 MHz), δ (ppm, DMSO-d$_6$): 10.56 (s, 1H), 7.61 (bs, 1H), 7.44 (d, J2=2.56 Hz, 1H), 7.31 (dd, J1=8.78 Hz, J2=2.56 Hz, 1H), 4.38 (q, J=7.07 Hz, 2H), 4.33 (s, 2H), 4.39-4.35 (m, 6H), 2.44 (m, 4H), 2.22 (s, 3H), 1.42 (s, 9H), 1.30 (t, J=7.07 Hz, 3H), 1.21 (s, 6H).

7,7-Dimethyl-3-(4-morpholin-4-yl-2-nitro-benzoylamino)-6,7-dihydro-4H-pyrazolo[4,3-c]pyridine-2,5-dicarboxylic acid 5-tert-butyl ester 2-ethyl ester [(IV), Q=ethyl, Ra=Rb=methyl, A=D=E=CH, B=CR2, R1=nitro, R2=morpholin-4-yl]

1H-NMR (400 MHz), δ (ppm, DMSO-d$_6$): 10.61 (s, 1H), 7.65 (bd, 1H), 7.50 (d, J=2.6 Hz, 1H), 7.34 (dd, J1=8.8 Hz, J2=2.6 Hz, 1H), 4.40 (q, J=7.1 Hz, 2H), 4.36 (bs, 2H), 3.77 (m, 4H), 3.42 (bs, 2H), 3.35 (m, 4H), 1.44 (s, 9H), 1.32 (t, J=7.1 Hz, 3H), 1.24 (s, 6H).

3-(4-Dimethylamino-2-nitro-benzoylamino)-7,7-dimethyl-6,7-dihydro-4H-pyrazolo[4,3-c]pyridine-2,5-dicarboxylic acid 5-tert-butyl ester 2-ethyl ester [(IV), Q=ethyl, Ra=Rb=methyl, A=D=E=CH, B=CR2, R1=nitro, R2=N,N-dimethylamino]

1H-NMR (400 MHz), δ (ppm, DMSO-d$_6$): 10.51 (s, 1H), 7.63 (bd, 1H), 7.18 (d, J=2.6 Hz, 1H), 7.03 (dd, J1=8.9 Hz, J2=2.6 Hz, 1H), 4.40 (q, J=7.1 Hz, 2H), 4.35 (bs, 2H), 3.41 (bs, 2H), 3.06 (s, 6H), 1.44 (s, 9H), 1.32 (t, J=7.1 Hz, 3H), 1.24 (s, 6H).

7,7-Dimethyl-3-(2-nitro-4-pyrrolidin-1-ylmethyl-benzoylamino)-6,7-dihydro-4H-pyrazolo[4,3-c]pyridine-2,5-dicarboxylic acid 5-tert-butyl ester 2-ethyl ester [(IV), Q=ethyl, Ra=Rb=methyl, A=D=E=CH, B=CR2, R1=nitro, R2=pyrrolidin-1-yl-methyl]

1H-NMR (400 MHz), δ (ppm, DMSO-d$_6$): 10.82 (s, 1H), 8.10, 8.06 (bs, 1H), 7.83 (m, 1H), 7.66 (m, 1H), 4.49, 4.38 (m, 4H), 3.74, 3.69 (s, 2H), 3.40 (s, 2H), 2.5-2.42 (m, 4H), 1.72 (m, 4H), 1.42 (s, 9H), 1.31 (t, J=7.20 Hz, 3H), 1.22 (s, 6H).

7,7-Dimethyl-3-(2-nitro-benzoylamino)-6,7-dihydro-4H-pyrazolo[4,3-c]pyridine-2,5-dicarboxylic acid 5-tert-butyl ester 2-ethyl ester [(IV), Q=ethyl, Ra=Rb=methyl, A=B=D=E=CH, R1=nitro]

1H-NMR (400 MHz), δ (ppm, DMSO-d$_6$): 10.87 (s, 1H), 8.18 (m, 1H), 7.93 (m, 1H), 7.80 (m, 1H), 7.73 (m, 1H), 4.42 (bs, 2H), 4.40 (q, J=7.2 Hz, 2H), 3.42 (bs, 2H), 1.43 (s, 9H), 1.32 (t, J=7.2 Hz, 3H), 1.23 (s, 6H).

EXAMPLE 10

Preparation of 3-[4-(4-Methyl-piperazin-1-yl)-2-nitro-benzoylamino]-4,5,6,7-tetrahydro-pyrazolo[4,3-c]pyridine-1-carboxylic acid ethyl ester dihydrochloride [(V), Q=ethyl, Ra=Rb=H, A=D=E=CH, B=CR2, R1=nitro, R2=4-methylpiperazin-1-yl]

A suspension of 3-[4-(4-methyl-piperazin-1-yl)-2-nitro-benzoylamino]-6,7-dihydro-4H-pyrazolo[4,3-c]pyridine-1, 5-dicarboxylic acid 5-tert-butyl ester 1-ethyl ester (1.29 g, 2.33 mmol) in 1,4-dioxane (15 mL) was treated with 4N HCl in 1,4-dioxane (20 eq., 11.6 mL) at room temperature for about 4 hours. After removal of the solvent, the crude material was treated with diethyl ether (20 mL) and evaporated to dryness. The title compound was obtained after crystallization from diethyl ether as colourless powder (1.23 g, quantitative).

1H-NMR (400 MHz), δ (ppm, DMSO-$d_6$): 11.46 (s, 1H), 9.25 (bs, NH2+), 7.72 (d, J1=8.78 Hz, 1H), 7.57 (d, J2=2.44 Hz, 1H), 7.36 (dd, J1=8.78 Hz, J2=2.44 Hz, 1H), 4.43 (q, J=7.07 Hz, 2H), 4.09 (m, 4H), 3.34 (m, 10H), 2.84 (s, 3H), 1.36 (t, J=7.07 Hz, 3H).

Operating in an analogous way, the following compounds were obtained:

3-[2-Nitro-4-[4-(2,2,2-trifluoro-acetyl)-piperazin-1-yl]-benzoylamino]-4,5,6,7-tetrahydro-pyrazolo[4,3-c]pyridine-1-carboxylic acid ethyl ester trifluoroacetate [(V), Q=ethyl, Ra=Rb=H, A=D=E=CH, B=CR2, R1=nitro, R2=4-(2,2,2-trifluoro-acetyl)-piperazin-1-yl]

1H-NMR (400 MHz), δ (ppm, DMSO-$d_6$): 11.44 (bs, 1H), 8.41 (bs, 2H), 7.69 (d, J=8.7 Hz, 1H), 7.49 (d, J=2.5 Hz, 1H), 7.26 (dd, J1=8.7 Hz, J2=2.5 Hz, 1H), 4.43 (q, J=7.1 Hz, 2H), 4.11 (bs, 2H), 3.75 (m, 4H), 3.54 (m, 4H), 3.45 (m, 2H), 3.22 (m, 2H), 1.36 (t, J=7.1 Hz, 3H).

3-[2-Fluoro-4-(4-methyl-piperazin-1-yl)-benzoylamino]-4,5,6,7-tetrahydro-pyrazolo[4,3-c]pyridine-1-carboxylic acid ethyl ester hydrochloride [(V), Q=ethyl, Ra=Rb=H, A=D=E=CH, B=CR2, R1=Fluoro, R2=4-methylpiperazin-1-yl]

1H-NMR (400 MHz), δ (ppm, DMSO-$d_6$): 10.60, 10.41 (bs, 1H), 9.27 (bs, NH2+), 7.78, 7.68 (m, 1H), 6.96-6.84 (m, 2H), 4.44 (q, J=7.07 Hz, 2H), 4.11-3.06 (m, bs, 14H), 2.83 (bs, 3H), 1.36, 1.23 (t, J=7.07 Hz, 3H), mixture of rotamers.

3-(4-Morpholin-4-yl-2-nitro-benzoylamino)-4,5,6,7-tetrahydro-pyrazolo[4,3-c]pyridine-1-carboxylic acid ethyl ester dihydrochloride [(V), Q=ethyl, Ra=Rb=H, A=D=E=CH, B=CR2, R1=nitro, R2=morpholin-4-yl]

1H-NMR (400 MHz), δ (ppm, DMSO-$d_6$): 11.41 (s, 1H), 9.18 (bs, 2H), 7.69 (d, J=8.7 Hz, 1H), 7.46 (d, J=2.5 Hz, 1H), 7.27 (dd, J1=2.5 Hz, J2=8.7 Hz, 1H), 4.44 (q, J=7.1 Hz, 2H), 4.09 (m, 2H), 3.76 (m, 4H), 3.50-3.30 (m, 6H), 3.23 (m, 2H), 1.36 (t, J=7.1 Hz, 3H).

3-{4-[(2-Dimethylamino-ethyl)-methyl-amino]-2-nitro-benzoylamino}-4,5,6,7-tetrahydro-pyrazolo[4,3-c]pyridine-1-carboxylic acid ethyl ester dihydrochloride [(V), Q=ethyl, Ra=Rb=H, A=D=E=CH, B=CR2, R1=nitro, R2=(2-dimethylamino-ethyl)-methyl-amino]

1H-NMR (400 MHz), δ (ppm, DMSO-$d_6$): ): 11.39 (s, 1H), 10.38 (bs, 1H), 9.25 (bs, 2H), 7.69 (d, J=8.8 Hz, 1H), 7.26 (d, J=2.7 Hz, 1H), 7.12 (dd, J1=2.7 Hz, J2=8.8 Hz, 1H), 4.44 (q, J=7.1 Hz, 2H), 4.06 (m, 2H), 3.86 (m, 2H), 3.45 (m, 2H), 3.29-3.20 (m, 4H), 3.07 (s, 3H), 2.83 (d, 6H), 1.36 (t, J=7.1 Hz, 3H).

3-[4-(2-Dimethylamino-ethoxy)-2-nitro-benzoylamino]-4,5,6,7-tetrahydro-pyrazolo[4,3-c]pyridine-1-carboxylic acid ethyl ester dihydrochloride [(V), Q=ethyl, Ra=Rb=H, A=D=E=CH, B=CR2, R1=nitro, R2=2-dimethylamino-ethoxy]

1H-NMR (400 MHz), δ (ppm, DMSO-$d_6$): 11.57 (s, 1H), 10.31 (bs, 1H), 9.35 (bs, 2H), 7.81 (d, J=8.5 Hz, 1H), 7.71 (d, J=2.5 Hz, 1H), 7.47 (dd, J1=2.5 Hz, J2=8.5 Hz, 1H), 4.55 (m, 2H), 4.44 (q, J=7.0 Hz, 2H), 4.12 (m, 2H), 3.57 (m, 2H), 3.46 (m, 2H), 3.24 (m, 2H), 2.88 (d, 6H), 1.36 (t, J=7.0 Hz, 3H).

3-[4-(1-Methyl-piperidin-4-yloxy)-2-nitro-benzoylamino]-4,5,6,7-tetrahydro-pyrazolo[4,3-c]pyridine-1-carboxylic acid ethyl ester dihydrochloride [(V), Q=ethyl, Ra=Rb=H, A=D=E=CH, B=CR2, R1=nitro, R2=1-methyl-piperidin-4-yloxy]

1H-NMR (400 MHz), δ (ppm, DMSO-$d_6$): 11.53 (bs, 1H), 10.32 (bs, 1H), 9.30 (bs, 2H), 7.79 (m, 1H), 7.73 (m, 1H), 7.51 (m, 1H), 5.00 (bs, 1H), 4.79 (m, 1H), 4.43 (q, J=7.2 Hz, 2H), 4.11 (bs, 2H), 3.50-3.25 (m, 8H), 2.80 (s, 3H), 2.28 (m, 2H), 1.93 (m, 2H), 1.36 (t, J=7.2 Hz, 3H).

3-(4-Methoxy-2-nitro-benzoylamino)-4,5,6,7-tetrahydro-pyrazolo[4,3-c]pyridine-1-carboxylic acid ethyl ester hydrochloride [(V), Q=ethyl, Ra=Rb=H, A=D=E=CH, B=CR2, R1=nitro, R2=methoxy]

1H-NMR (400 MHz), δ (ppm, DMSO-$d_6$): 11.53 (s, 1H), 9.15 (bs, 2H), 7.77 (d, J=8.5 Hz, 1H), 7.63 (d, J=2.6 Hz, 1H), 7.41 (dd, J1=8.5 Hz, J2=2.6 Hz, 1H), 4.44 (q, J=7.1 Hz, 2H), 4.13 (bs, 2H), 3.93 (s, 3H), 3.46 (m, 2H), 3.23 (m, 2H), 1.36 (t, J=7.1 Hz, 3H).

3-(4-Dimethylamino-2-nitro-benzoylamino)-4,5,6,7-tetrahydro-pyrazolo[4,3-c]pyridine-1-carboxylic acid ethyl ester hydrochlorid [(V), Q=ethyl, Ra=Rb=H, A=D=E=CH, B=CR2, R1=nitro, R2=N,N-dimethylamino]

1H-NMR (400 MHz), δ (ppm, DMSO-$d_6$): 11.34 (s, 1H), 9.16 (bs, NH2+), 7.66 (d, J=8.90 Hz, 1H), 7.14 (d, J=2.68 Hz, 1H), 6.97 (dd, J1=8.90 Hz, J2=2.68 Hz, 1H), 4.44 (q, J=7.07 Hz, 2H), 4.07 (m, bs, 2H), 3.48-3.33 (m, 2H), 3.23 (m, 2H), 3.06 (s, 6H), 1.36 (t, J=7.07 Hz, 3H).

3-(2-Fluoro-6-nitro-benzoylamino)-4,5,6,7-tetrahydro-pyrazolo[4,3-c]pyridine-1-carboxylic acid ethyl ester hydrochloride [(V), Q=ethyl, Ra=Rb=H, A=B=D=CH, E=CR2, R1=nitro, R2=fluoro]

1H-NMR (400 MHz), δ (ppm, DMSO-$d_6$): 11.76 (s, 1H), 9.16 (bs, 2H), 8.14 (m, 1H), 7.93-7.82 (m, 2H), 4.44 (q, J=7.1 Hz, 2H), 4.18 (bs, 2H), 3.48 (m, 2H), 3.24 (m, 2H), 1.36 (t, J=7.1 Hz, 3H).

3-(2-Nitro-benzoylamino)-4,5,6,7-tetrahydro-pyrazolo[4,3-c]pyridine-1-carboxylic acid ethyl ester hydrochloride [(V), Q=ethyl, Ra=Rb=H, A=B=D=E=CH, R1=nitro]

1H-NMR (400 MHz), δ (ppm, DMSO-$d_6$): 11.59 (s, 1H), 9.16 (bs, NH2+), 8.17, 8.18 (d, J1=8.29 Hz, 1H), 7.90 (ddd, J1=8.30 Hz, J2=7.44 Hz, J3=1.09 Hz, 1H), 7.81-7.77 (m, 2H), 4.44 (q, J=7.19 Hz, 2H), 4.17 (m, 2H), 3.48 (m, 2H), 3.24 (m, 2H), 1.86 (t, J=7.19 Hz, 3H).

3-(2-Nitro-benzoylamino)-4,5,6,7-tetrahydro-pyrazolo[4,3-c]pyridine-2-carboxylic acid ethyl ester hydrochloride [(V), Q=ethyl, Ra=Rb=H, A=B=D=E=CH, R1=nitro]

1H-NMR (400 MHz), δ (ppm, DMSO-$d_6$): 11.16 (s, 1H), 9.21 (bs, NH2+), 8.22 (d, J=8.42 Hz, 1H), 7.96 (ddd, bs, J1=8.05 Hz, J2=7.49 Hz, 1H), 7.83 (ddd, bs, J1=8.42 Hz, J2=8.05 Hz, J3=1.05 Hz, 1H), 7.78 (d, bs, J=7.49 Hz, 1H), 4.42 (q, J=7.07 Hz, 2H), 4.13 (s, 2H), 3.51 (m, 2H), 2.97 (m, 2H), 1.34 (t, J=7.07 Hz, 3H).

7,7-Dimethyl-3-[4-(4-methyl-piperazin-1-yl)-2-nitro-benzoylamino]-4,5,6,7-tetrahydro-pyrazolo[4,3-c]pyridine-2-carboxylic acid ethyl ester dihydrochloride [(V), Q=ethyl, Ra=Rb=methyl, A=D=E=CH, B=CR2, R1=nitro, R2=4-methylpiperazin-1-yl]

1H-NMR (400 MHz 6 ppm, DMSO-$d_6$): 10.94 (s, 1H), 9.37 (bs, NH2+), 7.72 (d, J1=8.65 Hz, 1H), 7.62 (d, J2=2.44 Hz, 1H), 7.42 (dd, J1=8.65 Hz, J2=2.44 Hz, 1H), 4.43 (q, J=7.07 Hz, 2H), 4.14 (m, 2H), 4.06 (s, 2H), 3.55-3.16 (m, 8H), 2.84 (s, 3H), 1.39 (s, 6H), 1.35 (t, J=7.07 Hz, 3H).

7,7-Dimethyl-3-(4-morpholin-4-yl-2-nitro-benzoylamino)-4,5,6,7-tetrahydro-pyrazolo[4,3-c]pyridine-2-carboxylic acid ethyl ester hydrochloride [(V), Q=ethyl, Ra=Rb=methyl, A=D=E=CH, B=CR2, R1=nitro, R2=morpholin-4-yl]

ESI(+) MS: m/z 473 (MH+).

7,7-Dimethyl-3-(2-nitro-4-pyrrolidin-1-ylmethyl-benzoylamino)-4,5,6,7-tetrahydro-pyrazolo[4,3-c]pyridine-2-carboxylic acid ethyl ester dihydrochloride [(V), Q=ethyl, Ra=Rb=methyl, A=D=E=CH, B=CR2, R1=nitro, R2=pyrrolidin-1-yl-methyl]

1H-NMR (400 MHz), δ (ppm, DMSO-$d_6$): 11.21 (s, 1H), 9.35 (bs, NH2+), 8.59, 8.50 (s, 1H), 8.15 (d, bs, J1=7.68 Hz, 1H), 7.82 (d, J1=7.68 Hz, 1H), 4.59-4.54 (m, 2H), 4.41 (q, J=7.07 Hz, 2H), 4.09 (bs, 2H), 3.40 (m, 2H), 3.32-3.11 (m, bs, 4H), 2.04-1.89 (m, bs, 4H), 1.38 (s, 6H), 1.32 (t, J=7.07 Hz, 3H), mixture of rotamers.

3-(4-Dimethylamino-2-nitro-benzoylamino)-7,7-dimethyl-4,5,6,7-tetrahydro-pyrazolo[4,3-c]pyridine-2-carboxylic acid ethyl ester hydrochloride [(V), Q=ethyl, Ra=Rb=methyl, A=D=E=CH, B=CR2, R1=nitro, R2=dimethylamino]

ESI (+) MS: m/z 431 (MH+).

7,7-Dimethyl-3-(2-nitro-benzoylamino)-4,5,6,7-tetrahydro-pyrazolo[4,3-c]pyridine-2-carboxylic acid ethyl ester hydrochloride [(V), Q=ethyl, Ra=Rb=methyl, A=B=D=E=CH, R1=nitro]

1H-NMR (400 MHz), δ (ppm, DMSO-$d_6$): 11.14 (s, 1H), 9.21 (bs, NH2+), 8.21 (d, J=8.29 Hz, 1H), 7.95 (dd, J1=7.93 Hz, J2=7.44 Hz, 1H), 7.82 (ddd, J1=8.29 Hz, J2=7.93 Hz, J3=0.85 Hz, 1H), 7.76 (d, J=7.44 Hz, 1H), 4.42 (q, J=7.08 Hz, 2H), 4.10 (s, 2H), 3.57 (s, 2H), 1.38 (s, 6H), 1.33 (t, J=7.08 Hz, 3H).

EXAMPLE 11

Preparation of 5-(3,5-Difluoro-benzenesulfonyl)-3-[4-(4-methyl-piperazin-1-yl)-2-nitro-benzoylamino]-4,5,6,7-tetrahydro-pyrazolo[4,3-c]pyridine-1-carboxylic acid ethyl ester [(VII), Q=ethyl, Ra=Rb=H, A=D=E=CH, B=CR2, R=3,5-difluorophenyl, R1=nitro, R2=4-methylpiperazin-1-yl]

A solution of 3,5-difluorobenzenesulfonyl chloride (1.1 eq., 2.62 g) in dry dichloromethane (15 mL) was added dropwise to a stirred solution of 3-[4-(4-methyl-piperazin-1-yl)-2-nitro-benzoylamino]-4,5,6,7-tetrahydro-pyrazolo[4,3-c]pyridine-1-carboxylic acid ethyl ester dihydrochloride (5.7 g, 10.85 mmol) and N,N-diisopropylethylamine (6 eq., 11.34 mL) in dry dichloromethane (100 mL) at room temperature. Stirring was continued for 20 hours. The reaction mixture was then washed with water (2×80 mL), saturated sodium hydrogenocarbonate (2×80 mL), brine (80 mL), dried over sodium sulfate, evaporated to dryness and purified by flash chromatography on silica gel, using acetone-dichloromethane 60:40 as eluant. The title compound was obtained as yellow powder (5 g, 73% yield).

1H-NMR (400 MHz), δ ppm, DMSO-$d_6$): 11.21 (s, 1H), 7.67 (m, 2H), 7.54 (m, 2H), 7.44 (d, J2=2.44 Hz, 1H), 7.27 (dd, J1=8.78 Hz, J2=2.44 Hz, 1H), 4.37 (q, J=7.07 Hz, 2H), 4.14 (s, 2H), 3.55 (m, 2H), 3.34 (m, 4H), 3.02 (m, 2H), 2.52 (m, 4H), 2.25 (s, 3H), 1.33 (t, J=7.07 Hz, 3H).

Operating in an analogous way, the following compounds were obtained:

5-(3,5-Difluoro-benzenesulfonyl)-3-{2-nitro-4-[4-(2,2,2-trifluoro-acetyl)-piperazin-1-yl]-benzoylamino}-4,5,6,7-tetrahydro-pyrazolo[4,3-c]pyridine-1-carboxylic acid ethyl ester [(VII), Q=ethyl, Ra=Rb=H, A=D=E=CH, B=CR2, R=3,5-difluorophenyl, R1=nitro, R2=4-(2,2,2-trifluoro-acetyl)-piperazin-1-yl]

1H-NMR (400 MHz), δ (ppm, DMSO-$d_6$): 11.26 (bs, 1H), 7.72-7.69 (m, 2H), 7.55 (m, 2H), 7.50 (d, J=2.5 Hz, 1H), 7.29 (dd, J1=8.6 Hz, J2=2.5 Hz, 1H), 4.37 (q, J=7.2 Hz, 2H), 4.16 (bs, 1H), 3.75 (m, 4H), 3.57-3.51 (m, 6H), 3.02 (m, 2H), 1.33 (t, J=7.2 Hz, 3H).

5-(3,5-Dichloro-benzenesulfonyl)-3-[4-(4-methyl-piperazin-1-yl)-2-nitro-benzoylamino]-4,5,6,7-tetrahydro-pyrazolo[4,3-c]pyridine-1-carboxylic acid ethyl ester [(VII), Q=ethyl, Ra=Rb=H, A=D=E=CH, B=CR2, R=3,5-dichlorophenyl, R1=nitro, R2=4-methylpiperazin-1-yl]

1H-NMR (400 MHz), δ (ppm, DMSO-$d_6$): 11.21 (bs, 1H), 7.99 (t, J=1.8 Hz, 1H), 7.80 (d, J=1.8 Hz, 2H), 7.64 (d, J=8.8 Hz, 1H), 7.44 (d, J=2.5 Hz, 1H), 7.24 (dd, J1=8.8 Hz, J2=2.5 Hz, 1H), 4.37 (q, J=7.2 Hz, 2H), 4.18 (bs, 2H), 3.58 (m, 2H), 3.37 (m, 4H), 3.00 (m, 2H), 2.46 (m, 4H), 2.24 (s, 3H), 1.33 (t, J=7.2 Hz, 3H).

5-(2-Fluoro-benzenesulfonyl)-3-[4-(4-methyl-piperazin-1-yl)-2-nitro-benzoylamino]-4,5,6,7-tetrahydro-pyrazolo[4,3-c]pyridine-1-carboxylic acid ethyl ester [(VII), Q=ethyl, Ra=Rb=H, A=D=E=CH, B=CR2, R=2-fluorophenyl, R1=nitro, R2=4-methylpiperazin-1-yl]

1H-NMR (400 MHz), δ (ppm, DMSO-$d_6$): 11.21 (bs, 1H), 7.85 (m, 1H), 7.74 (m, 1H), 7.61 (d, J=8.7 Hz, 1H), 7.45-7.39

(m, 3H), 7.24 (dd, J1=8.7 Hz, J2=2.7 Hz, 1H), 4.35 (q, J=7.1 Hz, 2H), 4.19 (bs, 2H), 3.57 (m, 2H), 3.34 (m, 4H), 2.98 (m, 2H), 2.44 (m, 4H), 2.23 (s, 3H), 1.31 (t, J=7.1 Hz, 2H).

5-(3-Fluoro-benzenesulfonyl)-3-[4-(4-methyl-piperazin-1-yl)-2-nitro-benzoylamino]-4,5,6,7-tetrahydro-pyrazolo[4,3-c]pyridine-1-carboxylic acid ethyl ester [(VII), Q=ethyl, Ra=Rb=H, A=D=E=CH, B=CR2, R=3-fluorophenyl, R1=nitro, R2=4-methylpiperazin-1-yl]

1H-NMR (400 MHz), δ (ppm, DMSO-$d_6$): 11.20 (bs, 1H), 7.70-7.55 (m, 5H), 7.45 (d, J=2.5 Hz, 1H), 7.27 (dd, J1=8.8 Hz, J2=2.5 Hz, 1H), 4.37 (q, J=7.2 Hz, 2H), 4.11 (bs, 2H), 3.50 (m, 2H), 3.38 (m, 4H), 3.01 (m, 2H), 2.46 (m, 4H), 2.25 (s, 3H), 1.31 (t, J=7.2 Hz, 2H).

5-(3-Chloro-benzenesulfonyl)-3-[4-(4-methyl-piperazin-1-yl)-2-nitro-benzoylamino]-4,5,6,7-tetrahydro-pyrazolo[4,3-c]pyridine-1-carboxylic acid ethyl ester [(VII), Q=ethyl, Ra=Rb=H, A=D=E=CH, B=CR2, R=3-chlorophenyl, R1=nitro, R2=4-methylpiperazin-1-yl]

1H-NMR (400 MHz), δ (ppm, DMSO-$d_6$): 11.20 (bs, 1H), 7.82 (m, 1H), 7.80-7.75 (m, 2H), 7.66-7.62 (m, 2H), 7.45 (d, J=2.5 Hz, 1H), 7.27 (dd, J1=8.9 Hz, J2=2.5 Hz, 1H), 4.37 (q, J=7.1 Hz, 2H), 4.13 (bs, 2H), 3.51 (m, 2H), 3.38 (m, 4H), 3.00 (m, 2H), 2.47 (m, 4H), 2.25 (s, 3H), 1.33 (t, J=7.1 Hz, 2H).

5-(3-Methoxy-benzenesulfonyl)-3-[4-(4-methyl-piperazin-1-yl)-2-nitro-benzoylamino]-4,5,6,7-tetrahydro-pyrazolo[4,3-c]pyridine-1-carboxylic acid ethyl ester [(VII), Q=ethyl, Ra=Rb=H, A=D=E=CH, B=CR2, R=3-methoxyphenyl, R1=nitro, R2=4-methylpiperazin-1-yl]

1H-NMR (400 MHz), δ (ppm, DMSO-$d_6$): 11.20 (bs, 1H), 7.64 (d, J=8.7 Hz, 1H), 7.53 (m, 1H), 7.44 (d, J=2.4 Hz, 1H), 7.39 (m, 1H), 7.27-7.23 (m, 3H), 4.36 (q, J=7.2 Hz, 2H), 4.10 (bs, 2H), 3.82 (s, 3H), 3.44 (m, 2H), 3.38 (m, 4H), 2.99 (m, 2H), 2.46 (m, 4H), 2.25 (s, 3H), 1.32 (t, J=7.2 Hz, 3H).

5-Benzenesulfonyl-3-[4-(4-methyl-piperazin-1-yl)-2-nitro-benzoylamino]-4,5,6,7-tetrahydro-pyrazolo[4,3-c]pyridine-1-carboxylic acid ethyl ester [(VII), Q=ethyl, Ra=Rb=H, A=D=E=CH, B=CR2, R=phenyl, R1=nitro, R2=4-methylpiperazin-1-yl]

1H-NMR (400 MHz), δ (ppm, DMSO-$d_6$): 11.19 (bs, 1H), 7.80 (d, J=8.5 Hz, 2H), 7.71 (m, 1H), 7.66-7.70 (m, 3H), 7.45 (d, J=2.0 Hz, 1H), 7.27 (dd, J1=8.9 Hz, J2=2.5 Hz, 1H), 4.36 (q, J=7.2 Hz, 2H), 4.07 (bs, 2H), 3.44 (m, 2H), 3.38 (m, 4H), 2.99 (m, 2H), 2.47 (m, 4H), 2.25 (s, 3H).

5-(3,5-Difluoro-benzenesulfonyl)-3-(4-morpholin-4-yl-2-nitro-benzoylamino)-4,5,6,7-tetrahydro-pyrazolo[4,3-c]pyridine-1-carboxylic acid ethyl ester [(VII), Q=ethyl, Ra=Rb=H, A=D=E=CH, B=CR2, R=3,5-difluorophenyl, R1=nitro, R2=morpholin-4-yl]

1H-NMR (400 MHz), δ (ppm, DMSO-$d_6$): 11.24 (s, 1H), 7.72-7.66 (m, 2H), 7.57-7.53 (m, 2H), 7.47 (d, J=2.5 Hz, 1H), 7.27 (dd, J1=2.5 Hz, J2=8.8 Hz, 1H), 4.38 (q, J=7.1 Hz, 2H), 4.15 (bs, 2H), 3.76 (m, 4H), 3.56 (m, 2H), 3.35 (m, 4H), 3.02 (m, 2H), 1.33 (t, J=7.1 Hz, 3H).

5-(3,5-Difluoro-benzenesulfonyl)-3-{4-[(2-dimethylamino-ethyl)-methyl-amino]-2-nitro-benzoylamino}-4,5,6,7-tetrahydro-pyrazolo[4,3-c]pyridine-1-carboxylic acid ethyl ester [(VII), Q=ethyl, Ra=Rb=H, A=D=E=CH, B=CR2, R=3,5-difluorophenyl, R1=nitro, R2=(2-dimethylamino-ethyl)-methyl-amino]

1H-NMR (400 MHz), δ (ppm, DMSO-$d_6$): 11.14 (s, 1H), 7.69 (m, 1H), 7.63 (d, J=8.8 Hz, 1H), 7.57-7.53 (m, 2H), 7.15 (d, J=2.6 Hz, 1H), 6.96 (dd, J1=2.6 Hz, J2=8.8 Hz, 1H), 4.38 (q, J=7.1 Hz, 2H), 4.12 (bs, 2H), 3.59-3.51 (m, 4H), 3.04 (s, 3H), 3.02 (m, 2H), 2.42 (m, 2H), 2.21 (s, 6H), 1.33 (t, J=7.1 Hz, 3H).

5-(3,5-Difluoro-benzenesulfonyl)-3-[4-(2-dimethylamino-ethoxy)-2-nitro-benzoylamino]-4,5,6,7-tetrahydro-pyrazolo[4,3-c]pyridine-1-carboxylic acid ethyl ester [(VII), Q=ethyl, Ra=Rb=H, A=D=E=CH, B=CR2, R=3,5-difluorophenyl, R1=nitro, R2=2-dimethylamino-ethoxy]

1H-NMR (400 MHz), δ (ppm, DMSO-$d_6$): 11.34 (s, 1H), 7.75 (d, J=8.4 Hz, 1H), 7.69 (m, 1H), 7.63 (d, J=2.4 Hz, 1H), 7.57-7.53 (m, 2H), 7.40 (dd, J1=2.4 Hz, J2=8.4 Hz, 1H), 4.38 (q, J=7.1 Hz, 2H), 4.24 (m, 2H), 4.20 (m, 2H), 3.56 (m, 2H), 3.03 (m, 2H), 2.69 (m, 2H), 2.25 (s, 6H), 1.33 (t, J=7.1 Hz, 3H).

5-(3,5-Difluoro-benzenesulfonyl)-3-[4-(1-methyl-piperidin-4-yloxy)-2-nitro-benzoylamino]-4,5,6,7-tetrahydro-pyrazolo[4,3-c]pyridine-1-carboxylic acid ethyl ester [(VII), Q=ethyl, Ra=Rb=H, A=D=E=CH, B=CR2, R=3,5-difluorophenyl, R1=nitro, R2=1-methyl-piperidin-4-yloxy]

1H-NMR (400 MHz), δ (ppm, DMSO-$d_6$): 11.33 (bs, 1H), 7.73 (d, J=8.7 Hz, 1H), 7.69 (m, 1H), 7.62 (d, J=2.4 Hz, 1H), 7.54 (m, 2H), 7.43 (dd, J1=8.7 Hz, J2=2.4 Hz, 1H), 4.65 (m, 1H), 4.37 (q, J=7.1 Hz, 2H), 4.18 (bs, 2H), 3.56 (m, 2H), 3.03 (m, 2H), 2.68 (m, 2H), 2.40-2.20 (m, 5H), 1.98 (m, 2H), 1.73 (m, 2H), 1.33 (t, J=7.1 Hz, 3H).

5-(3,5-Difluoro-benzenesulfonyl)-3-(4-methoxy-2-nitro-benzoylamino)-4,5,6,7-tetrahydro-pyrazolo[4,3-c]pyridine-1-carboxylic acid ethyl ester [(VII), Q=ethyl, Ra=Rb=H, A=D=E=CH, B=CR2, R=3,5-difluorophenyl, R1=nitro, R2=methoxy]

1H-NMR (400 MHz), δ (ppm, DMSO-$d_6$): 11.35 (s, 1H), 7.77 (d, J=8.5 Hz, 1H), 7.69 (m, 1H), 7.62 (d, J=2.5 Hz, 1H), 7.55 (m, 2H), 7.40 (dd, J1=8.5 Hz, J2=2.5 Hz, 1H), 4.38 (q, J=7.1 Hz, 2H), 4.20 (bs, 2H), 3.93 (s, 3H), 3.57 (m, 2H), 3.03 (m, 2H), 1.33 (t, J=7.1 Hz, 3H).

5-(3,5-Difluoro-benzenesulfonyl)-3-(4-dimethylamino-2-nitro-benzoylamino)-4,5,6,7-tetrahydro-pyrazolo[4,3-c]pyridine-1-carboxylic acid ethyl ester [(VII), Q=ethyl, Ra=Rb=H, A=D=E=CH, B=CR2, R=3,5-difluorophenyl, R1=nitro, R2=N,N-dimethylamino]

1H-NMR (400 MHz), δ (ppm, DMSO-$d_6$): 11.14 (s, 1H), 7.67 (m, 1H), 7.63 (d, J=8.78 Hz, 1H), 7.56-7.50 (m, 2H), 7.14 (d, J=2.56 Hz, 1H), 6.95 (dd, J1=8.78 Hz, J2=2.56 Hz, 1H), 4.37 (q, J=7.07 Hz, 2H), 4.12 (s, 2H), 3.54 (m, 2H), 3.04 (s, 6H), 3.01 (m, 2H), 1.32 (t, J=7.07 Hz, 3H).

5-(3,5-Difluoro-benzenesulfonyl)-3-(2-fluoro-6-nitro-benzoylamino)-4,5,6,7-tetrahydro-pyrazolo[4,3-c]pyridine-1-carboxylic acid ethyl ester [(VII), Q=ethyl, Ra=Rb=H, A=B=D=CH, E=CR2, R=3,5-difluorophenyl, R1=nitro, R2=fluoro]

1H-NMR (400 MHz), δ (ppm, DMSO-$d_6$): 11.57 (s, 1H), 8.14 (d, J=7.8 Hz, 1H), 7.92-7.82 (m, 2H), 7.69 (m, 1H), 7.52 (m, 2H), 4.39 (q, J=7.1 Hz, 2H), 4.27 (bs, 2H), 3.60 (m, 2H), 3.04 (m, 2H), 1.33 (t, J=7.1 Hz, 3H).

5-(3,5-Difluoro-benzenesulfonyl)-3-(2-nitro-benzoylamino)-4,5,6,7-tetrahydro-pyrazolo[4,3-c]pyridine-1-carboxylic acid ethyl ester [(VII), Q=ethyl, Ra=Rb=H, A=B=D=E=CH, R=3,5-difluorophenyl, R1=nitro]

1H-NMR (400 MHz), δ (ppm, DMSO-$d_6$): 11.42 (s, 1H), 8.16 (dd, J1=8.29 Hz, J2=1.09 Hz, 1H), 7.89 (dd, J1=8.78 Hz, J2=7.44 Hz, 1H), 7.81 (m, 2H), 7.69 (m, 1H), 7.55 (m, 2H), 4.39 (q, J=7.07 Hz, 2H), 4.25 (m, 2H), 3.58 (m, 2H), 3.04 (m, 2H), 1.83 (t, J1=7.07 Hz, 3H).

5-(3,5-Difluoro-benzenesulfonyl)-7,7-dimethyl-3-[4-(4-methyl-piperazin-1-yl)-2-nitro-benzoylamino]-4,5,6,7-tetrahydro-pyrazolo[4,3-c]pyridine-2-carboxylic acid ethyl ester [(VII), Q=ethyl, Ra=Rb=methyl, A=D=E=CH, B=CR2, R1=nitro, R2=4-methylpiperazin-1-yl]

1H-NMR (400 MHz), δ (ppm, DMSO-$d_6$): 10.64 (s, 1H), 7.71 (m, 1H), 7.60 (d, J1=8.78 Hz, 1H), 7.54 (m, 2H), 7.47 (d, J2=2.56 Hz, 1H), 7.29 (dd, J1=8.78 Hz, J2=2.56 Hz, 1H), 4.37 (q, J=7.19 Hz, 2H), 4.00 (s, 2H), 3.37 (m, 4H), 3.20 (s, 2H), 2.42 (m, 4H), 2.22, 2.20 (s, 3H), 1.29 (t, J=7.19 Hz, 3H).

5-(3,5-Difluoro-benzenesulfonyl)-7,7-dimethyl-3-(4-morpholin-4-yl-2-nitro-benzoylamino)-4,5,6,7-tetrahydro-pyrazolo[4,3-c]pyridine-2-carboxylic acid ethyl ester [(VII), Q=ethyl, Ra=Rb=methyl, A=D=E=CH, B=CR2, R=3,5-difluorophenyl, R1=nitro, R2=morpholin-4-yl]

1H-NMR (400 MHz), δ ppm, DMSO-$d_6$): 10.69 (s, 1H), 7.74 (m, 1H), 7.65 (d, J=8.8 Hz, 1H), 7.56 (m, 2H), 7.49 (d, J=2.6 Hz, 1H), 7.33 (dd, J1=8.8 Hz, J2=2.6 Hz, 1H), 4.40 (q, J=7.1 Hz, 2H), 4.03 (bs, 2H), 3.77 (m, 4H), 3.36 (m, 4H), 3.23 (bs, 2H), 1.31 (t, J=7.1 Hz, 3H), 1.30 (s, 6H).

5-(3,5-Difluoro-benzenesulfonyl)-7,7-dimethyl-3-(2-nitro-4-pyrrolidin-1-ylmethyl-benzoylamino)-4,5,6,7-tetrahydro-pyrazolo[4,3-c]pyridine-2-carboxylic acid ethyl ester [(VII), Q=ethyl, Ra=Rb=methyl, A=D=E=CH, B=CR2, R1=nitro, R2=pyrrolidin-1-yl-methyl]

1H-NMR (400 MHz), δ (ppm, DMSO-$d_6$): 10.95 (s, 1H), 8.08 (s, 1H), 7.85 (d, bs, J1=7.80 Hz, 1H), 7.74 (m, 1H), 7.70 (d, J1=7.80 Hz, 1H), 7.54 (m, 2H), 4.41 (q, J=7.08 Hz, 2H), 4.08 (s, 2H), 3.77 (s, 2H), 3.37-3.29 (m, 4H), 3.24 (s, 2H), 1.75 (m, 4H), 1.35-1.31 (m, 9H).

5-(3,5-Difluoro-benzenesulfonyl)-7,7-dimethyl-3-(2-nitro-benzoylamino)-4,5,6,7-tetrahydro-pyrazolo[4,3-c]pyridine-2-carboxylic acid ethyl ester [(VII), Q=ethyl, Ra=Rb=methyl, A=B=D=E=CH, R=3,5-difluorophenyl, R1=nitro]

1H-NMR (400 MHz), δ (ppm, DMSO-$d_6$): 10.98 (s, 1H), 8.20 (d, J=8.05 Hz, 1H), 7.95 (ddd, J1=8.05 Hz, J2=7.44 Hz, J3=0.85 Hz, 1H), 7.83 (m, 1H), 7.77-7.72 (m, 2H), 7.55 (m, 2H), 4.41 (q, J=7.07 Hz, 2H), 4.10 (s, 2H), 3.25 (s, 2H), 1.85-1.29 (m, 9H).

3-[4-(4-Methyl-piperazin-1-yl)-2-nitro-benzoylamino]-5-(pyridine-3-sulfonyl)-4,5,6,7-tetrahydro-pyrazolo[4,3-c]pyridine-1-carboxylic acid ethyl ester [(VII), Q=ethyl, Ra=Rb=H, A=D=E=CH, B=CR2, R=3-pyridyl, R1=nitro, R2=4-methylpiperazin-1-yl]

1H-NMR (400 MHz), δ (ppm, DMSO-$d_6$): 11.21 (s, 1H), 8.96 (m, 1H), 8.86 (m, 1H), 8.21 (m, 1H), 7.67-7.63 (m, 2H), 7.45 (d, J=2.6 Hz, 1H), 7.25 (dd, J1=2.6 Hz, J2=8.8 Hz, 1H), 4.37 (q, J=7.1 Hz, 2H), 4.17 (bs, 2H), 3.54 (m, 2H), 3.38 (m, 4H), 3.00 (m, 2H), 2.47 (m, 4H), 2.25 (s, 3H), 1.32 8t, J=7.1 Hz, 3H).

5-Methanesulfonyl-3-[4-(4-methyl-piperazin-1-yl)-2-nitro-benzoylamino]-4,5,6,7-tetrahydro-pyrazolo[4,3-c]pyridine-1-carboxylic acid ethyl ester [(VII), Q=ethyl, Ra=Rb=H, A=D=E=CH, B=CR2, R=methyl, R1=nitro, R2=4-methylpiperazin-1-yl]

1H-NMR (400 MHz), δ (ppm, DMSO-$d_6$): 11.20 (s, 1H), 7.65 (d, J1=8.78 Hz, 1H), 7.43 (d, J2=2.56 Hz, 1H), 7.24 (dd, J1=8.78 Hz, J2=2.56 Hz, 1H), 4.41 (q, J=7.07 Hz, 2H), 4.19 (s, 2H), 3.52 (m, 2H), 3.37 (m, 4H), 3.11 (m, 2H), 2.94 (s, 3H), 2.45 (m, 4H), 2.24 (s, 3H), 1.35 (t, J=7.07 Hz, 3H).

3-[4-(4-Methyl-piperazin-1-yl)-2-nitro-benzoylamino]-5-phenylmethanesulfonyl-4,5,6,7-tetrahydro-pyrazolo[4,3-c]pyridine-1-carboxylic acid ethyl ester [(VII), Q=ethyl, Ra=Rb=H, A=D=E=CH, B=CR2, R=benzyl, R1=nitro, R2=4-methylpiperazin-1-yl]

1H-NMR (400 MHz), δ (ppm, DMSO-$d_6$): 11.17 (s, 1H), 7.63 (d, J=8.70 Hz, 1H), 7.42 (d, J=2.29 Hz, 1H), 7.32 (m, 5H), 7.23 (dd, J1=8.70 Hz, J2=2.29 Hz, 1H), 4.45 (s, 2H), 4.39 (q, J=7.09 Hz, 2H), 4.15 (s, 2H), 3.45 (m, 2H), 3.36 (m, 4H), 2.87 (m, 2H), 2.44 (m, 4H), 2.23 (s, 3H), 1.33 (t, J=7.07 Hz, 3H).

EXAMPLE 12

Preparation of 3-[2-Amino-4-(4-methyl-piperazin-1-yl)-benzoylamino]-5-(3,5-difluoro-benzenesulfonyl)-4,5,6,7-tetrahydro-pyrazolo[4,3-c]pyridine-1-carboxylic acid ethyl ester hydrochloride [(VII), Q=ethyl, Ra=Rb=H, A=D=E=CH, B=CR2, R=3,5-difluorophenyl, R1=amino, R2=4-methylpiperazin-1-yl]

A suspension of ethyl 5-(3,5-difluoro-benzenesulfonyl)-3-[4-(4-methyl-piperazin-1-yl)-2-nitro-benzoylamino]-4,5,6,7-tetrahydro-pyrazolo[4,3-c]pyridine-1-carboxylic acid ethyl ester (2.50 g, 3.95 mmol) in THF:water:ethanol (1:1.5:2, 90 mL) was treated with cyclohexene (20 eq., 20 mL), 23% HCl (2 eq., 1.1 mL) and 10% Pd—C (0.77 g) at reflux for 1 hour. The reaction mixture was filtered, washed thoroughly with ethanol and evaporated to dryness. The title compound was obtained as beige powder (2.5 g, quantitative) and it was used in the next steps without any further purification.

1H-NMR (400 MHz), δ (ppm, DMSO-$d_6$): 10.52 (s, 1H), 7.72 (d, J=9.02 Hz, 1H), 7.68 (m, 1H), 7.57 (m, 2H), 6.32 (d, J=9.02 Hz, 1H), 6.27 (m, 1H), 4.37 (q, J=7.07 Hz, 2H), 4.15 (s, 2H), 3.90 (m, 2H), 3.55-3.00 (m, 10H), 2.85, 2.83 (s, 3H), 1.32 (t, J=7.07 Hz, 3H), mixture of rotamers.

Operating in an analogous way, the following compounds were obtained:

3-[2-Amino-4-(4-methyl-piperazin-1-yl)-benzoylamino]-5-(3-fluoro-benzenesulfonyl)-4,5,6,7-tetrahydro-pyrazolo[4,3-c]pyridine-1-carboxylic acid ethyl ester hydrochloride [(VII), Q=ethyl, Ra=Rb=H, A=D=E=CH, B=CR2, R=3-fluorophenyl, R1=amino, R2=4-methylpiperazin-1-yl]

1H-NMR (400 MHz), δ (ppm, DMSO-$d_6$): 10.52 (bs, 1H), 10.41 (bs, 1H), 7.73 (d, J=9.0 Hz, 1H), 7.69-7.55 (m, 5H), 6.34 (dd, J1=9.0 Hz, J2=2.2 Hz, 1H), 6.28 (d, J=2.2 Hz, 1H), 4.37 (q, J=7.2 Hz, 2H), 4.11 (bs, 2H), 3.89 (m, 2H), 3.13 (m, 4H), 2.99 (m, 2H), 2.83 (d, J=4.4 Hz, 3H), 1.32 (t, J=7.2 Hz, 3H).

3-[2-Amino-4-(4-methyl-piperazin-1-yl)-benzoylamino]-5-(2-fluoro-benzenesulfonyl)-4,5,6,7-tetrahydro-pyrazolo[4,3-c]pyridine-1-carboxylic acid ethyl ester [(VII), Q=ethyl, Ra=Rb=H, A=D=E=CH, B=CR2, R=2-fluorophenyl, R1=amino, R2=4-methylpiperazin-1-yl]

1H-NMR (400 MHz), δ (ppm, DMSO-$d_6$): 10.43 (bs, 1H), 7.85 (m, 1H), 7.72 (m, 1H), 7.64 (d, J=9.1 Hz, 1H), 7.40 (m, 2H), 6.53 (bs, 2H), 6.19 (dd, J1=9.1 Hz, J2=2.4 Hz, 1H), 6.15 (d, J=2.4 Hz, 1H), 4.35 (q, J=7.1 Hz, 2H), 4.15 (bs, 2H), 3.57 (m, 2H), 3.19 (m, 4H), 2.97 (m, 2H), 2.41 (m, 4H), 2.21 (s, 3H), 1.31 (t, J=7.1 Hz, 3H).

3-[2-Amino-4-(4-methyl-piperazin-1-yl)-benzoylamino]-5-benzenesulfonyl-4,5,6,7-tetrahydro-pyrazolo[4,3-c]pyridine-1-carboxylic acid ethyl ester [(VII), Q=ethyl, Ra=Rb=H, A=D=E=CH, B=CR2, R=phenyl, R1=amino, R2=4-methylpiperazin-1-yl]

1H-NMR (400 MHz), δ (ppm, DMSO-$d_6$): 10.40 (bs, 1H), 7.79 (d, J=7.1 Hz, 2H), 7.73-7.70 (m, 5H), 6.56 (bs, 1H), 6.21 (dd, J1=9.0 Hz, J2=2.3 Hz, 1H), 6.18 (d, J=2.3 Hz, 1H), 4.36 (q, J=7.1 Hz, 2H), 4.04 (bs, 2H), 3.45 (m, 2H), 3.22 (m, 4H), 2.97 (m, 2H), 2.44 (m, 4H), 2.20 (s, 3H), 1.32 (t, J=7.1 Hz, 3H).

3-(2-Amino-4-morpholin-4-yl-benzoylamino)-5-(3,5-difluoro-benzenesulfonyl)-4,5,6,7-tetrahydro-pyrazolo[4,3-c]pyridine-1-carboxylic acid ethyl ester hydrochloride [(VII), Q=ethyl, Ra=Rb=H, A=D=E=CH, B=CR2, R=3,5-difluorophenyl, R1=amino, R2=morpholin-4-yl]

1H-NMR (400 MHz), δ (ppm, DMSO-$d_6$): 10.52 (s, 1H), 7.75-7.65 (m, 2H), 7.61-7.56 (m, 2H), 6.37-6.24 (m, 2H), 4.38 (q, J=7.1 Hz, 2H), 4.16 (bs, 2H), 3.74 (m, 4H), 3.56 (m, 2H), 3.19 (m, 4H), 3.01 (m, 2H), 1.33 (t, J=7.1 Hz, 3H).

3-{2-Amino-4-[(2-dimethylamino-ethyl)-methylamino]-benzoylamino}-5-(3,5-difluoro-benzenesulfonyl)-4,5,6,7-tetrahydro-pyrazolo[4,3-c]pyridine-1-carboxylic acid ethyl ester [(VII), Q=ethyl, Ra=Rb=H, A=D=E=CH, B=CR2, R=3,5-difluorophenyl, R1=amino, R2=(2-dimethylamino-ethyl)-methyl-amino]

1H-NMR (400 MHz), δ (ppm, DMSO-$d_6$): 10.30 (s, 1H), 7.66 (m, 1H), 7.62 (d, J=9.1 Hz, 1H), 7.57-7.55 (m, 2H), 6.57 (bs, 2H), 5.99 (dd, J1=2.6 Hz, J2=9.1 Hz, 1H), 5.91 (d, J=2.6 Hz, 1H), 4.36 (q, J=7.1 Hz, 2H), 4.12 (bs, 2H), 3.54 (m, 2H), 3.40 (m, 2H), 2.98 (m, 2H), 2.91 (s, 3H), 2.37 (m, 2H), 2.19 (s, 6H), 1.31 (t, J=7.1 Hz, 3H).

3-[2-Amino-4-(2-dimethylamino-ethoxy)-benzoylamino]-5-(3,5-difluoro-benzenesulfonyl)-4,5,6,7-tetrahydro-pyrazolo[4,3-c]pyridine-1-carboxylic acid ethyl ester [(VII) Q=ethyl, Ra=Rb=H, A=D=E=CH, B=CR2, R=3,5-difluorophenyl, R1=amino, R2=2-dimethylamino-ethoxy]

1H-NMR (400 MHz), δ (ppm, DMSO-$d_6$): 10.54 (s, 1H), 7.71 (d, J=9.0 Hz, 1H), 7.66 (m, 1H), 7.59-7.55 (m, 2H), 6.70 (bs, 2H), 6.27 (d, J=2.6 Hz, 1H), 6.14 (dd, J1=2.6 Hz, J2=9.0 Hz, 1H), 4.36 (q, J=7.1 Hz, 2H), 4.14 (bs, 2H), 4.02 (m, 2H), 3.54 (m, 2H), 2.99 (m, 2H), 2.62 (m, 2H), 2.22 (s, 6H), 1.31 (t, J=7.1 Hz, 3H).

3-(2-Amino-4-methoxy-benzoylamino)-5-(3,5-difluoro-benzenesulfonyl)-4,5,6,7-tetrahydro-pyrazolo[4,3-c]pyridine-1-carboxylic acid ethyl ester [(VII), Q=ethyl, Ra=Rb=H, A=D=E=CH, B=CR2, R=3,5-difluorophenyl, R1=amino, R2=methoxy]

1H-NMR (400 MHz), δ (ppm, DMSO-$d_6$): 10.54 (bs, 1H), 7.73 (d, J=8.9 Hz, 1H), 7.66 (m, 1H), 7.57 (m, 2H), 6.73 (bs, 2H), 6.27 (d, J=2.6 Hz, 1H), 6.14 (dd, J1=8.9 Hz, J2=2.6 Hz, 1H), 4.37 (q, J=7.1 Hz, 2H), 4.15 (bs, 2H), 3.73 (s, 3H), 3.54 (m, 2H), 2.99 (m, 2H), 1.31 (t, J=7.1 Hz, 3H).

3-(2-Amino-4-dimethylamino-benzoylamino)-5-(3,5-difluoro-benzenesulfonyl)-4,5,6,7-tetrahydro-pyrazolo[4,3-c]pyridine-1-carboxylic acid ethyl ester [(VII), Q=ethyl, Ra=Rb=H, A=D=E=CH, B=CR2, R=3,5-difluorophenyl, R1=amino, R2=N,N-dimethylamino]

ESI(+) MS: m/z 549 (MH$^+$).

3-(2-Amino-benzoylamino)-5-(3,5-difluoro-benzenesulfonyl)-4,5,6,7-tetrahydro-pyrazolo[4,3-c]pyridine-1-carboxylic acid ethyl ester [(VII), Q=ethyl, Ra=Rb=H, A=B=D=E=CH, R=3,5-difluorophenyl, R1=amino]

ESI(+) MS: m/z 506 (MH$^+$).

3-[2-Amino-4-(4-methyl-piperazin-1-yl)-benzoylamino]-5-(3,5-difluoro-benzenesulfonyl)-7,7-dimethyl-4,5,6,7-tetrahydro-pyrazolo[4,3-c]pyridine-2-carboxylic acid ethyl ester dihydrochloride [(VII), Q=ethyl, Ra=Rb=methyl, A=D=E=CH, B=CR2, R=3,5-difluorophenyl, R1=amino, R2=4-methylpiperazin-1-yl]

1H-NMR (400 MHz), δ (ppm, DMSO-$d_6$): 10.49 (bs, 1H), 7.69 (m, 1H), 7.59 (m, 2H), 7.57 (d, J1=8.91 Hz, 1H), 7.35

(dd, J1=8.91 Hz, J2=2.19 Hz, 1H), 6.25 (d, J2=2.19 Hz, 1H), 4.31 (q, J=7.07 Hz, 2H), 4.08 (s, 2H), 3.86 (m, 4H), 3.19 (s, 2H), 3.10 (m, 4H), 2.82, 2.80 (s, 3H), 1.27 (s, 6H), 1.23 (t, J=7.07 Hz, 3H), mixture of rotamers.

3-(2-Amino-benzoylamino)-5-(3,5-difluoro-benzenesulfonyl)-7,7-dimethyl-4,5,6,7-tetrahydro-pyrazolo[4,3-c]pyridine-2-carboxylic acid ethyl ester [(VII), Q=ethyl, Ra=Rb=methyl, A=B=D=E=CH, R=3,5-difluorophenyl, R1=amino]

1H-NMR (400 MHz), δ (ppm, DMSO-d₆): 10.14 (bs, 1H), 7.73-7.58 (m, 4H), 7.25 (ddd, bs, J1=8.42 Hz, J3=1.22 Hz, 1H), 6.78 (d, J=8.42 Hz, 1H), 6.62-6.58 (m, 1H), 6.53 (bs, 2H), 4.33 (q, J=7.07 Hz, 2H), 4.10 (s, 2H), 3.20 (s, 2H), 1.29 (s, 6H), 1.23 (t, J=7.07 Hz, 3H).

EXAMPLE 13

3-{2-Amino-4-[4-(2,2,2-trifluoro-acetyl)-piperazin-1-yl]-benzoylamino}-5-(3,5-difluoro-benzenesulfonyl)-4,5,6,7-tetrahydro-pyrazolo[4,3-c]pyridine-1-carboxylic acid ethyl ester [(VII), Q=ethyl, Ra=Rb=H, A=D=E=CH, B=CR2, R=3,5-difluorophenyl, R1=amino, R2=4-trifluoroacetylpiperazin-1-yl]

To a solution of 5-(3,5-difluoro-benzenesulfonyl)-3-{2-nitro-4-[4-(2,2,2-trifluoro-acetyl)-piperazin-1-yl]-benzoylamino}-4,5,6,7-tetrahydro-pyrazolo[4,3-c]pyridine-1-carboxylic acid ethyl ester (0.48 g, 0.67 mmol) in dioxane (20 mL) 10% Pd/C (0.15 g) and cyclohexene (5 mL) were added. The mixture was stiffed at 90° C. for 5 h, and then filtered while hot, washing with dioxane and dichloromethane. After evaporation the title compound (0.44 g, 95% yield) was obtained as violet solid.

1H-NMR (400 MHz), δ (ppm, DMSO-d₆): 10.45 (bs, 1H), 7.68 (d, J=9.3 Hz, 1H), 7.65 (m, 1H), 7.56 (m, 2H), 6.61 (bs, 2H), 6.22 (dd, J1=9.3 Hz, J2=2.4 Hz, 1H), 6.18 (d, J=2.4 Hz, 1H), 4.35 (q, J=7.1 Hz, 2H), 4.14 (bs, 2H), 3.70 (m, 4H), 3.57 (m, 2H), 3.32 (m, 4H), 2.98 (m, 2H), 1.31 (t, J=7.1 Hz, 3H).

EXAMPLE 14

Preparation of 5-(3,5-Difluoro-benzenesulfonyl)-3-[2-[(furan-2-carbonyl)-amino]-4-(4-methyl-piperazin-1-yl)-benzoylamino]-4,5,6,7-tetrahydro-pyrazolo[4,3-c]pyridine-1-carboxylic acid ethyl ester [(VII), Q=ethyl, Ra=Rb=H, A=D=E=CH, B=CR2, R=3,5-difluorophenyl, R1=NHCOR4, R2=4-methylpiperazin-1-yl, R4=2-furyl]

2-Furoyl chloride (3.4 eq., 0.22 mL, 2.14 mmol) was slowly added to a solution of 3-[(2-amino-4-(4-methyl-piperazin-1-yl)-benzoylamino]-5-(3,5-difluoro-benzenesulfonyl)-4,5,6,7-tetrahydro-pyrazolo[4,3-c]pyridine-1-carboxylic acid ethyl ester hydrochloride (0.4 g, 0.63 mmol) and N,N-diisopropylethylamine (7 eq., 0.79 mL, 4.56 mmol) in dry THF (10 mL) at room temperature. The reaction mixture was stirred at 55° C. for 3 hours. After removal of the solvent, the crude material was diluted with dichloromethane (20 mL), washed with water (2×10 mL), saturated sodium hydrogenocarbonate (2×10 mL), brine (10 mL), dried over sodium sulfate, evaporated to dryness and purified by flash chromatography on silica gel, using acetone-dichloromethane 80:20 as eluant. The title compound was obtained as beige powder (0.30 g, 68% yield).

1H-NMR (400 MHz), δ (ppm, DMSO-d₆): 12.51 (s, 1H), 10.97 (s, 1H), 8.29 (d, J2=2.56 Hz, 1H), 7.96 (d, J1=9.15 Hz, 1H), 7.82 (d, J2=1.58 Hz, 1H), 7.58 (m, 3H), 7.19 (d, J1=3.78 Hz, 1H), 6.76 (dd, J1=9.15 Hz, J2=2.56 Hz, 1H), 6.69 (dd, J1=3.78 Hz, J2=1.58 Hz, 1H), 4.36 (q, J=7.08 Hz, 2H), 4.27 (s, 2H), 3.57 (m, 2H), 3.31 (m, 4H), 2.98 (m, 2H), 2.53 (m, 4H), 2.28 (s, 3H), 1.31 (t, J=7.08 Hz, 3H).

Operating in an analogous way, and using the suitable acid chloride, the following compounds were obtained:

5-(3,5-Difluoro-benzenesulfonyl)-3-(4-(4-methyl-piperazin-1-yl)-2-{[1-(toluene-4-sulfonyl)-1H-pyrrole-3-carbonyl]-amino}-benzoylamino)-4,5,6,7-tetrahydro-pyrazolo[4,3-c]pyridine-1-carboxylic acid ethyl ester [(VII), Q=ethyl, Ra=Rb=H, A=D=E=CH, B=CR2, R=3,5-difluorophenyl, R1=NHCOR4, R2=4-methylpiperazin-1-yl, R4=1-(toluene-4-sulfonyl)-1H-pyrrol-3-yl]

1H-NMR (400 MHz), δ (ppm, DMSO-d₆): 12.10 (s, 1H), 10.94 (s, 1H), 8.14 (d, J2=2.44 Hz, 1H), 7.91 (m, 3H), 7.81 (dd, J=2.2 Hz, 1H), 7.53 (m, 3H), 7.43 (d, J=8.17 Hz, 2H), 7.40 (dd, J1=3.30 Hz, J2=2.2 Hz, 1H), 6.73 (dd, J1=9.02 Hz, J2=2.44 Hz, 1H), 6.67 (dd, J1=3.30 Hz, J2=1.58 Hz, 1H), 4.36 (q, J=6.95 Hz, 2H), 4.23 (s, 2H), 3.55 (m, 2H), 3.31 (m, 4H), 2.98 (m, 2H), 2.44 (m, 4H), 2.36 (s, 3H), 2.22 (s, 3H), 1.33 (t, J=6.95 Hz, 3H).

5-(3,5-Difluoro-benzenesulfonyl)-3-[2-isobutyrylamino-4-(4-methyl-piperazin-1-yl)-benzoylamino]-4,5,6,7-tetrahydro-pyrazolo[4,3-c]pyridine-1-carboxylic acid ethyl ester [(VII), Q=ethyl, Ra=Rb=H, A=D=E=CH, B=CR2, R=3,5-difluorophenyl, R1=NHCOR4, R2=4-methylpiperazin-1-yl, R4=isopropyl]

1H-NMR (400 MHz), δ (ppm, DMSO-d₆): 11.61 (s, 1H), 10.93 (s, 1H), 8.18 (d, J2=2.56 Hz, 1H), 7.91 (d, J1=9.14 Hz, 1H), 7.68 (m, 1H), 7.58 (m, 2H), 6.70 (dd, J1=9.14 Hz, J2=2.56 Hz, 1H), 4.37 (q, J=7.07 Hz, 2H), 4.17 (s, 2H), 3.54 (m, 2H), 3.32 (m, 4H), 3.02 (m, 2H), 2.50 (m, 1H), 2.44 (m, 4H), 2.22 (s, 3H), 1.32 (t, J=7.07 Hz, 3H), 1.15 (d, J=6.95 Hz, 6H).

5-(3,5-Difluoro-benzenesulfonyl)-3-{4-dimethylamino-2-[(tetrahydro-pyran-4-carbonyl)-amino]-benzoylamino}-4,5,6,7-tetrahydro-pyrazolo[4,3-c]pyridine-1-carboxylic acid ethyl ester [(VII), Q=ethyl, Ra=Rb=H, A=D=E=CH, B=CR2, R=3,5-difluorophenyl, R1=NHCOR4, R2=N,N-dimethylamino, R4=tetrahydropyran-4-yl]

1H-NMR (400 MHz), δ (ppm, DMSO-d₆): 11.80 (s, 1H), 10.85 (s, 1H), 8.03 (d, J=2.44 Hz, 1H), 7.92 (d, J=9.14 Hz, 1H), 7.68 (m, 1H), 7.61 (m, 2H), 6.47 (dd, J1=9.14 Hz, J2=2.44 Hz, 1H), 4.38 (q, J=7.07 Hz, 2H), 4.21 (s, 2H), 3.87 (m, bs, 2H), 3.56 (m, 2H), 3.38-3.30 (m, bs, 3H), 3.04-2.97 (m, 8H), 1.81 (m, bs, 2H), 1.66 (m, bs, 2H), 1.33 (t, J=7.07 Hz, 3H).

5-(3,5-Difluoro-benzenesulfonyl)-3-{2-[(1H-pyrrole-2-carbonyl)-amino]-benzoylamino}-4,5,6,7-tetrahydro-pyrazolo[4,3-c]pyridine-1-carboxylic acid ethyl ester [(VII), Q=ethyl, Ra=Rb=H, A=B=D=E=CH, R=3,5-difluorophenyl, R1=NHCOR4, R4=pyrrol-2-yl]

1H-NMR (400 MHz), δ (ppm, DMSO-d₆): 11.79 (bs, 1H), 11.53 (bs, 1H), 11.30 (s, 1H), 8.51 (d, J=8.24 Hz, 1H), 7.99 (d, J=7.55 Hz, 1H), 7.65-7.56 (m, 4H), 7.17 (dd, bs, J=7.55 Hz, 1H), 6.99 (m, 1H), 6.75 (m, 1H), 6.14 (m, 1H), 4.37 (q, J=7.09 Hz, 2H), 4.30 (s, 2H), 3.57 (m, 2H), 3.00 (m, 2H), 1.31 (t, J=7.09 Hz, 3H).

5-(3,5-Difluoro-benzenesulfonyl)-7,7-dimethyl-3-(4-(4-methyl-piperazin-1-yl)-2-{[1-(toluene-4-sulfonyl)-1H-pyrrole-3-carbonyl]-amino}-benzoylamino)-4,5,6,7-tetrahydro-pyrazolo[4,3-c]pyridine-2-carboxylic acid ethyl ester [(VII), Q=ethyl, Ra=Rb=methyl, A=D=E=CH, B=CR2, R=3,5-difluorophenyl, R1=NHCOR4, R2=4-methylpiperazin-1-yl, R4=1-(toluene-4-sulfonyl)-1H-pyrrole-3-yl]

1H-NMR (400 MHz), δ (ppm, DMSO-$d_6$): 11.88 (s, 1H), 10.34 (s, 1H), 8.10 (d, bs, J=2.31 Hz, 1H), 7.92 (d, J=8.42 Hz, 2H), 7.83-7.80 (m, 2H), 7.63 (m, 1H), 7.53 (m, 2H), 7.44 (d, J=8.42 Hz, 2H), 7.43 (m, 1H), 6.82 (dd, bs, J1=8.78 Hz, J2=2.31 Hz, 1H), 6.65 (m, 1H), 4.29 (q, J=7.07 Hz, 2H), 4.13 (s, 2H), 3.40-3.27 (m, 4H), 3.19 (s, 2H), 2.45 (m, 4H), 2.37 (s, 3H), 2.23 (s, 3H), 1.29 (s, 6H), 1.19 (t, J=7.07 Hz, 3H).

5-(3,5-Difluoro-benzenesulfonyl)-7,7-dimethyl-3-{4-morpholin-4-yl-2-[(tetrahydro-pyran-4-carbonyl)-amino]-benzoylamino}-4,5,6,7-tetrahydro-pyrazolo[4,3-c]pyridine-2-carboxylic acid ethyl ester [(VII), Q=ethyl, Ra=Rb=methyl, A=D=E=CH, B=CR2, R=3,5-difluorophenyl, R1=NHCOR4, R2=4-methylpiperazin-1-yl, R4=tetrahydro-pyran-4-yl]

1H-NMR (400 MHz), δ (ppm, DMSO-$d_6$): 11.43 (s, 1H), 10.34 (s, 1H), 8.20 (d, J=2.5 Hz, 1H), 7.83 (d, J=9.1 Hz, 1H), 7.73 (m, 1H), 7.62 (m, 2H), 6.82 (dd, J1=2.5 HZ, J2=9.1 Hz, 1H), 4.35 (q, J=7.1 Hz, 2H), 4.14 (bs, 2H), 3.88 (m, 2H), 3.77 (m, 4H), 3.86 (m, 2H), 3.28 (m, 4H), 3.22 (bs, 2H), 2.55 (m, 1H), 1.78 (m, 2H), 1.64 (m, 2H), 1.31 (s, 6H), 1.24 (t, J=7.1 Hz, 3H).

EXAMPLE 15

Preparation of 2-Amino-N-[5-(3,5-difluoro-benzenesulfonyl)-4,5,6,7-tetrahydro-1H-pyrazolo[4,3-c]pyridin-3-yl]-4-(4-methyl-piperazin-1-yl)-benzamide [(I), Ra=Rb=H, A=D=E=CH, B=CR2, R=3,5-difluorophenyl, R1=amino, R2=4-methylpiperazin-1-yl]

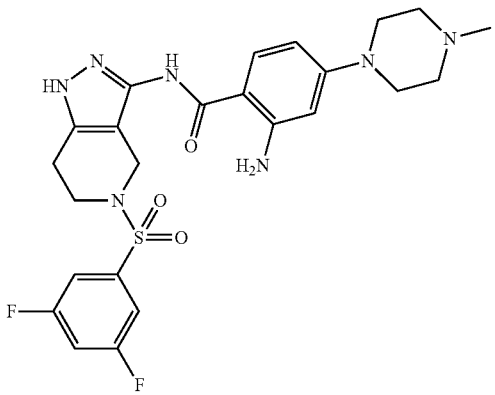

A solution of 3-[2-amino-4-(4-methyl-piperazin-1-yl)-benzoylamino]-5-(3,5-difluoro-benzenesulfonyl)-4,5,6,7-tetrahydro-pyrazolo[4,3-c]pyridine-1-carboxylic acid ethyl ester hydrochloride (0.13 g, 0.198 mmol) in methanol (5 mL) and triethylamine (20 eq., 0.55 mL) was stirred at room temperature for 20 hours and then evaporated. The crude material was chromatographed on silica gel, using dichloromethane-methanol-30% NH$_4$OH 95:5:0.5 as eluant. The title compound was obtained as colourless powder (0.08 g, 76% yield).

1H-NMR (400 MHz), δ (ppm, DMSO-$d_6$): 12.19 (s, 1H), 9.82 (s, H), 7.70-7.55 (m, 4H), 6.51 (s, 2H), 6.5-6.3 (m, 2H), 4.16 (s, 2H), 3.51 (m, 2H), 3.20 (m, 4H), 2.68 (m, 2H), 2.45 (m, 4H), 2.24 (s, 3H).

Operating in an analogous way, the following compounds were obtained:

N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-nitro-benzamide [(I), Ra=Rb=H, A=D=E=CH, B=CR2, R=3,5-difluorophenyl, R1=nitro, R2=4-methylpiperazin-1-yl]

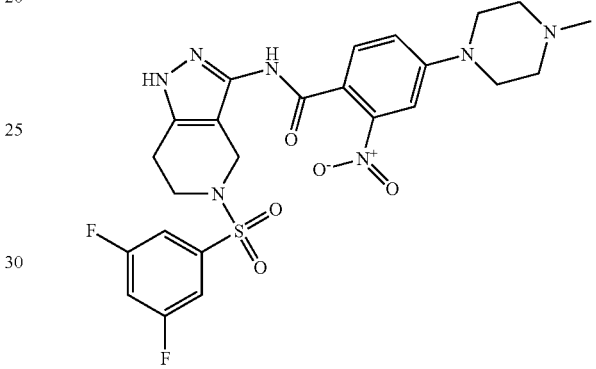

1H-NMR (400 MHz), δ (ppm, DMSO-$d_6$): 12.30 (s, 1H), 10.62 (s, 1H), 7.67 (m, 1H), 7.59 (d, J1=8.29 Hz, 1H), 7.52 (m, 2H), 7.43 (d, 1H), 7.25 (d, J1=8.29 Hz, 1H), 4.14 (s, 2H), 3.51 (m, 2H), 3.34 (m, 4H), 2.71 (m, 2H), 2.52 (m, 4H), 2.25 (s, 3H).

N-[5-(3,5-Difluoro-benzenesulfonyl)-4,5,6,7-tetrahydro-1H-pyrazolo[4,3-c]pyridin-3-yl]-2-fluoro-4-(4-methyl-piperazin-1-yl)-benzamide [(I), Ra=Rb=H, A=D=E=CH, B=CR2, R=3,5-difluorophenyl, R1=fluoro, R2=4-methylpiperazin-1-yl], cpd. 1

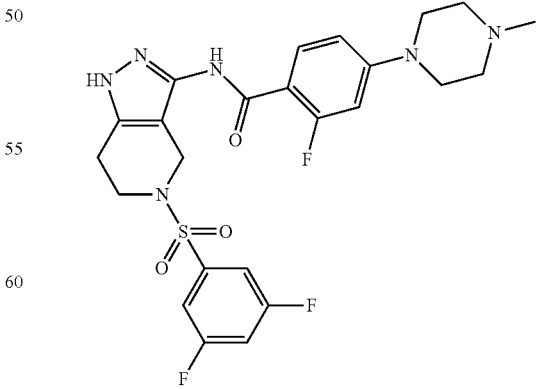

1H-NMR (400 MHz), δ (ppm, DMSO-$d_6$): 12.27 (s, 1H), 9.83 (s, 1H), 7.53-7.72 (m, 4H), 6.75-6.89 (m, 2H), 4.21 (s, 2H), 3.53 (t, J=5.67 Hz, 2H), 3.27-3.41 (m, 4H,) 2.63-2.74 (m, 2H), 2.45-2.58 (m, 4H), 2.29 (s, H).

2-Amino-N-[5-(3,5-difluoro-benzenesulfonyl)-7,7-dimethyl-4,5,6,7-tetrahydro-1H-pyrazolo[4,3-c]pyridin-3-yl]-4-(4-methyl-piperazin-1-yl)-benzamide [(I), Ra=Rb=methyl, A=D=E=CH, B=CR2, R=3,5-difluorophenyl, R1=amino, R2=4-methylpiperazin-1-yl]

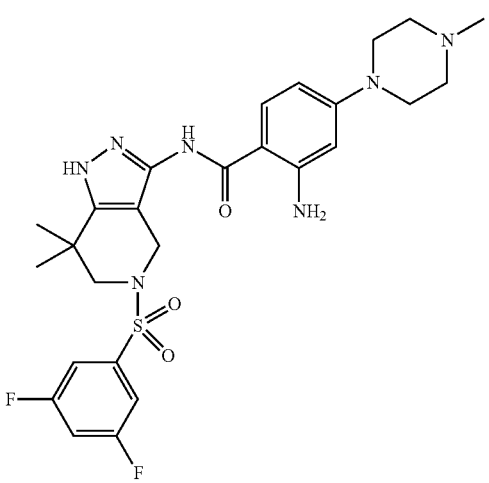

1H-NMR (400 MHz), δ (ppm, DMSO-d$_6$): 12.41, 12.33 (s, 1H), 9.78 (s, 1H), 7.70 (m, 1H), 7.61 (d, J1=9.15 Hz, 1H), 7.56 (m, 2H), 6.42 (bs, 2H), 6.21 (dd, J1=9.15 Hz, J2=2.08 Hz, 1H), 6.17 (d, J2=2.08 Hz, 1H), 3.97 (s, 2H), 3.19 (m, 4H), 3.15 (s, 2H), 2.43 (m, 4H), 2.22 (s, 3H), 1.28 (s, 6H), mixture of tautomers.

N-[5-(3,5-Difluoro-benzenesulfonyl)-7,7-dimethyl-4,5,6,7-tetrahydro-1H-pyrazolo[4,3-c]pyridin-3-yl]-4-dimethylamino-2-nitro-benzamide [(I), Ra=Rb=methyl, A=D=E=CH, B=CR2, R=3,5-difluorophenyl, R1=nitro, R2=dimethylamino]

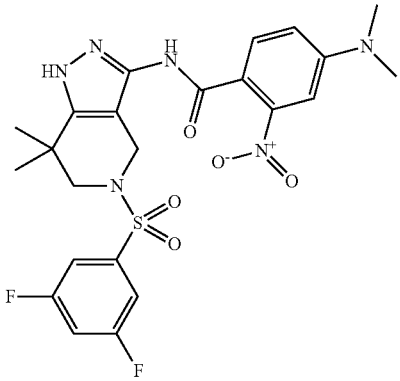

1H-NMR (400 MHz), δ (ppm, DMSO-d$_6$): 12.51 (s, 1H), 10.55 (bs, 1H), 7.72 (m, 1H), 7.60 (d, J=9.0 Hz, 1H), 7.53 (m, 2H), 7.13 (d, J=2.3 Hz, 1H), 6.96 (dd, J1=9.0 Hz, J2=2.3 Hz, 1H), 3.97 (bs, 2H), 3.15 (bs, 2H), 3.05 (s, 6H), 1.29 (s, 6H).

2-Amino-N-[5-(3,5-difluoro-benzenesulfonyl)-7,7-dimethyl-4,5,6,7-tetrahydro-1H-pyrazolo[4,3-c]pyridin-3-yl]-4-dimethylamino-benzamide [(I), Ra=Rb=methyl, A=D=E=CH, B=CR2, R=3,5-difluorophenyl, R1=amino, R2=dimethylamino]

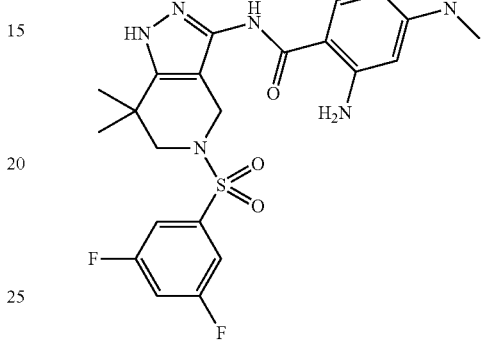

1H-NMR (400 MHz), δ (ppm, DMSO-d$_6$): 12.39 (bs, 1H), 9.70 (bs, 1H), 7.70 (m, 1H), 7.62-7.55 (m, 3H), 6.48 (bs, 2H), 6.02 (bd, 1H), 5.94 (d, J=2.4 Hz, 1H), 3.98 (bs, 2H), 3.15 (bs, 2H), 2.92 (bs, 6H), 1.28 (bs, 6H).

Furan-2-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide [(I), Ra=Rb=H, A=D=E=CH, B=CR2, R=3,5-difluorophenyl, R1=NHCOR4, R2=4-methylpiperazin-1-yl, R4=2-furyl], cpd. 31

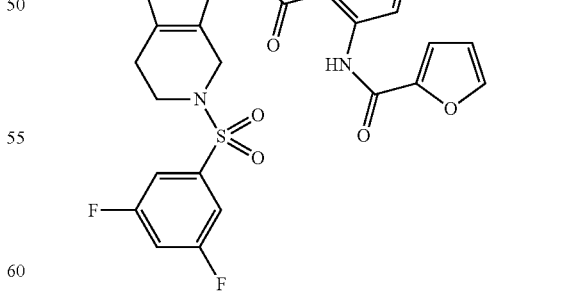

1H-NMR (400 MHz), δ (ppm, DMSO-d$_6$): 12.47 (s, 1H), 12.32 (s, 1H), 10.43 (s, 1H), 8.30 (d, J2=2.56 Hz, 1H), 7.93 (d, J1=9.03 Hz, 1H), 7.81 (m, 1H), 7.58 (m, 3H), 7.19 (d, J=3.29 Hz, 1H), 6.74 (dd, J1=9.03 Hz, J2=2.56 Hz, 1H), 6.68 (dd, J1=3.29 Hz, J2=1.71 Hz, 1H), 4.25 (s, 2H), 3.54 (m, 2H), 3.31 (m, 4H), 2.67 (m, 2H), 2.45 (m, 4H), 2.22 (s, 3H).

N-[5-(3,5-Difluoro-benzenesulfonyl)-4,5,6,7-tetrahydro-1H-pyrazolo[4,3-c]pyridin-3-yl]-2-isobutyrylamino-4-(4-methyl-piperazin-1-yl)-benzamide [(I), Ra=Rb=H, A=D=E=CH, B=CR2, R=3,5-difluorophenyl, R1=NHCOR4, R2=4-methylpiperazin-1-yl, R4=isopropyl], cpd. 5

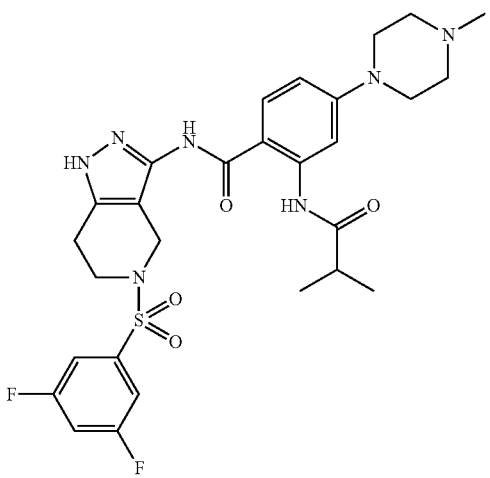

1H-NMR (400 MHz), δ (ppm, DMSO-d6): 12.32 (s, 1H), 11.81 (s, 1H), 10.38 (s, 1H), 8.19 (d, J2=2.44 Hz, 1H), 7.88 (d, J1=9.02 Hz, 1H), 7.65 (m, 1H), 7.56 (m, 2H), 6.68 (dd, J1=9.02 Hz, J2=2.44 Hz, 1H), 4.15 (s, 2H), 3.51 (m, 2H), 3.27 (m, 4H), 2.69 (m, 2H), 2.48 (m, 1H), 2.43 (m, 4H), 2.21 (s, 3H), 1.14 (d, J=6.95 Hz, 6H).

Tetrahydro-pyran-4-carboxylic acid {2-[5-(3,5-difluoro-benzenesulfonyl)-4,5,6,7-tetrahydro-1H-pyrazolo[4,3-c]pyridin-3-ylcarbamoyl]-5-dimethylaminophenyl}-amide [(I), Ra=Rb=H, A=D=E=CH, B=CR2, R=3,5-difluorophenyl, R1=NHCOR4, R2=N,N-dimethylamino, R4=tetrahydropyran-4-yl], cpd. 136

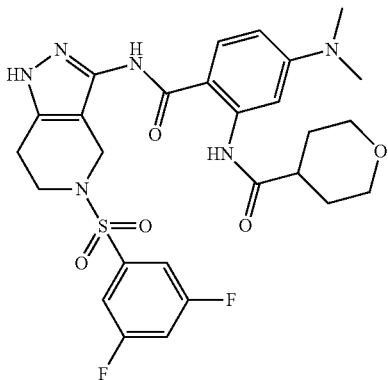

1H-NMR (400 MHz), δ (ppm, DMSO-d6): 12.44, 12.31 (s, 1H), 12.04, 11.73 (s, 1H), 10.30 (s, 1H), 8.04 (d, J=2.31 Hz, 1H), 7.90 (d, J=9.03 Hz, 1H), 7.66 (m, 1H), 7.60 (m, 2H), 6.46 (dd, bs, J1=9.03 Hz, J2=2.31 Hz, 1H), 4.21 (s, 2H), 3.87 (m, bs, 2H), 3.53 (m, 2H), 3.39-3.30 (m, bs, 3H), 3.04-2.97 (m, 8H), 1.81 (m, bs, 2H), 1.66 (m, bs, 2H).

1H-Pyrrole-2-carboxylic acid {2-[5-(3,5-difluoro-benzenesulfonyl)-4,5,6,7-tetrahydro-1H-pyrazolo[4,3-c]pyridin-3-ylcarbamoyl]-phenyl}-amide [(I), Ra=Rb=H, A=B=D=E=CH, R=3,5-difluorophenyl, R1=NHCOR4, R4=pyrrol-2-yl], cpd. 223

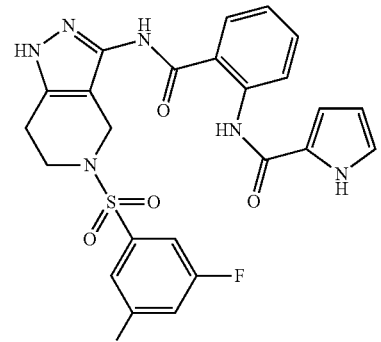

1H-NMR (400 MHz), δ (ppm, DMSO-d6): 12.41 (s, 1H), 11.82 (s, 1H), 11.81 (s, 1H), 10.80 (s, 1H), 8.59 (d, J=8.01 Hz, 1H), 7.99 (d, J=8.01 Hz, 1H), 7.62 (m, 1H), 7.56 (m, 1H), 7.16 (m, 1H), 6.99 (m, 1H), 6.73 (m, 1H), 6.14 (m, 1H), 4.29 (s, 2H), 3.54 (m, 2H), 2.69 (m, 2H).

3-Amino-N-[5-(3,5-difluoro-benzenesulfonyl)-4,5,6,7-tetrahydro-1H-pyrazolo[4,3-c]pyridin-3-yl]-isonicotinamide [(I), Ra=Rb=H, A=D=E=CH, B=N, R=3,5-difluorophenyl, R1=amino], cpd. 539

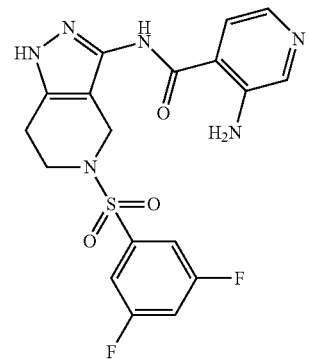

1H-NMR (400 MHz), δ (ppm, DMSO-d6): 12.35 (s, 1H), 10.50 (s, 1H), 8.20 (s, 1H), 7.78 (d, J=5.13 Hz, 1H), 7.66 (tt, J=9.12 Hz, 1H), 7.58 (m, 3H), 6.52 (bs, 2H), 4.19 (s, 2H), 3.52 (s, 2H), 2.70 (s, 2H).

2-Amino-N-[5-(3,5-difluoro-benzenesulfonyl)-7,7-dimethyl-4,5,6,7-tetrahydro-1H-pyrazolo[4,3-c]pyridin-3-yl]-benzamide [(I), Ra=Rb=methyl, A=B=D=E=CH, R=3,5-difluorophenyl, R1=amino], cpd. 541

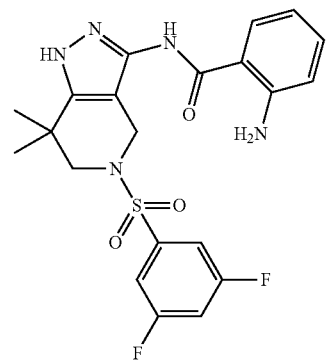

1H-NMR (400 MHz), δ (ppm, DMSO-d₆): 12.49 (s, 1H), 10.12 (s, 1H), 7.74, 7.66 (m, 2H), 7.58 (m, 2H), 7.20 (t, J=7.39 Hz, 1H), 6.76 (d, J=7.39 Hz, 1H), 6.55 (t, J=7.06 Hz, 1H), 6.44 (bs, 2H), 4.00 (s, 2H), 3.16 (s, 2H), 1.29 (s, 6H).

2-Amino-N-[5-(3-fluoro-benzenesulfonyl)-7,7-dimethyl-4,5,6,7-tetrahydro-1H-pyrazolo[4,3-c]pyridin-3-yl]-benzamide [(I), Ra=Rb=methyl, A=B=D=E=CH, R=3-fluorophenyl, R1=amino], cpd. 543

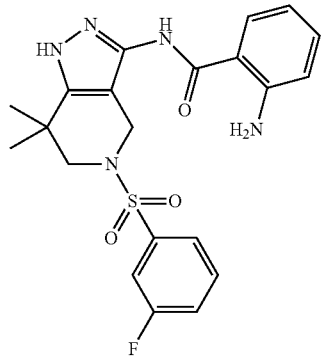

1H-NMR (400 MHz), δ (ppm, DMSO-d₆): 12.49 (s, 1H), 10.12 (s, 1H), 7.76-7.58 (m, 5H), 7.20 (t, J=7.31 Hz, 1H), 6.76 (d, J=7.31 Hz, 1H), 6.55 (t, J=7.31 Hz, 1H), 6.42 (bs, 2H), 3.95 (s, 2H), 3.10 (s, 2H), 1.29 (s, 6H).

2-Amino-N-[5-(3,5-difluoro-benzenesulfonyl)-4,5,6,7-tetrahydro-1H-pyrazolo[4,3-c]pyridin-3-yl]-benzamide [(I), Ra=Rb=H, A=B=D=E=CH, R=3,5-difluorophenyl, R1=amino], cpd. 546

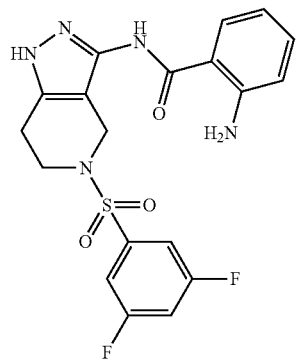

1H-NMR (400 MHz), δ (ppm, DMSO-d6): 12.27 (s, 1H), 10.16 (s, 1H), 7.75-7.63 (m, 2H), 7.62-7.54 (m, 2H), 7.20 (t, J=7.65 Hz, 1H), 6.75 (d, J=7.65 Hz, 1H), 6.55 (t, J=7.65 Hz, 1H), 6.47 (bs, 2H), 4.17 (s, 2H), 3.60-3.45 (m, 2H), 2.74-2.62 (m, 2H).

2-Amino-N-[5-(3,5-difluoro-benzenesulfonyl)-4,5,6,7-tetrahydro-1H-pyrazolo[4,3-c]pyridin-3-yl]-4-[(3-dimethylamino-propyl)-methyl-amino]-benzamide [(I), Ra=Rb=H, A=D=E=CH, B=CR2, R=3,5-difluorophenyl, R1=amino, R2=(3-dimethylamino-propyl)-methyl-amino], cpd. 550

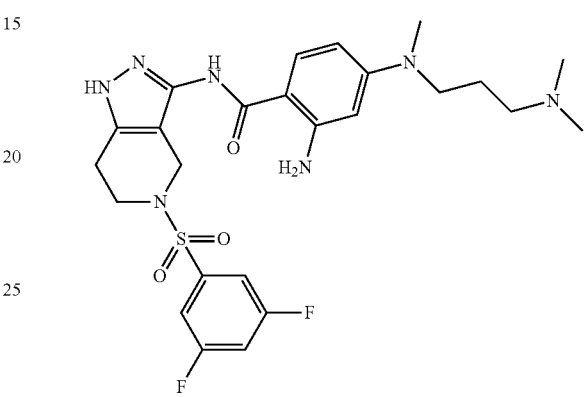

1H-NMR (400 MHz), δ (ppm, DMSO-d6): 12.16 (bs, 1H), 9.71 (s, 1H), 7.70-7.52 (m, 4H), 6.51 (bs, 2H), 6.02 (d, J=8.20 Hz, 1H), 5.95 (d, J=2.44 Hz, 1H), 4.16 (s, 2H), 3.51 (t, J=5.80 Hz, 2H), 3.40-3.30 (m, 2H), 2.90 (s, 3H), 2.67 (t, J=5.80 Hz, 2H), 2.35-2.23 (m, 2H), 2.19 (s, 6H), 1.72-1.60 (m, 2H).

N-[5-(3,5-Difluoro-benzenesulfonyl)-4,5,6,7-tetrahydro-1H-pyrazolo[4,3-c]pyridin-3-yl]-4-[methyl-(2-pyrrolidin-1-yl-ethyl)-amino]-2-nitro-benzamide hydrochloride [(I), Ra=Rb=H, A=D=E=CH, B=CR2, R=3,5-difluorophenyl, R1=nitro, R2=methyl-(2-pyrrolidin-1-yl-ethyl)-amino], cpd. 570

1H-NMR (400 MHz), δ (ppm, DMSO-d6): 10.63 (bs, 1H), 7.71-7.58 (m, 2H), 7.53-7.47 (m, 2H), 7.23 (d, J=2.68 Hz, 1H), 7.10 (dd, J=8.60 and 2.68 Hz, 1H), 4.11 (s, 2H), 3.82 (t, J=6.10 Hz, 2H), 3.40-3.24 (m, 7H), 3.13-2.99 (m, 5H), 2.70 (d, J=6.10 Hz, 2H), 2.07-1.95 (m, 2H), 1.94-1.81 (m, 2H).

2-Amino-N-[5-(3,5-difluoro-benzenesulfonyl)-4,5,6,7-tetrahydro-1H-pyrazolo[4,3-c]pyridin-3-yl]-4-[methyl-(2-pyrrolidin-1-yl-ethyl)-amino]-benzamide [(I), Ra=Rb=H, A=D=E=CH, B=CR2, R=3,5-difluorophenyl, R1=amino, R2=methyl-(2-pyrrolidin-1-yl-ethyl)-amino], cpd. 572

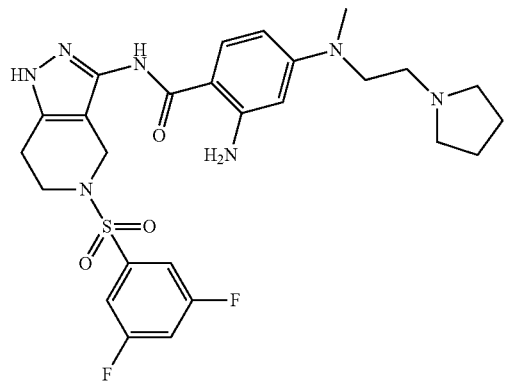

1H-NMR (400 MHz), δ (ppm, DMSO-d6): 12.15 (bs, 1H), 9.71 (bs, 1H), 7.69-7.53 (m, 1H), 7.61-7.53 (m, 3H), 6.52 (bs, 2H), 5.99 (d, J=8.60 Hz, 1H), 5.93 (d, J=2.32 Hz, 1H), 4.15 (bs, 2H), 3.53-3.49 (m, 2H), 3.46-3.41 (m, 2H), 2.92 (s, 3H), 2.70-2.64 (m, 2H), 2.59-2.53 (m, 2H), 2.51-2.47 (m, 4H), 1.71-1.67 (m, 4H).

N-[5-(3,5-Difluoro-benzenesulfonyl)-4,5,6,7-tetrahydro-1H-pyrazolo[4,3-c]pyridin-3-yl]-4-(2-diisopropylamino-ethoxy)-2-nitro-benzamide hydrochloride [(I), Ra=Rb=H, A=D=E=CH, B=CR2, R=3,5-difluorophenyl, R1=nitro, R2=2-diisopropylamino-ethoxy], cpd. 571

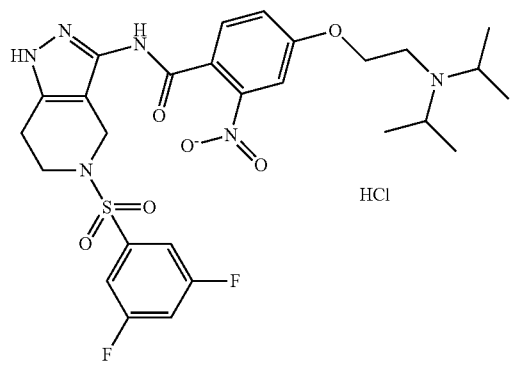

1H-NMR (400 MHz), δ (ppm, DMSO-d6): 10.89 (bs, 1H), 9.24 (bs, 1H), 7.24 (d, J=8.50 Hz, 1H), 7.71-7.61 (m, 2H), 7.55-7.49 (m, 2H), 7.41 (dd, J=8.50 and 2.44 Hz, 1H), 4.47 (t, J=4.40 Hz, 2H), 4.19 (m, 2H), 3.79-3.65 (m, 3H), 3.66-3.50 (m, 3H), 2.75-2.66 (m, 2H), 1.37 (d, J=6.58 Hz, 6H), 1.34 (d, J=6.46 Hz, 6H).

2-Amino-N-[5-(3,5-difluoro-benzenesulfonyl)-4,5,6,7-tetrahydro-1H-pyrazolo[4,3-c]pyridin-3-yl]-4-(2-diisopropylamino-ethoxy)-benzamide [(I), Ra=Rb=H, A=D=E=CH, B=CR2, R=3,5-difluorophenyl, R1=amino, R2=2-diisopropylamino-ethoxy], cpd. 573

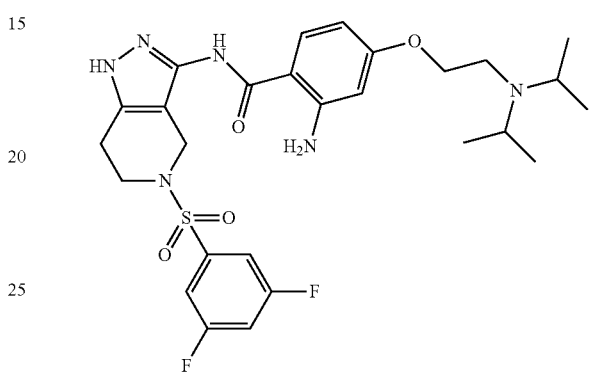

1H-NMR (400 MHz), δ (ppm, DMSO-d6): 12.21 (bs, 1H), 9.93 (s, 1H), 7.73-7.62 (m, 4H), 6.63 (bs, 2H), 6.26 (s, 1H), 6.16-6.05 (m, 1H), 4.15 (m, 2H), 3.84 (t, J=6.75 Hz, 2H), 3.55-3.45 (m, 2H), 3.08-2.95 (m, 2H), 2.75 (t, J=6.75 Hz, 2H), 2.71-2.60 (m, 2H), 0.99 (d, J=6.46 Hz, 12H).

N-[5-(3,5-Difluoro-benzenesulfonyl)-4,5,6,7-tetrahydro-1H-pyrazolo[4,3-c]pyridin-3-yl]-4-{[2-(isopropyl-methyl-amino)-ethyl]-methyl-amino}-2-nitro-benzamide hydrochloride [(I), Ra=Rb=H, A=D=E=CH, B=CR2, R=3,5-difluorophenyl, R1=nitro, R2=[2-(isopropyl-methyl-amino)-ethyl]-methyl-amino], cpd. 576

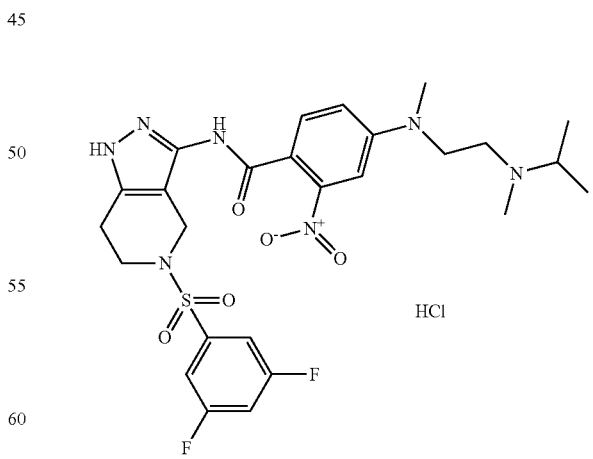

1H-NMR (400 MHz), δ (ppm, DMSO-d6): 10.64 (s, 1H), 10.15 (bs, 1H), 7.71-7.66 (m, 1H), 7.64 (d, J=8.90 Hz, 1H), 7.55-7.50 (m, 2H), 7.26 (d, J=2.50 Hz, 1H), 7.13 (dd, J=8.90 and 2.50 Hz, 1H), 4.13 (s, 2H), 3.93-3.85 (m, 2H), 3.65-3.58

(m, 1H), 3.54-3.51 (m, 2H), 3.24-3.14 (m, 2H), 3.07 (s, 3H), 2.73 (d, J=5.00 Hz, 3H), 2.71-2.66 (m, 2H), 1.29 (d, J=6.58, 3H), 1.25 (d, J=6.58 Hz, 3H).

2-Amino-N-[5-(3,5-difluoro-benzenesulfonyl)-4,5,6,7-tetrahydro-1H-pyrazolo[4,3-c]pyridin-3-yl]-4-{[2-(isopropyl-methyl-amino)-ethyl]-methyl-amino}-benzamide [(I), Ra=Rb=H, A=D=E=CH, B=CR2, R=3,5-difluorophenyl, R1=amino, R2=[2-(isopropyl-methyl-amino)-ethyl]-methyl-amino], cpd. 586

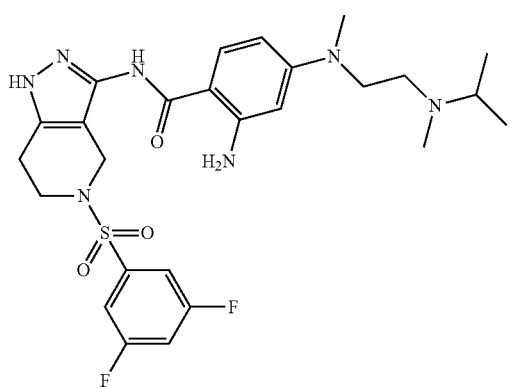

1H-NMR (400 MHz), δ (ppm, DMSO-d$_6$): 12.16 (bs, 1H), 9.71 (bs, 1H), 7.66 (m, 1H), 7.58-7.55 (m, 3H), 6.52 (bs, 2H), 5.99 (d, J=7.68 Hz, 1H), 5.92 (d, J=2.32 Hz, 1H), 4.16 (bs, 2H), 3.51 (m, 2H), 3.39 (m, 2H), 2.93 (bs, 3H), 2.78 (m, 1H), 2.68 (bs, 2H), 2.47 (m, 2H), 2.21 (bs, 3H), 0.95 (d, J=6.22 Hz).

2-Amino-N-[5-(3,5-difluoro-benzenesulfonyl)-4,5,6,7-tetrahydro-1H-pyrazolo[4,3-c]pyridin-3-yl]-4-[methyl-(2-morpholin-4-yl-ethyl)-amino]-benzamide [(I), Ra=Rb=H, A=D=E=CH, B=CR2, R=3,5-difluorophenyl, R1=amino, R2=methyl-(2-morpholin-4-yl-ethyl)-amino], cpd. 582

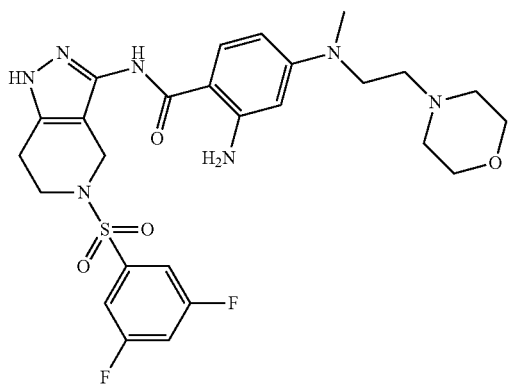

1H-NMR (400 MHz), δ (ppm, DMSO-d$_6$): 12.15 (bs, 1H), 9.70 (bs, 1H), 7.64 (m, 1H), 7.60-7.53 (m, 3H), 6.50 (bs, 2H), 5.99 (d, J=8.78 Hz, 1H), 5.93 (d, J=2.32 Hz, 1H), 4.13 (bs, 2H), 3.57 (t, J=4.63 Hz, 4H), 3.50 (t, J=5.37 Hz, 2H), 3.44 (t, J=7.07 Hz, 2H), 2.92 (bs, 3H), 2.66 (bs, 2H), 2.45-2.41 (m, 6H).

2-Amino-N-[5-(3,5-difluoro-benzenesulfonyl)-4,5,6,7-tetrahydro-1H-pyrazolo[4,3-c]pyridin-3-yl]-4-[methyl-(2-piperidin-1-yl-ethyl)-amino]-benzamide [(I), Ra=Rb=H, A=D=E=CH, B=CR2, R=3,5-difluorophenyl, R1=amino, R2=methyl-(2-piperidin-1-yl-ethyl)-amino], cpd. 584

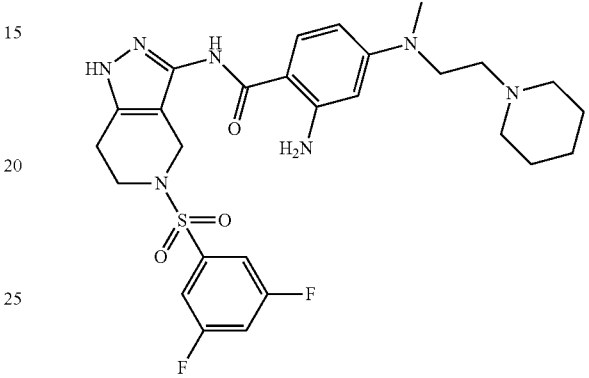

1H-NMR (400 MHz), δ (ppm, DMSO-d$_6$): 12.14 (bs, 1H), 9.69 (bs, 1H), 7.64 (m, 1H), 7.58-7.54 (m, 3H), 6.50 (bs, 2H), 5.98 (d, J=7.80 Hz, 1H), 5.92 (d, J=2.32 Hz, 1H), 4.14 (bs, 2H), 3.50 (t, J=5.49 Hz, 2H), 3.42 (t, J=7.32 Hz, 2H), 2.91 (bs, 3H), 2.66 (bs, 2H), 2.44-2.34 (m, 6H), 1.49 (m, 4H), 1.39 (m, 2H).

N-[5-(3,5-Difluoro-benzenesulfonyl)-4,5,6,7-tetrahydro-1H-pyrazolo[4,3-c]pyridin-3-yl]-4-[methyl-(2-piperidin-1-yl-ethyl)-amino]-2-nitro-benzamide hydrochloride [(I), Ra=Rb=H, A=D=E=CH, B=CR2, R=3,5-difluorophenyl, R1=nitro, R2=methyl-(2-piperidin-1-yl-ethyl)-amino], cpd. 585

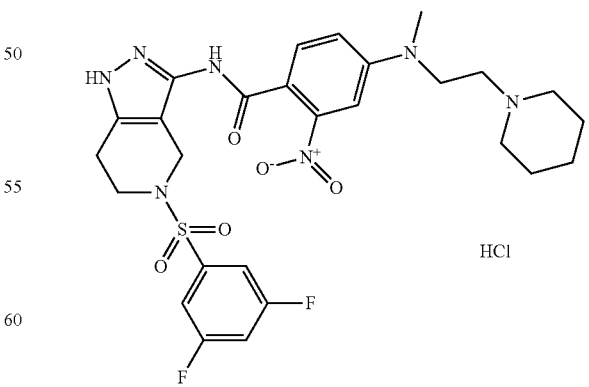

1H-NMR (400 MHz), δ (ppm, DMSO-d$_6$): 10.63 (bs, 1H), 10.14 (bs, 1H), 7.69-7.61 (m, 2H), 7.50 (m, 2H), 7.24 (d, J=2.32 Hz, 1H), 7.11 (dd, J1=8.90 Hz, J2=2.32 Hz, 1H), 4.11

(bs, 2H), 3.88 (t, J=8.17 Hz, 2H), 3.42 (m, 2H), 3.20 (m, 2H), 3.04 (bs, 3H), 2.95 (m, 4H), 2.70 (m, 2H), 1.81 (m, 6H).

EXAMPLE 16

Tetrahydro-pyran-4-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]amide [(I), Ra=Rb=H, A=D=E=CH, B=CR2, R=3,5-difluorophenyl, R1=NHCOR4, R2=4-methylpiperazin-1-yl, R4=tetrahydropyran-4-yl], cpd. 27

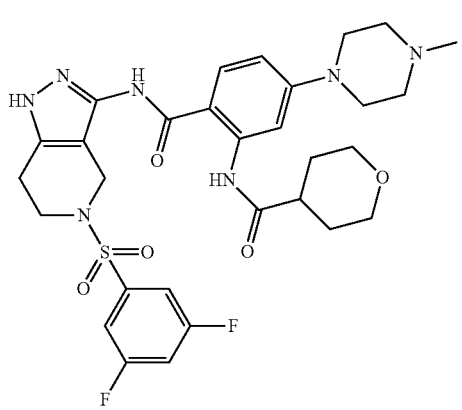

To a suspension of 3-[2-amino-4-(4-methyl-piperazin-1-yl)-benzoylamino]-5-(3,5-difluoro-benzenesulfonyl)-4,5,6,7-tetrahydro-pyrazolo[4,3-c]pyridine-1-carboxylic acid ethyl ester hydrochloride (0.3 g, 0.47 mmol) in anhydrous dichloromethane (10 mL), N,N-diisopropylethylamine (0.8 mL, 4.7 mmol) and tetrahydro-pyran-4-carbonyl chloride (0.2 g, 1.41 mmol) were added. The mixture was stirred at room temperature for 2 h, and then washed with 10% NaHCO₃, water, and brine. The organic phase was dried with sodium sulfate and evaporated. The crude was dissolved in a mixture of dichloromethane (5 mL) and methanol (10 mL). Triethylamine (1 mL) was added and the solution was stirred at room temperature overnight. After evaporation of the solvent the residue was purified by flash chromatography, using dichloromethane-methanol-30% aqueous NH₃ 9:1:0.1 as eluant, to obtain the title compound (0.2 g, 66% yield) as white solid.

1H-NMR (400 MHz), δ (ppm, DMSO-d₆): 12.33 (bs, 1H), 11.88 (bs, 1H), 10.39 (bs, 1H), 8.22 (s, 1H), 7.89 (d, J=9.1 Hz, 1H), 7.66 (m, 1H), 7.59 (d, J=4.5 Hz, 1H), 6.72 (d, J=9.1 Hz, 1H), 4.21 (bs, 2H), 3.86 (m, 2H), 3.53 (m, 2H), 3.45 (m, 1H), 3.42-3.35 (m, 6H), 2.69 (m, 2H), 2.45 (m, 4H), 2.24 (s, 3H), 1.79 (m, 2H), 1.65 (m, 2H).

Operating in a way analogous to that described above, the following compounds were obtained:

1H-Pyrrole-2-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide [(I), Ra=Rb=H, A=D=E=CH, B=CR2, R=3,5-difluorophenyl, R1=NHCOR4, R2=4-methylpiperazin-1-yl, R4=pyrrol-2-yl], cpd. 28

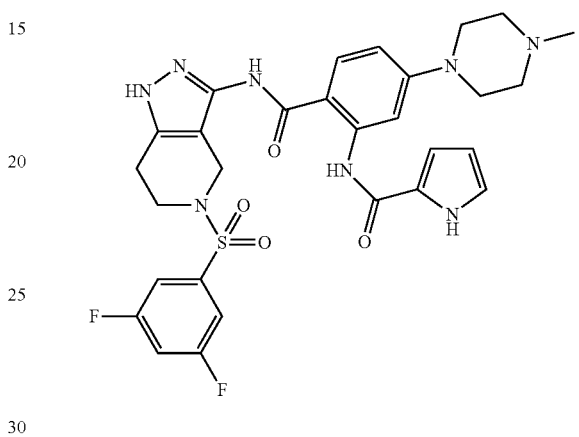

1H-NMR (400 MHz), δ (ppm, DMSO-d₆): 12.49 (bs, 1H), 12.35 (bs, 1H), 11.71 (s, 1H), 10.46 (s, 1H), 8.37 (d, J2=2.57 Hz, 1H), 7.95 (d, J1=8.90 Hz, 1H), 7.64 (m, 1H), 7.58 (m, 2H), 7.01 (m, 1H), 6.75 (m, 1H), 6.72 (dd, J1=8.90 Hz, 1H), 6.16 (m, 1H), 4.30 (s, 2H), 3.57 (m, 2H), 3.33 (m, 4H), 2.69 (m, 2H), 2.52 (m, 4H), 2.29 (s, 3H).

1H-Pyrrole-2-carboxylic acid [2-[5-(3-fluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide [(I), Ra=Rb=H, A=D=E=CH, B=CR2, R=3-fluorophenyl, R1=NHCOR4, R2=4-methylpiperazin-1-yl, R4=pyrrol-2-yl], cpd. 65

1H-NMR (400 MHz), δ (ppm, DMSO-d₆): 12.51 (bs, 1H), 12.35 (bs, 1H), 11.73 (bs, 1H), 10.45 (bs, 1H), 8.37 (d, J=2.5 Hz, 1H), 7.95 (d, J=9.0 Hz, 1H), 7.69-7.53 (m, 4H), 7.02 (m, 1H), 6.77-6.68 (m, 2H), 6.18 (m, 1H), 4.23 (bs, 2H), 3.51 (m, 2H), 3.34 (m, 4H), 2.70 (m, 2H), 2.49 (m, 4H), 2.26 (s, 3H).

1-Methyl-1H-pyrrole-2-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide [(I), Ra=Rb═H, A═D═E═CH, B═CR2, R=3,5-difluorophenyl, R1=NHCOR4, R2=4-methylpiperazin-1-yl, R4=1-methylpyrrol-2-yl], cpd. 29

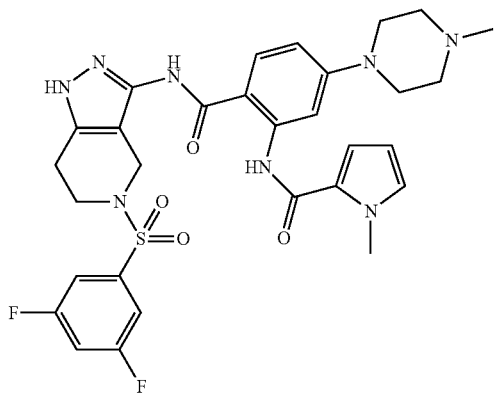

1H-NMR (400 MHz), δ (ppm, DMSO-$d_6$): 12.50 (s, 1H), 12.35 (s, 1H), 10.45 (s, 1H), 8.34 (d, J2=2.56 Hz, 1H), 7.95 (d, J1=9.14 Hz, 1H), 7.63 (m, 1H), 7.58 (m, 2H), 7.05 (m, 1H), 6.82 (d, bs, J=3.41 Hz, 1H), 6.70 (dd, bs, J1=9.14 Hz, J2=2.56 Hz, 1H), 6.06 (dd, bs, J1=3.41 Hz, 1H), 4.28 (s, 2H), 3.93 (s, 3H), 3.56 (m, 2H), 3.39-3.28 (m, 4H), 2.69 (m, 2H), 2.48 (m, 4H), 2.25 (s, 3H).

2-Ethyl-5-methyl-2H-pyrazole-3-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide [(I), Ra=Rb═H, A═D═E═CH, B═CR2, R=3,5-difluorophenyl, R1=NHCOR4, R2=4-methylpiperazin-1-yl, R4=2-ethyl-5-methyl-2H-pyrazol-3-yl], cpd. 35

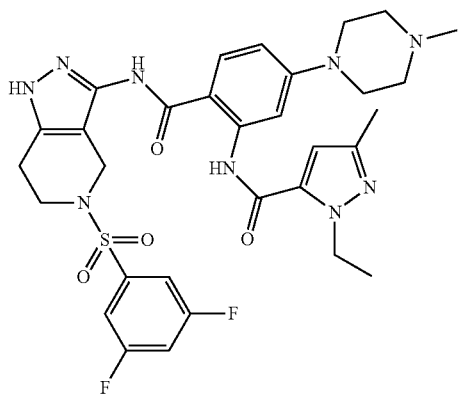

1H-NMR (400 MHz), δ (ppm, DMSO-$d_6$): 12.83 (s, 1H), 12.35 (s, 1H), 10.51 (s, 1H), 8.30 (d, J=2.12 Hz, 1H), 8.00 (d, J=9.03 Hz, 1H), 7.64-7.56 (m, 3H), 6.77 (dd, bs, J1=9.03 Hz, J2=2.12 Hz, 1H), 6.60 (s, 1H), 4.50 (q, J=7.20 Hz, 2H), 4.32 (s, 2H), 3.57 (m, 2H), 3.36-3.27 (m, 4H), 2.65 (m, 2H), 2.52-2.46 (m, 4H), 2.25 (s, 3H), 2.11 (s, 3H), 1.34 (t, J=7.20 Hz, 3H).

Pyridine-2-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide [(I), Ra=Rb═H, A═D═E═CH, B═CR2, R=3,5-difluorophenyl, R1=NHCOR4, R2=4-methylpiperazin-1-yl, R4=pyridin-2-yl], cpd. 45

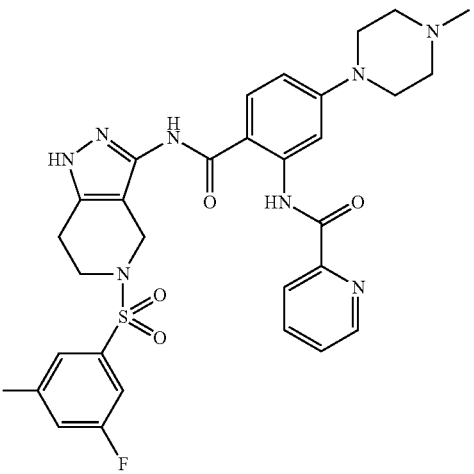

1H-NMR (400 MHz), δ (ppm, DMSO-$d_6$): 13.22 (s, 1H), 12.28 (s, 1H), 10.37 (s, 1H), 8.62 (d, J=4.39 Hz, 1H), 8.48 (d, J2=2.57 Hz, 1H), 8.16 (dm, J=7.81 Hz, 1H), 8.04 (ddd, J1=8.42 Hz, J2=7.81 Hz, J3=1.58 Hz, 1H), 7.88 (d, J1=9.15 Hz, 1H), 7.59 (m, 4H), 6.76 (dd, J1=9.15 Hz, J2=2.57 Hz, 1H), 4.31, 4.25 (s, 2H), 3.57 (m, 2H), 3.31 (m, 4H), 2.66 (m, 2H), 2.47 (m, 4H), 2.23 (s, 3H), mixture of tautomers.

N-[5-(3,5-Difluoro-benzenesulfonyl)-4,5,6,7-tetrahydro-1H-pyrazolo[4,3-c]pyridin-3-yl]-2-(2-dimethylamino-acetylamino)-4-(4-methyl-piperazin-1-yl)-benzamide [(I), Ra=Rb═H, A═D═E═CH, B═CR2, R=3,5-difluorophenyl, R1=NHCOR4, R2=4-methylpiperazin-1-yl, R4=N,N-dimethylaminomethyl], cpd. 12

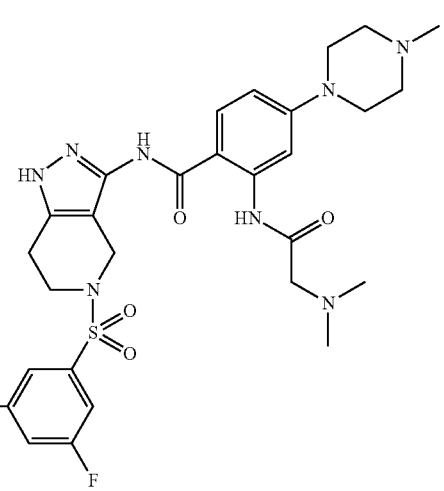

1H-NMR (400 MHz), δ (ppm, DMSO-d6): 12.28 (bs, 1H), 12.15 (bs, 1H), 10.31 (s, 1H), 8.31 (d, J2=2.31 Hz, 1H), 7.85 (d, J1=8.90 Hz, 1H), 7.61 (m, 3H), 6.72 (dd, J1=8.90 Hz, J2=2.31 Hz, 1H), 4.31 (s, 2H), 3.59 (m, 2H), 3.33 (m, 4H), 3.05 (s, 2H), 2.65 (m, 2H), 2.52 (m, 4H), 2.25 (s, 9H).

Tetrahydro-pyran-4-carboxylic acid {2-[5-(3,5-difluoro-benzenesulfonyl)-4,5,6,7-tetrahydro-1H-pyrazolo[4,3-c]pyridin-3-ylcarbamoyl]-5-morpholin-4-yl-phenyl}-amide [(I), Ra=Rb=H, A=D=E=CH, B=CR2, R=3,5-difluorophenyl, R1=NHCOR4, R2=morpholin-4-yl, R4=tetrahydropyran-4-yl], cpd. 110

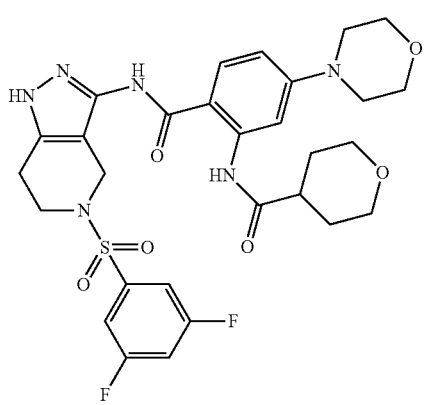

1H-NMR (400 MHz), δ (ppm, DMSO-d6): 12.35 (bs, 1H), 11.86 (bs, 1H), 10.42 (bs, 1H), 8.23 (d, J=2.2 Hz, 1H), 7.91 (d, J=8.9 Hz, 1H), 7.67 (m, 1H), 7.59 (d, J=4.6 Hz, 1H), 6.74 (d, J=8.9 Hz, 1H), 4.22 (bs, 2H), 3.86 (m, 2H), 3.76 (m, 4H), 3.53 (m, 2H), 3.26 (m, 4H), 2.69 (m, 2H), 1.80 (m, 2H), 1.66 (m, 2H).

1H-Pyrrole-2-carboxylic acid {2-[5-(3,5-difluoro-benzenesulfonyl)-4,5,6,7-tetrahydro-1H-pyrazolo[4,3-c]pyridin-3-ylcarbamoyl]-5-[(2-dimethylamino-ethyl)-methyl-amino]-phenyl}-amide [(I), Ra=Rb=H, A=D=E=CH, B=CR2, R=3,5-difluorophenyl, R1=NHCOR4, R2=(2-dimethylamino-ethyl)-methyl-amino), R4=pyrrol-2-yl], cpd. 142

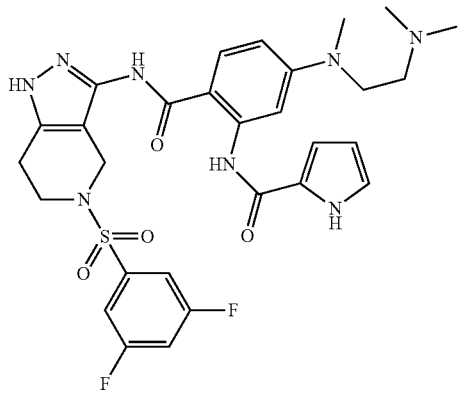

1H-NMR (400 MHz), δ (ppm, DMSO-d6): 12.64 (bs, 1H), 12.33 (bs, 1H), 11.77 (bs, 1H), 10.33 (bs, 1H), 8.20 (d, J=2.7

Hz, 1H), 7.92 (d, J=9.3 Hz, 1H), 7.63 (m, 1H), 7.59 (d, J=5.5 Hz, 2H), 6.99 (m, 1H), 6.75 (m, 1H), 6.44 (d, J=9.3 Hz, 1H), 6.15 (m, 1H), 4.29 (bs, 2H), 3.57 (m, 2H), 3.53 (t, J=7.1 Hz, 2H), 3.04 (s, 3H), 2.69 (m, 2H), 2.47 (t, J=7.1 Hz, 2H), 2.24 (s, 6H).

1H-Pyrrole-3-carboxylic acid {2-[5-(3,5-difluoro-benzenesulfonyl)-4,5,6,7-tetrahydro-1H-pyrazolo[4,3-c]pyridin-3-ylcarbamoyl]-5-[(2-dimethylamino-ethyl)-methyl-amino]-phenyl}-amide [(I), Ra=Rb=H, A=D=E=CH, B=CR2, R=3,5-difluorophenyl, R1=NHCOR4, R2=(2-dimethylamino-ethyl)-methyl-amino, R4=pyrrol-3-yl], cpd. 143

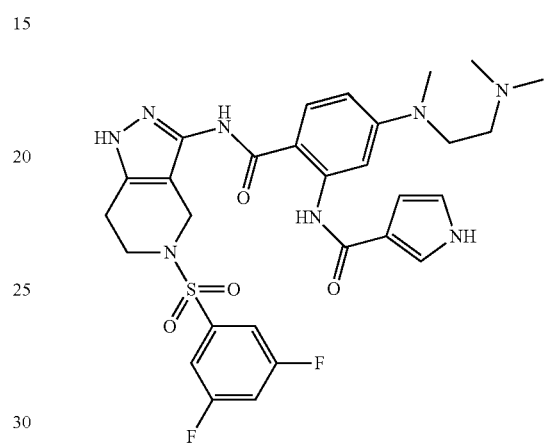

1H-NMR (400 MHz), δ (ppm, DMSO-d6): 12.41 (bs, 1H), 12.32 (bs, 1H), 11.34 (bs, 1H), 10.29 (bs, 1H), 8.26 (d, J=2.7 Hz, 1H), 7.89 (d, J=8.9 Hz, 1H), 7.63 (m, 1H), 7.58 (d, J=7.6 Hz, 2H), 7.37 (s, 1H), 6.81 (d, J=1.9 Hz, 1H), 6.51 (s, 1H), 6.43 (d, J=8.9 Hz, 1H), 4.29 (bs, 2H), 3.59-3.49 (m, 4H), 2.86 (s, 3H), 2.69 (m, 2H), 2.28 (s, 6H).

1H-Pyrrole-2-carboxylic acid [2-[5-(3,5-difluoro-benzenesulfonyl)-4,5,6,7-tetrahydro-1H-pyrazolo[4,3-c]pyridin-3-ylcarbamoyl]-5-(2-dimethylamino-ethoxy)-phenyl]-amide [(I), Ra=Rb=H, A=D=E=CH, B=CR2, R=3,5-difluorophenyl, R1=NHCOR4, R2=2-dimethylamino-ethoxy, R4=pyrrol-2-yl], cpd. 167

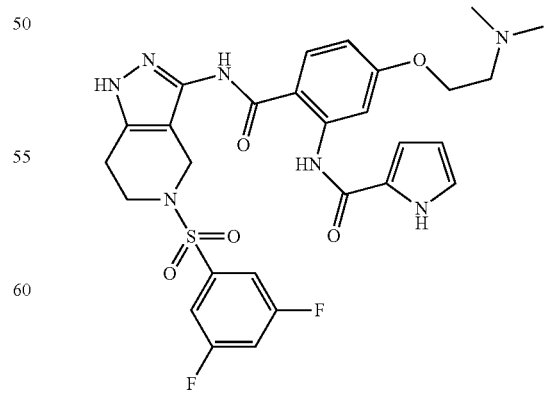

1H-NMR (400 MHz), δ (ppm, DMSO-d6): 12.40 (bs, 1H), 12.35 (bs, 1H), 11.82 (bs, 1H), 10.64 (bs, 1H), 8.34 (d, J=2.5

Hz, 1H), 8.03 (d, J=8.8 Hz, 1H), 7.64 (m, 1H), 7.58 (d, J=4.9 Hz, 2H), 7.02 (s, 1H), 6.79-6.73 (m, 2H), 6.17 (s, 1H), 4.31 (bs, 2H), 4.17 (t, J=5.6 Hz, 2H), 3.57 (m, 2H), 2.74-2.67 (m, 4H), 2.27 (s, 6H).

1H-Pyrrole-2-carboxylic acid {2-[5-(3,5-difluoro-benzenesulfonyl)-4,5,6,7-tetrahydro-1H-pyrazolo[4,3-c]pyridin-3-ylcarbamoyl]-5-methoxy-phenyl}-amide [(I), Ra=Rb=H, A=D=E=CH, B=CR2, R=3,5-difluorophenyl, R1=NHCOR4, R2=methoxy, R4=pyrrol-2-yl], cpd. 189

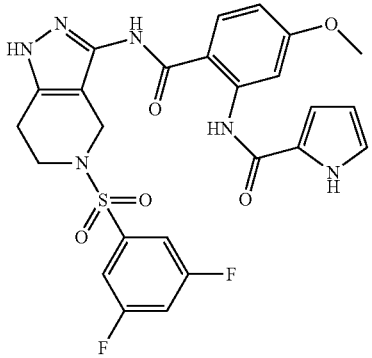

1H-NMR (400 MHz), δ (ppm, DMSO-d₆): 12.40 (bs, 1H), 12.37 (bs, 1H), 11.83 (bs, 1H), 10.85 (bs, 1H), 8.36 (d, J=2.7 Hz, 1H), 8.05 (d, J=8.9 Hz, 1H), 7.64 (m, 1H), 7.59 (d, J=4.8 Hz, 2H), 7.02 (m, 1H), 6.78-6.73 (m, 2H), 6.17 (m, 1H), 4.31 (bs, 2H), 3.87 (s, 3H), 3.58 (m, 2H), 2.71 (m, 2H).

1H-Pyrrole-2-carboxylic acid {5-methoxy-2-[5-(pyridine-3-sulfonyl)-4,5,6,7-tetrahydro-1H-pyrazolo[4,3-c]pyridin-3-ylcarbamoyl]-phenyl}-amide [(I), Ra=Rb=H, A=D=E=CH, B=CR2, R=3-pyridyl, R1=NHCOR4, R2=methoxy, R4=pyrrol-2-yl], cpd. 190

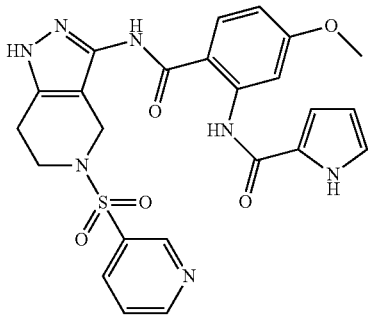

1H-NMR (400 MHz), δ (ppm, DMSO-d₆): 12.40 (bs, 2H), 11.84 (bs, 1H), 10.65 (bs, 1H), 9.01 (d, J=2.5 Hz, 1H), 8.85 (dd, J1=5.0 Hz, J2=1.5 Hz, 1H), 8.36 (d, J=2.7 Hz, 1H), 8.24 (m, 1H), 8.05 (d, J=8.8 Hz, 1H), 7.60 (m, 1H), 7.04 (m, 1H), 6.80-6.73 (m, 2H), 6.23 (m, 1H), 4.30 (bs, 2H), 3.87 (s, 3H), 3.56 (m, 2H), 2.70 (m, 2H).

1H-Pyrrole-2-carboxylic acid {2-[5-(3,5-difluoro-benzenesulfonyl)-4,5,6,7-tetrahydro-1H-pyrazolo[4,3-c]pyridin-3-ylcarbamoyl]-3-fluoro-phenyl}-amide [(I), Ra=Rb=H, A=D=E=CH, B=CR2, R=3,5-difluorophenyl, R1=NHCOR4, R2=fluoro, R4=pyrrol-2-yl], cpd. 197

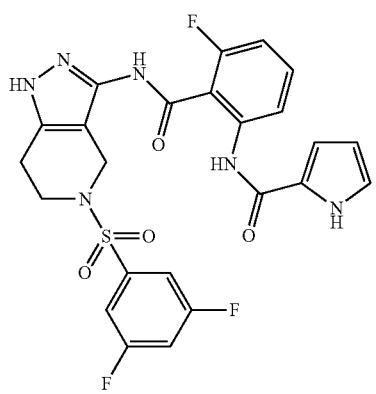

1H-NMR (400 MHz), δ (ppm, DMSO-d₆): 12.39 (bs, 1H), 11.80 (bs, 1H), 10.73 (bs, 1H), 10.24 (bs, 1H), 8.03 (d, J=8.2 Hz, 1H), 7.66 (m, 1H), 7.56-7.49 (m, 3H), 7.09 (t, J=9.3 Hz, 1H), 7.01 (s, 1H), 6.80 (s, 1H), 6.17 (m, 1H), 4.31 (bs, 2H), 3.54 (m, 2H), 2.71 (m, 2H).

1H-Pyrrole-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide [(I), Ra=Rb=methyl, A=D=E=CH, B=CR2, R=3,5-difluorophenyl, R1=NHCOR4, R2=4-methylpiperazin-1-yl, R4=pyrrol-2-yl], cpd. 294

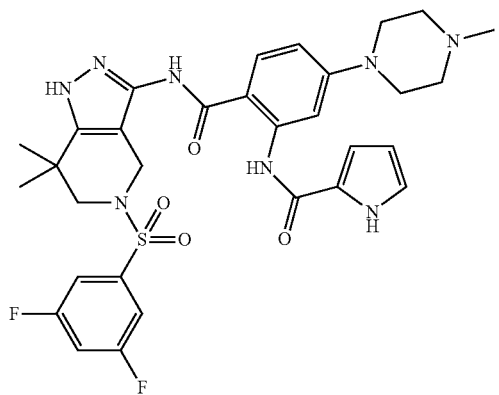

1H-NMR (400 MHz), δ (ppm, DMSO-d₆): 12.58 (s, 1H), 12.43 (s, 1H), 11.71 (s, 1H), 10.40 (s, 1H), 8.35 (d, J2=2.56 Hz, 1H), 7.94 (d, J1=9.14 Hz, 1H), 7.67 (m, 1H), 7.55 (m, 2H), 7.02 (m, 1H), 6.71 (m, 2H), 6.16 (m, 1H), 4.12 (s, 2H), 3.40-3.28 (m, 4H), 3.20 (s, 2H), 2.48 (m, 4H), 2.25 (s, 3H), 1.31 (s, 6H).

Tetrahydro-pyran-4-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-morpholin-4-yl-phenyl}-amide [(I), Ra=Rb=methyl, A=D=E=CH, B=CR2, R=3,5-difluorophenyl, R1=NHCOR4, R2=morpholin-4-yl, R4=tetrahydropyran-4-yl], cpd. 376

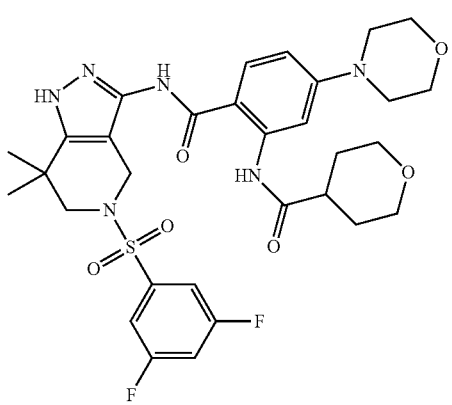

1H-NMR (400 MHz), δ (ppm, DMSO-$d_6$): 12.57 (s, 1H), 11.79 (s, 1H), 10.37 (s, 1H), 8.24 (bd, J=2.2 Hz, 1H), 7.91 (d, J=9.0 Hz, 1H), 7.72 (m, 1H), 7.60 (m, 2H), 6.73 (dd, J1=2.2 Hz, J2=9.0 Hz, 1H), 4.03 (bs, 2H), 3.88 (m, 2H), 3.76 (m, 4H), 3.37 (m, 2H), 3.26 (m, 4H), 3.16 (bs, 2H), 2.55 (m, 1H), 1.78 (m, 2H), 1.65 (m, 2H), 1.30 (s, 6H).

1H-Pyrrole-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-pyrrolidin-1-ylmethyl-phenyl}-amide [(I), Ra=Rb=methyl, A=D=E=CH, B=CR2, R=3,5-difluorophenyl, R1=NHCOR4, R2=1-pirrolidinylmethyl, R4=pyrrol-2-yl], cpd. 471

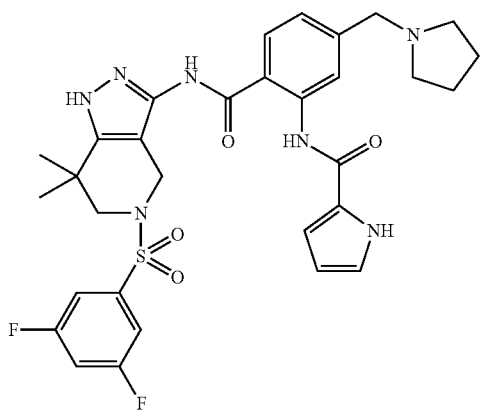

1H-NMR (400 MHz), δ (ppm, DMSO-$d_6$): 12.64 (s, 1H), 11.83 (s, 1H), 11.77 (s, 1H), 10.71 (s, 1H), 8.59 (bs, 1H), 7.96 (d, J1=8.54 Hz, 1H), 7.68 (m, 1H), 7.55 (m, 2H), 7.12 (d, bs, J1=8.54 Hz, 1H), 7.02 (m, 1H), 6.72 (m, 1H), 6.17 (m, 1H), 4.14 (s, 2H), 3.67 (m, bs, 2H), 3.20 (m, 2H), 2.52 (m, 4H), 1.75 (m, 4H), 1.31 (m, 6H).

1H-Pyrrole-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-phenyl}-amide [(I), Ra=Rb=methyl, A=B=D=E=CH, R=3,5-difluorophenyl, R1=NHCOR4, R4=pyrrol-2-yl], cpd. 489

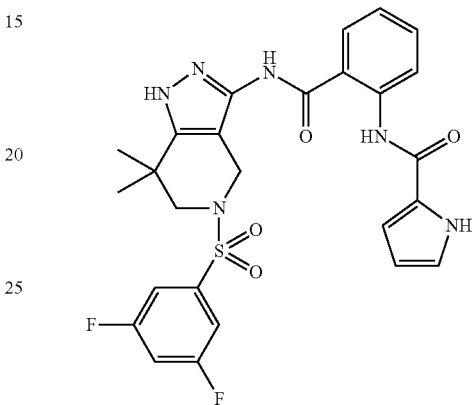

1H-NMR (400 MHz), δ (ppm, DMSO-$d_6$): 12.63 (s, 1H), 11.81 (s, 1H), 10.74 (s, 1H), 8.57 (d, J=8.42 Hz, 1H), 7.98 (d, J=7.56 Hz, 1H), 7.67 (m, 1H), 7.59-7.53 (m, 2H), 7.17 (m, 1H), 7.00 (m, 1H), 6.71 (m, 1H), 6.16 (m, 1H), 4.13 (s, 2H), 3.18 (s, 2H), 1.30 (s, 6H).

1H-Pyrrole-2-carboxylic acid [2-(5-methanesulfonyl-4,5,6,7-tetrahydro-1H-pyrazolo[4,3-c]pyridin-3-ylcarbamoyl)-5-(4-methyl-piperazin-1-yl)-phenyl]-amide [(I), Ra=Rb=H, A=D=E=CH, B=CR2, R=methyl, R1=NHCOR4, R2=4-methylpiperazin-1-yl, R4=pyrrol-2-yl], cpd. 89

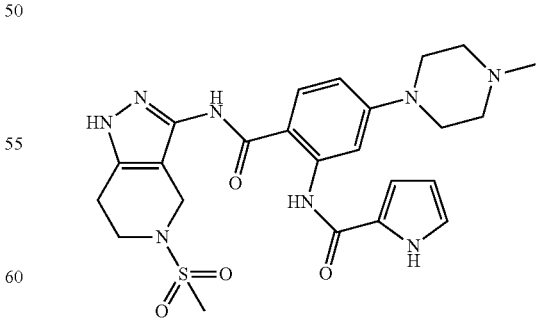

1H-NMR (400 MHz), δ (ppm, DMSO-$d_6$): 12.50 (s, 1H), 11.51 (s, 1H), 10.46 (s, 1H), 8.36 (d, J2=2.56 Hz, 1H), 8.22 (s, 2H), 7.95 (d, J1=9.02 Hz, 1H), 7.01 (m, 1H), 6.76 (m, 1H), 6.71 (dd, J1=9.02 Hz, J2=2.56 Hz, 1H), 6.18 (m, 1H), 4.24 (s, 1H), 3.53 (m, 2H), 3.40-3.30 (m, 4H), 2.93 (s, 3H), 2.82 (m, 2H), 2.48 (m, 4H), 2.25 (s, 3H).

N-[5-(3,5-Difluoro-benzenesulfonyl)-7,7-dimethyl-4,5,6,7-tetrahydro-1H-pyrazolo[4,3-c]pyridin-3-yl]-4-(4-methyl-piperazin-1-yl)-benzamide [(I), Ra=Rb=methyl, A=D=E=CH, B=CR2, R=3,5-difluorophenyl, R1=H, R2=4-methylpiperazin-1-yl], cpd. 2

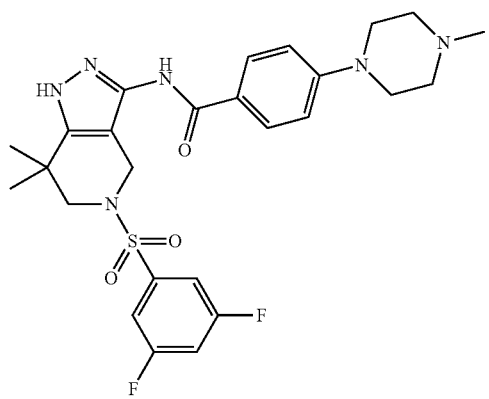

1H-NMR (400 MHz), δ (ppm, DMSO-d6): 12.47 (bs, 1H), 10.16 (s, 1H), 7.88 (d, J=8.90 Hz, 1H), 7.70 (m, 1H), 7.56 (m, 2H), 7.00 (d, J=8.90 Hz, 1H), 4.02 (s, 2H), 3.37-3.28 (m, 4H), 3.16 (s, 2H), 2.57-2.48 (m, bs, 4H), 2.29 (s, 3H), 1.29 (s, 6H).

N-[5-(3,5-Difluoro-benzenesulfonyl)-7,7-dimethyl-4,5,6,7-tetrahydro-1H-pyrazolo[4,3-c]pyridin-3-yl]-2-(2-pyridin-4-yl-acetylamino)-benzamide [(I), Ra=Rb=methyl, A=B=D=E=CH, R=3,5-difluorophenyl, R1=NHCOR4, R4=pyridin-4-yl-methyl], cpd. 500

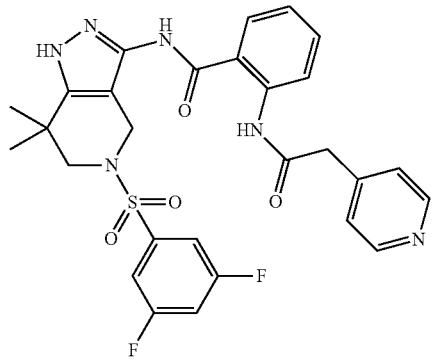

1H-NMR (400 MHz), δ (ppm, DMSO-d6): 12.58 (s, 1H), 10.84 (bs, 1H), 10.60 (bs, 1H), 8.41 (d, J=6.13 Hz, 2H), 8.12 (d, J=7.84 Hz, 1H), 7.82 (d, J=7.84 Hz, 1H), 7.70 (tt, J=9 Hz and 2.1 Hz, 1H), 7.60-7.51 (m, 3H), 7.32 (d, J=6.13 Hz, 2H), 7.22 (t, J=7.84 Hz, 1H), 4.07 (s, 2H), 3.76 (s, 2H), 3.16 (s, 2H), 1.31 (s, 6H).

1H-Pyrrole-2-carboxylic acid {2-[7,7-dimethyl-5-(pyridine-3-sulfonyl)-4,5,6,7-tetrahydro-1H-pyrazolo[4,3-c]pyridin-3-ylcarbamoyl]-phenyl}-amide [(I), Ra=Rb=methyl, A=B=D=E=CH, R=pyridin-3-yl, R1=NHCOR4, R4=pyrrol-2-yl], cpd. 540

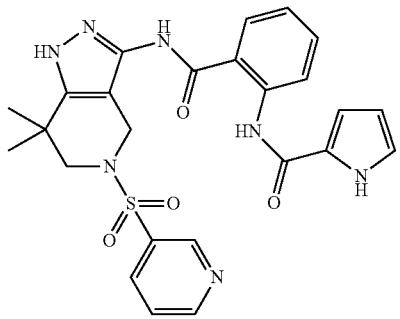

1H-NMR (400 MHz), δ (ppm, DMSO-d6): 12.63 (s, 1H), 11.81 (bs, 1H), 11.75 (bs, 1H), 10.75 (s, 1H), 8.98 (d, J=1.95 Hz, 1H), 8.88 (dd, J=4.85 and 195 Hz, 1H), 8.57 (d, J=8.24 Hz, 1H), 8.19 (dt, J=8.24 and 1.95 Hz, 1H), 7.97 (d, J=7.64 Hz, 1H), 7.65 (m, 1H), 7.58 (t, J=7.64 Hz, 1H), 7.17 (t, J=7.64 Hz, 1H), 7.01 (bs, 1H), 6.72 (bs, 1H), 6.23 (dd, J=1.66 Hz, 1H), 4.11 (s, 2H), 3.15 (s, 2H), 1.30 (s, 6H).

Tetrahydro-pyran-4-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-phenyl}-amide [(I), Ra=Rb=methyl, A=B=D=E=CH, R=3,5-difluorophenyl, R1=NHCOR4, R4=tetrahydro-pyran-4-yl], cpd. 496

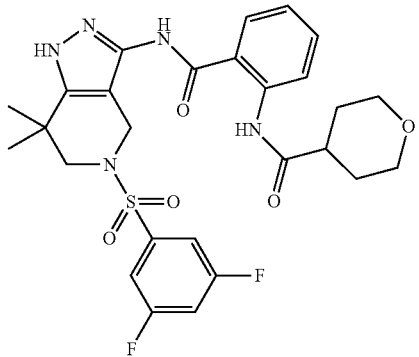

1H-NMR (400 MHz), δ (ppm, DMSO-d6): 12.61 (s, 1H), 10.96 (s, 1H), 10.63 (s, 1H), 8.34 (d, J=8.28 Hz, 1H), 7.89 (d, J=7.69 Hz, 1H), 7.72 (tt, J=9.07 and 2.17 Hz, 1H), 7.61-7.51

(m, 3H), 7.20 (t, J=7.69 Hz, 1H), 4.09 (s, 2H), 3.90-3.85 (m, 4H), 3.16 (s, 2H), 2.57 (m, 1H), 1.81-1.58 (m, 4H), 1.30 (m, 6H).

1H-Pyrrole-2-carboxylic acid {2-[5-(3,5-dimethyl-isoxazole-4-sulfonyl)-7,7-dimethyl-4,5,6,7-tetrahydro-1H-pyrazolo[4,3-c]pyridin-3-ylcarbamoyl]-phenyl}-amide [(I), Ra=Rb=methyl, A=B=D=E=CH, R=3,5-dimethyl-isoxazole-4-yl, R1=NHCOR4, R4=pyrrol-2-yl], cpd. 542

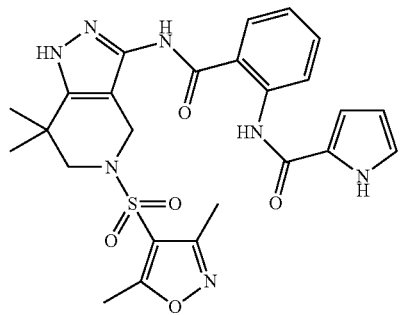

1H-NMR (400 MHz), δ (ppm, DMSO-d$_6$): 12.63 (s, 1H), 11.86 (bs, 1H), 11.81 (bs, 1H), 10.79 (s, 1H), 8.57 (d, J=8.55 Hz, 1H), 8.01 (d, J=8.1 Hz, 1H), 7.58 (t, J=7.2 Hz, 1H), 7.16 (t, J=8.1 Hz, 1H), 7.01 (m, 1H), 6.70 (bs, 1H), 6.17 (m, 1H), 4.17 (s, 2H), 3.22 (s, 2H), 2.57 (s, 3H), 2.31 (s, 3H), 1.29 (s, 6H).

N-[5-(3,5-Difluoro-benzenesulfonyl)-7,7-dimethyl-4,5,6,7-tetrahydro-1H-pyrazolo[4,3-c]pyridin-3-yl]-2-(2-piperidin-1-yl-acetylamino)-benzamide [(I), Ra=Rb=methyl, A=B=D=E=CH, R=3,5-difluorophenyl, R1=NHCOR4, R4=piperidin-1-yl-methyl], cpd. 499

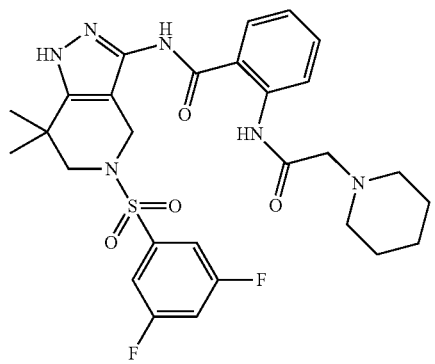

1H-NMR (400 MHz), δ (ppm, DMSO-d$_6$): 12.57 (s, 1H), 11.55 (s, 1H) 10.67 (s, 1H), 8.47 (d, J=8.19 Hz, 1H), 7.82 (d, J=7.34 Hz, 1H), 7.72 (tt, J=9.2 and 2.32 Hz, 1H), 7.59 (m, 2H), 7.55-7.50 (m, 1H), 7.17 (t, J=8.19 Hz, 1H), 4.07 (s, 2H), 3.16 (s, 2H), 2.99 (s, 2H), 2.33 (m, 4H), 1.37 (m, 4H), 1.30 (s, 6H), 1.14 (m, 2H).

1-Methyl-piperidine-4-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-phenyl}-amide [(I), Ra=Rb=methyl, A=B=D=E=CH, R=3,5-difluorophenyl, R1=NHCOR4, R4=1-methyl-piperidine-4-yl], cpd. 498

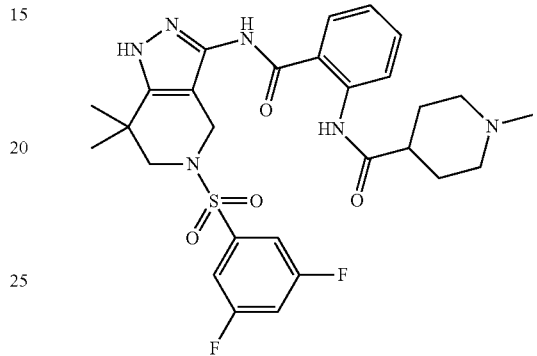

1H-NMR (400 MHz), δ (ppm, DMSO-d$_6$): 12.60 (s, 1H), 10.93 (s, 1H), 10.61 (s, 1H), 8.31 (d, J=8.1 Hz, 1H), 7.86 (d, J=7.65 Hz, 1H), 7.70 (tt, J=8.94 and 2.19 Hz, 1H), 7.61-7.56 (m, 2H), 7.53 (t, J=8.1 Hz, 1H), 7.18 (t, J=7.65 Hz, 1H), 4.07 (s, 2H), 3.15 (s, 2H), 2.86 (bs, 4H), 2.27-2.18 (m, 4H), 1.86-1.80 (m, 2H), 1.67 (m, 2H), 1.29 (s, 6H).

Tetrahydro-pyran-4-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide [(I), Ra=Rb=methyl, A=D=E=CH, B=CR2, R=3,5-difluorophenyl, R1=NHCOR4, R2=4-methylpiperazin-1-yl, R4=tetrahydro-pyran-4-yl], cpd. 293

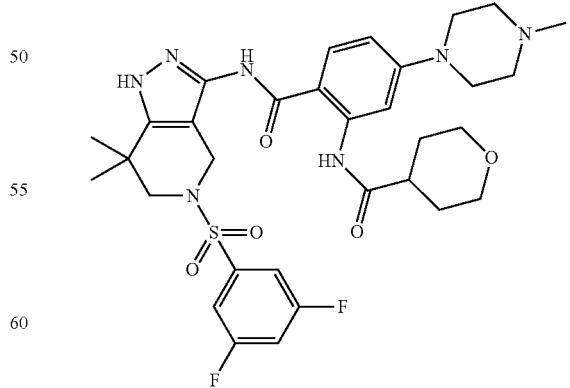

1H-NMR (400 MHz), δ (ppm, DMSO-d$_6$): 12.55 (bs, 1H), 11.79 (bs, 1H), 10.32 (s, 1H), 8.21 (m, 1H), 7.86 (m, 1H), 7.70 (m, 1H), 7.56 (m, 2H), 6.68 (m, 1H), 4.01 (bs, 2H), 3.85 (m, 2H), 3.26-3.38 (m, 4H), 3.14 (s, 2H), 2.44 (m, 4H), 2.22 (bs, 3H), 1.77 (m, 2H), 1.28 (s, 6H).

1-Methyl-1H-pyrrole-2-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide [(I), Ra=Rb=methyl, A=D=E=CH, B=CR2, R=3,5-difluorophenyl, R1=NHCOR4, R2=4-methylpiperazin-1-yl, R4=1-methyl-1H-pyrrole-2-yl], cpd. 295

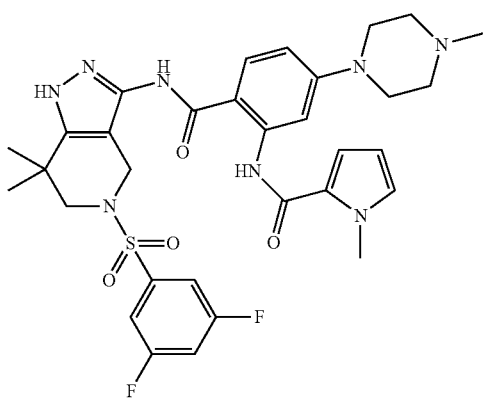

1H-NMR (400 MHz), δ (ppm, DMSO-$d_6$): 12.56 (bs, 1H), 12.40 (bs, 1H), 10.37 (bs, 1H), 8.30 (m, 1H), 7.90 (m, 1H), 7.66 (m, 1H), 7.53 (m, 2H), 7.03 (m, 1H), 6.75 (m, 1H), 6.70 (m, 1H), 6.05 (m, 1H), 4.07 (bs, 2H), 3.91 (s, 3H), 3.26-3.38 (m, 4H), 3.17 (m, 2H), 2.46 (m, 4H), 2.23 (bs, 3H), 1.29 (s, 6H).

1H-Pyrrole-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-morpholin-4-yl-phenyl}-amide [(I), Ra=Rb=methyl, A=D=E=CH, B=CR2, R=3,5-difluorophenyl, R1=NHCOR4, R2=morpholin-4-yl, R4=1H-pyrrole-2-yl], cpd. 363

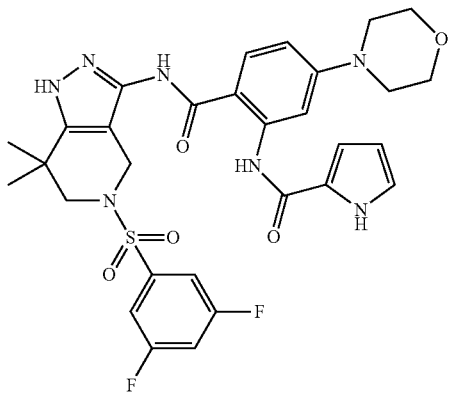

1H-NMR (400 MHz), δ (ppm, DMSO-$d_6$): 12.59 (bs, 1H), 12.42 (bs, 1H), 11.72 (bs, 1H), 10.43 (bs, 1H), 8.35 (m, 1H), 7.95 (m, 1H), 7.68 (m, 1H), 7.56 (m, 2H), 7.02 (m, 1H), 6.71 (m, 2H), 6.17 (m, 1H), 4.12 (s, 2H), 3.78 (m, 4H), 3.32 (m, 4H), 3.20 (s, 2H), 1.31 (s, 6H).

(S)-1-Methyl-pyrrolidine-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-morpholin-4-yl-phenyl}-amide [(I), Ra=Rb=methyl, A=D=E=CH, B=CR2, R=3,5-difluorophenyl, R1=NHCOR4, R2=morpholin-4-yl, R4=(S)-1-methyl-pyrrolidine-2-yl], cpd. 368

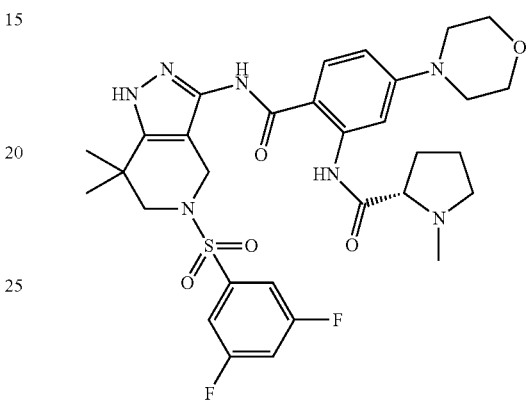

1H-NMR (400 MHz), δ (ppm, DMSO-$d_6$): 12.54 (bs, 1H), 12.15 (bs, 1H), 10.28 (bs, 1H), 8.32 (m, 1H), 7.86 (m, 1H), 7.71 (m, 1H), 7.55 (m, 2H), 6.73 (m, 1H), 4.09 (s, 2H), 3.76 (m, 4H), 3.25 (m, 5H), 3.03 (m, 1H), 2.87 (m, 1H), 2.30 (s, 3H), 2.09-2.34 (m, 2H), 1.63-1.84 (m, 3H), 1.30 (s, 6H).

1H-Pyrrole-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-dimethylamino-phenyl}-amide [(I), Ra=Rb=methyl, A=D=E=CH, B=CR2, R=3,5-difluorophenyl, R1=NHCOR4, R2=dimethylamino, R4=1H-pyrrole-2-yl], cpd. 389

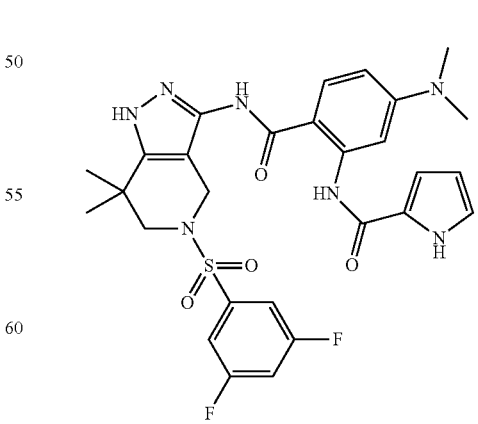

1H-NMR (400 MHz), δ (ppm, DMSO-$d_6$): 12.56 (bs, 1H), 11.73 (bs, 1H), 10.31 (bs, 1H), 8.17 (d, J=2.68 Hz, 1H), 7.92

(bd, 1H), 7.68 (m, 1H), 7.56 (m, 2H), 7.01 (m, 1H), 6.70 (m, 1H), 6.46 (m, 1H), 6.15 (m, 1H), 4.12 (bs, 2H), 3.19 (m, 2H), 3.04 (s, 6H), 1.31 (s, 6H).

1-Methyl-1H-pyrrole-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-dimethylamino-phenyl}-amide [(I), Ra=Rb=methyl, A=D=E=CH, B=CR2, R=3,5-difluorophenyl, R1=NHCOR4, R2=dimethylamino, R4=1-methyl-1H-pyrrol-2-yl], cpd. 545

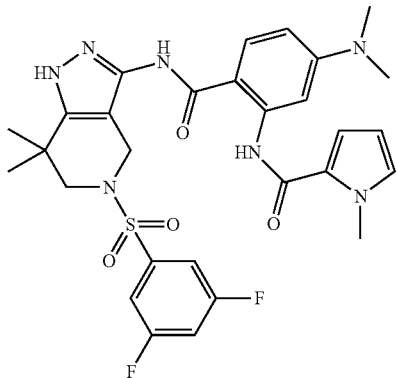

1H-NMR (400 MHz), δ (ppm, DMSO-$d_6$): 12.56 (bs, 1H), 10.30 (bs, 1H), 8.13 (d, J=2.68 Hz, 1H), 7.91 (d, J=9.03 Hz, 1H), 7.68 (m, 1H), 7.56 (m, 2H), 7.05 (m, 1H), 6.77 (m, 1H), 6.46 (m, 1H), 6.07 (m, 1H), 4.09 (bs, 2H), 3.93 (s, 3H), 3.19 (s, 2H), 3.04 (s, 6H), 1.31 (s, 6H).

Tetrahydro-pyran-4-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-dimethylamino-phenyl}-amide [(I), Ra=Rb=methyl, A=D=E=CH, B=CR2, R=3,5-difluorophenyl, R1=NHCOR4, R2=dimethylamino, R4=tetrahydro-pyran-4-yl], cpd. 402

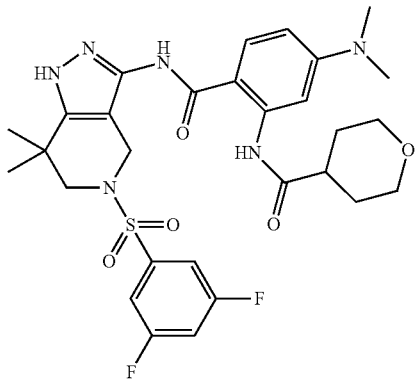

1H-NMR (400 MHz), δ (ppm, DMSO-$d_6$): 12.55 (bs, 1H), 11.96 (bs, 1H), 10.25 (bs, 1H), 8.05 (d, J=2.56 Hz, 1H), 7.87 (d, J=9.14 Hz, 1H), 7.72 (m, 1H), 7.58 (m, 2H), 6.47 (m, 1H), 4.03 (s, 2H), 3.88 (m, 2H), 3.27-3.43 (m, 2H), 3.16 (s, 2H), 3.01 (s, 6H), 1.77 (m, 2H), 1.66 (m, 2H), 1.30 (s, 6H).

(S)-1-Methyl-pyrrolidine-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-dimethylamino-phenyl}-amide [(I), Ra=Rb=methyl, A=D=E=CH, B=CR2, R=3,5-difluorophenyl, R1=NHCOR4, R2=dimethylamino, R4=(S)-1-methyl-pyrrolidine-2-yl], cpd. 394

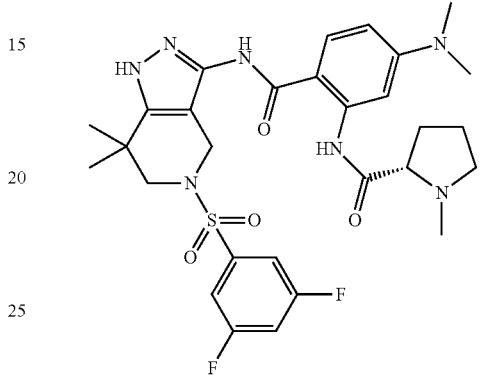

1H-NMR (400 MHz), δ (ppm, DMSO-$d_6$): 12.52 (bs, 1H), 12.26 (bs, 1H), 10.16 (bs, 1H), 8.14 (bd, 1H), 7.84 (d, J=8.90 Hz, 1H), 7.70 (m, 1H), 7.55 (m, 2H), 6.46 (m, 1H), 4.08 (s, 2H), 3.15-3.29 (m, 1H), 2.96-3.08 (m, 8H), 2.86 (m, 1H), 2.23-2.34 (m, 5H), 2.10-2.22 (m, 1H), 1.64-1.83 (m, 3H), 1.30 (s, 6H).

EXAMPLE 17

1H-Pyrrole-3-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide [(I), Ra=Rb=H, A=D=E=CH, B=CR2, R=3,5-difluorophenyl, R1=NHCOR4, R2=4-methylpiperazin-1-yl, R4=pyrrol-3-yl], cpd. 30

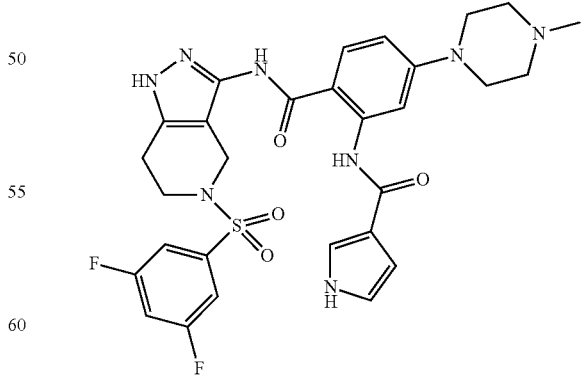

A solution of ethyl 5-(3,5-difluoro-benzenesulfonyl)-3-(4-(4-methyl-piperazin-1-yl)-2-{[1-(toluene-4-sulfonyl)-1H-pyrrole-3-carbonyl]-amino}-benzoylamino)-4,5,6,7-tetrahydro-pyrazolo[4,3-c]pyridine-1-carboxylic acid ethyl ester (0.4 g, 0.57 mmol) in 1,4-dioxane (30 mL) was treated with 1N NaOH (10 mL) and water (20 mL) at room temperature for 20 hours. The reaction mixture was then diluted with dichloromethane-water 1:1 (200 mL). The organic layer was separated, washed with brine, dried over sodium sulphate and evaporated to dryness. The reaction mixture was first purified by silica gel column chromatography, using dichloromethane-methanol-30% NH$_4$OH 100:10:1 as eluant, followed by preparative HPLC, and furnished the title compound as beige solid (0.09 g, 29% yield).

1H-NMR (400 MHz), δ (ppm, DMSO-d$_6$): 12.25 (s, 1H), 11.34 (s, 1H), 10.40 (s, 1H), 8.40 (d, J2=2.56 Hz, 1H), 7.90 (d, J1=9.03 Hz, 1H), 7.60 (m, 1H), 7.56 (m, 2H), 7.34 (m, 1H), 6.78 (m, 1H), 6.66 (dd, J1=9.03 Hz, J2=2.56 Hz, 1H), 6.47 (m, 1H), 4.27, 4.25 (s, 2H), 3.54 (m, 2H), 3.31 (m, 4H), 2.66 (m, 2H), 2.45 (m, 4H), 2.23 (s, 3H), mixture of tautomers.

The following compound (beige solid, 0.02 g) was also isolated from preparative HPLC.

1H-Pyrrole-3-carboxylic acid [2-[5-(3-fluoro-5-methoxy-benzenesulfonyl)-4,5,6,7-tetrahydro-1H-pyrazolo[4,3-c]pyridin-3-ylcarbamoyl]-5-(4-methyl-piperazin-1-yl)-phenyl]amide [(I), Ra=Rb=H, A=D=E=CH, B=CR2, R=3-fluoro-5-methoxyphenyl, R1=NHCOR4, R2=4-methylpiperazin-1-yl, R4=pyrrol-3-yl], cpd. 67

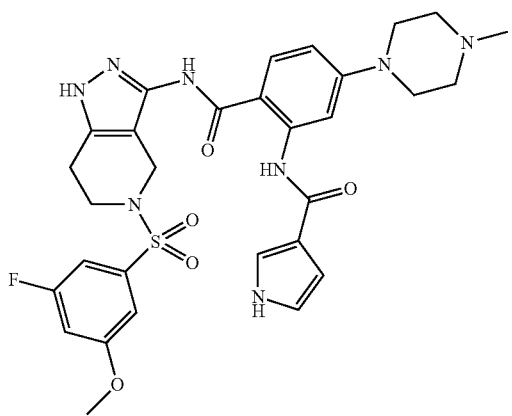

1H-NMR (400 MHz), δ (ppm, DMSO-d$_6$): 12.26 (s, 1H), 11.34 (s, 1H), 10.42 (s, 1H), 8.41 (d, J2=2.56 Hz, 1H), 7.90 (d, J1=9.03 Hz, 1H), 7.34 (m, 1H), 7.22-7.14 (m, 2H), 7.12 (m, 1H), 6.79 (m, 1H), 6.66 (dd, J1=9.03 Hz, J2=2.56 Hz, 1H), 6.48 (m, 1H), 4.27, 4.25 (s, 2H), 3.71 (s, 3H), 3.60-3.29 (m, 6H), 2.64 (m, 2H), 2.45 (m, 4H), 2.23 (s, 3H), mixture of tautomers.

Operating as described above, the following compound was prepared:

1H-Pyrrole-3-carboxylic acid [2-[5-(3,5-difluoro-benzenesulfonyl)-7,7-dimethyl-4,5,6,7-tetrahydro-1H-pyrazolo[4,3-c]pyridin-3-ylcarbamoyl]-5-(4-methyl-piperazin-1-yl)-phenyl]-amide [(I), Ra=Rb=methyl, A=D=E=CH, B=CR2, R=3,5-difluorophenyl, R1=NHCOR4, R2=4-methylpiperazin-1-yl, R4=pyrrol-3-yl], cpd. 296

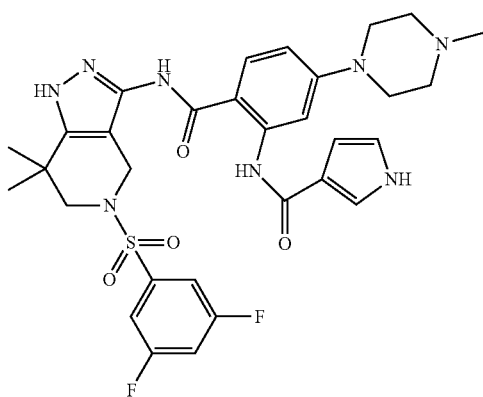

1H-NMR (400 MHz), δ (ppm, DMSO-d$_6$): 12.58 (s, 1H), 12.21 (s, 1H), 11.36 (s, 1H), 10.35 (s, 1H), 8.41 (d, J2=2.56 Hz, 1H), 7.91 (d, J1=9.02 Hz, 1H), 7.66 (m, 1H), 7.55 (m, 2H), 7.35 (bs, 1H), 6.82 (d, bs, J=2.07 Hz, 1H), 6.68 (d, bs, J1=9.02 Hz, 1H), 6.46 (m, bs, 1H), 4.11 (s, 2H), 3.83-3.24 (m, 4H), 3.19 (s, 2H), 2.47 (m, 4H), 2.25 (s, 3H), 1.31 (s, 6H).

1H-Pyrrole-3-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-phenyl}-amide [(I), Ra=Rb=methyl, A=B=D=E=CH, R=3,5-difluorophenyl, R1=NHCOR4, R4=pyrrol-3-yl], cpd. 490

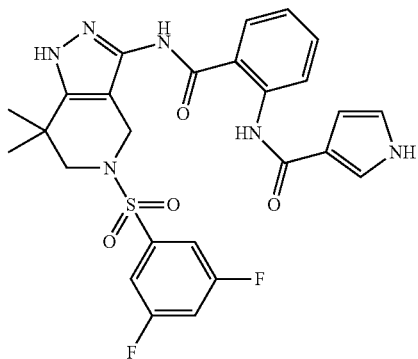

1H-NMR (400 MHz), δ (ppm, DMSO-d$_6$): 12.64 (bs, 1H), 11.52 (bs, 1H), 11.38 (bs, 1H), 10.69 (s, 1H), 8.59 (d, J=8.42 Hz, 1H), 7.96 (dd, J=7.77 Hz, 1H), 7.67 (tt, J=9.06 and 2.14

Hz, 1H), 7.59-7.52 (m, 3H), 7.39 (m, 1H), 7.16 (t, J=7.77 Hz, 1H), 6.83 (q, J=2.46 Hz, 1H), 6.47 (bs, 1H), 4.13 (bs, 2H), 3.18 (bs, 2H), 1.31 (s, 6H).

EXAMPLE 18

Preparation of 2-(2-Amino-acetylamino)-N-[5-(3,5-difluoro-benzenesulfonyl)-4,5,6,7-tetrahydro-1H-pyrazolo[4,3-c]pyridin-3-yl]-4-(4-methyl-piperazin-1-yl)-benzamide [(I), Ra=Rb=H, A=D=E=CH, B=CR2, R=3,5-difluorophenyl, R1=NHCOR4, R2=4-methylpiperazin-1-yl, R4=aminomethyl], cpd. 10

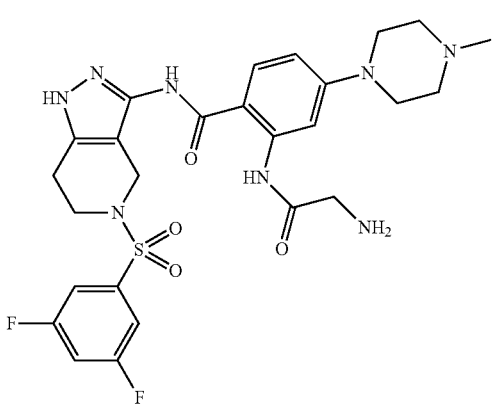

A solution of N-FMOC-glycine carbonyl chloride (4 eq., 3.04 mmol) in dry THF (3 mL) was added to the solution of 3-[2-amino-4-(4-methyl-piperazin-1-yl)-benzoylamino]-5-(3,5-difluoro-benzenesulfonyl)-4,5,6,7-tetrahydro-pyrazolo[4,3-c]pyridine-1-carboxylic acid ethyl ester hydrochloride (0.48 g, 0.76 mmol) and N,N-diisopropylethylamine (6 eq., 0.80 mL, 4.56 mmol) in dry THF (10 mL), maintained under stirring at room temperature. The mixture was heated to 50° C. for 2 hours, evaporated to dryness, taken up in dichloromethane (20 mL), washed with water (20 mL), brine (20 mL), dried over sodium sulphate and evaporated. Piperidine (20 eq., 1.5 mL) and methanol (10 mL) were added to the crude material and stirring was continued for 2 hours at 40° C. After evaporation of the solvent, the mixture was purified by preparative HPLC-MS. The fractions containing the product were evaporated, and the residue was triturated with cold methanol to yield the title compound as colourless solid (0.150 g, 33% yield).

1H-NMR (400 MHz), δ (ppm, DMSO-$d_6$): 12.30 (bs, 1H), 10.31 (s, 1H), 8.26 (d, J2=2.44 Hz, 1H), 7.77 (d, J1=8.90 Hz, 1H), 7.65 (m, 1H), 7.60 (m, 2H), 6.72 (d, J1=8.90 Hz, 1H), 4.19 (s, 2H), 3.52 (m, 2H), 3.28 (m, 6H), 2.70 (m, 2H), 2.46 (m, 4H), 2.24 (s, 3H).

Operating in an analogous way, the following compounds were obtained:

N-[5-(3,5-Difluoro-benzenesulfonyl)-4,5,6,7-tetrahydro-1H-pyrazolo[4,3-c]pyridin-3-yl]-2-(2-methylamino-acetylamino)-4-(4-methyl-piperazin-1-yl)-benzamide [(I), Ra=Rb=H, A=D=E=CH, B=CR2, R=3,5-difluorophenyl, R1=NHCOR4, R2=4-methylpiperazin-1-yl, R4=N-methylaminomethyl], cpd. 11

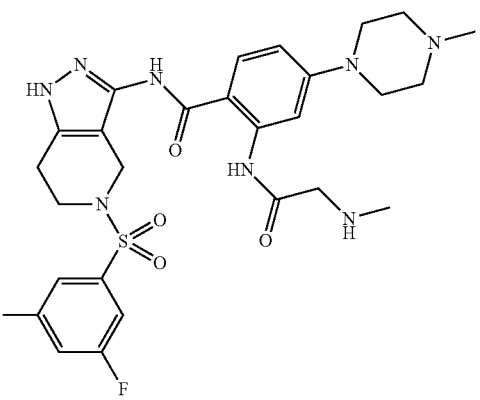

1H-NMR (400 MHz), δ (ppm, DMSO-$d_6$): 12.29 (s, 1H), 10.29 (s, 1H), 8.30 (d, J2=2.19 Hz, 1H), 7.81 (d, J1=9.02 Hz, 1H), 7.65 (m, 1H), 7.59 (m, 2H), 6.70 (d, J1=9.02 Hz, 1H), 4.21 (s, 2H), 3.54 (m, 2H), 3.29 (m, 4H), 3.22 (s, 2H), 2.69 (m, 2H), 2.46 (m, 4H), 2.29 (s, 3H), 2.25 (s, 3H).

2-((R)-2-Amino-propionylamino)-N-[5-(3,5-difluoro-benzenesulfonyl)-4,5,6,7-tetrahydro-1H-pyrazolo[4,3-c]pyridin-3-yl]-4-(4-methyl-piperazin-1-yl)-benzamide [(I), Ra=Rb=H, A=D=E=CH, B=CR2, R=3,5-difluorophenyl, R1=NHCOR4, R2=4-methylpiperazin-1-yl, R4=(R)-1-aminoethyl], cpd. 13

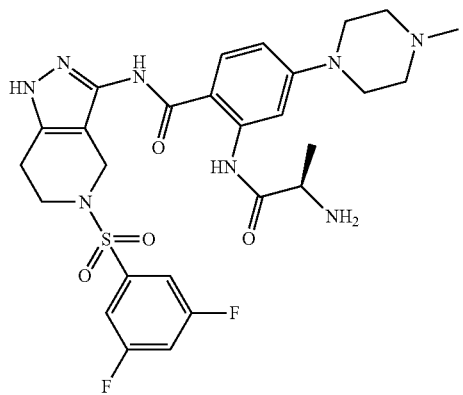

1H-NMR (400 MHz), δ (ppm, DMSO-$d_6$): 12.27 (s, 1H), 10.28 (bs, 1H), 8.25 (d, J2=2.43 Hz, 1H), 7.76 (d, J1=8.91 Hz, 1H), 7.63 (m, 1H), 7.58 (m, 2H), 6.67 (d, bs, J1=8.91 Hz, 1H), 4.17 (s, 2H), 3.50 (m, 2H), 3.40 (q, J=6.96 Hz, 1H), 3.25 (m, 4H), 2.68 (m, 2H), 2.44 (m, 4H), 2.22 (s, 3H), 1.23 (d, J=6.96 Hz, 3H).

2-((S)-2-Amino-propionylamino)-N-[5-(3,5-difluoro-benzenesulfonyl)-4,5,6,7-tetrahydro-1H-pyrazolo[4,3-c]pyridin-3-yl]-4-(4-methyl-piperazin-1-yl)-benzamide [(I), Ra=Rb=H, A=D=E=CH, B=CR2, R=3,5-difluorophenyl, R1=NHCOR4, R2=4-methylpiperazin-1-yl, R4=(S)-1-aminoethyl], cpd. 14

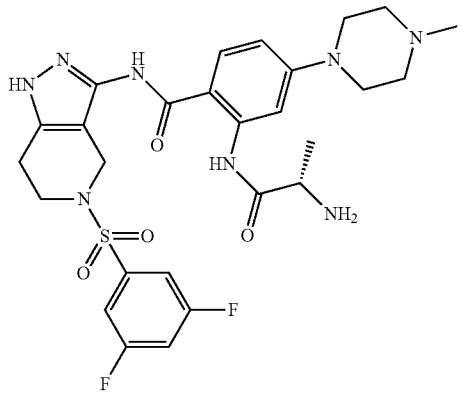

1H-NMR (400 MHz), δ (ppm, DMSO-d_6): 12.78 (s, 1H), 10.28 (s, 1H), 8.26 (d, J2=2.44 Hz, 1H), 7.77 (d, J1=8.90 Hz, 1H), 7.64 (m, 1H), 7.58 (m, 2H), 6.68 (d, bs, J1=8.90 MHz, 1H), 4.18 (s, 2H), 3.51 (m, 2H), 3.11 (q, J=6.95 Hz, 1H), 3.27-3.25 (m, 4H), 2.69 (m, 2H), 2.45 (m, 4H), 2.23 (s, 3H), 1.23 (d, J=6.95 Hz, 3H).

2-(3-Amino-propionylamino)-N-[5-(3,5-difluoro-benzenesulfonyl)-4,5,6,7-tetrahydro-1H-pyrazolo[4,3-c]pyridin-3-yl]-4-(4-methyl-piperazin-1-yl)-benzamide [(I), Ra=Rb=H, A=D=E=CH, B=CR2, R=3,5-difluorophenyl, R1=NHCOR4, R2=4-methylpiperazin-1-yl, R4=2-aminoethyl], cpd. 19

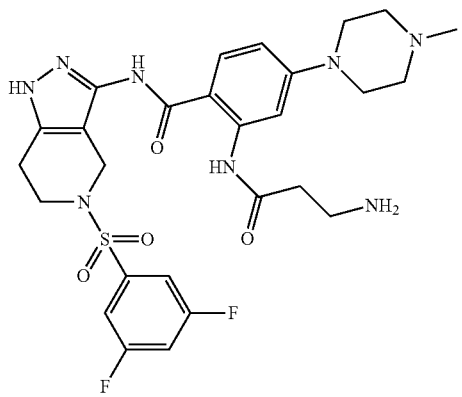

1H-NMR (400 MHz), δ (ppm, DMSO-d_6): 12.31 (bs, 1H), 8.14 (d, J2=2.44 Hz, 1H), 7.83 (d, J1=8.90 Hz, 1H), 7.65 (m, 1H), 7.58 (m, 2H), 6.68 (dd, J1=8.90 Hz, J2=2.44 Hz, 1H), 4.15 (s, 2H), 3.49 (m, 2H), 3.27 (m, 4H), 2.85 (t, J=6.58 Hz, 2H), 2.68 (m, 2H), 2.43 (m, 4H), 2.40 (t, J=6.58 Hz, 2H), 2.21 (s, 3H).

(R)-Pyrrolidine-2-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide [(I), Ra=Rb=H, A=D=E=CH, B=CR2, R=3,5-difluorophenyl, R1=NHCOR4, R2=4-methylpiperazin-1-yl, R4=(R)-pyrrolidin-2-yl], cpd. 16

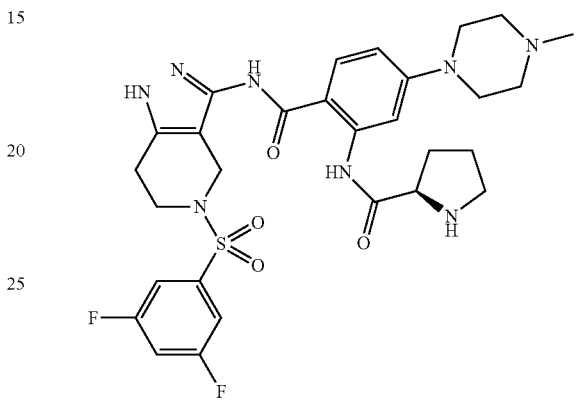

1H-NMR (400 MHz), δ (ppm, DMSO-d_6): 12.28 (bs, 1H), 12.20 (bs, 1H), 10.27 (bs, 1H), 8.30 (d, J2=2.44 Hz, 1H), 7.77 (d, J1=8.90 Hz, 1H), 7.65 (m, 1H), 7.59 (m, 2H), 6.70 (d, J1=8.90 Hz, 1H), 4.24 (s, 2H), 3.72 (dd, J1=8.90 Hz, J2=5.00 Hz, 1H), 3.65-3.5 (m, 2H), 3.27 (m, 4H), 2.90-2.80 (m, 2H), 2.68 (m, 2H), 2.46 (m, 4H), 2.24 (s, 3H), 2.03 (m, 1H), 1.82 (m, 1H), 1.61 (m, 2H).

(S)-Pyrrolidine-2-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide [(I), Ra=Rb=H, A=D=E=CH, B=CR2, R=3,5-difluorophenyl, R1=NHCOR4, R2=4-methylpiperazin-1-yl, R4=(S)-pyrrolidin-2-yl], cpd. 15

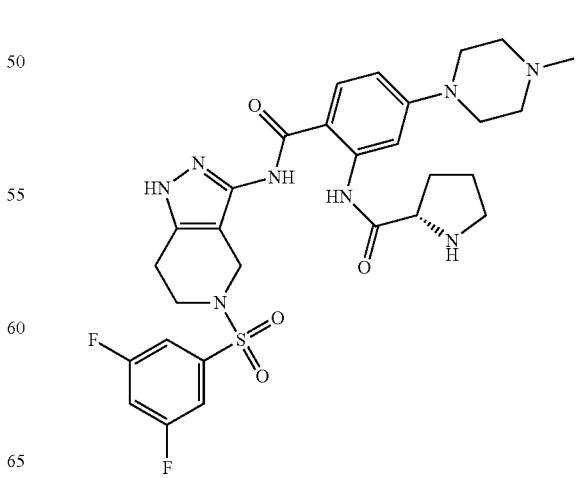

1H-NMR (400 MHz), δ (ppm, DMSO-d$_6$): 12.28 (s, 1H), 12.20 (bs, 1H), 10.27 (bs, 1H), 8.30 (d, J2=2.44 Hz, 1H), 7.78 (d, J1=8.90 Hz, 1H), 7.65 (m, 1H), 7.59 (m, 2H), 6.68 (d, J1=8.90 Hz, 1H), 4.24 (s, 2H), 3.72 (dd, J1=9.14 Hz, J2=5.12 Hz, 1H), 3.65-3.47 (m, 2H), 3.27 (m, 4H), 2.89 (m, 1H), 2.80 (m, 1H), 2.68 (m, 2H), 2.46 (m, 4H), 2.24 (s, 3H), 2.04 (m, 1H), 1.82 (m, 1H), 1.61 (m, 2H).

Piperidine-4-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide [(I), Ra=Rb=H, A=D=E=CH, B=CR2, R=3,5-difluorophenyl, R1=NHCOR4, R2=4-methylpiperazin-1-yl, R4=piperidin-4-yl], cpd. 23

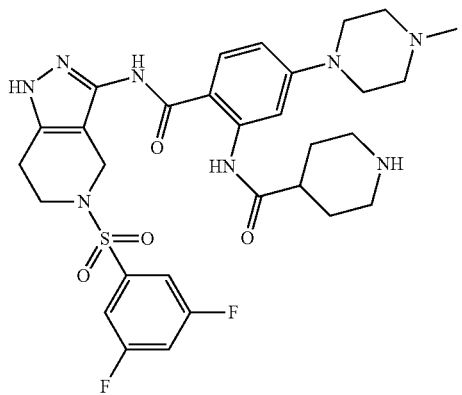

1H-NMR (400 MHz), δ (ppm, DMSO-d$_6$): 12.32 (s, 1H), 11.79 (s, 1H), 10.36 (s, 1H), 8.21 (d, J=2.57 Hz, 1H), 7.86 (d, J1=9.14 Hz, 1H), 7.63 (m, 1H), 7.57 (m, 2H), 6.68 (dd, J1=9.14 Hz, J2=2.57 Hz, 1H), 4.19 (s, 2H), 3.51 (m, 2H), 3.31 (m, 4H), 2.92 (m, 2H), 2.65 (m, 2H), 2.43 (m, 6H), 2.29 (m, 1H), 2.21 (s, 3H), 1.75 (m, 2H), 1.47 (m, 2H).

Piperidine-3-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide [(I), Ra=Rb=H, A=D=E=CH, B=CR2, R=3,5-difluorophenyl, R1=NHCOR4, R2=4-methylpiperazin-1-yl, R4=piperidin-3-yl], cpd. 22

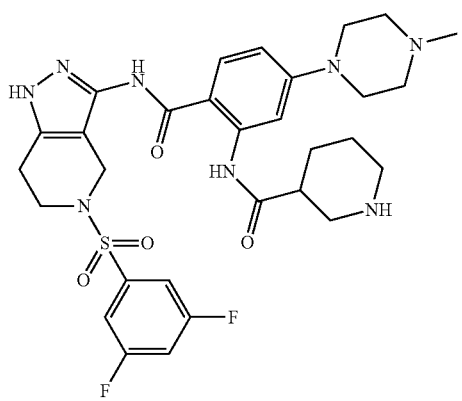

1H-NMR (400 MHz), δ (ppm, DMSO-d$_6$): 12.36, 12.31 (bs, 1H), 11.78 (bs, 1H), 10.52, 10.35 (bs, 1H), 8.18, 8.17 (d, J2=2.56 Hz, 1H), 7.98, 7.85 (d, J1=8.78 Hz, 1H), 7.64 (m, 1H), 7.57 (m, 2H), 6.84, 6.88 (d, bs, J1=8.78 Hz, 1H), 4.19 (s, 2H), 3.51 (m, 2H), 3.35-3.22 (m, 4H), 3.06 (dd, J1=11.83 Hz, J2=3.41 Hz, 1H), 2.80 (m, 1H), 2.66 (m, 2H), 2.60 (dd, J1=11.83 Hz, J2=9.87 Hz, 1H), 2.44-2.37 (m, 5H), 2.31 (m, 1H), 2.21 (s, 3H), 1.92 (m, 1H), 1.62-1.53 (m, 2H), 1.36 (m, 1H), mixture of tautomers.

Piperidine-2-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide [(I), Ra=Rb=H, A=D=E=CH, B=CR2, R=3,5-difluorophenyl, R1=NHCOR4, R2=4-methylpiperazin-1-yl, R4=piperidin-2-yl], cpd. 21

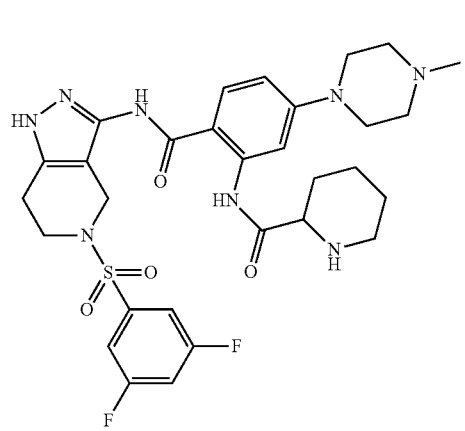

1H-NMR (400 MHz), δ (ppm, DMSO-d$_6$): 12.40, 12.26 (bs, 1H), 11.91 (bs, 1H), 10.26 (bs, 1H), 8.27 (d, J2=2.44 Hz, 1H), 7.79 (d, J1=8.90 Hz, 1H), 7.65-7.58 (m, 3H), 6.67 (d, bs, J1=8.90 Hz, 1H), 4.23 (s, 2H), 3.53 (m, 2H), 3.25 (m, 4H), 3.16 (dd, J1=9.51 Hz, J2=3.01 Hz, 1H), 2.85 (m, 1H), 2.64 (m, 2H), 2.55-2.50 (m, 1H), 2.44 (m, 4H), 2.22 (s, 3H), 1.82-1.23 (m, 6H), mixture of tautomers.

Piperidine-4-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-phenyl}-amide [(I), Ra=Rb=methyl, A=B=D=E=CH, R=3,5-difluorophenyl, R1=NHCOR4, R4=piperidine-4-yl], cpd. 497

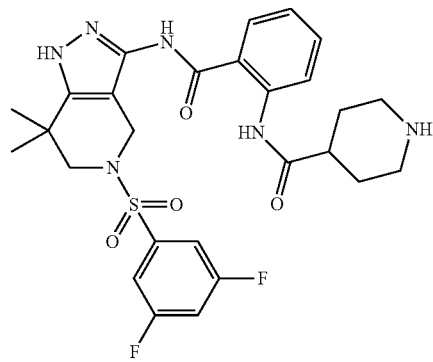

1H-NMR (400 MHz), δ (ppm, DMSO-d$_6$): 12.61 (bs, 1H), 10.94 (bs, 1H), 10.63 (bs, 1H), 8.37 (d, J=8.53 Hz, 1H), 7.89 (d, J=7.88 Hz, 1H), 7.71 (tt, J=9.18 and 2.27 Hz, 1H), 7.61-7.51 (m, 3H), 7.19 (t, J=7.88 Hz, 1H), 4.09 (s, 2H), 3.16 (s, 2H), 2.98 (dt, J=12.3 and 3.35 Hz, 2H), 2.52 (m, 2H), 2.39 (m, 1H), 1.77 (m, 2H), 1.53 (m, 2H), 1.30 (s, 6H).

(S)-Pyrrolidine-2-carboxylic acid {2-[5-(3,5-difluoro-benzenesulfonyl)-7,7-dimethyl-4,5,6,7-tetrahydro-1H-pyrazolo[4,3-c]pyridin-3-ylcarbamoyl]-5-morpholin-4-yl-phenyl}-amide [(I), Ra=Rb=methyl, A=D=E=CH, B=CR2, R=3,5-difluorophenyl, R1=NHCOR4, R2=morpholin-4-yl, R4=(S)-pyrrolidine-2-yl], cpd. 366

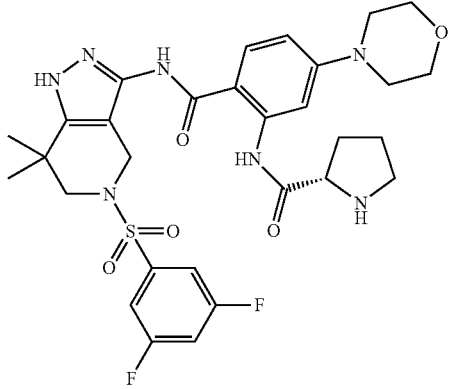

1H-NMR (400 MHz), δ (ppm, DMSO-d$_6$): 12.52 (bs, 1H), 12.14 (bs, 1H), 10.24 (bs, 1H), 8.31 (m, 1H), 7.71 (m, 1H), 7.58 (m, 2H), 6.70 (m, 1H), 4.05 (s, 2H), 3.76 (m, 4H), 3.71 (m, 1H), 3.27-3.29 (m, 2H), 3.23 (m, 1H), 3.13 (m, 1H), 2.88 (m, 3H), 2.09 (m, 1H), 1.83 (m, 1H), 1.60 (m, 2H), 1.30 (s, 6H).

(R)-Pyrrolidine-2-carboxylic acid {2-[5-(3,5-difluoro-benzenesulfonyl)-4,5,6,7-tetrahydro-1H-pyrazolo[4,3-c]pyridin-3-ylcarbamoyl]-phenyl}-amide [(I), Ra=Rb=H, A=B=D=E=CH, R=3,5-difluorophenyl, R1=NHCOR4, R4=(R)-pyrrolidine-2-yl], cpd. 236

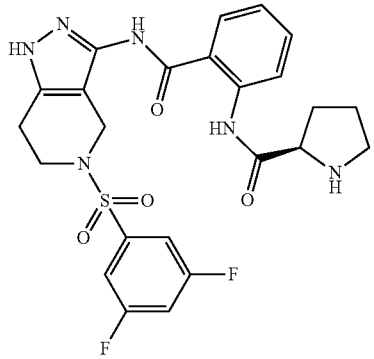

1H-NMR (400 MHz), δ (ppm, DMSO-d6): 12.35 (bs, 1H), 11.70 (bs, 1H), 10.61 (bs, 1H), 8.51 (d, J=8.10 Hz, 1H), 7.80 (d, J=8.10 Hz, 1H), 7.70-7.56 (m, 3H), 7.52 (t, J=8.10 Hz, 1H), 7.16 (t, J=8.10 Hz, 1H), 4.33-4.22 (m, 2H), 3.74 (dd, J=9.02 and J=5.12, 1H), 3.67-3.44 (m, 2H), 3.03 (bs, 1H), 2.96-2.85 (m, 1H), 2.83-2.74 (m, 1H), 2.73-2.64 (m, 2H), 2.11-1.98 (m, 1H), 1.88-1.77 (m, 1H), 1.68-1.56 (m, 2H).

(R)-Pyrrolidine-2-carboxylic acid {2-[5-(3,5-difluoro-benzenesulfonyl)-4,5,6,7-tetrahydro-1H-pyrazolo[4,3-c]pyridin-3-ylcarbamoyl]-3-fluoro-phenyl}-amide [(I), Ra=Rb=H, A=B=D=CH, E=CR2, R=3,5-difluorophenyl, R1=NHCOR4, R2=fluoro, R4=(R)-pyrrolidine-2-yl], cpd. 547

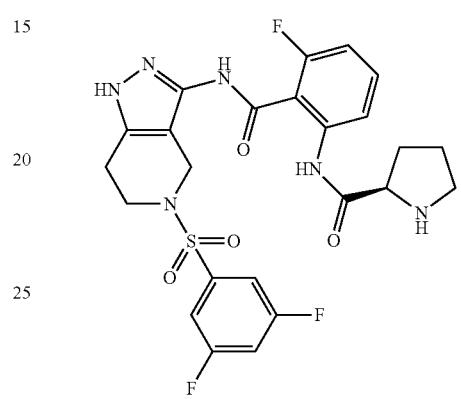

1H-NMR (400 MHz), δ (ppm, DMSO-d6): 12.33 (bs, 1H), 10.79 (s, 1H), 10.76 (s, 1H), 8.15 (d, J=8.15 Hz, 1H), 7.70-7.62 (m, 1H), 7.60-7.41 (m, 3H), 7.03 (t, J=8.15 Hz, 1H), 4.42-4.19 (m, 2H), 3.80-3.78 (m, 1H), 3.65-3.45 (m, 2H), 3.19-2.99 (m, 1H), 2.95-2.80 (m, 1H), 2.75-2.60 (m, 2H), 2.10-1.95 (m, 1H), 1.88-1.68 (m, 1H), 1.65-1.49 (m, 2H).

EXAMPLE 19

Preparation of 3H-Imidazole-4-carboxylic acid [2-[5-(3,5-difluoro-benzenesulfonyl)-4,5,6,7-tetrahydro-1H-pyrazolo[4,3-c]pyridin-3-ylcarbamoyl]-5-(4-methyl-piperazin-1-yl)-phenyl]-amide [(I), Ra=Rb=H, A=D=E=CH, B=CR2, R=3,5-difluorophenyl, R1=NHCOR4, R2=4-methylpiperazin-1-yl, R4=imidazol-4-yl], cpd. 38

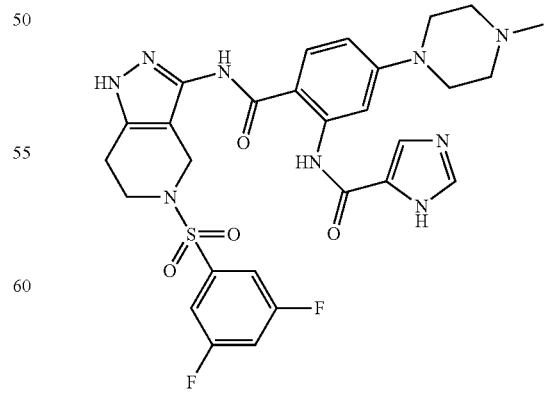

Oxalyl chloride (4.4 eq., 0.191 mL, 2.2 mmol) was added to a solution of 1-trityl-imidazol-4-yl carboxylic acid (4 eq., 0.71 g, 2.00 mmol), N,N-diisopropylethylamine (24 eq., 2.1 mL, 12 mmol) and 4-(N,N-dimethylamino)pyridine (4.4 eq., 0.27 g, 2.2 mmol) in dry THF (20 mL), maintained under stirring at room temperature. After about 3 hours 3-[2-amino-4-(4-methyl-piperazin-1-yl)-benzoylamino]-5-(3,5-difluoro-benzenesulfonyl)-4,5,6,7-tetrahydro-pyrazolo[4,3-c]pyridine-1-carboxylic acid ethyl ester hydrochloride (0.32 g, 0.5 mmol) was added and stirring was continued for 6 hours at 50° C. The mixture was evaporated, diluted with dichloromethane (50 mL), washed with water (30 mL), saturated sodium hydrogenocarbonate (100 mL), dried over sodium sulphate and evaporated to dryness. The resulting dark brown oil was treated with 4N HCl in 1,4-dioxane (5 mL) at room temperature for 2 hours, evaporated, added with triethylamine (10 mL) and methanol (10 mL) and stirred for 48 hours at room temperature. After removal of the solvents, the crude material was purified by flash chromatography on silica gel, using dichloromethane-methanol-30% $NH_4OH$ 100:10:1 as eluant, to give the title compound as colourless solid (0.087 g, 28% yield).

1H-NMR (400 MHz), δ (ppm, DMSO-$d_6$): 12.55 (bs, 1H), 12.30 (s, 1H), 12.26 (s, 1H), 10.29 (s, 1H), 8.42 (d, J2=2.32 Hz, 1H), 7.79 (d, J1=8.91 Hz, 1H), 7.72 (s, 1H), 7.66 (s, 1H), 7.59 (m, 3H), 6.68 (dd, J1=8.91 Hz, J2=2.32 Hz, 1H), 4.18 (s, 2H), 3.51 (m, 2H), 3.31 (m, 4H), 2.71 (m, 2H), 2.49 (m, 4H), 2.26 (bs, 3H).

Operating in an analogous way, the following compound was obtained:

3H-Imidazole-4-carboxylic acid {2-[5-(3,5-difluoro-benzenesulfonyl)-4,5,6,7-tetrahydro-1H-pyrazolo[4,3-c]pyridin-3-ylcarbamoyl]-phenyl}-amide [(I), Ra=Rb=H, A=B=D=E=CH, R=3,5-difluorophenyl, R1=NHCOR4, R4=imidazol-4-yl], cpd. 225

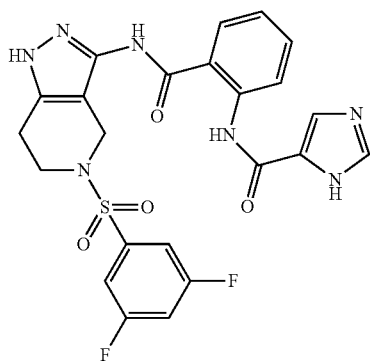

1H-NMR (400 MHz), δ (ppm, DMSO-$d_6$): 12.62-12.28 (bs, 2H), 11.70 (bs, 1H), 10.69 (bs, 1H), 8.63 (d, J=8.52 Hz, 1H), 7.90 (bs, 1H), 7.77 (bs, 1H), 7.70 (s, 1H), 7.52 (m, 1H), 7.55 (m, 3H), 7.12 (m, bs, 1H), 4.26 (bs, 2H), 3.50 (m, bs, 2H), 2.69 (m, bs, 2H).

EXAMPLE 20

N-[5-(3,5-Difluoro-benzenesulfonyl)-4,5,6,7-tetrahydro-1H-pyrazolo[4,3-c]pyridin-3-yl]-3-[(1H-pyrrole-3-carbonyl)-amino]-isonicotinamide [(I), Ra=Rb=H, A=D=E=CH, B=N, R=3,5-difluorophenyl, R1=NHCOR4, R4=pyrrol-3-yl], cpd. 239

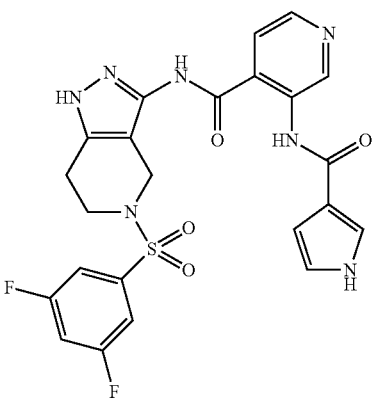

Step 1. 3-aminophthalimido-4-pyridine carboxylic acid

In order to avoid side reactions in the amidation step, 3-amino-4-pyridine carboxylic acid was first protected as phthalimido derivative. A mixture of phthalic anhydride (0.97 g, 6.57 mmol) and 3-amino-4-pyridine carboxylic acid (0.91 g, 6.57 mmol) was vigorously stirred at 125° C. for 24 hours in 20 mL of acetic acid. After cooling the solvent was removed under reduced pressure and the resulting solid dried at 70° C. in vacuum to give the title compound (1.23 g, 70% yield).

Step 2. 3-{[3-(1,3-Dioxo-1,3-dihydro-isoindol-2-yl)-pyridine-4-carbonyl]-amino}-6,7-dihydro-4H-pyrazolo[4,3-c]pyridine-1,5-dicarboxylic acid 5-tert-butyl ester 1-ethyl ester The 3-aminophthalimido-4-pyridine carboxylic acid was transformed into the corresponding acyl chloride and reacted with 3-amino-6,7-dihydro-4H-pyrazolo[4,3-c]pyridine-1,5-dicarboxylic acid 5-tert-butyl ester 1-ethyl ester as described above.

1H-NMR (400 MHz), δ (ppm, DMSO-$d_6$): 11.53 (s, 1H), 8.87 (d, J=4.9 Hz, 1H), 8.83 (s, 1H), 8.08-7.91 (m, 4H), 7.88 (d, J=4.9 Hz, 1H), 4.39 (q, J=7.1 Hz, 2H), 4.17 (bs, 2H), 3.56 (m, 2H), 2.93 (m, 2H), 1.38 (bs, 9H), 1.34 (t, J=7.1 Hz, 3H).

Step 3. 3-[(3-Amino-pyridine-4-carbonyl)-amino]-6,7-dihydro-4H-pyrazolo[4,3-c]pyridine-1,5-dicarboxylic acid 5-tert-butyl ester 1-ethyl ester [(IV), Q=ethyl, Ra=Rb=H, A=D=E=CH, B=N, R1=amino]

To a mixture of 3-{[3-(1,3-dioxo-1,3-dihydro-isoindol-2-yl)-pyridine-4-carbonyl]-amino}-6,7-dihydro-4H-pyrazolo

[4,3-c]pyridine-1,5-dicarboxylic acid 5-tert-butyl ester 1-ethyl ester (1.68 g, 3 mmol) in 35 mL of EtOH was added hydrazine hydrate (0.37 mL) and the solution was heated to reflux for 1 hour. After cooling, the precipitate was filtered off and the filtrate evaporated in vacuum. The product was chromatographed twice, using dichloromethane-MeOH 95:5 as eluant, to afford 3-[(3-amino-pyridine-4-carbonyl)-amino]-1,4,6,7-tetrahydro-pyrazolo[4,3-c]pyridine-5-carboxylic acid tert-butyl ester (0.8 g, 74% yield).

A solution of this compound (0.37 g, 1.02 mmol) was dissolved in 10 mL of dry THF and treated with 0.23 mL of N,N-diisopropylethylamine, 0.095 mL of ethyl chloroformate. The resulting solution was stirred for 4 hours. The solvent was evaporated and the crude was chromatographed, using dichloromethane-EtOH 95:5 as eluant, affording the title compound as brown-yellow solid (0.22 g, 50% yield).

1H-NMR (400 MHz), δ (ppm, DMSO-$d_6$): 11.06 (s, 1H), 8.20 (s, 1H), 7.76 (d, J=5.4 Hz, 1H), 7.61 (d, J=4.9 Hz, 1H), 6.65 (bs, 2H), 4.39 (q, J=7.3 Hz, 2H), 4.27 (bs, 2H), 3.63 (m, 2H), 2.98 (m, 2H), 1.40 (bs, 9H), 1.33 (t, J=7.3 Hz, 3H).

Step 4. 3-[(3-{[1-(Toluene-4-sulfonyl)-1H-pyrrole-3-carbonyl]-amino}-pyridine-4-carbonyl)-amino]-6,7-dihydro-4H-pyrazolo[4,3-c]pyridine-1,5-dicarboxylic acid 5-tert-butyl ester 1-ethyl ester [(IV), Q=ethyl, Ra=Rb=H, A=D=E=CH, B=N, R1=NHCOR4, R4=1-(toluene-4-sulfonyl)-1H-pyrrol-3-yl]

To a solution of 1-(toluene-4-sulfonyl)-1H-pyrrol-3-yl carboxylic acid chloride (50 mg, 0.174 mmol) and 3-[(3-amino-pyridine-4-carbonyl)-amino]-6,7-dihydro-4H-pyrazolo[4,3-c]pyridine-1,5-dicarboxylic acid 5-tert-butyl ester 1-ethyl ester (50 mg, 0.116 mmol) in 2 mL of anhydrous THF under argon atmosphere was dropped N,N-diisopropylethylamine (0.35 mmol) and the resulting mixture was stirred at 65° C. for 90 minutes. The solvent was evaporated under reduced pressure, the residue was taken up with dichloromethane, washed with saturated NaHCO₃, and evaporated. The crude was chromatographed, using dichloromethane-EtOH 95:5 as eluant, to give the title compound as pale yellow solid (33 mg, 40% yield).

1H-NMR (400 MHz), δ (ppm, DMSO-$d_6$): 11.25 (s, 1H), 10.56 (s, 1H), 8.97 (s, 1H), 8.51 (d, J=5.0 Hz, 1H), 8.06 (bs, 1H), 7.93 (m, 2H), 7.69 (d, J=5.0 Hz, 1H), 7.53-7.43 (m, 3H), 6.84 (bs, 1H), 4.40 (q, J=7.1 Hz, 2H), 4.35 (bs, 2H), 3.63 (m, 2H), 2.98 (m, 2H), 2.40 (s, 3H), 1.41 (bs, 9H), 1.34 (t, J=7.1 Hz, 3H).

Step 5. 3-[(3-{[1-(Toluene-4-sulfonyl)-1H-pyrrole-3-carbonyl]-amino}-pyridine-4-carbonyl)-amino]-4,5,6,7-tetrahydro-pyrazolo[4,3-c]pyridine-1-carboxylic acid ethyl ester dihydrochloride [(V), Q=ethyl, Ra=Rb=H, A=D=E=CH, B=N, R1=NHCOR4, R4=1-(toluene-4-sulfonyl)-1H-pyrrol-3-yl]

A suspension of 3-[(3-{[1-(toluene-4-sulfonyl)-1H-pyrrole-3-carbonyl]-amino}-pyridine-4-carbonyl)-amino]-6,7-dihydro-4H-pyrazolo[4,3-c]pyridine-1,5-dicarboxylic acid 5-tert-butyl ester 1-ethyl ester (30 mg) in 1,4-dioxane (5 mL) was treated with 4N HCl in 1,4-dioxane at room temperature for 4 hours. After removal of the solvent, the crude material was treated with diethyl ether (20 mL) and evaporated to dryness. The residue was triturated with diethyl ether, filtered, and dried in vacuum. The solid was used in the next step without further purification.

Step 6. N-[5-(3,5-Difluoro-benzenesulfonyl)-4,5,6,7-tetrahydro-1H-pyrazolo[4,3-c]pyridin-3-yl]-3-[(1H-pyrrole-3-carbonyl)-amino]-isonicotinamide To a solution of 3-[(3-{[1-(toluene-4-sulfonyl)-1H-pyrrole-3-carbonyl]-amino}-pyridine-4-carbonyl)-amino]-4,5,6,7-tetrahydro-pyrazolo[4,3-c]pyridine-1-carboxylic acid ethyl ester dihydrochloride (0.069 mmol) in 1 mL of dry dichloromethane at 0° C. was added N,N-diisopropylethylamine (0.207 mmol) and 3,5-difluorobenzenesulfonyl chloride (0.069 mmol) in 10 minute time. After 30 minutes, the reaction mixture was washed with saturated NaHCO₃, and the organic phase evaporated to dryness. The compound was used without further purification.

To a solution of starting material (0.069 mmol) in 1 mL of dioxane was added 2N NaOH (0.200 mL) and the resulting mixture was stirred at room temperature for 2 days. The mixture was then evaporated to dryness, and the crude was chromatographed, using dichloromethane-MeOH—NH₃ 90:10:1 as eluant, affording the title compound (15 mg, 51% yield).

1H-NMR (400 MHz), δ (ppm, DMSO-$d_6$): 12.43 (bs, 1H), 11.43 (bs, 1H), 10.97 (bs, 2H), 9.60 (s, 1H), 8.43 (d, J=5.0 Hz, 1H), 7.82 (d, J=5.0 Hz, 1H), 7.64 (m, 1H), 7.55-7.51 (m, 2H), 7.47 (bs, 1H), 6.85 (bs, 1H), 6.54 (bs, 1H), 4.29 (bs, 2H), 3.54 (m, 2H), 2.71 (m, 2H).

N-[5-(3,5-Difluoro-benzenesulfonyl)-4,5,6,7-tetrahydro-1H-pyrazolo[4,3-c]pyridin-3-yl]-3-[(1-methyl-1H-pyrrole-2-carbonyl)-amino]-isonicotinamide [(I), Ra=Rb=H, A=D=E=CH, B=N, R=3,5-difluorophenyl, R1=NHCOR4, R4=1-methyl-1H-pyrrol-2-yl], cpd. 544

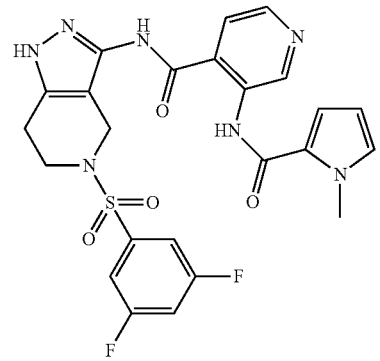

1H-NMR (400 MHz), δ (ppm, DMSO-$d_6$): 12.44 (s, 1H), 11.13 (s, 1H), 11.01 (s, 1H), 9.55 (s, 1H), 8.45 (d, J=5.13 Hz, 1H), 7.85 (d, J=5.13 Hz, 1H), 7.65 (tt, J=8.97 and 2.56 Hz, 1H), 7.53-7.49 (m, 2H), 7.09-7.07 (m, 2H), 6.11 (dd, J=4.08 and 2.5 Hz, 1H), 4.26 (s, 2H), 3.92 (s, 3H), 3.53 (t, J=5.56 Hz, 2H), 2.72 (t, J=5.56 Hz, 2H).

EXAMPLE 21

Preparation of 3-{[2-[5-(3,5-Difluoro-benzenesulfonyl)-4,5,6,7-tetrahydro-1H-pyrazolo[4,3-c]pyridin-3-ylcarbamoyl]-5-(4-methyl-piperazin-1-yl)-phenylamino]-methyl}-piperidine-1-carboxylic acid tert-butyl ester [(I), Ra=Rb=H, A=D=E=CH, B=CR2, R=3,5-difluorophenyl, R1=NR5R6, R2=4-methylpiperazin-1-yl, R5=(1-tert-butyloxycarbonyl)-piperidin-3-yl-methyl, R6=H]

To a stirred solution of 3-[2-amino-4-(4-methyl-piperazin-1-yl)-benzoylamino]-5-(3,5-difluoro-benzenesulfonyl)-4,5,6,7-tetrahydro-pyrazolo[4,3-c]pyridine-1-carboxylic acid ethyl ester hydrochloride (0.3 g, 0.469 mmol) in anhydrous methanol (5 mL) 3-formyl-piperidine-1-carboxylic acid tert-butylester (1.5 eq., 0.15 g, 0.704 mmol) and glacial acetic acid (0.081 mL, 1.41 mmol) were added. After few minutes, sodium cyanoborohydride (3 eq., 0.088 g, 1.41 mmol) was added and the reaction was stirred at room temperature overnight. The resulting mixture was partitioned between dichloromethane (30 mL) and an excess of 1M aqueous sodium carbonate (30 mL). The organic layer was washed with water, brine, dried over sodium sulphate and evaporated under vacuum. The residue was dissolved in methanol (20 mL) and triethylamine (10%) was added. The mixture was stiffed at room temperature overnight. After evaporation of the solvent the crude was chromatographed on silica gel, using dichloromethane-ethanol-$NH_4OH$ 90:10:0.5 as eluant, to give the title compound as colorless solid (0.17 g, 50% yield).

1H-NMR (400 MHz), δ (ppm, DMSO-$d_6$): 12.27, 12.19 (s, 1H), 9.89 (s, 1H), 8.27, 8.16 (m, bs, 1H), 7.69 (d, J1=8.78 Hz, 1H), 7.63 (m, 1H), 7.53 (m, 2H), 6.18 (dd, bs, J1=8.78 Hz, 1H), 6.00 (d, J2=1.96 Hz, 1H), 4.08 (m, 2H), 3.85 (m, 1H), 3.69 (m, 1H), 3.47 (m, 2H), 3.38-3.21 (m, 4H), 3.02 (m, 2H), 2.82 (m, 1H), 2.68 (m, 3H), 2.41 (m, 4H), 2.21 (s, 3H), 1.83-1.22 (m, 14H), mixture of tautomers.

Operating in an analogous way, the following compounds were obtained:

(R)-2-{[2-[5-(3,5-Difluoro-benzenesulfonyl)-4,5,6,7-tetrahydro-1H-pyrazolo[4,3-c]pyridin-3-ylcarbamoyl]-5-(4-methyl-piperazin-1-yl)-phenylamino]-methyl}-pyrrolidine-1-carboxylic acid tert-butyl ester [(I), Ra=Rb=H, A=D=E=CH, B=CR2, R=3,5-difluorophenyl, R1=NR5R6, R2=4-methylpiperazin-1-yl, R5=(R)-1-(tert-butyloxycarbonyl)-pirrolidin-2-yl-methyl, R6=H]

1H-NMR (400 MHz), δ (ppm, DMSO-$d_6$): 12.29, 12.21 (s, 1H), 9.89 (s, 1H), 8.34, 8.29 (bs, 1H), 7.71-7.65 (m, 2H), 7.56 (m, 2H), 6.57 (s, 1H), 6.19 (d, bs, J1=8.66 Hz, 1H), 4.17-4.08 (m, 2H), 3.92 (m, bs, 1H), 3.53-3.04 (m, 8H), 2.70 (m, 2H), 2.43 (m, 4H), 2.23 (s, 3H), 1.91-1.77 (m, 4H), 1.43, 1.38 (s, 9H), mixture of tautomers.

EXAMPLE 22

Preparation of 3-[2-[5-(3,5-Difluoro-benzenesulfonyl)-4,5,6,7-tetrahydro-1H-pyrazolo[4,3-c]pyridin-3-ylcarbamoyl]-5-(4-methyl-piperazin-1-yl)-phenylamino]-piperidine-1-carboxylic acid tert-butyl ester [(I), Ra=Rb=H, A=D=E=CH, B=CR2, R=3,5-difluorophenyl, R1=NR5R6, R2=4-methylpiperazin-1-yl, R5=(1-tert-butyloxycarbonyl)-piperidin-3-yl, R6=H]

To a stirred solution of 3-[2-amino-4-(4-methyl-piperazin-1-yl)-benzoylamino]-5-(3,5-difluoro-benzenesulfonyl)-4,5,6,7-tetrahydro-pyrazolo[4,3-c]pyridine-1-carboxylic acid ethyl ester hydrochloride (0.3 g, 0.469 mmol) in anhydrous N,N-dimethylformamide (2.5 mL) tert-butyl 3-oxo-piperidine-1-carboxylate (1.2 eq., 0.112 g, 0.564 mmol) and trifluoroacetic acid (0.25 mL) were added. After few minutes sodium triacetoxyborohydride (3 eq., 0.300 g, 1.41 mmol) was added and the reaction was stirred at room temperature overnight. The resulting mixture was partitioned between dichloromethane (30 mL) and an excess of 1M aqueous sodium carbonate (30 mL). The organic layer was washed with water, brine, dried over sodium sulphate and evaporated under vacuum. The residue was dissolved in methanol (20 mL) and triethylamine (10%) was added. The mixture was stiffed at room temperature overnight. After evaporation of the solvent the crude was purified by preparative HPLC to obtain the title compound as colourless solid (0.067 g, 20% yield).

1H-NMR (400 MHz), δ (ppm, DMSO-$d_6$): 12.14-11.98 (bs, 1H), 9.91-9.80 (bs, 1H), 8.20-8.10 (bs, 1H), 7.65-7.50 (m, 3H), 6.96 (d, 1H), 6.54-6.45 (s, 1H), 6.20-6.12 (d, 1H), 4.30-4.10 (m, 2H), 3.66-3.35 (m, 5H), 3.20-2.88 (m, 8H), 2.62-2.47 (m, 4H), 2.30 (s, 3H), 2.01-1.93 (m, 2H), 1.71-1.69 (m, 2H), 1.48 (s, 9H).

Operating in a way analogous to that described above, the following compounds were obtained:

(S)-2-{[2-[5-(3,5-Difluoro-benzenesulfonyl)-4,5,6,7-tetrahydro-1H-pyrazolo[4,3-c]pyridin-3-ylcarbamoyl]-5-(4-methyl-piperazin-1-yl)-phenylamino]-methyl}-pyrrolidine-1-carboxylic acid tert-butyl ester [(I), Ra=Rb=H, A=D=E=CH, B=CR2, R=3,5-difluorophenyl, R1=NR5R6, R2=4-methylpiperazin-1-yl, R5=(S)-1-(tert-butyloxycarbonyl)-pirrolidin-2-yl-methyl, R6=H]

1H-NMR (400 MHz), δ (ppm, DMSO-$d_6$): 12.29, 12.21 (s, 1H), 9.89 (s, 1H), 8.34 (d, bs, 1H), 7.67 (m, 2H), 7.55 (m, 2H), 6.57 (m, 1H), 6.19 (d, J=7.19 Hz, 1H), 4.12 (m, 2H), 3.91 (m, bs, 1H), 3.50-3.00 (m, 10H), 2.70 (m, 2H), 2.43 (m, 4H), 2.23 (s, 3H), 1.90-1.76 (m, 4H), 1.43 (s, 9H), mixture of tautomers.

4-[2-[5-(3,5-Difluoro-benzenesulfonyl)-4,5,6,7-tetrahydro-1H-pyrazolo[4,3-c]pyridin-3-ylcarbamoyl]-5-(4-methyl-piperazin-1-yl)-phenylamino]-piperidine-1-carboxylic acid tert-butyl ester [(I), Ra=Rb=H, A=D=E=CH, B=CR2, R=3,5-difluorophenyl, R1=NR5R6, R2=4-methylpiperazin-1-yl, R5=(1-tert-butyloxycarbonyl)-piperidin-3-yl, R6=H]

1H-NMR (400 MHz), δ (ppm, DMSO-$d_6$): 12.05-11.85 (bs, 1H), 9.90-9.80 (bs, 1H), 8.18-8.10 (bs, 1H), 7.63-7.48 (m, 3H), 6.94 (d, 1H), 6.50-6.40 (s, 1H), 6.18-6.10 (d, 1H), 4.40-4.20 (m, 2H), 3.90-3.59 (m, 7H), 3.15-3.05 (m, 4H), 3.03-2.90 (m, 2H), 2.34 (s, 3H), 2.60-2.52 (m, 4H), 1.98-1.76 (m, 4H), 1.46 (s, 9H).

N-[5-(3,5-Difluoro-benzenesulfonyl)-7,7-dimethyl-4,
5,6,7-tetrahydro-1H-pyrazolo[4,3-c]pyridin-3-yl]-2-
isobutylamino-4-(4-methyl-piperazin-1-yl)-benza-
mide [(I), Ra=Rb=methyl, A=D=E=CH, B=CR2,
R=3,5-difluorophenyl, R1=NR5R6, R2=4-meth-
ylpiperazin-1-yl R5=1-(2-methyl)propyl, R6=H],
cpd. 317

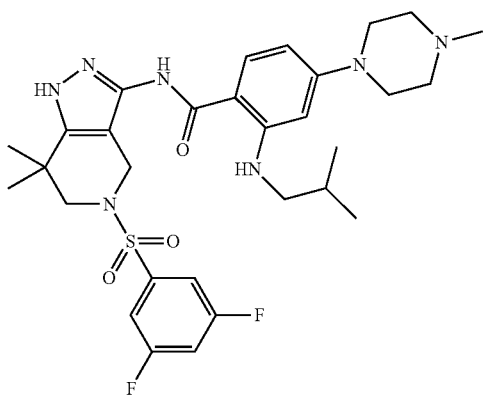

1H-NMR (400 MHz), δ (ppm, DMSO-d$_6$): 12.43, 12.31 (s, 1H), 9.88 (s, 1H), 8.26, 8.16 (t, bs, J=4.58 Hz, 1H), 7.74-7.67 (m, 2H), 7.53 (m, 2H), 6.19 (d, bs, J=8.54 Hz, 1H), 6.01 (bs, 1H), 4.03, 3.94 (s, 2H), 3.25 (m, 4H), 3.16 (s, 2H), 2.95 (m, 2H), 2.43 (m, 4H), 2.23 (s, 3H), 1.87 (m, 1H), 1.29, 1.25 (s, 6H), 0.98 (d, J=6.71 Hz, 6H), mixture of tautomers.

N-[5-(3,5-Difluoro-benzenesulfonyl)-7,7-dimethyl-4,
5,6,7-tetrahydro-1H-pyrazolo[4,3-c]pyridin-3-yl]-2-
[(furan-2-ylmethyl)-amino]-4-(4-methyl-piperazin-1-
yl)-benzamide [(I), Ra=Rb=methyl, A=D=E=CH,
B=CR2, R=3,5-difluorophenyl, R1=NR5R6, R2=4-
methylpiperazin-1-yl, R5=fur-2-yl-methyl, R6=H],
cpd. 318

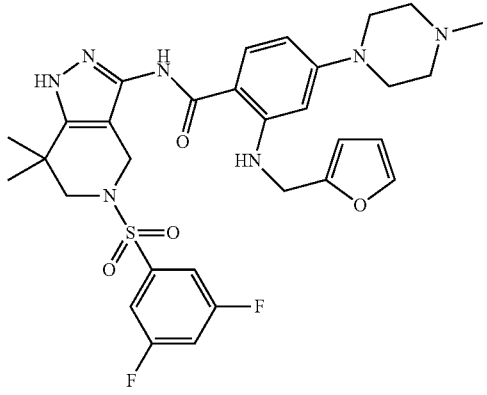

1H-NMR (400 MHz), δ (ppm, DMSO-d$_6$): 12.41, 12.32 (s, 1H), 9.86 (s, 1H), 8.83 (bs, 1H), 7.68 (m, 2H), 7.56 (d, J=1.10 Hz, 1H), 7.53 (m, 2H), 6.39 (dd, J1=3.17 Hz, J2=1.83 Hz, 1H), 6.82 (d, J=3.17 Hz, 1H), 6.21 (d, bs, J1=9.02 Hz, 1H), 6.16 (d, J2=2.19 Hz, 1H), 4.36 (d, J=5.49 Hz, 2H), 3.92 (s, 2H), 3.24 (m, 4H), 3.12 (s, 2H), 2.41 (m, 4H), 2.21 (s, 3H), 1.26 (s, 6H), mixture of tautomers.

N-[5-(3,5-Difluoro-benzenesulfonyl)-7,7-dimethyl-4,
5,6,7-tetrahydro-1H-pyrazolo[4,3-c]pyridin-3-yl]-4-
(4-methyl-piperazin-1-yl)-2-(tetrahydro-pyran-4-
ylamino)-benzamide [(I), Ra=Rb=methyl,
A=D=E=CH, B=CR2, R=3,5-difluorophenyl,
R1=NR5R6, R2=4-methylpiperazin-1-yl,
R5=tetrahydropyran-4-yl, R6=H], cpd. 329

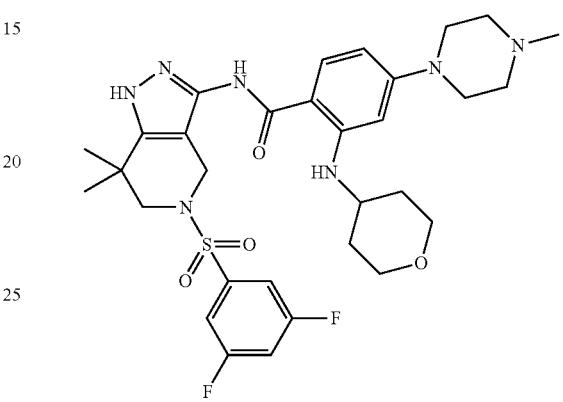

1H-NMR (400 MHz), δ (ppm, DMSO-d$_6$): 12.43 (bs, 1H), 9.88 (s, 1H), 8.21 (d, J1=6.57 Hz, 1H), 7.69 (m, 2H), 7.55 (m, 2H), 6.22 (m, 2H), 3.95 (bs, 2H), 3.81 (m, 2H), 3.68 (m, 1H), 3.52 (m, 2H), 3.26 (m, 4H), 3.15 (sb, 2H), 2.46 (m, 4H), 2.25 (s, 3H), 1.94 (m, 2H), 1.38 (m, 2H), 1.29 (s, 6H).

N-[5-(3,5-Difluoro-benzenesulfonyl)-4,5,6,7-tetrahy-
dro-1H-pyrazolo[4,3-c]pyridin-3-yl]-2-isobuty-
lamino-4-(4-methyl-piperazin-1-yl)-benzamide [(I),
Ra=Rb=H, A=D=E=CH, B=CR2, R=3,5-difluo-
rophenyl, R1=NR5R6, R2=4-methylpiperazin-1-yl,
R5=1-(2-methyl)propyl, R6=H], cpd. 51

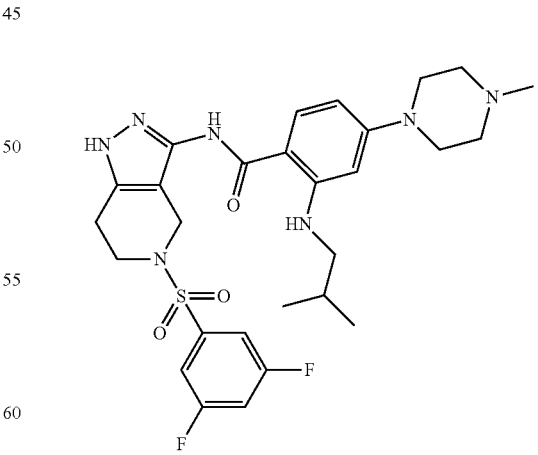

1H-NMR (400 MHz), δ (ppm, DMSO-d$_6$): 12.29, 12.22 (s, 1H), 9.91 (s, 1H), 8.30 (bs, 1H), 7.69 (m, 2H), 7.55 (m, 2H), 6.19 (d, J1=8.29 Hz, 1H), 6.02 (d, J2=2.07 Hz, 1H), 4.11 (s, 1H), 3.52 (m, 2H), 3.28 (m, 4H), 2.96 (m, 2H), 2.71 (m, 2H), 2.53-2.49 (m, 4H), 2.28 (s, 3H), 1.88 (m, 1H), 0.99 (d, J=6.70 Hz, 6H), mixture of tautomers.

N-[5-(3,5-Difluoro-benzenesulfonyl)-4,5,6,7-tetrahydro-1H-pyrazolo[4,3-c]pyridin-3-yl]-2-[(furan-2-ylmethyl)-amino]-4-(4-methyl-piperazin-1-yl)-benzamide [(I), Ra=Rb=H, A=D=E=CH, B=CR2, R=3,5-difluorophenyl, R1=NR5R6, R2=4-methylpiperazin-1-yl, R5=fur-2-yl-methyl, R6=H], cpd. 52

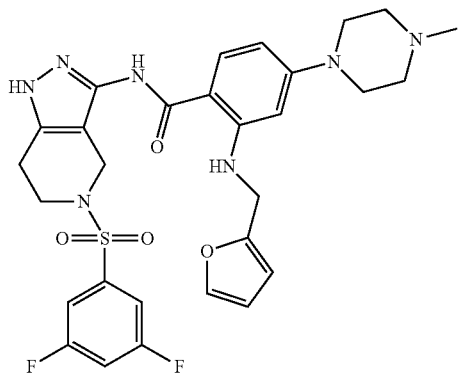

1H-NMR (400 MHz), δ (ppm, DMSO-d$_6$): 12.33, 12.22 (s, 1H), 9.92 (s, 1H), 8.42 (t, J=5.49 Hz, 1H), 7.70 (d, J1=8.90 Hz, 1H), 7.66 (m, 1H), 7.58 (m, 1H), 7.56 (m, 2H), 6.41 (dd, J1=3.05 Hz, J2=1.83 Hz, 1H), 6.35 (d, bs, J1=3.05 Hz, 1H), 6.24 (d, bs, J1=8.90 Hz, 1H), 6.19 (d, J2=1.83 Hz, 1H), 4.40 (d, J=5.49 Hz, 2H), 4.18, 4.11 (s, 2H), 3.51 (m, 2H), 3.31-3.26 (m, 4H), 2.70 (m, 2H), 2.43 (m, 4H), 2.23 (s, 3H), mixture of tautomers.

N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-[(1H-pyrrol-2-ylmethyl)-amino]-benzamide [(I), Ra=Rb=H, A=D=E=CH, B=CR2, R=3,5-difluorophenyl, R1=NR5R6, R2=4-methylpiperazin-1-yl, R5=pyrrol-2-yl-methyl, R6=H], cpd. 53

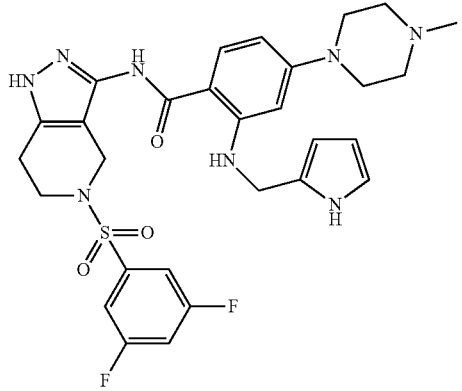

1H-NMR (400 MHz), δ (ppm, DMSO-d$_6$): 12.27, 12.18 (bs, 1H), 10.78 (s, 1H), 9.86 (s, 1H), 8.19 (m, bs, 1H), 7.65 (m, 2H), 7.53 (m, 2H), 6.63 (m, 1H), 6.20 (m, 1H), 6.12 (m, 1H), 5.96-5.92 (m, 2H), 4.23 (d, J=4.76 Hz, 2H), 4.06 (m, 2H), 3.47 (m, 2H), 3.30-3.03 (m, 4H), 2.67 (m, 2H), 2.41 (m, 4H), 2.21 (s, 3H), mixture of tautomers.

N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-[(1-methyl-1H-pyrrol-2-ylmethyl)-amino]-benzamide [(I), Ra=Rb=H, A=D=E=CH, B=CR2, R=3,5-difluorophenyl, R1=NR5R6, R2=4-methylpiperazin-1-yl, R5=1-methylpyrrol-2-yl-methyl, R6=H], cpd. 54

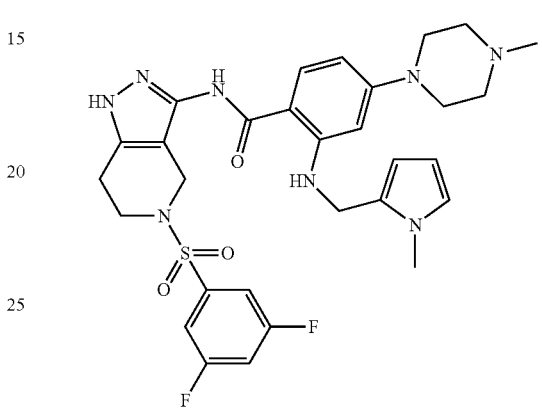

1H-NMR (400 MHz), δ (ppm, DMSO-d$_6$): 12.31, 12.21 (s, 1H), 9.91 (s, 1H), 8.29, 8.17 (m, bs, 1H), 7.72-7.65 (m, 2H), 7.64 (m, 2H), 6.67 (m, 1H), 6.24-6.22 (m, 2H), 6.03 (dd, J1=3.29 Hz, J2=1.58 Hz, 1H), 5.91 (dd, bs, J1=3.29 Hz, 1H), 4.81 (d, J=5.00 Hz, 2H), 4.09 (s, 2H), 3.58 (s, 3H), 3.51 (m, 2H), 3.31-3.27 (m, 4H), 2.69 (m, 2H), 2.45 (m, 4H), 2.24 (s, 3H), mixture of tautomers.

N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-(tetrahydro-pyran-4-ylamino)-benzamide [(I), Ra=Rb=H, A=D=E=CH, B=CR2, R=3,5-difluorophenyl, R1=NR5R6, R2=4-methylpiperazin-1-yl, R5=tetrahydropyran-4-yl, R6=H], cpd. 63

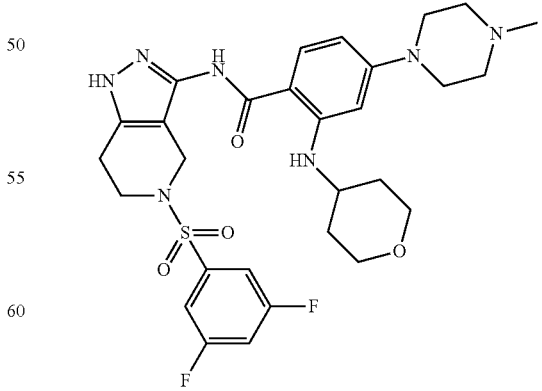

1H-NMR (400 MHz), δ (ppm, DMSO-d$_6$): 12.24 (s, 1H), 9.91 (s, 1H), 8.26 (d, J=6.95 Hz, 1H), 7.68 (m, 2H), 7.56 (m, 2H), 6.21 (d, bs, J1=8.54 Hz, 1H), 6.13 (d, J2=1.95 Hz, 1H), 4.10 (s, 2H), 3.84 (m, 2H), 3.70 (m, 1H), 3.55-3.49 (m, 4H), 3.26 (m, 4H), 2.71 (m, bs, 2H), 2.45 (m, 4H), 2.24 (s, 3H), 1.96 (m, bs, 2H), 1.88 (m, 2H).

2-Cyclohexylamino-N-[5-(3,5-difluoro-benzenesulfonyl)-4,5,6,7-tetrahydro-1H-pyrazolo[4,3-c]pyridin-3-yl]-4-(4-methyl-piperazin-1-yl)-benzamide [(I), Ra=Rb=H, A=D=E=CH, B=CR2, R=3,5-difluorophenyl, R1=NR5R6, R2=4-methylpiperazin-1-yl, R5=cyclohexyl, R6=H], cpd. 57

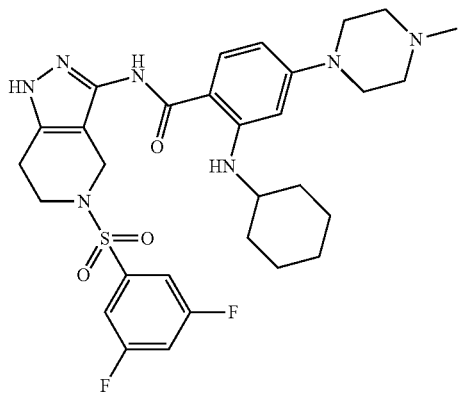

1H-NMR (400 MHz), δ (ppm, DMSO-$d_6$): 12.30, 12.22 (bs, 1H), 9.88 (s, 1H), 8.25, 8.17 (d, bs, J=7.19 Hz, 1H), 7.68 (m, 2H), 7.55 (m, H), 6.18 (d, bs, J1=8.78 Hz, 1H), 6.08 (d, J2=1.83 Hz, 1H), 4.10 (m, 2H), 3.51 (m, 2H), 3.24 (m, 4H), 2.71 (m, 2H), 2.44 (m, 4H), 2.24 (s, 3H), 1.91 (m, 2H), 1.68-1.27 (m, 8H), mixture of tautomers.

N-[5-(3,5-Difluoro-benzenesulfonyl)-4,5,6,7-tetrahydro-1H-pyrazolo[4,3-c]pyridin-3-yl]-4-piperazin-1-yl-2-(tetrahydro-pyran-4-ylamino)-benzamide [(I), Ra=Rb=H, A=D=E=CH, B=CR2, R=3,5-difluorophenyl, R1=NR5R6, R2=piperazin-1-yl, R5=tetrahydropyran-4-yl, R6=H], cpd. 75

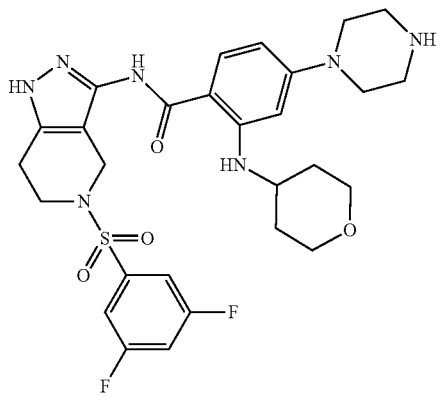

The title compound was obtained by the procedure described above starting from 3-{2-amino-4-[4-(2,2,2-trifluoro-acetyl)-piperazin-1-yl]-benzoylamino}-5-(3,5-difluoro-benzenesulfonyl)-4,5,6,7-tetrahydro-pyrazolo[4,3-c]pyridine-1-carboxylic acid ethyl ester.

1H-NMR (400 MHz), δ (ppm, DMSO-$d_6$): 12.22 (bs, 1H), 9.90 (bs, 1H), 8.24 (bs, 1H), 7.71-7.64 (m, 2H), 7.55 (m, 2H), 6.21 (d, J=8.3 Hz, 1H), 6.11 (d, J=2.2 Hz, 1H), 4.10 (bs, 2H), 3.86 (m, 2H), 3.70 (m, 1H), 3.56-3.47 (m, 4H), 3.18 (m, 4H), 2.84 (m, 4H), 2.71 (m, 2H), 1.95 (m, 2H), 1.38 (m, 2H).

N-[5-(3,5-Difluoro-benzenesulfonyl)-4,5,6,7-tetrahydro-1H-pyrazolo[4,3-c]pyridin-3-yl]-4-dimethylamino-2-isobutylamino-benzamide [(I), Ra=Rb=H, A=D=E=CH, B=CR2, R=3,5-difluorophenyl, R1=NR5R6, R2=N,N-dimethylamino, R5=1-(2-methyl)propyl, R6=H], cpd. 534

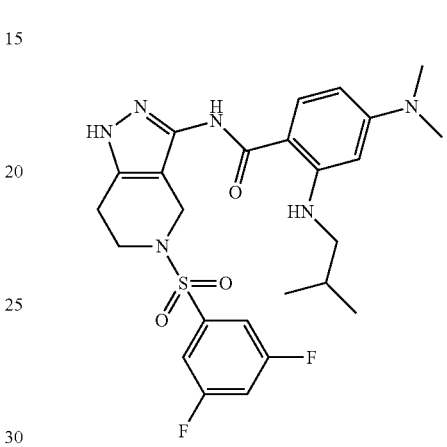

1H-NMR (400 MHz), δ (ppm, DMSO-$d_6$): 12.25, 12.17 (s, 1H), 9.79 (s, 1H), 8.36, 8.25 (m, bs, 1H), 7.71-7.62 (m, 2H), 7.54 (m, 2H), 5.98 (d, bs, J=8.90 Hz, 1H), 5.74 (d, bs, J=2.08 Hz, 1H), 4.14, 4.10 (s, 2H), 3.50 (m, 2H), 2.95 (m, 8H), 2.69 (m, 2H), 1.89 (m, 1H), 0.98 (d, J=6.70 Hz, 6H), mixture of tautomers.

N-[5-(3,5-Difluoro-benzenesulfonyl)-4,5,6,7-tetrahydro-1H-pyrazolo[4,3-c]pyridin-3-yl]-4-dimethylamino-2-(tetrahydro-pyran-4-ylamino)-benzamide [(I), Ra=Rb=H, A=D=E=CH, B=CR2, R=3,5-difluorophenyl, R1=NR5R6, R2=N,N-dimethylamino, R5=tetrahydropyran-4-yl, R6=H], cpd. 141

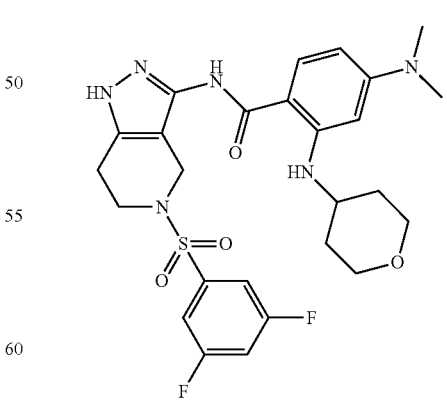

1H-NMR (400 MHz), δ (ppm, DMSO-$d_6$): 12.26, 12.18 (s, 1H), 9.80 (s, 1H), 8.33, 8.22 (d, J=7.44 Hz, 1H), 7.67 (m, 2H), 7.54 (m, 2H), 6.05, 5.99 (d, bs, J=8.78 Hz, 1H), 5.86 (d, bs, J=2.20 Hz, 1H), 4.16, 4.08 (bs, 2H), 3.85-3.80 (m, 2H), 3.65

(m, 1H), 3.53-3.46 (m, 6H), 2.96 (s, 6H), 2.70 (m, 2H), 1.97 (m, 1H), 1.37 (m, 2H), mixture of tautomers.

N-[5-(3,5-Difluoro-benzenesulfonyl)-4,5,6,7-tetrahydro-1H-pyrazolo[4,3-c]pyridin-3-yl]-2-(tetrahydropyran-4-ylamino)-benzamide [(I), Ra=Rb=H, A=B=D=E=CH, R=3,5-difluorophenyl, R1=NR5R6, R5=tetrahydropyran-4-yl, R6=H], cpd. 235

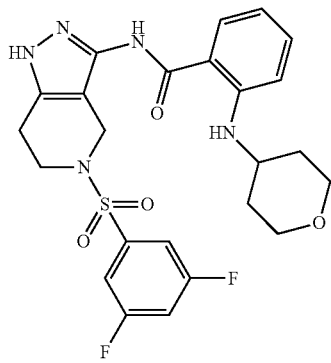

1H-NMR (400 MHz), δ (ppm, DMSO-d$_6$): 12.43, 12.28 (s, 1H), 10.25 (s, 1H), 7.79-7.74 (m, 2H), 7.66 (m, 1H), 7.55 (m, 2H), 7.30 (ddd, bs, J1=8.66 Hz, J2=7.93 Hz, 1H), 6.82 (d, bs, J=8.66 Hz, 1H), 6.57 (ddd, bs, J1=8.70 Hz, J2=7.93 Hz, 1H), 4.15, 4.10 (s, 2H), 3.85-3.80 (m, 2H), 3.62 (m, 1H), 3.51-3.44 (m, 4H), 2.70, 2.66 (m, 2H), 1.94 (m, 2H), 1.35 (m, 2H) mixture of tautomers.

EXAMPLE 23

Preparation of N-[5-(3,5-Difluoro-benzenesulfonyl)-4,5,6,7-tetrahydro-1H-pyrazolo[4,3-c]pyridin-3-yl]-2-(4-hydroxy-cyclohexylamino)-4-(4-methyl-piperazin-1-yl)-benzamide [(I), Ra=Rb=H, A=D=E=CH, B=CR2, R=3,5-difluorophenyl, R1=NR5R6, R2=4-methylpiperazin-1-yl, R5=4-hydroxycyclohexyl, R6=H], cpd. 58

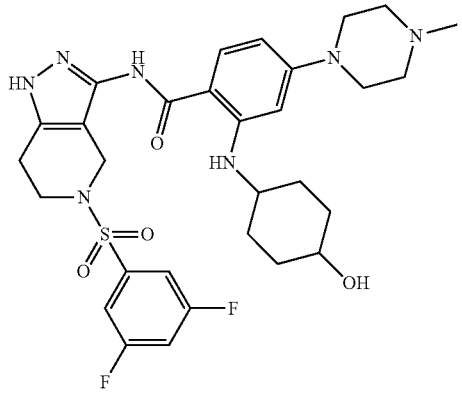

To a stirred solution of 3-[2-amino-4-(4-methyl-piperazin-1-yl)-benzoylamino]-5-(3,5-difluoro-benzenesulfonyl)-4,5,6,7-tetrahydro-pyrazolo[4,3-c]pyridine-1-carboxylic acid ethyl ester hydrochloride (0.3 g, 0.469 mmol) in anhydrous N,N-dimethylformamide (5 mL) benzoic acid 4-oxo-cyclohexyl ester (1.5 eq., 0.123 g, 0.563 mmol) and trifluoroacetic acid (0.5 mL) were added. After few minutes sodium triacetoxyborohydride (4 eq., 0.397 g, 1.88 mmol) was added and the reaction was stirred at room temperature overnight. The resulting mixture was partitioned between dichloromethane (30 mL) and an excess of 1M aqueous sodium carbonate (30 mL). The organic layer was washed with water, brine, dried over sodium sulphate and evaporated under vacuum. The residue was dissolved in a mixture of methanol (5 mL) and 2N sodium hydroxide (1 mL) and stiffed at room temperature overnight. After evaporation of the solvent the crude was purified by flash chromatography silica gel, using dichloromethane-methanol-NH$_4$OH 90:10:1 as eluant, to obtain the title compound as colourless solid (0.12 g, 42% yield).

1H-NMR (400 MHz), δ (ppm, DMSO-d$_6$): 12.32, 12.21 (s, 1H), 9.87, 9.85 (s, 1H), 8.33, 8.15 (bs, 1H), 7.71-7.53 (m, 3H), 6.18 (m, 1H), 6.08 (m, 1H), 4.55, 4.41 (d, J1=4.15 Hz, 1H), 4.18-4.07 (m, bs, 3H), 3.65-3.47 (m, bs, 3H), 3.25 (m, bs, 4H), 2.71 (m, bs, 2H), 2.44 (m, bs, 4H), 2.24, 2.23 (bs, 3H), 2.03-1.09 (m, bs, 8H), mixture of tautomers.

Operating in an analogous way, the following compounds was obtained:

N-[5-(3,5-Difluoro-benzenesulfonyl)-4,5,6,7-tetrahydro-1H-pyrazolo[4,3-c]pyridin-3-yl]-4-dimethylamino-2-(4-hydroxy-cyclohexylamino)-benzamide [(I), Ra=Rb=H, A=D=E=CH, B=CR2, R=3,5-difluorophenyl, R1=NR5R6, R2=N,N-dimethylamino, R5=4-hydroxycyclohexyl, R6=H], cpd. 535

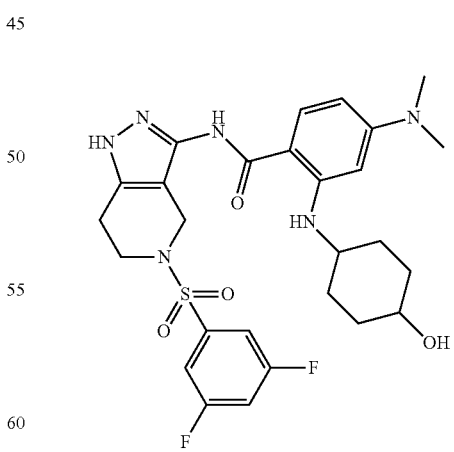

1H-NMR (400 MHz), δ (ppm, DMSO-d$_6$): 12.26, 12.17 (s, 1H), 9.77, 9.75 (s, 1H), 8.38, 8.19 (bs, 1H), 7.69-7.53 (m, 3H), 5.97 (m, 1H), 5.81 (m, 1H), 4.53, 4.39 (d, J1=4.15 Hz, 1H), 4.18-4.07 (m, bs, 2H), 3.63-3.26 (m, bs, 4H), 2.95 (s, 6H), 2.69 (m, bs, 2H), 2.04-1.09 (m, bs, 8H), mixture of tautomers.

EXAMPLE 24

Preparation of N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-[(piperidin-3-ylmethyl)-amino]-benzamide dihydrochloride [(I), Ra=Rb=H, A=D=E=CH, B=CR2, R=3,5-difluorophenyl, R1=NR5R6, R2=4-methylpiperazin-1-yl, R5=piperidin-3-yl-methyl, R6=H], cpd. 536

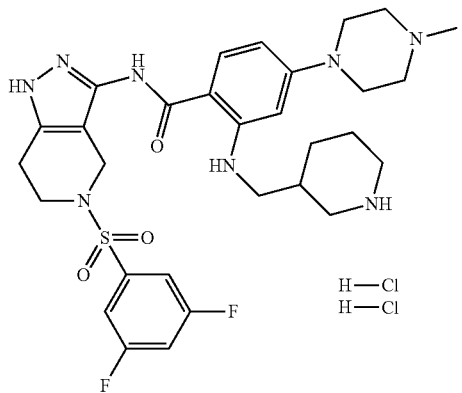

To a solution of 3-{[2-[5-(3,5-Difluoro-benzenesulfonyl)-4,5,6,7-tetrahydro-1H-pyrazolo[4,3-c]pyridin-3-ylcarbamoyl]-5-(4-methyl-piperazin-1-yl)-phenylamino]-methyl}-piperidine-1-carboxylic acid tert-butyl ester (0.12 g, 0.162 mmol) in dichloromethane (20 mL) 4N HCl in 1,4-dioxane (0.5 mL) was added. The mixture was stirred at room temperature overnight. The suspension was then diluted with diethyl ether (20 mL), the solid was filtered, washed with diethyl ether and dried under vacuum at 40° C. to obtain the title compound as colourless solid (0.108 g, 95% yield).

1H-NMR (400 MHz), δ (ppm, DMSO-$d_6$): 10.83 (bs, 1H), 10.03 (s, 1H), 8.88 (bs, 1H), 8.71 (m, bs, 1H), 7.76 (d, J1=9.03 Hz, J2=2.20 Hz, 1H), 7.67 (m, 1H), 7.57 (m, 2H), 6.30 (dd, J1=9.03 Hz, 1H), 6.15 (d, J2=2.20 Hz, 1H), 4.16 (bs, 2H), 4.02 (m, 2H), 3.26-3.05 (m, 10H), 2.83 (s, 3H), 2.69 (m, 2H), 2.09 (m, 1H), 1.80 (m, 4H), 1.67 (m, 2H), 1.26 (m, 2H).

Operating in an analogous way, the following compounds were obtained:

N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-[((S)-1-pyrrolidin-2-ylmethyl)-amino]-benzamide dihydrochloride [(I), Ra=Rb=H, A=D=E=CH, B=CR2, R=3,5-difluorophenyl, R1=NR5R6, R2=4-methylpiperazin-1-yl, R5=(S)-pirrolidin-2-yl-methyl, R6=H], cpd. 55

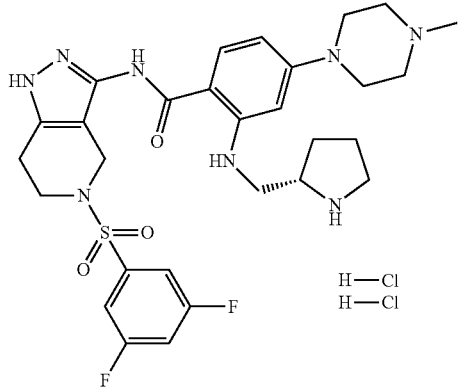

1H-NMR (400 MHz), δ (ppm, DMSO-$d_6$): 10.80 (s, 1H), 10.06 (s, 1H), 9.42 (s, 1H), 8.35 (bs, 1H), 7.77 (d, J1=9.02 Hz, 1H), 7.68 (m, 1H), 7.56 (m, 2H), 6.36 (dd, J1=9.02 Hz, J2=1.59 Hz, 1H), 6.24 (d, J2=1.59 Hz, 1H), 4.11 (s, 2H), 4.07 (m, 2H), 3.69 (m, 1H), 3.53-3.14 (m, 12H), 2.83, 2.82 (s, 3H), 2.69 (m, 2H), 2.11-1.66 (m, 4H), mixture of tautomers.

N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-[((R)-1-pyrrolidin-2-ylmethyl)-amino]-benzamide dihydrochloride [(I), Ra=Rb=H, A=D=E=CH, B=CR2, R=3,5-difluorophenyl, R1=NR5R6, R2=4-methylpiperazin-1-yl, R5=(R)-pirrolidin-2-yl-methyl, R6=H], cpd. 537

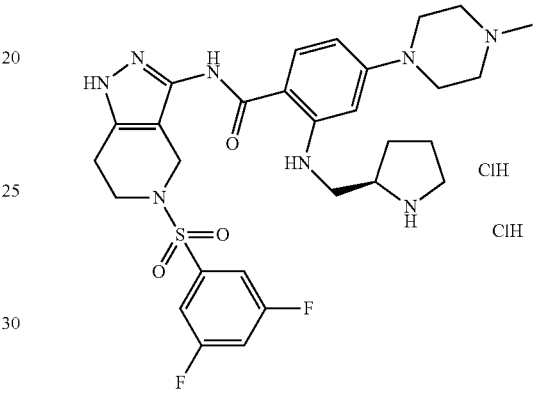

1H-NMR (400 MHz), δ (ppm, DMSO-$d_6$): 10.83 (bs, 1H), 10.08 (s, 1H), 9.45 (bs, 1H), 8.80 (bs, 1H), 7.78 (d, J1=9.03 Hz, 1H), 7.69 (m, 1H), 7.57 (m, 2H), 6.34 (dd, J1=9.03 Hz, J2=2.08 Hz, 1H), 6.25 (d, J2=2.08 Hz, 1H), 4.13-4.08 (m, 4H), 3.70 (m, 1H), 3.58-3.11 (m, 10H), 2.85 (s, 3H), 2.72 (m, 2H), 2.13-1.68 (m, 4H).

N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-(piperidin-3-ylamino)-benzamide dihydrochloride [(I), Ra=Rb=H, A=D=E=CH, B=CR2, R=3,5-difluorophenyl, R1=NR5R6, R2=4-methylpiperazin-1-yl, R5=piperidin-3-yl-methyl, R6=H], cpd. 60

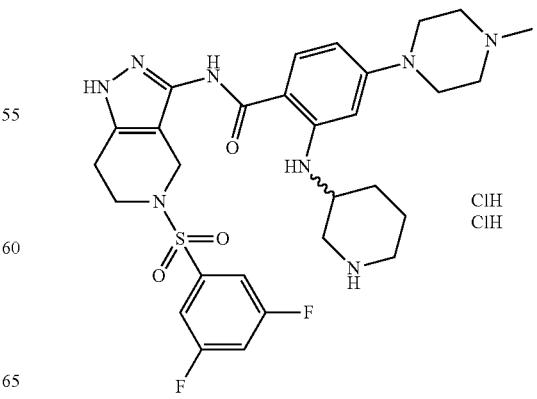

1H-NMR (400 MHz), δ (ppm, DMSO-d$_6$): 10.65 (bs, 1H), 9.67 (bs, 1H), 8.81 (m, bs, 1H), 7.78 (d, J1=9.02 Hz, 1H), 7.69 (m, 1H), 7.57 (m, 2H), 6.36 (m, bs, 1H), 6.33 (dd, J1=9.02 Hz, J2=2.07 Hz, 1H), 4.18 (m, bs, 2H), 4.12 (s, 2H), 4.04 (m, 1H), 3.25-2.63 (m, 17H), 2.06-1.79 (m, 4H), 1.55 (m, 1H).

N-[5-(3,5-Difluoro-benzenesulfonyl)-4,5,6,7-tetrahydro-1H-pyrazolo[4,3-c]pyridin-3-yl]-4-(4-methyl-piperazin-1-yl)-2-(piperidin-4-ylamino)-benzamide dihydrochloride [(I), Ra=Rb=H, A=D=E=CH, B=CR2, R=3,5-difluorophenyl, R1=NR5R6, R2=4-methylpiperazin-1-yl, R5=piperidin-4-yl, R6=H], cpd. 61

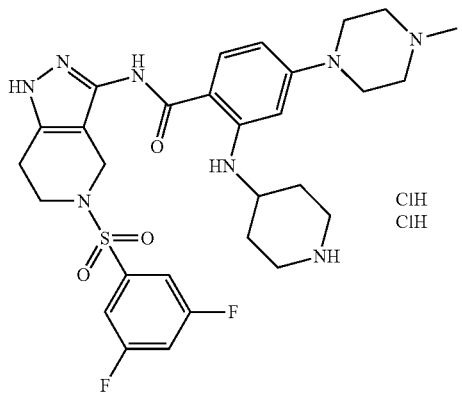

1H-NMR (400 MHz), δ (ppm, DMSO-d$_6$): 11.83 (bs, 1H), 10.03 (s, 1H), 8.94 (bs, 1H), 8.59 (bs, 1H), 7.75 (d, J1=9.03 Hz, 1H), 7.66 (m, 1H), 7.56 (m, 2H), 6.29 (d, J1=9.03 Hz, J2=2.20 Hz, 1H), 6.19 (d, J2=2.08 Hz, 1H), 4.13 (m, 2H), 4.02 (m, 2H), 3.78 (m, 1H), 3.57-3.04 (m, 12H), 2.83, 2.81 (s, 3H), 2.68 (m, 2H), 2.12 (m, 2H), 1.54 (m, 2H), mixture of tautomers.

N-[5-(3,5-Difluoro-benzenesulfonyl)-4,5,6,7-tetrahydro-1H-pyrazolo[4,3-c]pyridin-3-yl]-2-[((S)-1-pyrrolidin-2-ylmethyl)-amino]-benzamide hydrochloride [(I), Ra=Rb=H, A=B=D=E=CH, R=3,5-difluorophenyl, R1=NR5R6, R5=(S)-pirrolidin-2-yl-methyl R6=H], cpd. 237

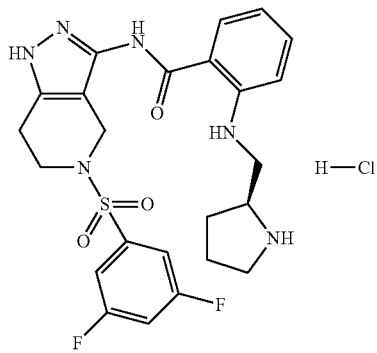

1H-NMR (400 MHz), δ (ppm, DMSO-d$_6$): 10.34 (s, 1H), 9.11 (bs, 1H), 7.89 (m, 1H), 7.78 (dd, J1=7.93 Hz, J2=1.58 Hz, 1H), 7.66 (m, 1H), 7.55 (m, 2H), 7.36 (ddd, J1=8.78 Hz, J2=7.19 Hz, J3=1.58 Hz, 1H), 6.85 (d, bs, J=8.78 Hz, 1H), 6.67 (ddd, bs, J1=7.93 Hz, J2=7.19 Hz, J3=0.73 Hz, 1H), 4.14 (s, 2H), 3.70 (m, 1H), 3.50-3.10 (m, 6H), 2.70 (m, 2H), 2.11 (m, 1H), 2.00-1.81 (m, 2H), 1.63 (m, 1H).

EXAMPLE 25

N-[5-(2-Fluoro-benzenesulfonyl)-4,5,6,7-tetrahydro-1H-pyrazolo[4,3-c]pyridin-3-yl]-4-(4-methyl-piperazin-1-yl)-2-(tetrahydro-pyran-4-ylamino)-benzamide [(I), Ra=Rb=H, A=D=E=CH, B=CR2, R=2-fluorophenyl, R1=NR5R6, R2=4-methylpiperazin-1-yl, R5=tetrahydropyran-4-yl, R6=H], cpd. 69

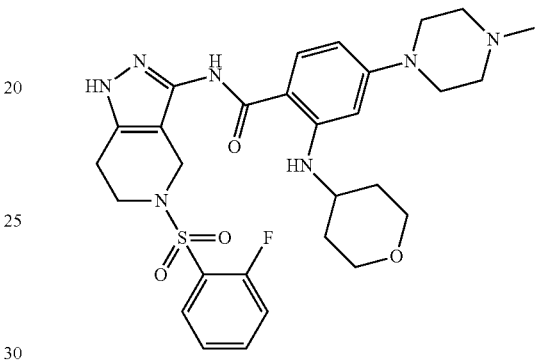

To a solution of 5-(2-fluoro-benzenesulfonyl)-3-[4-(4-methyl-piperazin-1-yl)-2-nitro-benzoylamino]-4,5,6,7-tetrahydro-pyrazolo[4,3-c]pyridine-1-carboxylic acid ethyl ester (0.38 g, 0.62 mmol) in a mixture of tetrahydrofuran (5 mL), ethanol (10 mL), water (7.5 mL) and 37% HCl (1 mL), 10% palladium on carbon (0.1 g) and cycloexene (2 mL) were added. The mixture was refluxed for 2 h, filtered while hot, washed with ethanol, and the resulting solution was evaporated. The residue was treated with 10% NaHCO$_3$ solution and extracted several times with dichloromethane. The organic phase was washed with water, brine, dried with sodium sulfate and evaporated to give the crude amino intermediate.

The amino compound (0.25 g, 0.43 mmol) was dissolved in a mixture of dichloromethane (2 mL) and methanol (8 mL). Triethylamine (1 mL) was added and the mixture was stirred at room temperature overnight. The solution was evaporated and the residue dried under vacuum.

The crude obtained (0.43 mmol) was suspended in anhydrous dichloromethane (10 mL) and trifluoroacetic acid (0.66 mL, 8.54 mmol) was added. After few minutes, to the resulting solution were added tetramethylammonium triacetoxyborohydride (0.17 g, 0.64 mmol) and tetrahydro-4H-pyran-4-one (0.051 mL, 0.56 mmol). The mixture was stirred at room temperature for 2 h, and then washed with 10% NaHCO$_3$, water, and brine. The organic phase was dried with sodium sulfate and evaporated to give a residue, which was purified by flash chromatography, using dichloromethane-methanol-30% NH$_4$OH 9:1:0.05 as eluant, to obtain the title compound (0.2 g, 79% yield) as white powder.

1H-NMR (400 MHz), δ (ppm, DMSO-d$_6$): 12.24 (bs, 1H), 9.82 (bs, 1H), 8.22 (bs, 1H), 7.86 (m, 1H), 7.76 (m, 1H), 7.68 (d, J=8.9 Hz, 1H), 7.44 (m, 2H), 6.21 (m, 1H), 6.12 (d, J=2.0 Hz, 1H), 4.07 (bs, 2H), 3.82 (m, 2H), 3.70 (m, 1H), 3.57-3.50 (m, 4H), 3.26 (m, 4H), 2.74 (m, 2H), 2.45 (m, 4H), 2.24 (s, 3H), 1.94 (m, 2H), 1.37 (m, 2H).

Using a procedure analogous to that described above, the following compounds were prepared:

N-[5-(3-Fluoro-benzenesulfonyl)-4,5,6,7-tetrahydro-1H-pyrazolo[4,3-c]pyridin-3-yl]-4-(4-methyl-piperazin-1-yl)-2-(tetrahydro-pyran-4-ylamino)-benzamide [(I), Ra=Rb=H, A=D=E=CH, B=CR2, R=3-fluorophenyl, R1=NR5R6, R2=4-methylpiperazin-1-yl, R5=tetrahydropyran-4-yl, R6=H], cpd. 68

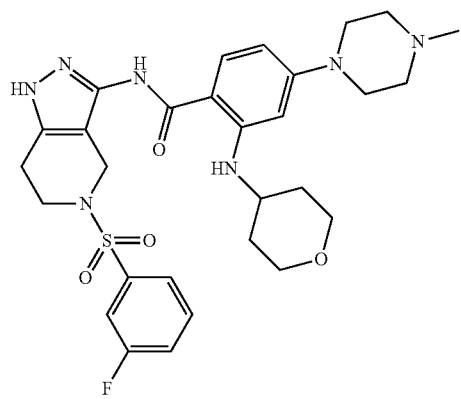

1H-NMR (400 MHz), δ (ppm, DMSO-d₆): 12.21 (bs, 1H), 9.90 (bs, 1H), 8.26 (bs, 1H), 7.75-7.56 (m, 5H), 6.22 (m, 1H), 6.13 (d, J=2.0 Hz, 1H), 4.04 (bs, 2H), 3.82 (m, 2H), 3.70 (m, 1H), 3.52 (m, 2H), 3.45 (m, 2H), 3.26 (m, 4H), 2.71 (m, 2H), 2.44 (m, 4H), 2.24 (s, 3H), 1.95 (m, 2H), 1.39 (m, 2H).

N-[5-(3-Chloro-benzenesulfonyl)-4,5,6,7-tetrahydro-1H-pyrazolo[4,3-c]pyridin-3-yl]-4-(4-methyl-piperazin-1-yl)-2-(tetrahydro-pyran-4-ylamino)-benzamide [(I), Ra=Rb=H, A=D=E=CH, B=CR2, R=3-chlorophenyl, R1=NR5R6, R2=4-methylpiperazin-1-yl, R5=tetrahydropyran-4-yl, R6=H], cpd. 71

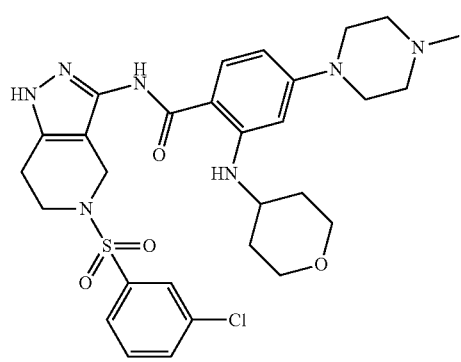

1H-NMR (400 MHz), δ (ppm, DMSO-d₆): 12.21 (bs, 1H), 9.91 (bs, 1H), 8.25 (bs, 1H), 7.84-7.77 (m, 3H), 7.69 (d, J=8.5 Hz, 1H), 7.65 (m, 1H), 6.22 (m, 1H), 6.14 (d, J=2.2 Hz, 1H), 4.05 (bs, 2H), 3.83 (m, 2H), 3.70 (m, 1H), 3.53 (m, 2H), 3.46 (m, 2H), 3.26 (m, 4H), 2.71 (m, 2H), 2.44 (m, 4H), 2.24 (s, 3H), 1.95 (m, 2H), 1.40 (m, 2H).

N-[5-(3-Methoxy-benzenesulfonyl)-4,5,6,7-tetrahydro-1H-pyrazolo[4,3-c]pyridin-3-yl]-4-(4-methyl-piperazin-1-yl)-2-(tetrahydro-pyran-4-ylamino)-benzamide [(I), Ra=Rb=H, A=D=E=CH, B=CR2, R=3-methoxyphenyl, R1=NR5R6, R2=4-methylpiperazin-1-yl, R5=tetrahydropyran-4-yl, R6=H], cpd. 70

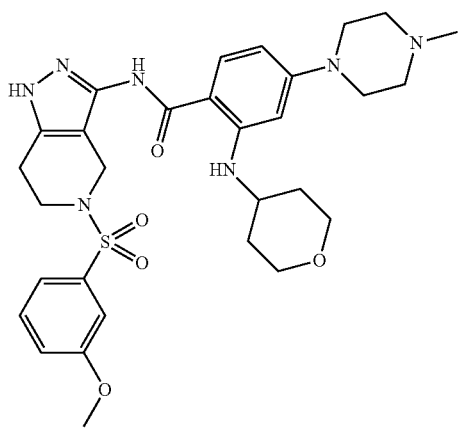

1H-NMR (400 MHz), δ (ppm, DMSO-d₆): 12.20 (bs, 1H), 9.91 (bs, 1H), 8.22 (bs, 1H), 7.68 (d, J=9.0 Hz, 1H), 7.54 (m, 1H), 7.38 (d, J=8.0 Hz, 1H), 7.29 (dd, J1=8.0 Hz, J2=2.4 Hz, 1H), 7.24 (m, 1H), 6.21 (d, J=9.0 Hz, 1H), 6.14 (d, J=2.0 Hz, 1H), 4.02 (bs, 2H), 3.88-3.80 (m, 5H), 3.71 (m, 1H), 3.41 (m, 2H), 2.68 (m, 2H), 2.31 (s, 3H), 1.95 (m, 2H), 1.38 (m, 2H).

N-[5-(3,5-Dichloro-benzenesulfonyl)-4,5,6,7-tetrahydro-1H-pyrazolo[4,3-c]pyridin-3-yl]-4-(4-methyl-piperazin-1-yl)-2-(tetrahydro-pyran-4-ylamino)-benzamide [(I), Ra=Rb=H, A=D=E=CH, B=CR2, R=3,5-dichlorophenyl, R1=NR5R6, R2=4-methylpiperazin-1-yl, R5=tetrahydropyran-4-yl, R6=H], cpd. 72

1H-NMR (400 MHz), δ (ppm, DMSO-d₆): 12.21 (bs, 1H), 9.92 (bs, 1H), 8.24 (bs, 1H), 8.01 (t, J=1.8 Hz, 1H), 7.83 (d, J=1.8 Hz, 2H), 7.69 (d, J=8.8 Hz, 1H), 6.22 (d, J=8.8 Hz, 1H), 6.14 (d, J=2.0 Hz, 1H), 4.13 (bs, 2H), 3.82 (m, 2H), 3.71 (m, 1H), 3.55-3.47 (m, 4H), 3.26 (m, 4H), 2.69 (m, 2H), 2.45 (m, 4H), 2.24 (s, 3H), 1.95 (m, 2H), 1.39 (m, 2H).

N-(5-Benzenesulfonyl-4,5,6,7-tetrahydro-1H-pyrazolo[4,3-c]pyridin-3-yl)-4-(4-methyl-piperazin-1-yl)-2-(tetrahydro-pyran-4-ylamino)-benzamide [(I), Ra=Rb=H, A=D=E=CH, B=CR2, R=phenyl, R1=NR5R6, R2=4-methylpiperazin-1-yl, R5=tetrahydropyran-4-yl, R6=H], cpd. 74

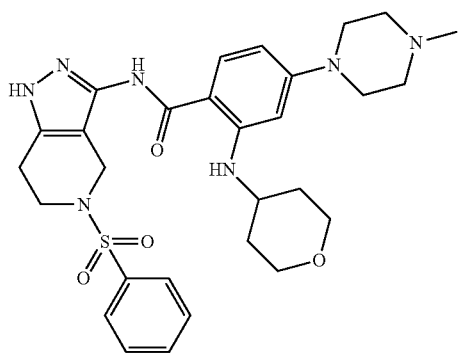

1H-NMR (400 MHz), δ (ppm, DMSO-d$_6$): 12.21 (bs, 1H), 9.89 (bs, 1H), 8.28 (bs, 1H), 7.80 (d, J=7.3 Hz, 2H), 7.75-7.68 (m, 2H), 7.63 (m, 2H), 6.22 (m, 1H), 6.13 (d, J=2.0 Hz, 1H), 3.96 (bs, 2H), 3.83 (m, 2H), 3.71 (m, 1H), 3.54 (m, 2H), 3.39 (m, 2H), 3.26 (m, 4H), 2.72 (m, 2H), 2.45 (m, 4H), 2.24 (s, 3H), 1.95 (m, 2H), 1.39 (m, 2H).

4-(4-Methyl-piperazin-1-yl)-N-[5-(pyridine-3-sulfonyl)-4,5,6,7-tetrahydro-1H-pyrazolo[4,3-c]pyridin-3-yl]-2-(tetrahydro-pyran-4-ylamino)-benzamide [(I), Ra=Rb=H, A=D=E=CH, B=CR2, R=pyridin-3-yl, R1=NR5R6, R2=4-methylpiperazin-1-yl, R5=tetrahydropyran-4-yl, R6=H], cpd. 73

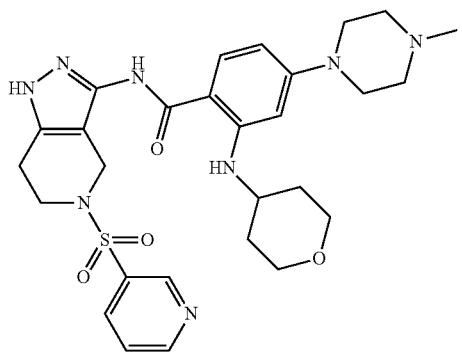

1H-NMR (400 MHz), δ (ppm, DMSO-d$_6$): 12.21 (bs, 1H), 9.90 (bs, 1H), 8.97 (d, J=2.1 Hz, 1H), 8.86 (dd, J1=4.9 Hz, J2=1.6 Hz, 1H), 8.28-8.20 (m, 2H), 7.68 (d, J=8.8 Hz, 1H), 7.65 (m, 1H), 6.22 (d, J=8.8 Hz, 1H), 6.14 (d, J=1.9 Hz, 1H), 4.09 (bs, 1H), 3.83 (m, 2H), 3.70 (m, 1H), 3.52 (m, 4H), 3.27 (m, 4H), 2.69 (m, 2H), 2.51 (m, 4H), 2.26 (s, 3H), 1.95 (m, 2H), 1.40 (m, 2H).

N-[5-(3,5-Difluoro-benzenesulfonyl)-4,5,6,7-tetrahydro-1H-pyrazolo[4,3-c]pyridin-3-yl]-4-morpholin-4-yl-2-(tetrahydro-pyran-4-ylamino)-benzamide [(I), Ra=Rb=H, A=D=E=CH, B=CR2, R=3,5-difluorophenyl, R1=NR5R6, R2=morpholin-4-yl, R5=tetrahydropyran-4-yl, R6=H], cpd. 118

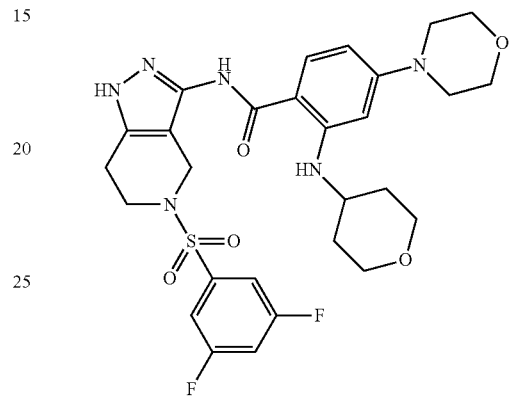

1H-NMR (400 MHz), δ (ppm, DMSO-d$_6$): 12.23 (bs, 1H), 9.93 (bs, 1H), 8.25 (bs, 1H), 7.74-7.65 (m, 2H), 7.56 (d, J=6.5 Hz, 2H), 6.22 (d, J=8.7 Hz, 1H), 6.15 (d, J=2.2 Hz, 1H), 4.10 (bs, 2H), 3.82 (m, 2H), 3.76-3.71 (m, 5H), 3.55-3.48 (m, 4H), 3.22 (m, 4H), 2.71 (m, 2H), 1.95 (m, 2H), 1.38 (m, 2H).

N-[5-(3,5-Difluoro-benzenesulfonyl)-4,5,6,7-tetrahydro-1H-pyrazolo[4,3-c]pyridin-3-yl]-2-(1-methyl-piperidin-4-ylamino)-4-morpholin-4-yl-benzamide [(I), Ra=Rb=H, A=D=E=CH, B=CR2, R=3,5-difluorophenyl, R1=NR5R6, R2=morpholin-4-yl, R5=1-methyl-piperidin-4-yl, R6=H], cpd. 117

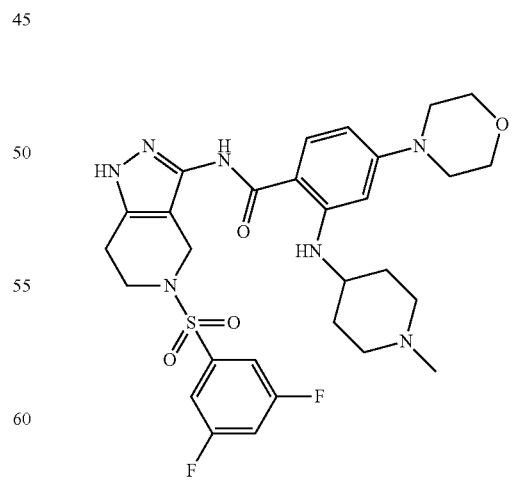

1H-NMR (400 MHz), δ (ppm, DMSO-d$_6$): 12.22 (bs, 1H), 9.91 (bs, 1H), 8.23 (bs, 1H), 7.73-7.64 (m, 2H), 7.56 (d, J=4.5 Hz, 2H), 6.21 (d, J=8.7 Hz, 1H), 6.10 (d, J=2.1 Hz, 1H), 4.12

(bs, 2H), 3.74 (m, 4H), 3.54-3.49 (m, 3H), 3.21 (m, 4H), 2.70 (m, 2H), 2.62 (m, 2H), 2.22-2.14 (m, 5H), 1.92 (m, 2H), 1.44 (m, 2H).

N-[5-(3,5-Difluoro-benzenesulfonyl)-4,5,6,7-tetrahydro-1H-pyrazolo[4,3-c]pyridin-3-yl]-4-[(2-dimethylamino-ethyl)-methyl-amino]-2-(tetrahydro-pyran-4-ylamino)-benzamide [(I), Ra=Rb=H, A=D=E=CH, B=CR2, R=3,5-difluorophenyl, R1=NR5R6, R2=(2-dimethylamino-ethyl)-methyl-amino, R5=tetrahydropyran-4-yl, R6=H], cpd. 148

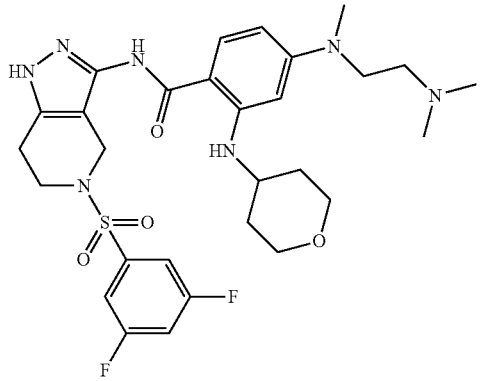

1H-NMR (400 MHz), δ (ppm, DMSO-d$_6$): 8.32 (bs, 1H), 7.70-7.64 (m, 2H), 7.57-7.52 (m, 2H), 5.98 (m, 1H), 5.85 (m, 1H), 4.08 (bs, 2H), 3.87-3.80 (m, 2H), 3.61 (m, 1H), 3.54-3.39 (m, 6H), 2.96 (s, 3H), 2.69 (m, 2H), 2.38 (m, 2H), 2.19 (s, 6H), 1.97 (m, 2H), 1.38 (m, 2H).

N-[5-(3,5-Difluoro-benzenesulfonyl)-4,5,6,7-tetrahydro-1H-pyrazolo[4,3-c]pyridin-3-yl]-4-(2-dimethylamino-ethoxy)-2-(tetrahydro-pyran-4-ylamino)-benzamide [(I), Ra=Rb=H, A=D=E=CH, B=CR2, R=3,5-difluorophenyl, R1=NR5R6, R2=2-dimethylamino-ethoxy, R5=tetrahydropyran-4-yl, R6=H], cpd. 173

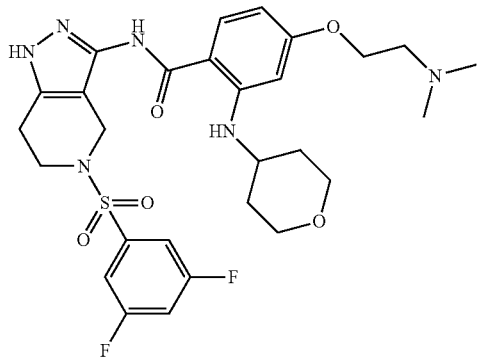

1H-NMR (400 MHz), δ (ppm, DMSO-d$_6$): 12.25 (bs, 1H), 10.05 (s, 1H), 8.19 (bs, 1H), 7.76 (m, 1H), 7.67 (m, 1H), 7.57-7.53 (m, 2H), 6.25 (m, 1H), 6.18 (m, 1H), 4.14-4.06 (m, 4H), 3.86-3.78 (m, 2H), 3.65 (m, 1H), 3.54-3-46 (m, 4H), 2.73-2.65 (m, 4H), 2.26 (bs, 6H), 1.95 (m, 2H), 1.36 (m, 2H).

N-[5-(3,5-Difluoro-benzenesulfonyl)-4,5,6,7-tetrahydro-1H-pyrazolo[4,3-c]pyridin-3-yl]-4-(1-methyl-piperidin-4-yloxy)-2-(tetrahydro-pyran-4-ylamino)-benzamide [(I), Ra=Rb=H, A=D=E=CH, B=CR2, R=3,5-difluorophenyl, R1=NR5R6, R2=1-methyl-piperidin-4-yloxy, R5=tetrahydropyran-4-yl, R6=H], cpd. 188

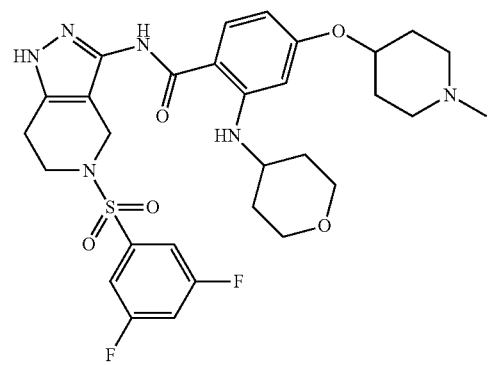

1H-NMR (400 MHz), δ (ppm, DMSO-d$_6$): 12.26 (bs, 1H), 10.07 (bs, 1H), 8.16 (bs, 1H), 7.75 (d, J=8.7 Hz, 1H), 7.68 (m, 1H), 7.56 (d, J=4.5 Hz, 1H), 6.26-6.19 (m, 2H), 4.48 (m, 1H), 4.11 (bs, 2H), 3.82 (m, 2H), 3.64 (m, 1H), 3.55-3.48 (m, 4H), 2.74-2.61 (m, 4H), 2.33-2.17 (m, 5H), 1.99-1.90 (m, 4H), 1.67 (m, 2H), 1.38 (m, 2H).

N-[5-(3,5-Difluoro-benzenesulfonyl)-4,5,6,7-tetrahydro-1H-pyrazolo[4,3-c]pyridin-3-yl]-4-methoxy-2-(tetrahydro-pyran-4-ylamino)-benzamide [(I), Ra=Rb=H, A=D=E=CH, B=CR2, R=3,5-difluorophenyl, R1=NR5R6, R2=methoxy, R5=tetrahydropyran-4-yl, R6=H], cpd. 196

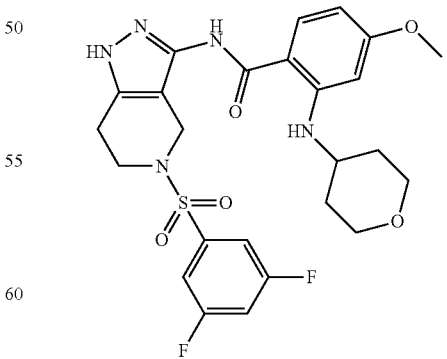

1H-NMR (400 MHz), δ (ppm, DMSO-d$_6$): 12.26 (bs, 1H), 10.07 (bs, 1H), 8.22 (d, J=7.3 Hz, 1H), 7.77 (d, J=8.7 Hz, 1H), 7.68 (m, 1H), 7.56 (d, J=4.6 Hz, 2H), 6.26 (d, J=2.0 Hz, 1H), 6.20 (d, J=8.7 Hz, 1H), 4.11 (bs, 1H), 3.82 (m, 2H), 3.80 (s, 3H), 3.65 (m, 1H), 3.55-3.48 (m, 4H), 2.71 (m, 2H), 1.95 (m, 2H), 1.39 (m, 2H).

N-[5-(3,5-Difluoro-benzenesulfonyl)-4,5,6,7-tetrahydro-1H-pyrazolo[4,3-c]pyridin-3-yl]-2-fluoro-6-(tetrahydro-pyran-4-ylamino)-benzamide [(I), Ra=Rb=H, A=B=D=H, E=CR2, R=3,5-difluorophenyl, R1=NR5R6, R2=fluoro, R5=tetrahydropyran-4-yl, R6=H], cpd. 204

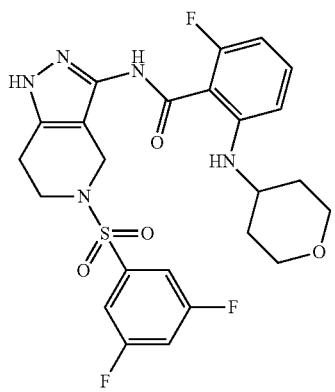

1H-NMR (400 MHz), δ (ppm, DMSO-d₆): 12.34 (bs, 1H), 10.33 (bs, 1H), 7.69 (m, 1H), 7.55 (d, J=4.8 Hz, 2H), 7.28 (m, 1H), 6.67 (d, J=8.4 Hz, 1H), 6.47 (m, 1H), 6.20 (d, J=7.4 Hz, 1H), 4.18 (bs, 1H), 3.84 (m, 2H), 3.66-3.37 (m, 5H), 2.72 (m, 2H), 1.93 (m, 2H), 1.39 (m, 2H).

N-[5-(3,5-Difluoro-benzenesulfonyl)-4,5,6,7-tetrahydro-1H-pyrazolo[4,3-c]pyridin-3-yl]-4-morpholin-4-ylmethyl-2-(tetrahydro-pyran-4-ylamino)-benzamide [(I), Ra=Rb=H, A=D=E=CH, B=CR2, R=3,5-difluorophenyl, R1=NR5R6, R2=morpholin-4-ylmethyl, R5=tetrahydropyran-4-yl, R6=H], cpd. 219

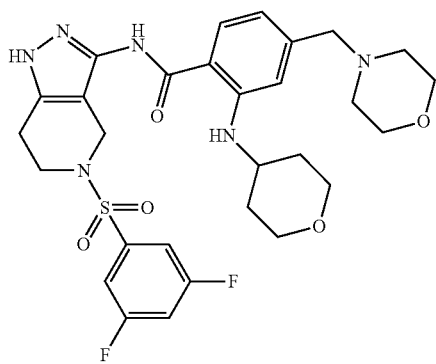

1H-NMR (400 MHz), δ (ppm, DMSO-d₆): 12.28 (bs, 1H), 10.21 (bs, 1H), 7.88 (bd, 1H), 7.73 (d, J=8.2 Hz, 1H), 7.67 (m, 1H), 7.55 (m, 2H), 6.75 (bs, 1H), 6.55 (bd, 1H), 4.10 (bs, 2H), 3.84 (m, 2H), 3.63 (m, 1H), 3.58 (m, 4H), 3.54-3.46 (m, 4H), 3.43 (s, 2H), 2.71 (m, 2H), 2.37 (m, 4H), 1.95 (m, 2H), 1.37 (m, 2H).

N-[5-(3,5-Difluoro-benzenesulfonyl)-4,5,6,7-tetrahydro-1H-pyrazolo[4,3-c]pyridin-3-yl]-4-(2-methoxyethylamino)-2-(tetrahydro-pyran-4-ylamino)-benzamide [(I), Ra=Rb=H, A=D=E=CH, B=CR2, R=3,5-difluorophenyl, R1=NR5R6, R2=2-methoxyethylamino, R5=tetrahydropyran-4-yl, R6=H], cpd. 536

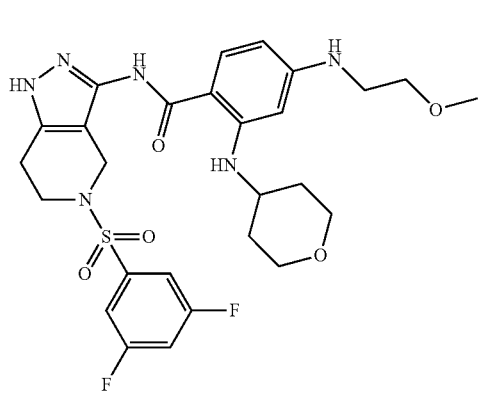

1H-NMR (400 MHz), δ (ppm, DMSO-d₆): 12.17 (bs, 1H), 9.72 (bs, 1H), 8.31 (bd, 1H), 7.68 (m, 1H), 7.64-7.53 (m, 3H), 6.11-5.78 (m, 3H), 4.09 (bs, 2H), 3.85 (m, 2H), 3.59-3.44 (m, 7H), 3.30 (s, 3H), 3.25 (m, 2H), 2.71 (m, 2H), 1.97 (m, 2H), 1.38 (m, 2H).

4-Amino-N-[5-(3,5-difluoro-benzenesulfonyl)-4,5,6,7-tetrahydro-1H-pyrazolo[4,3-c]pyridin-3-yl]-2-(tetrahydro-pyran-4-ylamino)-benzamide [(I), Ra=Rb=H, A=D=E=CH, B=CR2, R=3,5-difluorophenyl, R1=NR5R6, R2=amino, R5=tetrahydropyran-4-yl, R6=H], cpd. 537

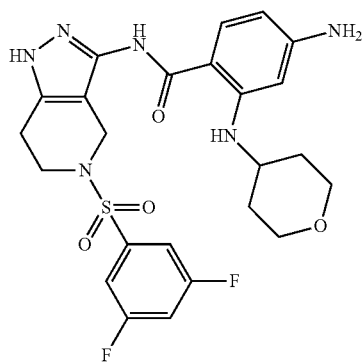

1H-NMR (400 MHz), δ (ppm, DMSO-d₆): 12.17 (bs, 1H), 9.69 (bs, 1H), 8.27 (bd, 1H), 7.68 (m, 1H), 7.61-7.52 (m, 3H), 5.92 (bs, 1H), 5.83 (bd, 1H), 5.52 (bs, 2H), 4.09 (bs, 2H), 3.86 (m, 2H), 3.54-3.41 (m, 5H), 2.70 (m, 2H), 1.96 (m, 2H), 1.37 (m, 2H).

N-[5-(3,5-Difluoro-benzenesulfonyl)-4,5,6,7-tetrahydro-1H-pyrazolo[4,3-c]pyridin-3-yl]-4-(2-dimethylamino-1-methyl-ethylamino)-2-(tetrahydro-pyran-4-ylamino)-benzamide [(I), Ra=Rb=H, A=D=E=CH, B=CR2, R=3,5-difluorophenyl, R1=NR5R6, R2=2-dimethylamino-1-methyl-ethylamino, R5=tetrahydropyran-4-yl, R6=H], cpd. 538

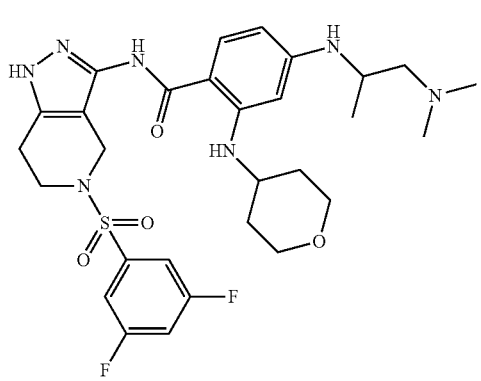

1H-NMR (400 MHz), δ (ppm, DMSO-d$_6$): 12.15 (bs, 1H), 9.74 (bs, 1H), 8.30 (bd, 1H), 7.67 (m, 1H), 7.60 (m, 1H), 7.54 (m, 2H), 5.96-5.78 (m, 3H), 4.08 (bs, 2H), 3.85 (m, 2H), 3.59-3.41 (m, 6H), 3.08 (m, 2H), 2.69 (m, 2H), 2.43 (bs, 6H), 1.95 (m, 2H), 1.37 (m, 2H), 1.13 (d, J=6.3 Hz, 3H).

N-[5-(3,5-Difluoro-benzenesulfonyl)-7,7-dimethyl-4,5,6,7-tetrahydro-1H-pyrazolo[4,3-c]pyridin-3-yl]-4-morpholin-4-yl-2-(tetrahydro-pyran-4-ylamino)-benzamide [(I), Ra=Rb=methyl, A=D=E=CH, B=CR2, R=3,5-difluorophenyl, R1=NR5R6, R2=morpholin-4-yl, R5=tetrahydropyran-4-yl, R6=H], cpd. 384

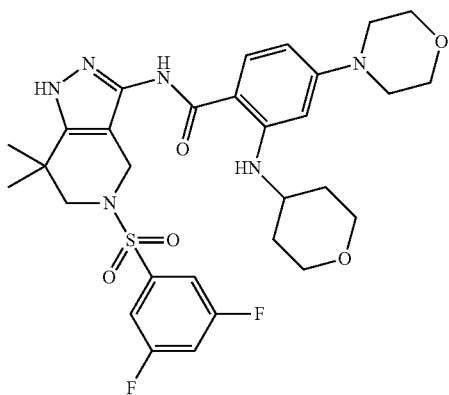

1H-NMR (400 MHz), δ (ppm, DMSO-d$_6$): 12.43 (bs, 1H), 9.89 (bs, 1H), 8.19 (bs, 1H), 7.71 (m, 1H), 7.53 (m, 2H), 6.21 (m, 1H), 6.13 (m, 1H), 3.93 (s, 2H), 3.80 (m, 2H), 3.73 (m, 4H), 3.50 (m, 2H), 3.30 (m, 1H), 3.21 (m, 2H), 3.13 (s, 2H), 1.93 (m, 2H), 1.36 (m, 2H), 1.27 (s, 6H).

N-[5-(3,5-Difluoro-benzenesulfonyl)-7,7-dimethyl-4,5,6,7-tetrahydro-1H-pyrazolo[4,3-c]pyridin-3-yl]-4-dimethylamino-2-(tetrahydro-pyran-4-ylamino)-benzamide [(I), Ra=Rb=methyl, A=D=E=CH, B=CR2, R=3,5-difluorophenyl, R1=NR5R6, R2=dimethylamino, R5=tetrahydropyran-4-yl, R6=H], cpd. 407

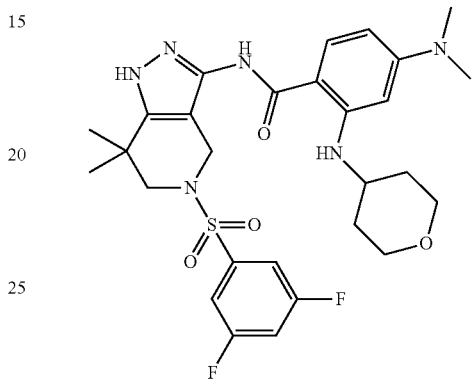

1H-NMR (400 MHz), δ (ppm, DMSO-d$_6$): 12.41 (bs, 1H), 9.73 (bs, 1H), 7.74 (m, 1H), 7.68 (m, 1H), 7.55 (m, 2H), 6.01 (m, 1H), 5.87 (m, 1H), 3.94 (s, 2H), 3.79-3.88 (m, 2H), 3.66 (m, 1H), 3.52 (m, 2H), 3.15 (s, 2H), 2.97 (s, 6H), 1.98 (m, 2H), 1.38 (m, 2H), 1.29 (s, 6H).

N-[5-(3,5-Difluoro-benzenesulfonyl)-4,5,6,7-tetrahydro-1H-pyrazolo[4,3-c]pyridin-3-yl]-4-(4-ethyl-piperazin-1-yl)-2-(tetrahydro-pyran-4-ylamino)-benzamide [(I), Ra=Rb=H, A=D=E=CH, B=CR2, R=3,5-difluorophenyl, R1=NR5R6, R2=4-ethyl-piperazin-1-yl, R5=tetrahydropyran-4-yl, R6=H], cpd. 76

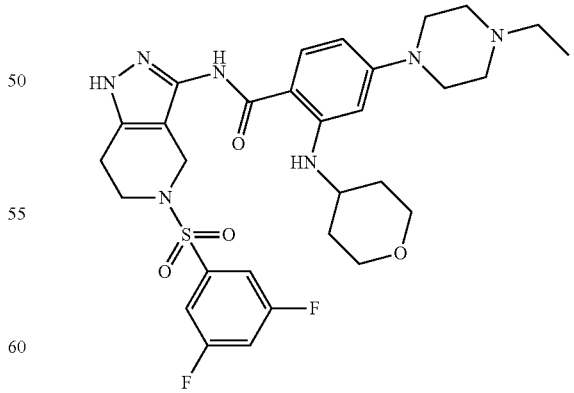

1H-NMR (400 MHz), δ (ppm, DMSO-d6): 12.22 (bs, 1H), 9.91 (s, 1H), 8.26 (bs, 1H), 7.73-7.63 (m, 2H), 7.60-7.52 (m, 2H), 6.21 (s, J=8.40 Hz, 1H) 6.13 (s, 1H), 4.10 (s, 2H), 3.89-3.79 (m, 2H), 3.75-3.63 (m, 1H), 3.56-3.45 (m, 4H), 3.29-3.16 (m, 4H), 2.75-2.66 (m, 2H), 2.51-2.45 (m, 4H), 2.39 (q, J=7.07 Hz, 2H), 2.02-1.91 (m, 2H), 1.44-1.30 (m, 2H), 1.05 (t, J=7.07, 3H).

N-[5-(3,5-Difluoro-benzenesulfonyl)-4,5,6,7-tetrahydro-1H-pyrazolo[4,3-c]pyridin-3-yl]-4-(4-isopropyl-piperazin-1-yl)-2-(tetrahydro-pyran-4-ylamino)-benzamide [(I), Ra=Rb=H, A=D=E=CH, B=CR2, R=3,5-difluorophenyl, R1=NR5R6, R2=4-isopropyl-piperazin-1-yl, R5=tetrahydropyran-4-yl, R6=H], cpd. 78

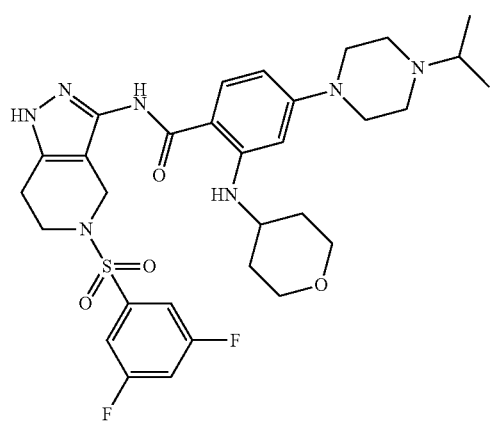

1H-NMR (400 MHz), δ (ppm, DMSO-d6): 12.22 (bs, 1H), 9.90 (s, 1H), 8.24 (bs, 1H), 7.73-7.63 (m, 2H), 7.59-7.53 (m, 2H), 6.20 (s, J=7.80 Hz, 1H) 6.12 (s, 1H), 4.10 (bs, 2H), 3.88-3.78 (m, 2H), 3.74-3.62 (m, 1H), 3.56-3.46 (m, 4H), 3.27-3.19 (m, 4H), 2.75-2.64 (m, 3H), 2.63-2.43 (m, 4H), 2.02-1.91 (m, 2H), 1.44-1.30 (m, 2H), 1.02 (d, J=6.46 Hz, 6H).

N-[5-(3,5-Difluoro-benzenesulfonyl)-4,5,6,7-tetrahydro-1H-pyrazolo[4,3-c]pyridin-3-yl]-4-(2-pyrrolidin-1-yl-ethoxy)-2-(tetrahydro-pyran-4-ylamino)-benzamide [(I), Ra=Rb=H, A=D=E=CH, B=CR2, R=3,5-difluorophenyl, R1=NR5R6, R2=2-pyrrolidin-1-yl-ethoxy, R5=tetrahydropyran-4-yl, R6=H], cpd. 174

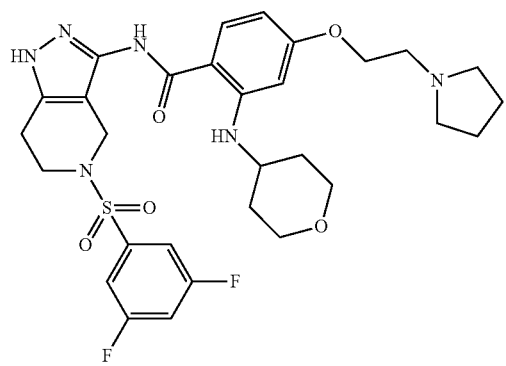

1H-NMR (400 MHz), δ (ppm, DMSO-d6): 12.25 (bs, 1H), 10.05 (s, 1H), 8.19 (bs, 1H), 7.75 (d, J=8.40 Hz, 1H), 7.71-7.62 (m, 1H), 7.59-7.51 (m, 2H), 6.25 (s, 1H), 6.18 (d, J=8.40 Hz, 1H), 4.18-4.06 (m, 4H), 3.86-3.77 (m, 2H), 3.72-3.59 (m, 1H), 3.56-3.44 (m, 4H), 2.83-2.75 (m, 2H), 2.74-2.65 (m, 2H), 2.57-2.51 (m, 4H), 1.99-1.89 (m, 2H), 1.74-1.63 (m, 4H), 1.43-1.29 (m, 2H).

N-(5-Cyclopropanesulfonyl-4,5,6,7-tetrahydro-1H-pyrazolo[4,3-c]pyridin-3-yl)-4-(4-methyl-piperazin-1-yl)-2-(tetrahydro-pyran-4-ylamino)-benzamide [(I), Ra=Rb=H, A=D=E=CH, B=CR2, R=cyclopropyl, R1=NR5R6, R2=4-methyl-piperazin-1-yl, R5=tetrahydropyran-4-yl, R6=H], cpd. 549

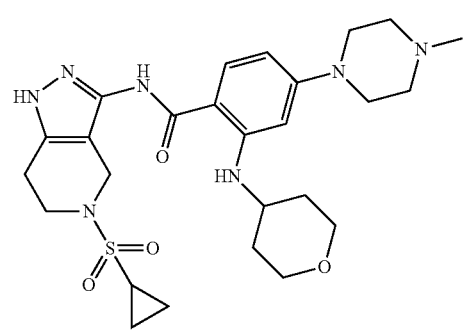

1H-NMR (400 MHz), δ (ppm, DMSO-d6): 12.26 (bs, 1H), 9.89 (s, 1H), 8.23 (bs, 1H), 7.69 (d, J=8.70 Hz, 1H), 6.21 (d, J=8.70 Hz, 1H) 6.12 (s, 1H), 4.18 (bs, 2H), 3.87-3.77 (m, 2H), 3.76-3.64 (m, 1H), 3.60-3.46 (m, 4H), 3.29-3.21 (m, 4H), 2.84-2.74 (m, 2H), 2.66-2.56 (m, 1H), 2.49-2.42 (m, 4H), 2.25 (s, 3H), 2.00-1.94 (m, 2H), 1.44-1.30 (m, 2H), 0.99-0.92 (m, 4H).

N-[5-(3,5-Difluoro-benzenesulfonyl)-4,5,6,7-tetrahydro-1H-pyrazolo[4,3-c]pyridin-3-yl]-4-(4-propyl-piperazin-1-yl)-2-(tetrahydro-pyran-4-ylamino)-benzamide [(I), Ra=Rb=H, A=D=E=CH, B=CR2, R=3,5-difluorophenyl, R1=NR5R6, R2=4-propyl-piperazin-1-yl, R5=tetrahydropyran-4-yl, R6=H], cpd. 77

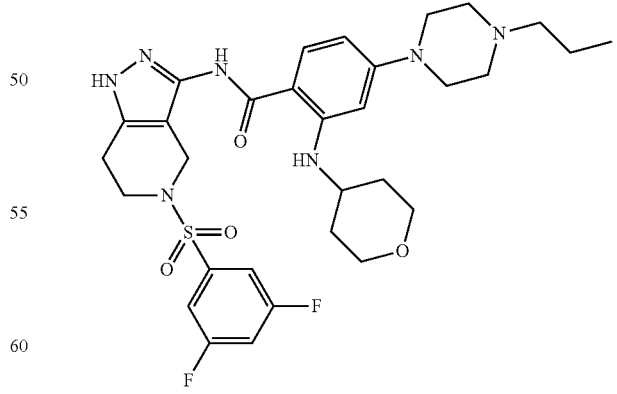

1H-NMR (400 MHz), δ (ppm, DMSO-d6): 12.22 (bs, 1H), 9.91 (s, 1H), 8.25 (bs, 1H), 7.74-7.62 (m, 2H), 7.61-7.52 (m, 2H), 6.21 (d, J=8.40 Hz, 1H) 6.13 (s, 1H), 4.10 (s, 2H), 3.89-3.77 (m, 2H), 3.75-3.63 (m, 1H), 3.58-3.45 (m, 4H), 3.29-3.18 (m, 4H), 2.76-2.66 (m, 2H), 2.51-2.43 (m, 4H), 2.35-2.22 (m, 2H), 2.01-1.90 (m, 2H), 1.56-1.29 (m, 4H), 0.90 (t, J=7.20 Hz, 3H).

N-[5-(3,5-Difluoro-benzenesulfonyl)-4,5,6,7-tetrahydro-1H-pyrazolo[4,3-c]pyridin-3-yl]-4-pyrrolidin-1-ylmethyl-2-(tetrahydro-pyran-4-ylamino)-benzamide [(I), Ra=Rb=H, A=D=E=CH, B=CR2, R=3,5-difluorophenyl, R1=NR5R6, R2=pyrrolidin-1-ylmethyl, R5=tetrahydropyran-4-yl, R6=H], cpd. 211

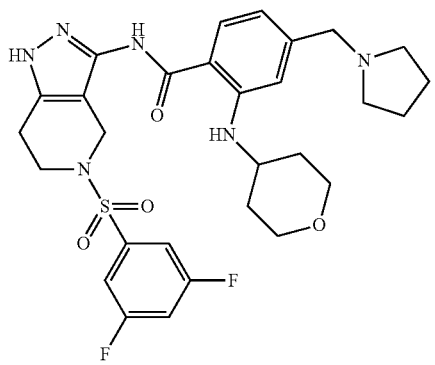

1H-NMR (400 MHz), δ (ppm, DMSO-d6): 12.30 (bs, 1H), 10.22 (s, 1H), 7.89 (bs, 1H), 7.74 (d, J=8.10 Hz, 1H), 7.72-7.64 (m, 1H), 7.61-7.53 (m, 2H), 6.76 (s, 1H), 6.57 (d, J=8.10 Hz, 1H), 4.12 (s, 2H), 3.90-3.78 (m, 2H), 3.72-3.45 (m, 7H), 2.78-2.60 (m, 2H), 2.51-2.40 (m, 4H), 2.04-1.89 (m, 2H), 1.79-1.66 (m, 4H), 1.47-1.30 (m, 2H).

N-[5-(3,5-Difluoro-benzenesulfonyl)-4,5,6,7-tetrahydro-1H-pyrazolo[4,3-c]pyridin-3-yl]-2,4-bis-(tetrahydro-pyran-4-ylamino)-benzamide [(I), Ra=Rb=H, A=D=E=CH, B=CR2, R=3,5-difluorophenyl, R1=NR5R6, R2=tetrahydro-pyran-4-ylamino, R5=tetrahydropyran-4-yl, R6=H], cpd. 155

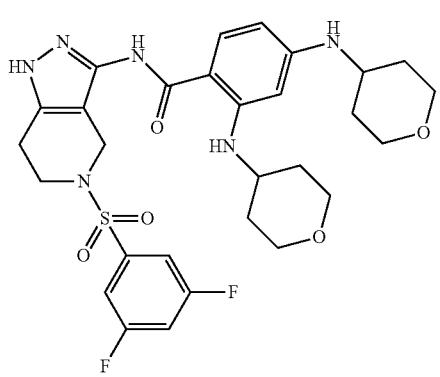

1H-NMR (400 MHz), δ (ppm, DMSO-d6): 12.19 (bs, 1H), 9.73 (s, 1H), 8.27 (bs, 1H), 7.73-7.64 (m, 1H), 7.60 (d, J=8.60 Hz, 1H), 7.58-7.53 (m, 2H), 6.05-5.88 (m, 3H), 4.10 (s, 2H), 3.85-3.78 (m, 4H), 3.62-3.40 (m, 8H), 2.76-2.63 (m, 2H), 2.02-1.81 (m, 4H), 1.49-1.31 (m, 4H).

N-[5-(3,5-Difluoro-benzenesulfonyl)-4,5,6,7-tetrahydro-1H-pyrazolo[4,3-c]pyridin-3-yl]-4-(1-methyl-piperidin-4-ylamino)-2-(tetrahydro-pyran-4-ylamino)-benzamide [(I), Ra=Rb=H, A=D=E=CH, B=CR2, R=3,5-difluorophenyl, R1=NR5R6, R2=1-methyl-piperidin-4-ylamino, R5=tetrahydropyran-4-yl, R6=H], cpd. 157

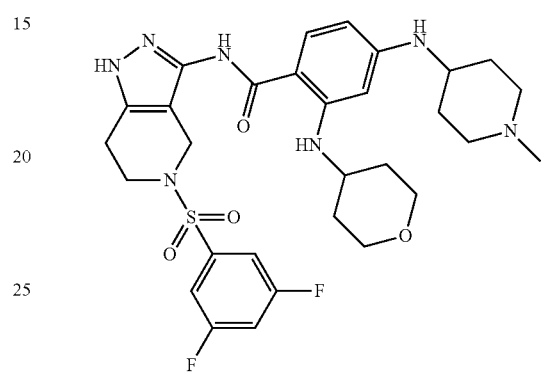

1H-NMR (400 MHz), δ (ppm, DMSO-d6): 12.27 (bs, 1H), 11.02 (bs, 1H), 7.98-7.65 (m, 1H), 7.70-7.53 (m, 3H), 6.97 (d, J=2.20 Hz, 1H) 6.73-7.55 (m, 1H), 4.17 (bs, 2H), 3.60-3.44 (m, 2H), 3.29-3.17 (m, 4H), 3.10-2.78 (m, 3H), 2.75-2.64 (m, 2H), 2.50-2.43 (m, 2H), 2.25 (s, 3H), 1.17-1.04 (m, 2H).

N-[5-(3,5-Difluoro-benzenesulfonyl)-4,5,6,7-tetrahydro-1H-pyrazolo[4,3-c]pyridin-3-yl]-4-[(3-dimethylamino-propyl)-methyl-amino]-2-(tetrahydro-pyran-4-ylamino)-benzamide [(I), Ra=Rb=H, A=D=E=CH, B=CR2, R=3,5-difluorophenyl, R1=NR5R6, R2=(3-dimethylamino-propyl)-methyl-amino, R5=tetrahydropyran-4-yl, R6=H], cpd. 149

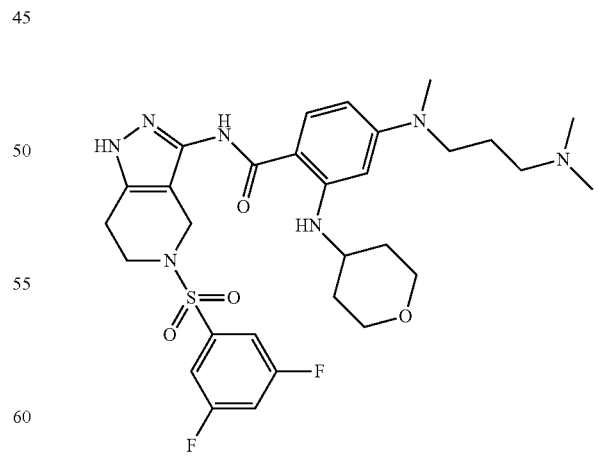

1H-NMR (400 MHz), δ (ppm, DMSO-d6): 12.19 (bs, 1H), 9.80 (s, 1H), 8.32 (bs, 1H), 7.74-7.62 (m, 2H), 7.61-7.52 (m, 2H), 6.02 (d, J=7.70 Hz, 1H), 5.86 (d, J=2.19 Hz, 1H), 4.10 (s, 2H), 3.92-3.79 (m, 2H), 3.73-3.59 (m, 1H), 3.58-3.44 (m, 4H), 3.44-3.36 (m, 2H), 2.95 (s, 3H), 2.76-2.62 (m, 2H), 2.37-2.26 (m, 2H), 2.22 (s, 6H), 2.03-1.92 (m, 2H), 1.75-1.60 (m, 2H), 1.46-1.32 (m, 2H).

N-[5-(3,5-Difluoro-benzenesulfonyl)-4,5,6,7-tetrahydro-1H-pyrazolo[4,3-c]pyridin-3-yl]-4-[4-(2-fluoroethyl)-piperazin-1-yl]-2-(tetrahydro-pyran-4-ylamino)-benzamide [(I), Ra=Rb=H, A=D=E=CH, B=CR2, R=3,5-difluorophenyl, R1=NR5R6, R2=4-(2-fluoro-ethyl)-piperazin-1-yl, R5=tetrahydropyran-4-yl, R6=H], cpd. 551

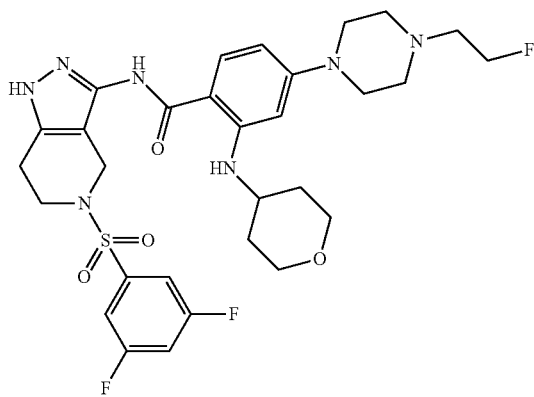

1H-NMR (400 MHz), δ (ppm, DMSO-d6): 12.22 (bs, 1H), 9.91 (s, 1H), 8.26 (bs, 1H), 7.74-7.63 (m, 2H), 7.60-7.52 (m, 2H), 6.21 (d, J=8.30 Hz, 1H) 6.13 (s, 1H), 4.62 (t, J=4.88 Hz, 1H), 4.53 (t, J=4.88 Hz. 1H), 4.10 (s, 2H), 3.88-3.78 (m, 2H), 3.76-3.63 (m, 1H), 3.57-3.45 (m, 4H), 3.30-3.22 (m, 2H), 2.78-2.62 (m, 4H), 2.62-2.54 (m, 4H), 2.51-2.43 (m, 2H), 2.03-1.90 (m, 2H), 1.45-1.31 (m, 2H).

N-[5-(3,5-Difluoro-benzenesulfonyl)-4,5,6,7-tetrahydro-1H-pyrazolo[4,3-c]pyridin-3-yl]-2-(tetrahydro-pyran-4-ylamino)-4-((3R,5S)-3,4,5-trimethyl-piperazin-1-yl)-benzamide [(I), Ra=Rb=H, A=D=E=CH, B=CR2, R=3,5-difluorophenyl, R1=NR5R6, R2=(3R,5S)-3,4,5-trimethyl-piperazin-1-yl, R5=tetrahydropyran-4-yl, R6=H], cpd. 552

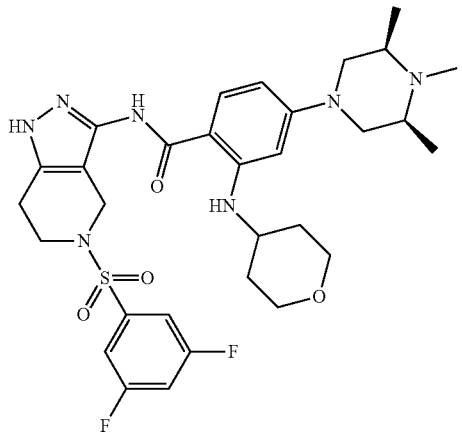

1H-NMR (400 MHz), δ (ppm, DMSO-d6): 12.20 (bs, 1H), 9.90 (s, 1H), 8.27 (bs, 1H), 7.73-7.62 (m, 2H), 7.59-7.51 (m, 2H), 6.21 (d, J=8.40 Hz, 1H), 6.10 (s, 1H), 4.09 (s, 2H), 3.87-3.77 (m, 2H), 3.76-3.62 (m, 3H), 3.57-3.45 (m, 4H), 2.75-2.63 (m, 2H), 2.48-2.41 (m, 2H), 2.30-2.10 (m, 5H), 2.01-1.90 (m, 2H), 1.43-1.29 (m, 2H), 1.17-0.99 (m, 6H).

Acetic acid 2-{[4-[5-(3,5-difluoro-benzenesulfonyl)-4,5,6,7-tetrahydro-1H-pyrazolo[4,3-c]pyridin-3-yl-carbamoyl]-3-(tetrahydro-pyran-4-ylamino)-phenyl]-methyl-amino}-ethyl ester [(I), Ra=Rb=H, A=D=E=CH, B=CR2, R=3,5-difluorophenyl, R1=NR5R6, R2=(2-acetoxy-ethyl)-methyl-amino, R5=tetrahydropyran-4-yl, R6=H], cpd. 553

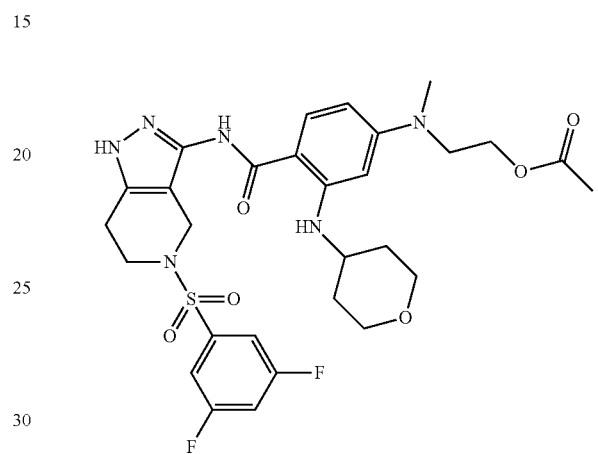

1H-NMR (400 MHz), δ (ppm, DMSO-d6): 12.18 (bs, 1H), 9.81 (s, 1H), 8.31 (bs, 1H), 7.72-7.60 (m, 2H), 7.60-7.51 (m, 2H), 6.01 (d, J=8.20 Hz, 1H), 5.90 (d, J=2.32 Hz, 1H), 4.18 (t, J=5.90 Hz, 2H), 4.08 (s, 2H), 3.88-3.77 (m, 2H), 3.73-3.57 (m, 3H), 3.55-3.41 (m, 4H), 2.97 (s, 3H), 2.76-2.60 (m, 2H), 2.03-1.90 (m, 5H), 1.45-1.30 (m, 2H).

N-[5-(3,5-Difluoro-benzenesulfonyl)-4,5,6,7-tetrahydro-1H-pyrazolo[4,3-c]pyridin-3-yl]-4-[(2-hydroxy-ethyl)-methyl-amino]-2-(tetrahydro-pyran-4-ylamino)-benzamide [(I), Ra=Rb=H, A=D=E=CH, B=CR2, R=3,5-difluorophenyl, R1=NR5R6, R2=(2-hydroxy-ethyl)-methyl-amino, R5=tetrahydropyran-4-yl, R6=H], cpd. 554

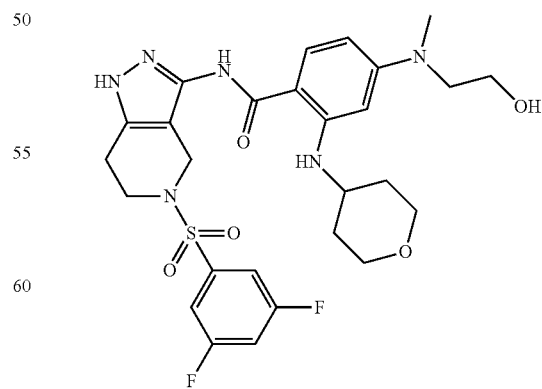

1H-NMR (400 MHz), δ (ppm, DMSO-d6): 12.18 (bs, 1H), 9.78 (s, 1H), 8.34 (bs, 1H), 7.71-7.60 (m, 2H), 7.59-7.50 (m, 2H), 5.99 (d, J=7.80 Hz, 1H), 5.85 (d, J=2.19 Hz, 1H), 4.69 (t, J=5.37 Hz, 1H), 4.08 (s, 2H), 3.87-3.77 (m, 2H), 3.70-3.58 (m, 1H), 3.58-3.35 (m, 8H), 2.98 (s, 3H), 2.75-2.58 (m, 2H), 2.03-1.90 (m, 2H), 1.45-1.29 (m, 2H).

N-[5-(3,5-Difluoro-benzenesulfonyl)-4,5,6,7-tetrahydro-1H-pyrazolo[4,3-c]pyridin-3-yl]-4-(4-methyl-[1,4]diazepan-1-yl)-2-(tetrahydro-pyran-4-ylamino)-benzamide [(I), Ra=Rb═H, A═D═E═CH, B═CR2, R=3,5-difluorophenyl, R1=NR5R6, R2=4-methyl-[1,4]diazepan-1-yl, R5=tetrahydropyran-4-yl, R6═H], cpd. 555

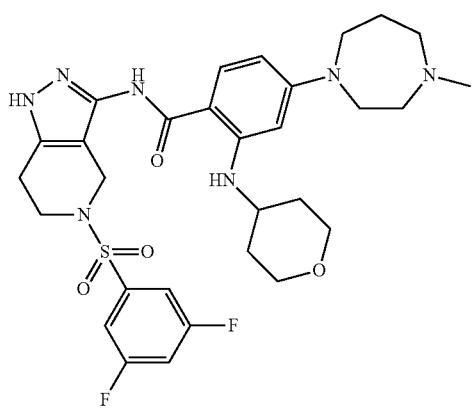

1H-NMR (400 MHz), δ (ppm, DMSO-d6): 12.17 (bs, 1H), 9.78 (s, 1H), 8.31 (bs, 1H), 7.72-7.60 (m, 2H), 7.60-7.51 (m, 2H), 6.01 (s, J=8.20 Hz, 1H) 5.85 (d, J=1.83 Hz, 1H), 4.09 (s, 2H), 3.87-3.76 (m, 2H), 3.71-3.60 (m, 1H), 3.60-3.43 (m, 8H), 2.73-2.61 (m, 4H), 2.55-2.52 (m, 2H), 2.38-2.26 (m, 3H), 2.00-1.83 (m, 4H), 1.45-1.30 (m, 2H).

4-[(2-Diethylamino-ethyl)-methyl-amino]-N-[5-(3,5-difluoro-benzenesulfonyl)-4,5,6,7-tetrahydro-1H-pyrazolo[4,3-c]pyridin-3-yl]-2-(tetrahydro-pyran-4-ylamino)-benzamide [(I), Ra=Rb═H, A═D═E═CH, B═CR2, R=3,5-difluorophenyl, R1=NR5R6, R2=(2-diethylamino-ethyl)-methyl-amino, R5=tetrahydropyran-4-yl, R6═H], cpd. 556

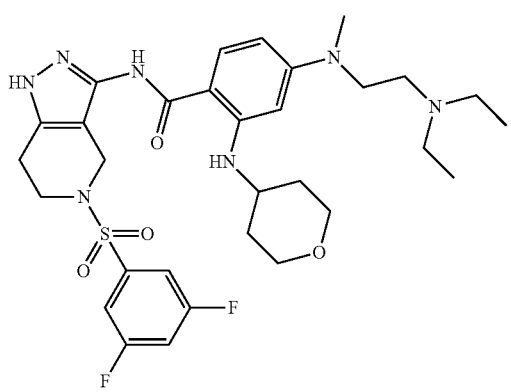

1H-NMR (400 MHz), δ (ppm, DMSO-d6): 12.19 (bs, 1H), 9.79 (s, 1H), 8.33 (bs, 1H), 7.74-7.62 (m, 2H), 7.61-7.52 (m, 2H), 5.98 (d, J=8.40 Hz, 1H), 5.85 (d, J=2.07 Hz, 1H), 4.09 (s, 2H), 3.90-3.79 (m, 2H), 3.71-3.58 (m, 1H), 3.55-3.36 (m, 6H), 2.98 (s, 3H), 2.78-2.60 (m, 2H), 2.61-2.54 (m, 6H), 2.03-1.92 (m, 2H), 1.49-1.32 (m, 2H), 0.98 (t, J=7.07 Hz, 6H).

N-[5-(3,5-Difluoro-benzenesulfonyl)-4,5,6,7-tetrahydro-1H-pyrazolo[4,3-c]pyridin-3-yl]-4-(2-methoxy-ethoxy)-2-(tetrahydro-pyran-4-ylamino)-benzamide [(I), Ra=Rb═H, A═D═E═CH, B═CR2, R=3,5-difluorophenyl, R1=NR5R6, R2=2-methoxy-ethoxy, R5=tetrahydropyran-4-yl, R6═H], cpd. 557

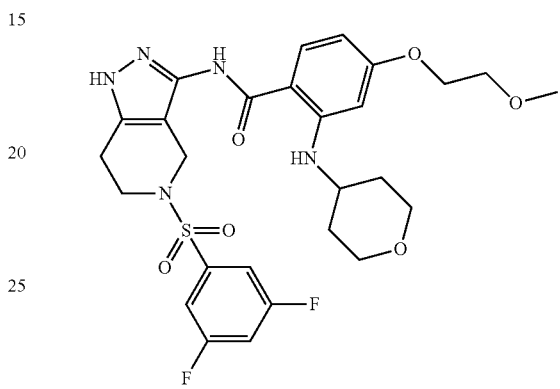

1H-NMR (400 MHz), δ (ppm, DMSO-d6): 12.26 (bs, 1H), 10.07 (s, 1H), 8.20 (bs, 1H), 7.78 (d, J=8.90 Hz, 1H), 7.72-7.62 (m, 1H), 7.61-7.52 (m, 2H), 6.27 (s, 1H), 6.19 (d, J=8.90 Hz, 1H), 4.15 (t, J=4.40 Hz, 2H), 4.11 (m, 2H), 3.89-3.78 (m, 2H), 3.73-3.61 (m, 3H), 3.58-3.42 (m, 4H), 3.33 (s, 3H), 2.76-2.64 (m, 2H), 2.02-1.89 (m, 2H), 1.45-1.30 (m, 2H).

N-[5-(3,5-Difluoro-benzenesulfonyl)-4,5,6,7-tetrahydro-1H-pyrazolo[4,3-c]pyridin-3-yl]-2-(2,2-dimethyl-tetrahydro-pyran-4-ylamino)-4-(4-methyl-piperazin-1-yl)-benzamide [(I), Ra=Rb═H, A═D═E═CH, B═CR2, R=3,5-difluorophenyl, R1=NR5R6, R2=4-methyl-piperazin-1-yl, R5=2,2-dimethyl-tetrahydro-pyran-4-yl, R6═H], cpd. 558

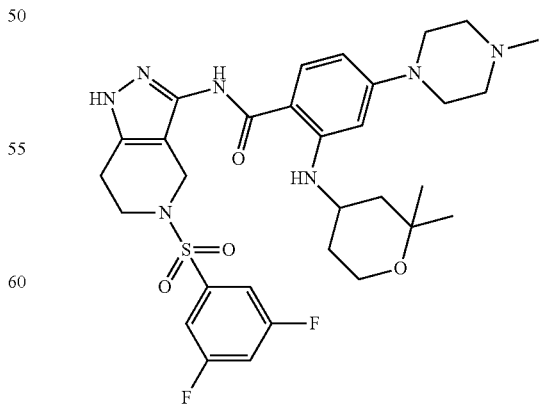

ESI(+) MS: m/z 644 (MH+).

N-[5-(3,5-Difluoro-benzenesulfonyl)-4,5,6,7-tetrahydro-1H-pyrazolo[4,3-c]pyridin-3-yl]-2-((2R,6S)-2,6-dimethyl-tetrahydro-pyran-4-ylamino)-4-(4-methyl-piperazin-1-yl)-benzamide [(I), Ra=Rb=H, A=D=E=CH, B=CR2, R=3,5-difluorophenyl, R1=NR5R6, R2=4-methyl-piperazin-1-yl, R5=(2R,6S)-2,6-dimethyl-tetrahydro-pyran-4-yl, R6=H], cpd. 596

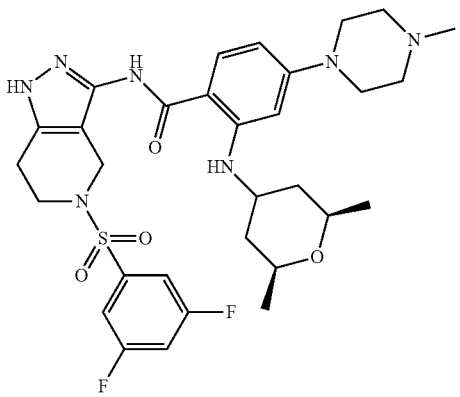

1H-NMR (400 MHz), δ (ppm, DMSO-d₆): 12.20 (bs, 1H), 9.89 (bs, 1H), 8.74, 8.04 (2bd, 1H), 7.72-7.59 (m, 2H), 7.54 (m, 2H), 6.20 (m, 1H), 6.13, 6.04 (2bs, 1H), 4.17, 4.08 (2bs, 2H), 4.00-3.45 (m, 4H), 3.26 (m, 4H), 2.67 (m, 2H), 2.47 (m, 4H), 2.26 (bs, 3H), 2.00 (m, 1H), 1.67 (m, 1H), 1.41 (m, 1H), 1.12, 1.06 (2d, J=6.2 Hz, 6H), 0.87 (m, 1H), mixture of diastereoisomers.

N-[5-(3,5-Difluoro-benzenesulfonyl)-4,5,6,7-tetrahydro-1H-pyrazolo[4,3-c]pyridin-3-yl]-4-[(2-dimethylamino-ethyl)-ethyl-amino]-2-(tetrahydro-pyran-4-ylamino)-benzamide [(I), Ra=Rb=H, A=D=E=CH, B=CR2, R=3,5-difluorophenyl, R1=NR5R6, R2=(2-dimethylamino-ethyl)-ethyl-amino, R5=tetrahydropyran-4-yl, R6=H], cpd. 559

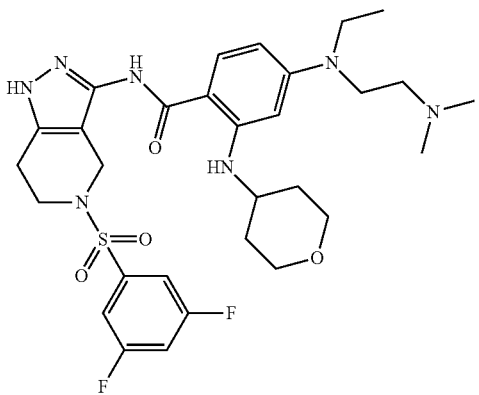

1H-NMR (400 MHz), δ (ppm, DMSO-d6): 12.17 (bs, 1H), 9.76 (s, 1H), 8.32 (bs, 1H), 7.72-7.59 (m, 2H), 7.59-7.50 (m, 2H), 5.94 (d, J=8.50 Hz, 1H), 5.82 (d, J=2.07 Hz, 1H), 4.07 (s, 2H), 3.89-3.78 (m, 2H), 3.65-3.55 (m, 1H), 3.53-3.34 (m, 8H), 2.74-2.60 (m, 2H), 2.46-2.34 (m, 2H), 2.22 (s, 6H), 2.01-1.92 (m, 2H), 1.46-1.30 (m, 2H), 1.15-1.04 (m, 3H).

N-[5-(3,5-Difluoro-benzenesulfonyl)-4,5,6,7-tetrahydro-1H-pyrazolo[4,3-c]pyridin-3-yl]-4-[(2-methoxy-ethyl)-methyl-amino]-2-(tetrahydro-pyran-4-ylamino)-benzamide [(I), Ra=Rb=H, A=D=E=CH, B=CR2, R=3,5-difluorophenyl, R1=NR5R6, R2=(2-methoxy-ethyl)-methyl-amino, R5=tetrahydropyran-4-yl, R6=H], cpd. 560

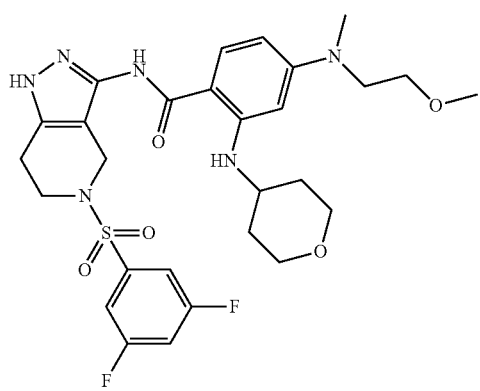

1H-NMR (400 MHz), δ (ppm, DMSO-d6): 12.18 (bs, 1H), 9.79 (s, 1H), 8.30 (bs, 1H), 7.71-7.61 (m, 2H), 7.59-7.50 (m, 2H), 5.99 (d, J=8.60 Hz, 1H), 5.88 (d, J=2.07 Hz, 1H), 4.09 (s, 2H), 3.88-3.76 (m, 2H), 3.69-3.58 (m, 1H), 3.57-3.43 (m, 8H), 3.26 (s, 3H), 2.97 (s, 3H), 2.75-2.64 (m, 2H), 2.03-1.90 (m, 2H), 1.45-1.29 (m, 2H).

Acetic acid (S)-1-[4-[5-(3,5-difluoro-benzenesulfonyl)-4,5,6,7-tetrahydro-1H-pyrazolo[4,3-c]pyridin-3-ylcarbamoyl]-3-(tetrahydro-pyran-4-ylamino)-phenyl]-pyrrolidin-2-ylmethyl ester [(I), Ra=Rb=H, A=D=E=CH, B=CR2, R=3,5-difluorophenyl, R1=NR5R6, R2=(S)-2-acetoxymethyl-pyrrolidin-1-yl, R5=tetrahydropyran-4-yl, R6=H], cpd. 561

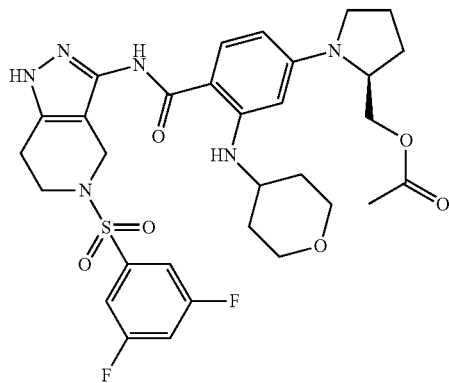

1H-NMR (400 MHz), δ (ppm, DMSO-d6): 12.18 (bs, 1H), 9.80 (s, 1H), 8.33 (bs, 1H), 7.72-7.61 (m, 2H), 7.59-7.50 (m, 2H), 6.02-5.91 (m, 2H), 4.30 (dd, J=11.10 and 3.54 Hz, 1H), 4.15-4.04 (m, 2H), 4.03-3.93 (m, 1H), 3.89-3.78 (m, 2H), 3.76-3.64 (m, 2H), 3.57-3.40 (m, 5H), 3.20-3.09 (m, 1H), 2.74-2.62 (m, 2H), 2.06 (s, 3H), 2.03-1.87 (m, 6H), 1.44-1.30 (m, 2H).

N-[5-(3,5-Difluoro-benzenesulfonyl)-4,5,6,7-tetrahydro-1H-pyrazolo[4,3-c]pyridin-3-yl]-4-((S)-2-hydroxymethyl-pyrrolidin-1-yl)-2-(tetrahydro-pyran-4-ylamino)-benzamide [(I), Ra=Rb=H, A=D=E=CH, B=CR2, R=3,5-difluorophenyl, R1=NR5R6, R2=(S)-2-hydroxymethyl-pyrrolidin-1-yl, R5=tetrahydropyran-4-yl, R6=H], cpd. 562

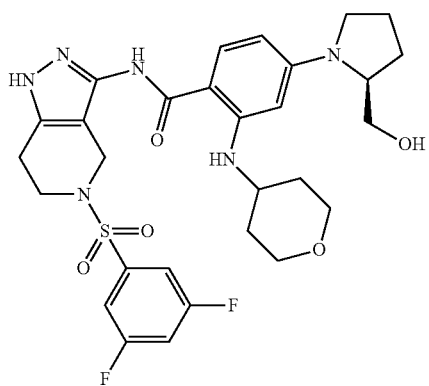

1H-NMR (400 MHz), δ (ppm, DMSO-d6): 12.19 (bs, 1H), 9.79 (s, 1H), 8.36 (bs, 1H), 7.73-7.61 (m, 2H), 7.61-7.52 (m, 2H), 5.93 (d, J=8.20 Hz, 1H), 5.80 (d, J=1.83 Hz, 1H), 4.80 (t, J=5.60 Hz, 1H), 4.10 (s, 2H), 3.90-3.72 (m, 3H), 3.70-3.58 (m, 1H), 3.57-3.36 (m, 5H), 3.27-3.07 (m, 3H), 2.76-2.63 (m, 2H), 2.08-1.81 (m, 6H), 1.47-1.31 (m, 2H).

N-[5-(3,5-Difluoro-benzenesulfonyl)-4,5,6,7-tetrahydro-1H-pyrazolo[4,3-c]pyridin-3-yl]-4-[4-(2-methoxy-ethyl)-piperazin-1-yl]-2-[(tetrahydro-furan-3-ylmethyl)-amino]benzamide [(I), Ra=Rb=H, A=D=E=CH, B=CR2, R=3,5-difluorophenyl, R1=NR5R6, R2=4-(2-methoxy-ethyl)-piperazin-1-yl, R5=tetrahydro-furan-3-ylmethyl, R6=H], cpd. 563

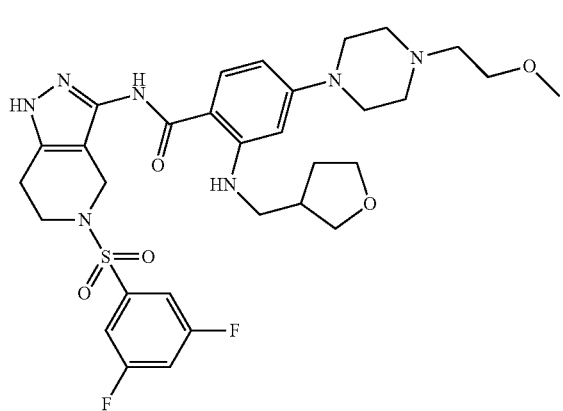

1H-NMR (400 MHz), δ (ppm, DMSO-d6): 12.20 (bs, 1H), 9.89 (s, 1H), 8.25 (bs, 1H), 7.74-7.60 (m, 2H), 7.60-7.51 (m, 2H), 6.19 (d, J=8.90 Hz, 1H), 6.05 (d, J=1.83 Hz, 1H), 4.11 (s, 2H), 3.83-3.72 (m, 2H), 3.70-3.60 (m, 1H), 3.56-3.42 (m, 6H), 3.27-3.19 (m, 5H), 3.17-3.03 (m, 2H), 2.75-2.62 (m, 2H), 2.10-1.93 (m, 1H), 1.69-1.55 (m, 1H).

N-[5-(3,5-Difluoro-benzenesulfonyl)-4,5,6,7-tetrahydro-1H-pyrazolo[4,3-c]pyridin-3-yl]-4-[4-(2-methoxy-ethyl)-piperazin-1-yl]-2-(tetrahydro-pyran-4-ylamino)-benzamide [(I), Ra=Rb=H, A=D=E=CH, B=CR2, R=3,5-difluorophenyl, R1=NR5R6, R2=4-(2-methoxy-ethyl)-piperazin-1-yl, R5=tetrahydropyran-4-yl, R6=H], cpd. 564

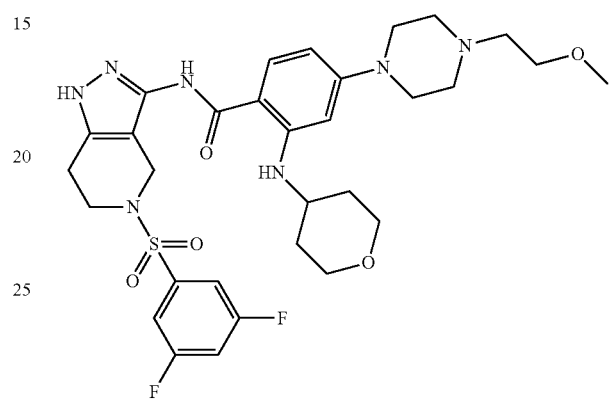

1H-NMR (400 MHz), δ (ppm, DMSO-d6): 12.22 (bs, 1H), 9.90 (s, 1H), 8.25 (bs, 1H), 7.74-7.62 (m, 2H), 7.61-7.52 (m, 2H), 6.20 (d, J=8.60 Hz, 1H), 6.12 (d, J=1.95 Hz, 1H), 4.10 (s, 2H), 3.89-3.78 (m, 2H), 3.75-3.62 (m, 1H), 3.57-3.44 (m, 6H), 3.28-3.19 (m, 7H), 2.76-2.65 (m, 2H), 2.59-2.52 (m, 6H), 2.02-1.91 (m, 2H), 1.44-1.28 (m, 2H).

N-[5-(3,5-Difluoro-benzenesulfonyl)-4,5,6,7-tetrahydro-1H-pyrazolo[4,3-c]pyridin-3-yl]-4-(4-pyrrolidin-1-yl-piperidin-1-yl)-2-(tetrahydro-pyran-4-ylamino)-benzamide [(I), Ra=Rb=H, A=D=E=CH, B=CR2, R=3,5-difluorophenyl, R1=NR5R6, R2=4-pyrrolidin-1-yl-piperidin-1-yl, R5=tetrahydropyran-4-yl, R6=H], cpd. 565

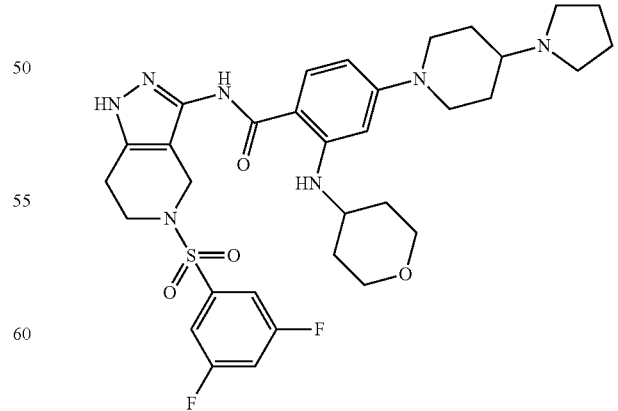

1H-NMR (400 MHz), δ (ppm, DMSO-d6): 12.20 (bs, 1H), 9.88 (s, 1H), 8.25 (bs, 1H), 7.72-7.62 (m, 2H), 7.59-7.50 (m, 2H), 6.20 (d, J=8.10 Hz, 1H), 6.11 (d, J=1.83 Hz, 1H), 4.09 (s, 2H), 3.88-3.75 (m, 4H), 3.74-3.60 (m, 1H), 3.55-3.44 (m, 4H), 2.89-2.76 (m, 2H), 2.75-2.61 (m, 5H), 2.01-1.87 (m, 4H), 1.80-1.64 (m, 4H), 1.58-1.42 (m, 2H), 1.42-1.28 (m, 2H).

N-[5-(3,5-Difluoro-benzenesulfonyl)-4,5,6,7-tetrahydro-1H-pyrazolo[4,3-c]pyridin-3-yl]-4-(4-dimethylamino-piperidin-1-yl)-2-(tetrahydro-pyran-4-ylamino)-benzamide [(I), Ra=Rb=H, A=D=E=CH, B=CR2, R=3,5-difluorophenyl, R1=NR5R6, R2=4-dimethylamino-piperidin-1-yl, R5=tetrahydropyran-4-yl, R6=H], cpd. 568

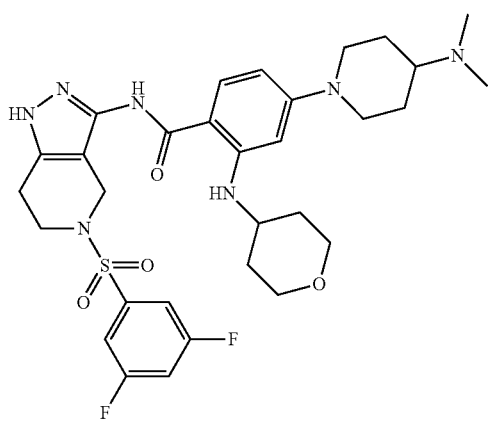

1H-NMR (400 MHz), δ (ppm, DMSO-d6): 12.20 (bs, 1H), 9.87 (s, 1H), 8.25 (bs, 1H), 7.72-7.61 (m, 2H), 7.59-7.51 (m, 2H), 6.21 (d, J=8.30 Hz, 1H), 6.10 (d, J=2.07 Hz, 1H), 4.08 (s, 2H), 3.80-3.76 (m, 4H), 3.73-3.61 (m, 1H), 3.57-3.44 (m, 4H), 2.84-2.62 (m, 4H), 2.31-2.21 (m, 1H), 2.19 (s, 6H), 1.99-1.89 (m, 2H), 1.86-1.76 (m, 2H), 1.48-1.30 (m, 4H).

N-[5-(3,5-Difluoro-benzenesulfonyl)-4,5,6,7-tetrahydro-1H-pyrazolo[4,3-c]pyridin-3-yl]-4-(2-diisopropylamino-ethoxy)-2-(tetrahydro-pyran-4-ylamino)-benzamide [(I), Ra=Rb=H, A=D=E=CH, B=CR2, R=3,5-difluorophenyl, R1=NR5R6, R2=2-diisopropylamino-ethoxy, R5=tetrahydropyran-4-yl, R6=H], cpd. 574

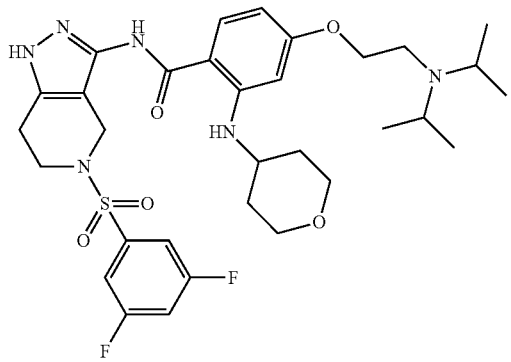

1H-NMR (400 MHz), δ (ppm, DMSO-d6): 12.25 (bs, 1H), 10.06 (s, 1H), 8.21 (bs, 1H), 7.77 (d, J=8.40 Hz, 1H), 7.72-7.63 (m, 1H), 7.60-7.52 (m, 2H), 6.22 (s, 1H), 6.16 (d, J=8.40 Hz, 1H), 4.10 (s, 2H), 3.94 (t, J=6.85 Hz, 2H), 3.88-3.69 (m, 2H), 3.72-3.70 (m, 1H), 3.56-3.44 (m, 4H), 3.08-2.97 (m, 2H), 2.76 (t, J=7.07 Hz, 2H), 2.73-2.65 (m, 2H), 2.00-1.90 (m, 2H), 1.44-1.28 (m, 2H), 0.99 (d, J=6.58 Hz, 12H).

N-[5-(3,5-Difluoro-benzenesulfonyl)-4,5,6,7-tetrahydro-1H-pyrazolo[4,3-c]pyridin-3-yl]-4-[methyl-(2-pyrrolidin-1-yl-ethyl)-amino]-2-(tetrahydro-pyran-4-ylamino)-benzamide [(I), Ra=Rb=H, A=D=E=CH, B=CR2, R=3,5-difluorophenyl, R1=NR5R6, R2=methyl-(2-pyrrolidin-1-yl-ethyl)-amino, R5=tetrahydropyran-4-yl, R6=H], cpd. 575

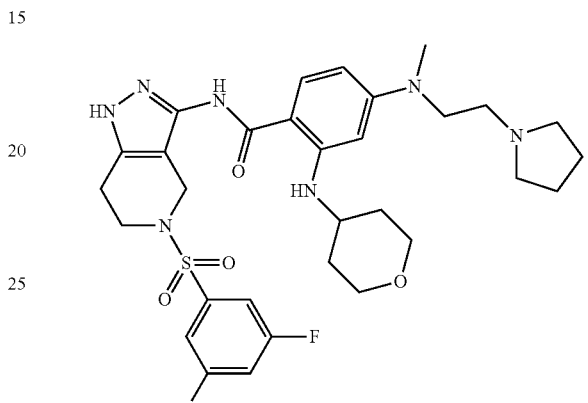

1H-NMR (400 MHz), δ (ppm, DMSO-d6): 12.17 (bs, 1H), 9.77 (s, 1H), 8.30 (bs, 1H), 7.70-7.60 (m, 2H), 7.57-7.50 (m, 2H), 5.96 (d, J=8.20 Hz, 1H), 5.84 (d, J=2.19 Hz, 1H), 4.07 (bs, 2H), 3.88-3.77 (m, 2H), 3.64-3.56 (m, 1H), 3.50-3.41 (m, 6H), 2.95 (s, 3H), 2.71-2.64 (m, 2H), 2.59-2.53 (m, 2H), 2.50-2.44 (m, 4H), 2.01-1.91 (m, 2H), 1.72-1.64 (m, 4H), 1.44-1.30 (m, 2H).

N-[5-(3,5-Difluoro-benzenesulfonyl)-4,5,6,7-tetrahydro-1H-pyrazolo[4,3-c]pyridin-3-yl]-4-[methyl-(2-morpholin-4-yl-ethyl)-amino]-2-(tetrahydro-pyran-4-ylamino)-benzamide [(I), Ra=Rb=H, A=D=E=CH, B=CR2, R=3,5-difluorophenyl, R1=NR5R6, R2=methyl-(2-morpholin-4-yl-ethyl)-amino, R5=tetrahydropyran-4-yl, R6=H], cpd. 581

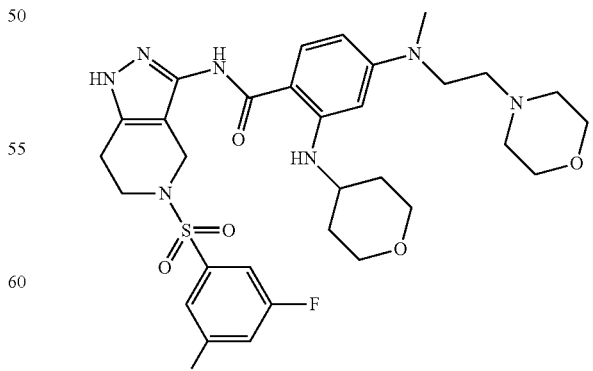

1H-NMR (400 MHz), δ (ppm, DMSO-d6): 12.19 (bs, 1H), 9.80 (bs, 1H), 8.35 (d, J=7.93 Hz, 1H), 7.71-7.66 (m, 2H), 7.57 (m, 2H), 6.00 (d, J=9.15 Hz, 1H), 5.86 (d, J=2.07 Hz, 1H), 4.09 (bs, 2H), 3.85 (m, 2H), 3.59 (t, J=4.63 Hz, 4H), 3.50 (m, 6H), 2.98 (bs, 3H), 2.71 (bs, 2H), 2.44 (m, 2H), 2.00 (m, 2H), 1.41 (m, 2H).

N-[5-(3,5-Difluoro-benzenesulfonyl)-4,5,6,7-tetrahydro-1H-pyrazolo[4,3-c]pyridin-3-yl]-4-[methyl-(2-piperidin-1-yl-ethyl)-amino]-2-(tetrahydro-pyran-4-ylamino)-benzamide [(I), Ra=Rb=H, A=D=E=CH, B=CR2, R=3,5-difluorophenyl, R1=NR5R6, R2=methyl-(2-piperidin-1-yl-ethyl)-amino, R5=tetrahydropyran-4-yl, R6=H], cpd. 583

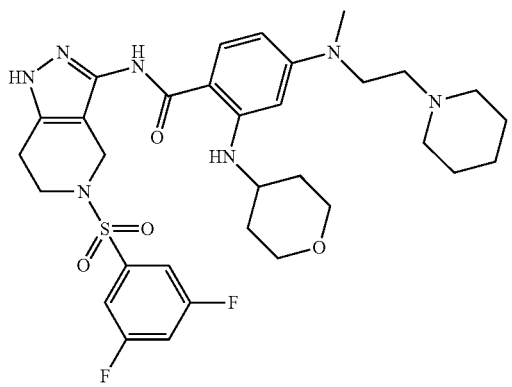

1H-NMR (400 MHz), δ (ppm, DMSO-d$_6$): 12.18 (bs, 1H), 9.78 (bs, 1H), 8.30 (bs, 1H), 7.69-7.64 (m, 2H), 7.54 (m, 2H), 5.98 (d, J=8.41 Hz, 1H), 5.84 (d, J=2.19 Hz, 1H), 4.08 (bs, 2H), 3.84 (m, 2H), 3.60 (m, 1H), 3.49-3.44 (m, 6H), 2.85 (bs, 3H), 2.67 (bs, 2H), 2.33 (m, 6H), 1.95 (m, 2H), 1.50-1.37 (m, 8H).

N-[5-(3,5-Difluoro-benzenesulfonyl)-4,5,6,7-tetrahydro-1H-pyrazolo[4,3-c]pyridin-3-yl]-4-{[2-(isopropyl-methyl-amino)-ethyl]-methyl-amino}-2-(tetrahydro-pyran-4-ylamino)-benzamide [(I), Ra=Rb=H, A=D=E=CH, B=CR2, R=3,5-difluorophenyl, R1=NR5R6, R2=[2-(isopropyl-methyl-amino)-ethyl]-methyl-amino, R5=tetrahydropyran-4-yl, R6=H], cpd. 587

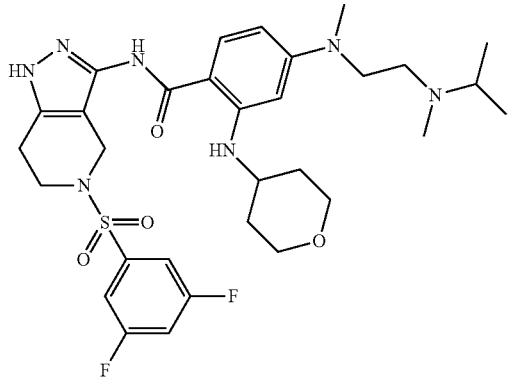

1H-NMR (400 MHz), δ (ppm, DMSO-d$_6$): 12.19 (bs, 1H), 9.79 (bs, 1H), 8.33 (bs, 1H), 7.71-7.65 (m, 2H), 7.56 (m, 2H), 5.99 (d, J=8.41 Hz, 1H), 5.86 (d, J=2.32 Hz, 1H), 4.10 (bs, 2H), 3.85 (m, 2H), 3.63 (m, 1H), 3.50-3.44 (m, 6H), 2.98 (bs, 3H), 2.78 (bs, 1H), 2.71 (bs, 2H), 2.22 (bs, 3H), 1.98 (m, 2H) 1.40 (m, 2H), 0.95 (d, J=6.34 Hz).

N-[5-(3,5-Difluoro-benzenesulfonyl)-4,5,6,7-tetrahydro-1H-pyrazolo[4,3-c]pyridin-3-yl]-4-(4-fluoro-piperidin-1-ylmethyl)-2-(tetrahydro-pyran-4-ylamino)-benzamide [(I), Ra=Rb=H, A=D=E=CH, B=CR2, R=3,5-difluorophenyl, R1=NR5R6, R2=4-fluoro-piperidin-1-ylmethyl, R5=tetrahydropyran-4-yl, R6=H], cpd. 590

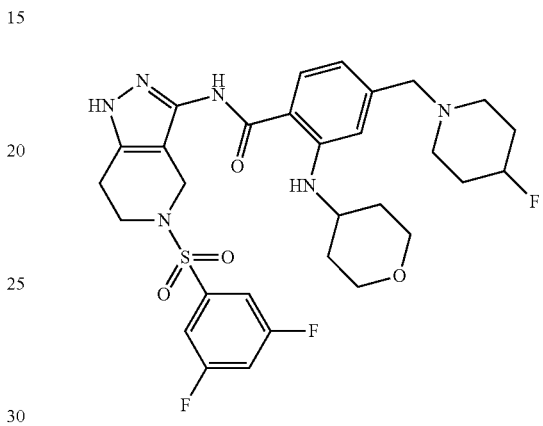

1H-NMR (400 MHz), δ (ppm, DMSO-d$_6$): 12.30 (bs, 1H), 10.22 (bs, 1H), 7.89 (bd, 1H), 7.75 (bd, 1H), 7.68 (m, 1H), 7.57 (m, 2H), 6.76 (bs, 1H), 6.55 (bd, 1H), 4.71 (m, 1H), 4.12 (bs, 2H), 3.85 (m, 2H), 3.65 (m, 1H), 3.55-3.44 (m, 6H), 2.72 (m, 2H), 2.55 (m, 2H), 2.32 (m, 2H), 1.96 (m, 2H), 1.86 (m, 2H), 1.73 (m, 2H), 1.38 (m, 2H).

N-[5-(3,5-Difluoro-benzenesulfonyl)-4,5,6,7-tetrahydro-1H-pyrazolo[4,3-c]pyridin-3-yl]-4-(1-propyl-piperidin-4-ylamino)-2-(tetrahydro-pyran-4-ylamino)-benzamide [(I), Ra=Rb=H, A=D=E=CH, B=CR2, R=3,5-difluorophenyl, R1=NR5R6, R2=1-propyl-piperidin-4-ylamino, R5=tetrahydropyran-4-yl, R6=H], cpd. 591

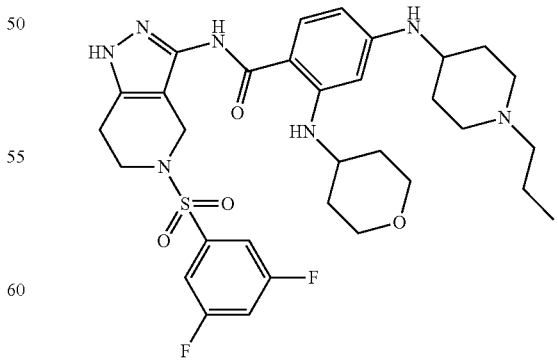

1H-NMR (400 MHz), δ (ppm, DMSO-d$_6$): 12.17 (bs, 1H), 9.71 (s, 1H), 8.28 (s, 1H), 7.68 (tt, 1H), 7.61-7.51 (m, 3H), 5.97-5.81 (m, 3H), 4.08 (m, 2H), 3.89-3.80 (m, 2H), 3.57-

3.44 (m, 5H), 3.36-3.17 (m, 1H), 2.82-2.74 (m, 2H), 2.74-2.65 (m, 2H), 2.30-2.18 (m, 2H), 2.01-1.86 (m, 4H), 1.44-1.25 (m, 8H), 0.92 (t, 3H).

N-[5-(3,5-Difluoro-benzenesulfonyl)-4,5,6,7-tetrahydro-1H-pyrazolo[4,3-c]pyridin-3-yl]-4-(1-ethyl-3-methyl-piperidin-4-ylamino)-2-(tetrahydro-pyran-4-ylamino)-benzamide [(I), Ra=Rb=H, A=D=E=CH, B=CR2, R=3,5-difluorophenyl, R1=NR5R6, R2=1-ethyl-3-methyl-piperidin-4-ylamino, R5=tetrahydropyran-4-yl, R6=H], cpd. 592

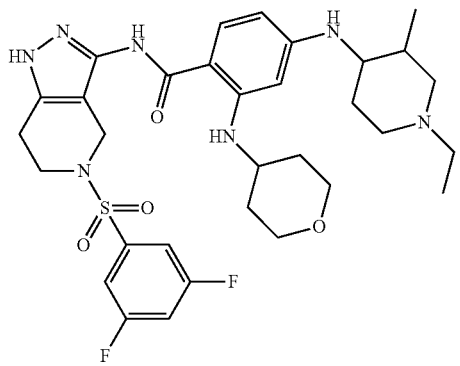

1H-NMR (400 MHz), δ (ppm, DMSO-d$_6$): 12.16 (bs, 1H), 9.70 (bs, 1H), 8.28 (bs, 1H), 7.67 (tt, 1H), 7.60-7.49 (m, 3H), 6.00-5.75 (m, 3H), 4.08 (m, 2H), 3.87-3.80 (m, 2H), 3.57-3.42 (m, 6H), 2.69 (m, 2H), 2.08 (m, 1H), 2.00-1.88 (m, 2H), 1.44-1.28 (m, "H), 1.12-0.99 (m, "H), 0.96-0.84 (d, 1H).

4-(2-Diethylamino-1-methyl-ethylamino)-N-[5-(3,5-difluoro-benzenesulfonyl)-4,5,6,7-tetrahydro-1H-pyrazolo[4,3-c]pyridin-3-yl]-2-(tetrahydro-pyran-4-ylamino)-benzamide [(I), Ra=Rb=H, A=D=E=CH, B=CR2, R=3,5-difluorophenyl, R1=NR5R6, R2=2-diethylamino-1-methyl-ethylamino, R5=tetrahydropyran-4-yl, R6=H], cpd. 593

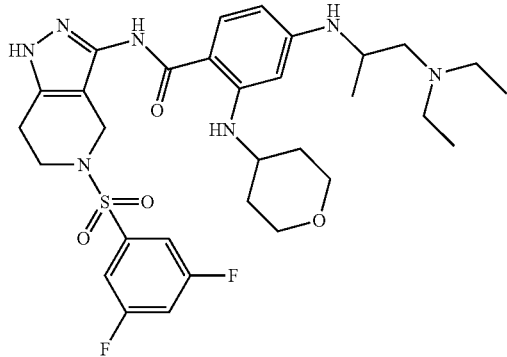

1H-NMR (400 MHz), δ (ppm, DMSO-d$_6$): 12.10 (bs, 1H), 9.69 (bs, 1H), 8.33 (m, 1H), 7.68 (tt, 1H), 7.60-7.52 (m, 3H), 5.91-5.70 (m, 3H), 4.08 (m, 2H), 3.90-3.80 (m, 2H), 3.61-

3.40 (m, 6H), 2.75-2.64 (m, 2H), 2.63-2.18 (m, 6H), 2.00-1.90 (m, 2H), 1.45-1.31 (m, 2H), 1.16 (d, 3H), 0.97 (t, 6H).

N-[5-(3,5-Difluoro-benzenesulfonyl)-4,5,6,7-tetrahydro-1H-pyrazolo[4,3-c]pyridin-3-yl]-4-(1-isopropyl-piperidin-4-ylamino)-2-(tetrahydro-pyran-4-ylamino)-benzamide [(I), Ra=Rb=H, A=D=E=CH, B=CR2, R=3,5-difluorophenyl, R1=NR5R6, R2=1-isopropyl-piperidin-4-ylamino, R5=tetrahydropyran-4-yl, R6=H], cpd. 595

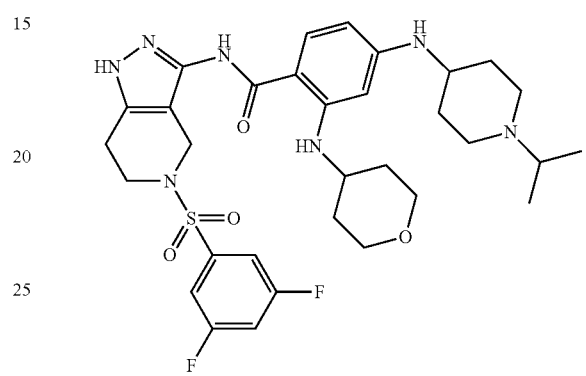

1H-NMR (400 MHz), δ (ppm, DMSO-d$_6$): 12.17 (bs, 1H), 9.71 (s, 1H), 8.28 (s, 1H), 7.68 (tt, 1H), 7.61-7.51 (m, 3H), 5.97-5.81 (m, 3H), 4.08 (m, 2H), 3.89-3.80 (m, 2H), 3.57-3.44 (m, 5H), 3.36-3.17 (m, 1H), 2.82-2.74 (m, 2H), 2.74-2.65 (m, 2H), 2.30-2.18 (m, 2H), 2.01-1.86 (m, 4H), 1.44-1.30 (m, 4H), 0.99 (d, 6H).

4-Acetylamino-N-[5-(3,5-difluoro-benzenesulfonyl)-4,5,6,7-tetrahydro-1H-pyrazolo[4,3-c]pyridin-3-yl]-2-(tetrahydro-pyran-4-ylamino)-benzamide [(I), Ra=Rb=H, A=D=E=CH, B=CR2, R=3,5-difluorophenyl, R1=NR5R6, R2=acetylamino, R5=tetrahydropyran-4-yl, R6=H], cpd. 594

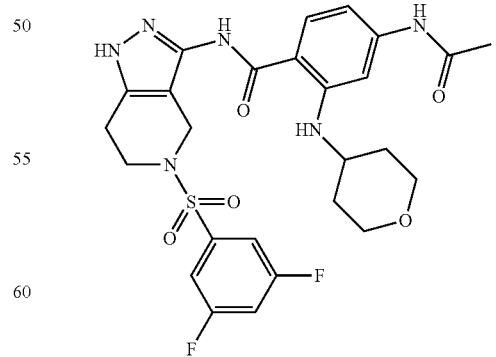

1H-NMR (400 MHz), δ (ppm, DMSO-d$_6$): 12.27 (bs, 1H), 10.11 (s, 1H), 9.94 (s, 1H), 8.07 (m, 1H), 7.73 (d, 1H), 7.68 (tt, 1H), 7.57 (m, 2H), 7.10 (bs, 1H), 6.85 (m, 1H), 4.11 (m, 2H), 3.87 (m, 2H), 3.54-3.44 (m, 5H), 2.71 (m, 2H), 2.06 (s, 3H), 2.01-1.96 (m, 2H), 1.46-1.34 (m, 2H).

N-[5-(3,5-Difluoro-benzenesulfonyl)-4,5,6,7-tetrahydro-1H-pyrazolo[4,3-c]pyridin-3-yl]-2-(2-methoxy-1-methyl-ethylamino)-4-(4-methyl-piperazin-1-yl)-benzamide [(I), Ra=Rb=H, A=D=E=CH, B=CR2, R=3,5-difluorophenyl, R1=NR5R6, R2=4-methyl-piperazin-1-yl, R5=2-methoxy-1-methyl-ethyl, R6=H], cpd. 577

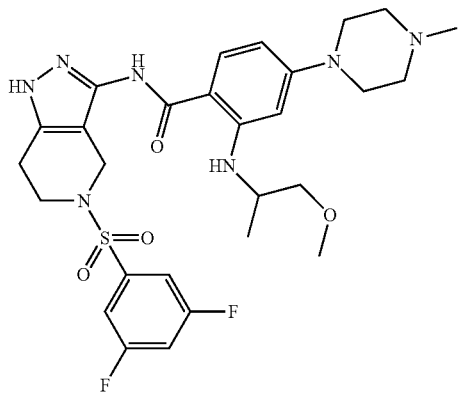

1H-NMR (400 MHz), δ (ppm, DMSO-d$_6$): 12.20 (bs, 1H), 9.86 (bs, 1H), 8.12 (d, J=7.44 Hz, 1H), 7.71-7.63 (m, 2H), 7.54 (m, 2H), 6.20 (d, J=8.17 Hz, 1H), 6.11 (d, J=2.07 Hz, 1H), 4.09 (bs, 2H), 3.78 (m, 1H), 3.49 (t, J=5.61 Hz, 2H), 3.39-3.25 (m, 6H), 3.28 (s, 3H), 2.69 (m, 2H), 2.48 (m, 4H), 2.26 (bs, 3H), 1.15 (d, J=6.34 Hz, 3H).

N-[5-(3,5-Difluoro-benzenesulfonyl)-4,5,6,7-tetrahydro-1H-pyrazolo[4,3-c]pyridin-3-yl]-2-(2-methoxy-1-methoxymethyl-ethylamino)-4-(4-methyl-piperazin-1-yl)-benzamide [(I), Ra=Rb=H, A=D=E=CH, B=CR2, R=3,5-difluorophenyl, R1=NR5R6, R2=4-methyl-piperazin-1-yl, R5=2-methoxy-1-methoxymethyl-ethyl, R6=H], cpd. 588

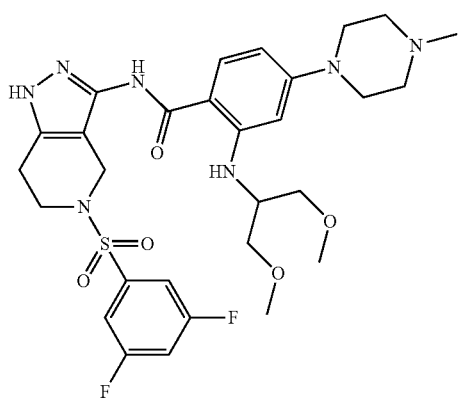

1H-NMR (400 MHz), δ (ppm, DMSO-d$_6$): 12.21 (bs, 1H), 9.87 (bs, 1H), 8.29 (d, J=7.80 1H), 7.70-7.64 (m, 2H), 7.57 (m, 2H), 6.23 (d, J=8.54 Hz, 1H), 6.17 (d, J=1.95 Hz, 1H), 4.11 (bs, 2H), 3.84 (m, 1H), 3.51 (m, 2H), 3.44 (d, J=5.00 Hz, 6H), 3.29 (s, 6H), 3.27 (m, 4H), 2.69 (m, 2H), 2.47 (m, 4H), 2.26 (bs, 3H).

N-[5-(3,5-Difluoro-benzenesulfonyl)-4,5,6,7-tetrahydro-1H-pyrazolo[4,3-c]pyridin-3-yl]-4-[(2-methoxy-ethyl)-methyl-amino]-2-(2-methoxy-1-methyl-ethylamino)-benzamide [(I), Ra=Rb=H, A=D=E=CH, B=CR2, R=3,5-difluorophenyl, R1=NR5R6, R2=(2-methoxy-ethyl)-methyl-amino, R5=2-methoxy-1-methyl-ethyl, R6=H], cpd. 589

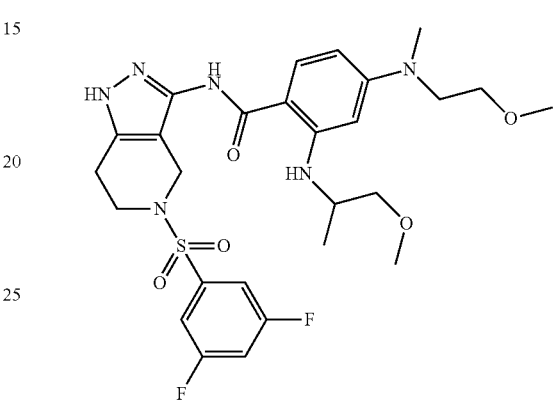

1H-NMR (400 MHz), δ (ppm, DMSO-d6): 12.17 (bs, 1H), 9.75 (s, 1H), 8.19 (bs, 1H), 7.71-7.59 (m, 2H), 7.58-7.51 (m, 2H), 5.99 (d, J=8.60 Hz, 1H), 5.86 (d, J=2.20 Hz, 1H), 4.08 (s, 2H), 3.78-3.65 (m, 1H), 3.69-3.58 (m, 1H), 3.58-3.45 (m, 5H), 3.44-3.36 (m, 2H), 3.28 (s, 3H), 3.26 (s, 3H), 2.97 (s, 3H), 2.73-2.62 (m, 2H), 1.16 (d, J=6.46 Hz, 3H).

N-[5-(3,5-Difluoro-benzenesulfonyl)-4,5,6,7-tetrahydro-1H-pyrazolo[4,3-c]pyridin-3-yl]-2-((3R,4S)-3,4,5-trihydroxy-pentylamino)-benzamide [(I), Ra=Rb=H, A=B=D=E=CH, R=3,5-difluorophenyl, R1=NR5R6, R5=(3R,4S)-3,4,5-trihydroxy-pentyl, R6=H], cpd. 566

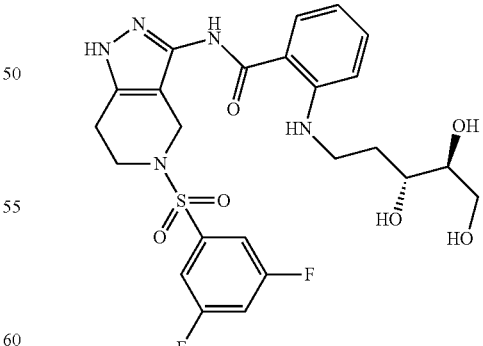

1H-NMR (400 MHz), δ (ppm, DMSO-d6): 12.29 (bs, 1H), 10.21 (bs, 1H), 7.75 (d, J=8.30 Hz, 1H), 7.71-7.62 (m, 2H), 7.62-7.54 (m, 2H), 7.39-7.30 (m, 1H), 6.75 (d, J=8.10 Hz, 1H), 6.64-6.54 (m, 1H), 4.57 (d, J=5.97 Hz, 1H), 4.50 (d, J=5.24 Hz, 1H), 4.33 (t, J=4.37 Hz, 1H), 4.15 (s, 2H), 3.60-

3.36 (m, 6H), 3.26-3.16 (m, 2H), 2.76-2.67 (m, 2H), 1.97-1.84 (m, 1H), 1.75-1.52 (m, 1H).

N-[5-(3,5-Difluoro-benzenesulfonyl)-4,5,6,7-tetrahydro-1H-pyrazolo[4,3-c]pyridin-3-yl]-2-(2,3-dihydroxy-propylamino)-benzamide [(I), Ra=Rb=H, A=B=D=E=CH, R=3,5-difluorophenyl, R1=NR5R6, R5=2,3-dihydroxy-propyl, R6=H], cpd. 567

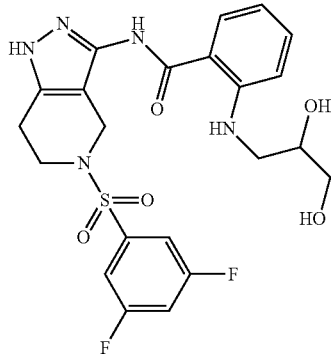

1H-NMR (400 MHz), δ (ppm, DMSO-d6): 12.29 (bs, 1H), 10.22 (bs, 1H), 7.81-7.70 (m, 2H), 7.70-7.62 (m, 1H), 7.33 (t, J=8.10 Hz, 1H), 6.75 (d, J=8.10 Hz, 1H), 6.58 (t, J=8.10 Hz, 1H), 4.84 (d, J=5.00 Hz, 1H), 4.63 (t, J=5.50 Hz, 1H), 4.13 (s, 2H), 3.71-3.61 (m, 1H), 3.58-3.47 (m, 2H), 3.47-3.30 (m, 5H), 3.08-2.97 (m, 1H), 2.78-2.68 (m, 2H).

N-[5-(3,5-Difluoro-benzenesulfonyl)-4,5,6,7-tetrahydro-1H-pyrazolo[4,3-c]pyridin-3-yl]-2-(3-hydroxy-1-methyl-propylamino)-benzamide [(I), Ra=Rb=H, A=B=D=E=CH, R=3,5-difluorophenyl, R1=NR5R6, R5=3-hydroxy-1-methyl-propyl, R6=H], cpd. 569

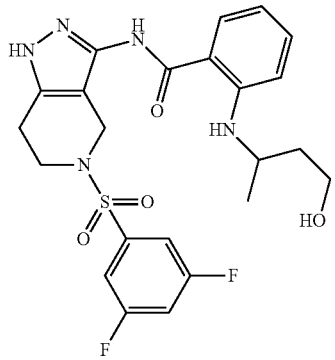

1H-NMR (400 MHz), δ (ppm, DMSO-d6): 12.24 (bs, 1H), 10.18 (bs, 1H), 7.69 (d, J=7.80 Hz, 1H), 7.66-7.56 (m, 2H), 7.55-7.47 (m, 2H), 7.26 (t, J=7.80 Hz, 1H), 6.73 (d, J=7.80 Hz, 1H), 6.51 (t, J=7.80 Hz, 1H), 4.44 (t, J=4.88 Hz, 1H), 4.06 (s, 2H), 3.74-3.59 (m, 1H), 3.52-3.39 (m, 4H), 2.73-2.59 (m, 2H), 1.71-1.45 (m, 2H), 1.11 (d, J=6.34, 3H).

EXAMPLE 26

Preparation of N-[5-(3,5-difluoro-benzenesulfonyl)-4,5,6,7-tetrahydro-1H-pyrazolo[4,3-c]pyridin-3-yl]-2-(isopropylamino-methyl)-benzamide hydrochloride [(I), Ra=Rb=H, A=B=D=E=CH, R=3,5-difluorophenyl, R1=isopropylamino-methyl], cpd. 534

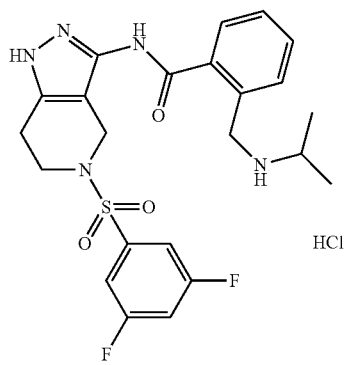

Step 1. Preparation of 2-(1,3-dioxo-1,3-dihydro-isoindol-2-ylmethyl)-benzoic acid To a solution of 3H-isobenzofuran-1-one (18 g, 134 mmol) in dry N,N-dimethylformamide (110 mL) was added potassium phthalimide (27 g, 145 mmol). The mixture was stirred at reflux for 6 hours then cooled to 0° C. and treated with 1N hydrochloric acid (180 mL). The yellow solid thus formed was filtered, washed with water, with ethanol and dried in oven. Crystallization with ethanol afforded the title compound as white solid (27 g).

1H-NMR (400 MHz), δ (ppm, DMSO-$d_6$): 13.21 (bs, 1H), 7.97-7.86 (m, 5H), 7.50 (m, 1H), 7.40 (m, 1H), 7.17 (m, 1H), 5.17 (s, 2H).

Step 2. Preparation of 3-[2-(1,3-dioxo-1,3-dihydro-isoindol-2-ylmethyl)-benzoylamino]-6,7-dihydro-4H-pyrazolo[4,3-c]pyridine-1,5-dicarboxylic acid 5-tert-butyl ester 1-ethyl ester [(IV), Ra=Rb=H, A=B=D=E=CH, Q=ethyl, R1=1,3-dioxo-1,3-dihydro-isoindol-2-ylmethyl]

To a suspension of 2-(1,3-dioxo-1,3-dihydro-isoindol-2-ylmethyl)-benzoic acid (1.82 g, 6.5 mmol) in dry dichloromethane (50 mL), at 0° C., under stirring, was added oxalyl chloride (2.8 mL, 32 mmol) and dry N,N-dimethylformamide (50 microL). The mixture was allowed to warm to room temperature, stirred for 1.5 hours then evaporated to dryness. The residue was diluted with dry toluene and evaporated again. The crude acyl chloride thus obtained (yellow solid) was dissolved in dry tetrahydrofuran (20 mL) and treated with N,N-diisopropylethylamine (1.1 mL, 6.3 mmol) and with a suspension of 3-amino-6,7-dihydro-4H-pyrazolo[4,3-c]pyridine-1,5-dicarboxylic acid 5-tert-butyl ester 1-ethyl ester (1.3 g, 4.2 mmol) in dry tetrahydrofuran and N,N-diisopropylethylamine (1.1 mL, 6.3 mmol). After stirring at room temperature for 2 days, the volatiles were removed under reduced pressure, the residue dissolved in dichloromethane and washed with 1N HCl, water, saturated solution of NaHCO₃, and brine, dried over sodium sulfate and evaporated to dryness. The crude was purified by flash chromatography on silica gel eluting with dichloromethane/methanol 98:2 affording 1.54 g of the title compound.

1H-NMR (400 MHz), δ (ppm, DMSO-d₆): 11.14 (bs, 1H), 7.95-7.87 (m, 4H), 7.68 (m, 1H), 7.49-7.38 (m, 2H), 7.24 (m, 1H), 5.03 (s, 2H), 4.45-4.38 (m, 4H), 3.66 (m, 2H), 3.00 (m, 2H), 1.39 (bs, 9H), 1.36 (t, J=7.1 Hz, 3H).

Step 3. Preparation of 3-[2-(1,3-dioxo-1,3-dihydro-isoindol-2-ylmethyl)-benzoylamino]-4,5,6,7-tetrahydro-pyrazolo[4,3-c]pyridine-1-carboxylic acid ethyl ester hydrochloride [(V), Ra=Rb=H, A=B=D=E=CH, Q=ethyl, R1=1,3-dioxo-1,3-dihydro-isoindol-2-ylmethyl]

To a stirred solution of 3-[2-(1,3-dioxo-1,3-dihydro-isoindol-2-ylmethyl)-benzoylamino]-6,7-dihydro-4H-pyrazolo[4,3-c]pyridine-1,5-dicarboxylic acid 5-tert-butyl ester 1-ethyl ester (1.54 g, 2.7 mmol) in 1,4-dioxane (20 mL) was added 4N HCl in 1,4-dioxane (15 mL, 60 mmol). After stirring for 4 hours at room temperature the volatiles were removed under reduced pressure and the solid residue stirred with diethylether, filtered and dried in oven at 45° C. affording the title compound as white solid (1.08 g).

1H-NMR (400 MHz), δ (ppm, DMSO-d₆): 11.38 (bs, 1H), 9.19 (bs, 2H), 7.95-7.87 (m, 4H), 7.70 (m, 1H), 7.51-7.39 (m, 2H), 7.28 (m, 1H), 5.05 (s, 2H), 4.45 (q, J=7.1 Hz, 2H), 4.24 (bs, 2H), 3.48 (m, 2H), 3.26 (m, 2H), 1.37 (t, J=7.1 Hz, 3H).

Step 4. Preparation of 5-(3,5-difluoro-benzenesulfonyl)-3-[2-(1,3-dioxo-1,3-dihydro-isoindol-2-ylmethyl)-benzoylamino]-4,5,6,7-tetrahydro-pyrazolo[4,3-c]pyridine-1-carboxylic acid ethyl ester [(VII), Ra=Rb=H, A=B=D=E=CH, Q=ethyl, R=3,5-difluorophenyl, R1=1,3-dioxo-1,3-dihydro-isoindol-2-ylmethyl]

To a suspension of 3-[2-(1,3-dioxo-1,3-dihydro-isoindol-2-ylmethyl)-benzoylamino]-4,5,6,7-tetrahydro-pyrazolo[4,3-c]pyridine-1-carboxylic acid ethyl ester hydrochloride (1.08 g, 2.1 mmol) in dry dichloromethane (25 mL) was added N,N-diisopropylethylamine (1.46 mL, 8.4 mmol) and then 3,5-difluorobenzenesulfonyl chloride (670 mg, 3.1 mmol). After stirring at room temperature for 1.5 hours, the mixture was diluted with dichloromethane (50 mL), washed with 1N HCl, water, saturated solution of NaHCO₃, brine, dried over sodium sulfate and evaporated to dryness. The solid residue was stirred with diethylether, filtered and dried affording 1.04 g of the title compound as white solid.

1H-NMR (400 MHz), δ (ppm, DMSO-d₆): 11.16 (bs, 1H), 7.93-7.85 (m, 4H), 7.69 (m, 1H), 7.64 (m, 1H), 7.58 (m, 2H), 7.49-7.37 (m, 2H), 7.28 (m, 1H), 5.03 (s, 2H), 4.38 (q, J=7.1 Hz, 2H), 4.29 (bs, 2H), 3.56 (m, 2H), 3.03 (m, 2H), 1.33 (t, J=7.1 Hz, 3H).

Step 5. Preparation of 2-aminomethyl-N-[5-(3,5-difluoro-benzenesulfonyl)-4,5,6,7-tetrahydro-1H-pyrazolo[4,3-c]pyridin-3-yl]-benzamide [(I), Ra=Rb=H, A=B=D=E=CH, R=3,5-difluorophenyl, R1=aminomethyl]

To a suspension of 5-(3,5-difluoro-benzenesulfonyl)-3-[2-(1,3-dioxo-1,3-dihydro-isoindol-2-ylmethyl)-benzoylamino]-4,5,6,7-tetrahydro-pyrazolo[4,3-c]pyridine-1-carboxylic acid ethyl ester (0.32 g, 0.5 mmol) in 20 mL of methanol and 2 mL of dichloromethane was added hydrazine hydrate (73 microL, 1.5 mmol). The mixture was stirred at reflux for 1 hour 45 min. then evaporated to dryness. The residue was purified by flash chromatography on silica gel eluting with dichloromethane/methanol/7N NH₃ in methanol 92:7:1 affording 70 mg of the title compound.

ESI(+) MS: m/z 448 (MH⁺).

Step 6. Preparation of N-[5-(3,5-difluoro-benzenesulfonyl)-4,5,6,7-tetrahydro-1H-pyrazolo[4,3-c]pyridin-3-yl]-2-(isopropylamino-methyl)-benzamide hydrochloride [(I), Ra=Rb=H, A=B=D=E=CH, R=3,5-difluorophenyl, R1=isopropylamino-methyl], cpd. 534

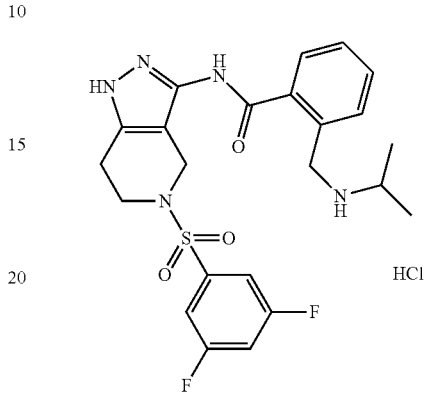

To a solution of 2-aminomethyl-N-[5-(3,5-difluoro-benzenesulfonyl)-4,5,6,7-tetrahydro-1H-pyrazolo[4,3-c]pyridin-3-yl]-benzamide (98 mg, 0.22 mmol) in dichloromethane (6 mL) was added acetone (24 microL, 0.33 mmol), sodium triacetoxyborohydride (65 mg, 0.31 mmol) and acetic acid (189 microL, 33 mmol). After stirring for 2 hours at room temperature the mixture was treated with 1M NaOH (3 mL). The organic layer was separated, washed with brine, dried over sodium sulfate and evaporated to dryness. The residue was purified by flash chromatography on silica gel eluting with dichloromethane/methanol/7N NH₃ in methanol 95:4:1. The oil thus obtained was dissolved in dichloromethane (1 mL) and treated with 2N HCl in Et₂O (0.15 mL). Evaporation of the volatiles afforded 6.5 mg of the title compound as white solid.

1H-NMR (400 MHz), δ (ppm, DMSO-d₆): 11.32 (bs, 1H), 10.86 (bs, 1H), 8.65 (bs, 2H) 7.90 (m, 1H), 7.72-7.53 (m, 6H), 4.28-4.22 (m, 4H), 3.54-3.46 (m, 3H), 2.71 (m, 2H), 1.30 (d, J=6.6 Hz, 6H).

Operating in an analogous way, the following compounds were obtained:

N-[5-(3,5-Difluoro-benzenesulfonyl)-4,5,6,7-tetrahydro-1H-pyrazolo[4,3-c]pyridin-3-yl]-2-[(tetrahydro-pyran-4-ylamino)-methyl]-benzamide hydrochloride [(I), Ra=Rb=H, A=B=D=E=CH, R=3,5-difluorophenyl, R1=(tetrahydro-pyran-4-ylamino)-methyl], cpd. 535

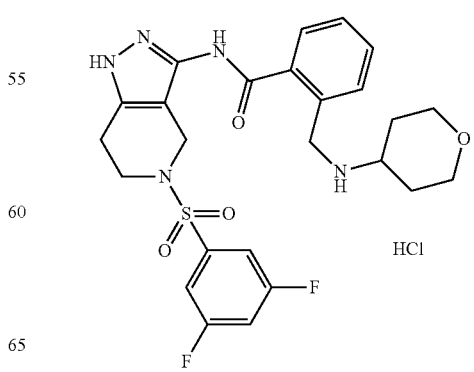

1H-NMR (400 MHz), δ (ppm, DMSO-d$_6$): 10.87 (bs, 1H), 8.87 (bs, 2H), 7.90 (m, 1H), 7.72-7.53 (m, 6H), 4.33-4.25 (m, 4H), 3.90 (m, 2H), 3.50 (m, 2H), 3.49-3.25 (m, 3H), 2.69 (m, 2H), 2.01 (m, 2H), 1.68 (m, 2H).

N-[5-(3,5-Difluoro-benzenesulfonyl)-4,5,6,7-tetrahydro-1H-pyrazolo[4,3-c]pyridin-3-yl]-2-fluoro-6-morpholin-4-ylmethyl-benzamide hydrochloride [(I), Ra=Rb=H, A=B=D=CH, E=CR2, R=3,5-difluorophenyl, R1=morpholin-4-ylmethyl, R2=fluoro], cpd. 266

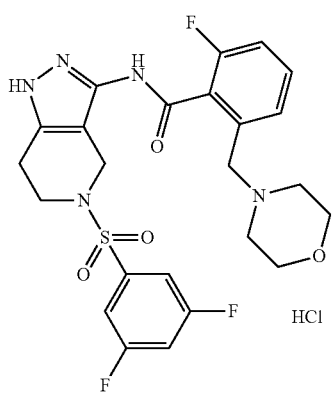

1H-NMR (400 MHz), δ (ppm, DMSO-d$_6$): 11.00 (bs, 1H), 10.47 (bs, 1H), 7.72-7.44 (m, 6H), 4.36 (bs, 2H), 4.27 (bs, 2H), 3.92 (m, 2H), 3.78 (m, 2H), 3.53 (m, 2H), 3.49-3.25 (m, 4H), 2.72 (m, 2H).

EXAMPLE 27

Preparation of 5-(3,5-difluoro-benzenesulfonyl)-1-trityl-4,5,6,7-tetrahydro-1H-pyrazolo[4,3-c]pyridin-3-ylamine [(XVI), Ra=Rb=H, R=3,5-difluorophenyl]

Step 1. Preparation of 3-amino-4,5,6,7-tetrahydro-pyrazolo[4,3-c]pyridine-2-carboxylic acid ethyl ester hydrochloride [(XI), Ra=Rb=H, Q=ethyl]

To a solution of 3-amino-6,7-dihydro-4H-pyrazolo[4,3-c]pyridine-2,5-dicarboxylic acid 5-tert-butyl ester 2-ethyl ester (40 g, 128.9 mmol) in dichloromethane (1 L), 4 N HCl in dioxane (161 mL, 644.5 mmol) was added dropwise. The mixture was stirred at room temperature for 4 hours. The solid was filtered, washed with dichloromethane and diethylether. After drying in vacuo the title compound was obtained as white solid (36.2 g, 99%).

1H-NMR (400 MHz), δ (ppm, DMSO-d$_6$): 9.20 (bs, 2H), 6.51 (bs, 2H), 4.36 (q, J=7.0 Hz, 2H), 3.90 (m, 2H), 3.33 (m, 2H), 2.75 (m, 2H), 1.31 (t, J=7.0 Hz, 3H).

Step 2. Preparation of 3-amino-5-(3,5-difluoro-benzenesulfonyl)-4,5,6,7-tetrahydro-pyrazolo[4,3-c]pyridine-2-carboxylic acid ethyl ester [(XII), Ra=Rb=H, R=3,5-difluorophenyl, Q=ethyl]

To a suspension of 3-amino-4,5,6,7-tetrahydro-pyrazolo[4,3-c]pyridine-2-carboxylic acid ethyl ester hydrochloride (36.2 g, 127.8 mmol) in anhydrous dichloromethane (1 L), at 0°-5° C., N,N-diisopropylethylamine (111.3 mL, 639 mmol) was added. To the resulting solution, 3,5-difluorobenzenesulfonyl chloride (27.17 g, 127.8 mmol) was added portionwise. The mixture was stirred at 0°-5° C. for 1 hour then at room temperature for 3 hours. The organic phase was washed with NaHCO$_3$ satured solution, water and brine, dried over sodium sulfate filtered and evaporated. The crude, was triturated with diethylether (500 mL) to obtain the title compound as yellowish solid (45.48 g, 92%).

1H-NMR (400 MHz), δ (ppm, DMSO-d$_6$): 7.71 (m, 1H), 7.51 (m, 2H), 6.38 (bs, 2H), 4.34 (q, J=7.1 Hz, 2H), 3.99 (s, 2H), 3.44 (m, 2H), 2.58 (m, 2H), 1.30 (t, J=7.1 Hz, 3H).

Step 3. Preparation of 5-(3,5-difluoro-benzenesulfonyl)-4,5,6,7-tetrahydro-2H-pyrazolo[4,3-c]pyridin-3-ylamine [(XIII), Ra=Rb=H, R=3,5-difluorophenyl]

3-Amino-5-(3,5-difluoro-benzenesulfonyl)-4,5,6,7-tetrahydro-pyrazolo[4,3-c]pyridine-2-carboxylic acid ethyl ester (45.4 g, 117.5 mmol) was dissolved in a mixture of dichloromethane (200 mL) and methanol (900 mL) then triethylamine (200 mL) was added. The solution was stirred at room temperature for 2 days and then evaporated to dryness. The solid was treated with diethylether (1 L), stirred for 1 hour, filtered and washed with diethylether. After drying in vacuo the title compound was obtained as white solid (34.68 g, 94%).

1H-NMR (400 MHz), δ (ppm, DMSO-d$_6$): 11.29 (bs, 1H), 7.67 (m, 1H), 7.50 (m, 2H), 5.00 (bs, 2H), 3.97 (s, 2H), 3.38 (m, 2H), 2.57 (m, 2H).

Step 4. Preparation of N-[5-(3,5-difluoro-benzenesulfonyl)-4,5,6,7-tetrahydro-2H-pyrazolo[4,3-c]pyridin-3-yl]-2,2,2-trifluoro-acetamide [(XIV), Ra=Rb=H, R=3,5-difluorophenyl]

To a suspension of 5-(3,5-difluoro-benzenesulfonyl)-4,5,6,7-tetrahydro-2H-pyrazolo[4,3-c]pyridin-3-ylamine (34.68 g, 110.44 mmol) in anhydrous dichloromethane (1 L), at 0°-5° C., trifluoroacetic anhydride (46.80 mL, 331.32 mmol) was added dropwise. The mixture was stirred at 0°-5° C. for 2 hours and then evaporated to dryness. The crude residue was treated with methanol (200 mL) and then evaporated to dryness. A mixture of methanol (130 mL) and water (300 mL) was added to the solid and the suspension stiffed at room temperature for 30 min. The white solid was then filtered and washed with water. After drying in vacuo at 50° C. the title compound was obtained as white solid (43.76 g, 96%).

1H-NMR (400 MHz), δ (ppm, DMSO-d$_6$): 12.57 (bs, 1H), 11.61 (bs, 1H), 7.65 (m, 1H), 7.55 (m, 2H), 4.17 (s, 2H), 3.51 (m, 2H), 2.68 (m, 2H).

Step 5. Preparation of N-[5-(3,5-difluoro-benzenesulfonyl)-1-trityl-4,5,6,7-tetrahydro-1H-pyrazolo[4,3-c]pyridin-3-yl]-2,2,2-trifluoro-acetamide [(XV), Ra=Rb=H, R=3,5-difluorophenyl]

To a mixture of N-[5-(3,5-difluoro-benzenesulfonyl)-4,5,6,7-tetrahydro-2H-pyrazolo[4,3-c]pyridin-3-yl]-2,2,2-trifluoro-acetamide (43.76 g, 106.65 mmol) and triethylamine (44.6 mL, 319.95 mmol) in dichloromethane (1 L), at room temperature, trityl chloride (31.22 g, 111.98 mmol) was added. The reaction was stirred at room temperature for 1 hour. The organic phase was washed with NaHCO$_3$ satured solution, water and brine, dried over sodium sulfate filtered and evaporated to dryness affording the crude title compound as white solid.

1H-NMR (400 MHz), δ (ppm, DMSO-d$_6$): 11.57 (bs, 1H), 7.74 (m, 1H), 7.47 (m, 2H), 7.37-7.28 (m, 9H), 6.99-6.93 (m, 6H), 4.20 (s, 2H), 3.24 (m, 2H), 1.53 (m, 2H).

Step 6. Preparation of 5-(3,5-difluoro-benzenesulfonyl)-1-trityl-4,5,6,7-tetrahydro-1H-pyrazolo[4,3-c]pyridin-3-ylamine [(XVI), Ra=Rb=H, R=3,5-difluorophenyl]

To a suspension of N-[5-(3,5-difluoro-benzenesulfonyl)-1-trityl-4,5,6,7-tetrahydro-1H-pyrazolo[4,3-c]pyridin-3-yl]-2,2,2-trifluoro-acetamide (106.65 mmol) in methanol (500 mL), triethylamine (150 mL) was added and the mixture was refluxed for 36 hours and then evaporated to dryness. The crude was treated with a mixture of diethylether (400 mL) and methanol (100 mL), stirred at room temperature for 30 min., filtered and washed with diethylether. After drying in vacuo the title compound was obtained as white solid (50.5 g, 86%).

1H-NMR (400 MHz), δ (ppm, DMSO-d$_6$): 7.75 (m, 1H), 7.44 (m, 2H), 7.34-7.23 (m, 9H), 7.06-7.01 (m, 6H), 4.68 (bs, 2H), 4.02 (s, 2H), 3.10 (m, 2H), 1.57 (m, 2H).

EXAMPLE 28

Preparation of N-[5-(3,5-difluoro-benzenesulfonyl)-4,5,6,7-tetrahydro-1H-pyrazolo[4,3-c]pyridin-3-yl]-2-((S)-2-methoxy-1-methyl-ethylamino)-4-(4-methyl-piperazin-1-yl)-benzamide [(I), Ra=Rb=H, A=D=E=CH, B=CR2, R=3,5-difluorophenyl, R1=NR5R6, R2=4-methyl-piperazin-1-yl, R5=(S)-2-methoxy-1-methyl-ethyl, R6=H], cpd. 578

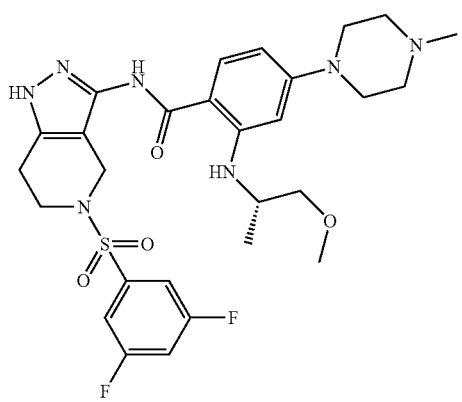

Step 1. Preparation of 2,4-difluoro-benzoic acid tert-butyl ester

To a solution of 2,4-difluorobenzoic acid (5 g, 31.62 mmol) in a mixture of dichloromethane (100 mL) and t-BuOH (50 mL) were added (BOC)$_2$O (13.8 g, 63.24 mmol) and N,N-dimethylaminopyridine (1.16 g, 9.49 mmol). The solution was stirred at room temperature for 24 hours then diluted with dichloromethane and washed with 1N HCl (2×), NaHCO$_3$ satured solution (1×), water (3×) and brine (1×). The organic phase was dried over sodium sulfate, filtered and evaporated to give the title compound (5.70 g, 84%) as yellowish oil.

1H-NMR (400 MHz), δ (ppm, DMSO-d$_6$): 7.91 (m, 1H), 7.36 (m, 1H), 7.20 (m, 1H), 1.53 (s, 9H).

Step 2. Preparation of 4-fluoro-2-((S)-2-methoxy-1-methyl-ethylamino)-benzoic acid tert-butyl ester A mixture of 2,4-difluoro-benzoic acid tert-butyl ester (30 g, 140.05 mmol) and (S)-2-methoxy-1-methyl-ethylamine (100 mL) was stirred at 65° C. for 2 days. A satured solution of NaHCO$_3$ was added and the mixture was extracted with dichloromethane (3×). The organic phase was washed with water (2×), brine, dried over sodium sulfate filtered and evaporated to dryness to obtain a crude, which was purified by column chromatography on silica gel (exane-EtOAc 9:1). The title compound (33.38 g, 84%) was obtained as oil.

1H-NMR (400 MHz), δ (ppm, DMSO-d$_6$): 7.87 (d, J=7.80 Hz, 1H), 7.80 (t, J=7.19 Hz, 1H), 6.60 (dd, J1=13.05 Hz, J2=2.44 Hz, 1H), 6.36 (m, 1H), 3.80 (m, 1H), 3.40 (d, J=4.76 Hz, 2H), 3.30 (s, 3H), 1.53 (s, 9H), 1.17 (d, J=6.58 Hz, 3H).

Step 3. Preparation of 4-fluoro-2-[((S)-2-methoxy-1-methyl-ethyl)-(2,2,2-trifluoro-acetyl)-amino]-benzoic acid tert-butyl ester A solution of 4-fluoro-2-((S)-2-methoxy-1-methyl-ethylamino)-benzoic acid tert-butyl ester (1.54 g, 5.44 mmol) in dichloromethane (30 mL) was cooled to 0°-5° C. Triethylamine (1.11 mL, 8.16 mmol) and trifluoroacetic anhydride (1.15 mL, 8.16 mmol) were added. After 3 hours at 0°-5° C. the mixture was washed with NaHCO$_3$ satured solution, water and brine. The organic layer was dried over sodium sulfate, filtered and evaporated to give the title compound as yellowish oil (2 g, 99%).

1H-NMR (400 MHz), δ (ppm, DMSO-d$_6$): (mixture of tautomers) 8.07 (m, 1H), 7.53 (m, 1H), 7.29 (dd, J1=9.39 Hz, J2=2.68 Hz, 1H), 4.83 (m, 1H), 3.44 (m, 1H), 3.30 (s, 3H), 1.49 (s, 9H), 0.86 (d, 3H).

Step 4. Preparation of 2-[((S)-2-methoxy-1-methyl-ethyl)-(2,2,2-trifluoro-acetyl)-amino]-4-(4-methyl-piperazin-1-yl)-benzoic acid tert-butyl ester A solution of 4-fluoro-2-[((S)-2-methoxy-1-methyl-ethyl)-(2,2,2-trifluoro-acetyl)-amino]-benzoic acid tert-butyl ester (2 g, 5.28 mmol) and N-methylpiperazine (5.86 mL, 52.8 mmol) in tetrahydrofuran (20 mL) was stirred at 60° C. for 7 days. The solution was then evaporated, NaHCO$_3$ satured solution was added and the mixture extracted with dichloromethane (3×). The organic layer was washed with water, brine, dried over sodium sulfate filtered and evaporated to obtain a crude, which was purified by column chromatography on silica gel (dichloromethane-methanol 93:7). The title compound (2.04 g, 84%) was obtained as yellowish solid.

1H-NMR (400 MHz), δ (ppm, DMSO-d$_6$): (mixture of tautomers) 7.81 (d, J=9.15 Hz, 1H), 7.06 (dd, J1=9.15 Hz, J2=2.56 Hz, 1H), 6.79 (d, J=2.56 Hz, 1H), 4.80 (m, 1H), 3.39 (m, 2H), 3.34-3.28 (m, 7H), 2.55 (m, 4H), 2.29 (bs, 3H), 1.46 (s, 9H), 0.83 (d, 3H).

Step 5. Preparation of 2-[((S)-2-methoxy-1-methyl-ethyl)-(2,2,2-trifluoro-acetyl)-amino]-4-(4-methyl-piperazin-1-yl)-benzoic acid trifluoroacetate To a solution of 2-[((S)-2-methoxy-1-methyl-ethyl)-(2,2,2-trifluoro-acetyl)-amino]-4-(4-methyl-piperazin-1-yl)-benzoic acid tert-butyl ester (2.03 g, 4.42 mmol) in dichloromethane (15 mL) trifluoroacetic acid (3.4 mL, 44.2 mmol) was added. The mixture was stirred at room temperature for 15 hours then the solution was evaporated to dryness affording the title compound as oil that was used for the next step without any further purification.

1H-NMR (400 MHz), δ (ppm, DMSO-d$_6$): (mixture of tautomers) 12.10 (bs, 1H), 9.74 (bs, 1H), 7.90 (d, J=8.90 Hz, 1H), 7.15 (dd, J1=8.90 Hz, J2=2.56 Hz, 1H), 6.89 (d, J=2.56 Hz, 1H), 4.76 (m, 1H), 4.03 (t, 2H), 3.55 (m, 2H), 3.37 (m, 2H), 3.30 (s, 3H), 3.18 (m, 2H), 2.88 (bs, 3H), 0.85 (d, 3H).

Step 6. Preparation of N-[5-(3,5-difluoro-benzene-sulfonyl)-1-trityl-4,5,6,7-tetrahydro-1H-pyrazolo[4,3-c]pyridin-3-yl]-2-[((S)-2-methoxy-1-methyl-ethyl)-(2,2,2-trifluoro-acetyl)-amino]-4-(4-methyl-piperazin-1-yl)-benzamide [(XVII), Ra=Rb=H, A=D=E=CH, B=CR2, R=3,5-difluorophenyl, R1=NR5R6, R2=4-methyl-piperazin-1-yl, R5=(S)-2-methoxy-1-methyl-ethyl, R6=2,2,2-trifluoro-acetyl]

To a suspension of 2-[((S)-2-methoxy-1-methyl-ethyl)-(2,2,2-trifluoro-acetyl)-amino]-4-(4-methyl-piperazin-1-yl)-benzoic acid trifluoroacetate (4.40 mmol) in anhydrous dichloromethane (40 mL), oxalyl chloride (1.15 mL, 13.2 mmol) and catalytic N,N-dimethylformamide (few drops) were added. The mixture was stirred at room temperature for 3 hours, evaporated to dryness and the residue dried in vacuo. The crude acyl chloride thus obtained was suspended in anhydrous tetrahydrofuran (40 mL) and 5-(3,5-difluoro-benzenesulfonyl)-1-trityl-4,5,6,7-tetrahydro-1H-pyrazolo[4,3-c]pyridin-3-ylamine (2 g, 3.67 mmol) was added. The mixture was cooled at 0°-5° C. and N,N-diisopropylethylamine (3.83 mL. 22 mmol) was added dropwise. After 2 hours at 0°-5° C. the solvent was evaporated and the crude dissolved in dichloromethane and washed with NaHCO$_3$ saturated solution, water and brine. The organic phase was dried over sodium sulfate, filtered and evaporated affording a crude which was purified by column chromatography on silica gel (dichloromethane-ethanol 95:5). The title compound (3.04 g, 88%) was obtained as orange solid.

1H-NMR (400 MHz), δ (ppm, DMSO-d$_6$): (mixture of tautomers) 10.53 (bs, 1H), 7.77-7.68 (m, 2H), 7.43 (m, 2H), 7.34 (m, 9H), 7.03-6.98 (m, 7H), 6.83 (d, J=2.44 Hz, 1H), 4.72 (m, 1H), 3.94 (d, J=14.14 Hz, 2H), 3.37-3.28 (m, 10H), 3.27 (s, 3H), 2.46 (m, 4H), 2.23 (bs, 3H), 0.90 (d, 3H).

Step 7. Preparation of N-[5-(3,5-difluoro-benzene-sulfonyl)-4,5,6,7-tetrahydro-1H-pyrazolo[4,3-c]pyridin-3-yl]-2-[((S)-2-methoxy-1-methyl-ethyl)-(2,2,2-trifluoro-acetyl)-amino]-4-(4-methyl-piperazin-1-yl)-benzamide hydrochloride [(I), Ra=Rb=H, A=D=E=CH, B=CR2, R=3,5-difluorophenyl, R1=NR5R6, R2=4-methyl-piperazin-1-yl, R5=(S)-2-methoxy-1-methyl-ethyl, R6=2,2,2-trifluoro-acetyl]

To a solution of N-[5-(3,5-difluoro-benzenesulfonyl)-1-trityl-4,5,6,7-tetrahydro-1H-pyrazolo[4,3-c]pyridin-3-yl]-2-[((S)-2-methoxy-1-methyl-ethyl)-(2,2,2-trifluoro-acetyl)-amino]-4-(4-methyl-piperazin-1-yl)-benzamide (2.97 g, 3.16 mmol) in dioxane (50 mL), 4 N HCl in dioxane (6.32 mL, 25.28 mmol) was added. The mixture was stirred at room temperature for 15 hours and then evaporated to dryness. The crude was suspended in a mixture of diethylether (400 mL) and methanol (20 mL) and stirred for 1 hour. The solid was filtered and washed with plenty of diethylether. After drying in vacuo the title compound (2.17 g, 93%) was obtained as pink solid.

1H-NMR (400 MHz), δ (ppm, DMSO-d$_6$): (mixture of tautomers) 10.52 (bs, 1H), 7.80 (d, J=8.90 Hz, 1H), 7.69 (m, 1H), 7.49 (m, 2H), 7.15 (dd, J1=8.90 Hz, J2=2.56 Hz, 1H), 6.92 (d, J=2.56 Hz, 1H), 4.73 (m, 1H), 4.02-3.98 (m, 4H), 3.50-3.33 (m, 6H), 3.29 (s, 3H), 3.10 (s, 3H), 2.85 (d, J=4.85 Hz, 3H), 2.73 (t, J=5.85 Hz, 2H), 2.23 (bs, 3H).

Step 8. Preparation of N-[5-(3,5-difluoro-benzene-sulfonyl)-4,5,6,7-tetrahydro-1H-pyrazolo[4,3-c]pyridin-3-yl]-2-[((S)-2-methoxy-1-methyl-ethylamino)-4-(4-methyl-piperazin-1-yl)-benzamide [(I), Ra=Rb=H, A=D=E=CH, B=CR2, R=3,5-difluorophenyl, R1=NR5R6, R2=4-methyl-piperazin-1-yl, R5=(S)-2-methoxy-1-methyl-ethyl, R6=H], cpd. 578

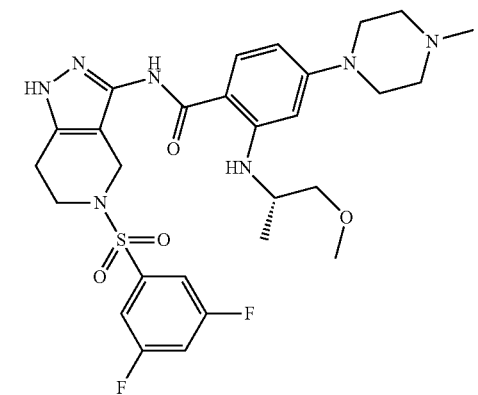

To a solution of N-[5-(3,5-difluoro-benzenesulfonyl)-4,5,6,7-tetrahydro-1H-pyrazolo[4,3-c]pyridin-3-yl]-2-[((S)-2-methoxy-1-methyl-ethyl)-(2,2,2-trifluoro-acetyl)-amino]-4-(4-methyl-piperazin-1-yl)-benzamide hydrochloride (2.15 g, 2.92 mmol) in methanol (100 mL) was added triethylamine (30 mL) and the mixture stirred at room temperature for 15 hours and then at reflux for 6 hours. The solution was then evaporated, the crude dissolved in dichloromethane and washed with NaHCO$_3$ saturated solution, water and brine. The organic phase was dried over sodium sulfate filtered and evaporated to give a crude, which was purified by column chromatography on silica gel (DCM-MeOH 92:8). The title compound (1.49 g, 85%) was obtained as white solid.

1H-NMR (400 MHz), δ (ppm, DMSO-d$_6$): 12.20 (bs, 1H), 9.86 (bs, 1H), 8.12 (d, J=7.44 Hz, 1H), 7.71-7.63 (m, 2H), 7.54 (m, 2H), 6.20 (d, J=8.17 Hz, 1H), 6.11 (d, J=2.07 Hz, 1H), 4.09 (bs, 2H), 3.78 (m, 1H), 3.49 (t, J=5.61 Hz, 2H), 3.39-3.25 (m, 6H), 3.28 (s, 3H), 2.69 (m, 2H), 2.48 (m, 4H), 2.26 (bs, 3H), 1.15 (d, J=6.34 Hz, 3H).

$[α]^{20}_D$=+9.08 (C=1% in methanol).

Operating in a way analogous to that described above, the following compounds were obtained:

Step 2

4-Fluoro-2-((R)-2-methoxy-1-methyl-ethylamino)-benzoic acid tert-butyl ester

1H-NMR (400 MHz), δ (ppm, DMSO-d$_6$): 7.87 (d, J=7.80 Hz, 1H), 7.80 (t, J=7.19 Hz, 1H), 6.60 (dd, J1=13.05 Hz, J2=2.44 Hz, 1H), 6.36 (m, 1H), 3.80 (m, 1H), 3.40 (d, J=4.76 Hz, 2H), 3.30 (s, 3H), 1.53 (s, 9H), 1.17 (d, J=6.58 Hz, 3H).

4-Fluoro-2-(2-methoxy-ethylamino)-benzoic acid tert-butyl ester

1H-NMR (400 MHz), δ (ppm, DMSO-d$_6$): 7.89 (t, J=5.00 Hz, 1H), 7.80 (t, J=7.07 Hz, 1H), 6.56 (dd, J1=12.80 Hz, J2=2.56 Hz, 1H), 6.37 (m, 1H), 3.55 (t, J=5.37 Hz, 2H), 3.33 (m, 2H), 3.29 (s, 3H), 1.53 (s, 9H).

Step 3

4-Fluoro-2-[((R)-2-methoxy-1-methyl-ethyl)-(2,2,2-trifluoro-acetyl)-amino]-benzoic acid tert-butyl ester 1H-NMR (400 MHz), δ (ppm, DMSO-$d_6$): (mixture of tautomers) 8.07 (m, 1H), 7.53 (m, 1H), 7.29 (dd, J1=9.39 Hz, J2=2.68 Hz, 1H), 4.83 (m, 1H), 3.44 (m, 1H), 3.30 (s, 3H), 1.49 (s, 9H), 0.86 (d, 3H).

4-Fluoro-2-[(2-methoxy-ethyl)-(2,2,2-trifluoro-acetyl)-amino]-benzoic acid tert-butyl ester 1H-NMR (400 MHz), δ (ppm, DMSO-$d_6$): 8.07 (m, 1H), 7.50 (m, 1H), 7.41 (dd, J1=9.39 Hz, J2=2.56 Hz, 1H), 4.28 (m, 1H), 3.55 (m, 1H), 3.46 (m, 1H), 3.38 (m, 1H), 3.18 (s, 3H), 1.49 (s, 9H).

Step 4

2-[((R)-2-Methoxy-1-methyl-ethyl)-(2,2,2-trifluoro-acetyl)-amino]-4-(4-methyl-piperazin-1-yl)-benzoic acid tert-butyl ester 1H-NMR (400 MHz), δ (ppm, DMSO-$d_6$): (mixture of tautomers) 7.81 (d, J=9.15 Hz, 1H), 7.06 (dd, J1=9.15 Hz, J2=2.56 Hz, 1H), 6.79 (d, J=2.56 Hz, 1H), 4.80 (m, 1H), 3.39 (m, 2H), 3.34-3.28 (m, 7H), 2.55 (m, 4H), 2.29 (bs, 3H), 1.46 (s, 9H), 0.83 (d, 3H).

2-[(2-Methoxy-ethyl)-(2,2,2-trifluoro-acetyl)-amino]-4-(4-methyl-piperazin-1-yl)-benzoic acid tert-butyl ester 1H-NMR (400 MHz), δ (ppm, DMSO-$d_6$): (mixture of tautomers) 7.83 (d, J=9.02 Hz, 1H), 7.05 (dd, J1=9.02 Hz, J2=2.68 Hz, 1H), 6.86 (d, J=2.68 Hz, 1H), 4.31 (m, 1H), 3.55 (m, 1H), 3.40 (m, 1H), 3.32 (m, 4H), 3.25 (m, 1H), 3.21 (s, 1H), 2.44 (t, J=5.12 Hz, 4H), 2.22 (bs, 3H), 1.46 (s, 9H).

Step 5

2-[((R)-2-Methoxy-1-methyl-ethyl)-(2,2,2-trifluoro-acetyl)-amino]-4-(4-methyl-piperazin-1-yl)-benzoic acid trifluoroacetate 1H-NMR (400 MHz), δ (ppm, DMSO-$d_6$): (mixture of tautomers) 12.10 (bs, 1H), 9.74 (bs, 1H), 7.90 (d, J=8.90 Hz, 1H), 7.15 (dd, J1=8.90 Hz, J2=2.56 Hz, 1H), 6.89 (d, J=2.56 Hz, 1H), 4.76 (m, 1H), 4.03 (t, 2H), 3.55 (m, 2H), 3.37 (m, 2H), 3.30 (s, 3H), 3.18 (m, 2H), 2.88 (bs, 3H), 0.85 (d, 3H).

2-[(2-Methoxy-ethyl)-(2,2,2-trifluoro-acetyl)-amino]-4-(4-methyl-piperazin-1-yl)-benzoic acid trifluoroacetate 1H-NMR (400 MHz), δ (ppm, DMSO-$d_6$): (mixture of tautomers) 12.76 (bs, 1H), 9.73 (bs, 1H), 7.91 (d, J=8.78 Hz, 1H), 7.10 (dd, J1=8.78 Hz, J2=2.68 Hz, 1H), 7.01 (d, J=2.68 Hz, 1H), 4.15 (m, 1H), 4.04 (m, 2H), 3.54 (m, 2H), 3.42 (m, 2H), 3.38 (m, 2H), 3.33 (m, 2H), 3.19 (s, 3H), 3.14 (m, 2H), 2.86 (bs, 3H).

Step 6

N-[5-(3,5-Difluoro-benzenesulfonyl)-1-trityl-4,5,6,7-tetrahydro-1H-pyrazolo[4,3-c]pyridin-3-yl]-2-[((R)-2-methoxy-1-methyl-ethyl)-(2,2,2-trifluoro-acetyl)-amino]-4-(4-methyl-piperazin-1-yl)-benzamide [(XVII), Ra=Rb=H, A=D=E=CH, B=CR2, R=3,5-difluorophenyl, R1=NR5R6, R2=4-methyl-piperazin-1-yl, R5=(R)-2-methoxy-1-methyl-ethyl, R6=2,2,2-trifluoro-acetyl]

1H-NMR (400 MHz), δ (ppm, DMSO-$d_6$): (mixture of tautomers) 10.53 (bs, 1H), 7.77-7.68 (m, 2H), 7.43 (m, 2H), 7.34 (m, 9H), 7.03-6.98 (m, 7H), 6.83 (d, J=2.44 Hz, 1H), 4.72 (m, 1H), 3.94 (d, J=14.14 Hz, 2H), 3.37-3.28 (m, 10H), 3.27 (s, 3H), 2.46 (m, 4H), 2.23 (bs, 3H), 0.90 (d, 3H).

N-[5-(3,5-Difluoro-benzenesulfonyl)-1-trityl-4,5,6,7-tetrahydro-1H-pyrazolo[4,3-c]pyridin-3-yl]-2-[(2-methoxy-ethyl)-(2,2,2-trifluoro-acetyl)-amino]-4-(4-methyl-piperazin-1-yl)-benzamide [(XVII), Ra=Rb=H, A=D=E=CH, B=CR2, R=3,5-difluorophenyl, R1=NR5R6, R2=4-methyl-piperazin-1-yl, R5=2-methoxy-ethyl, R6=2,2,2-trifluoro-acetyl]

1H-NMR (400 MHz), δ (ppm, DMSO-$d_6$): (mixture of tautomers) 10.43 (bs, 1H), 7.77-7.70 (m, 2H), 7.42 (m, 2H), 7.32 (m, 9H), 7.00-6.95 (m, 7H), 6.90 (d, J=2.44 Hz, 1H), 4.09 (m, 2H), 3.90 (bs, 2H), 3.51-3.26 (m, 10H), 3.16 (s, 3H), 2.43 (m, 4H), 2.21 (bs, 3H).

Step 7

N-[5-(3,5-Difluoro-benzenesulfonyl)-4,5,6,7-tetrahydro-1H-pyrazolo[4,3-c]pyridin-3-yl]-2-[((R)-2-methoxy-1-methyl-ethyl)-(2,2,2-trifluoro-acetyl)-amino]-4-(4-methyl-piperazin-1-yl)-benzamide hydrochloride [(I), Ra=Rb=H, A=D=E=CH, B=CR2, R=3,5-difluorophenyl, R1=NR5R6, R2=4-methyl-piperazin-1-yl, R5=(R)-2-methoxy-1-methyl-ethyl, R6=2,2,2-trifluoro-acetyl]

1H-NMR (400 MHz), δ (ppm, DMSO-$d_6$): (mixture of tautomers) 10.52 (bs, 1H), 7.80 (d, J=8.90 Hz, 1H), 7.69 (m, 1H), 7.49 (m, 2H), 7.15 (dd, J1=8.90 Hz, J2=2.56 Hz, 1H), 6.92 (d, J=2.56 Hz, 1H), 4.73 (m, 1H), 4.02-3.98 (m, 4H), 3.50-3.33 (m, 6H), 3.29 (s, 3H), 3.10 (s, 3H), 2.85 (d, J=4.85 Hz, 3H), 2.73 (t, J=5.85 Hz, 2H), 2.23 (bs, 3H).

N-[5-(3,5-Difluoro-benzenesulfonyl)-4,5,6,7-tetrahydro-1H-pyrazolo[4,3-c]pyridin-3-yl]-2-[(2-methoxy-ethyl)-(2,2,2-trifluoro-acetyl)-amino]-4-(4-methyl-piperazin-1-yl)-benzamide hydrochloride [(I), Ra=Rb=H, A=D=E=CH, B=CR2, R=3,5-difluorophenyl, R1=NR5R6, R2=4-methyl-piperazin-1-yl, R5=2-methoxy-ethyl, R6=2,2,2-trifluoro-acetyl]

1H-NMR (400 MHz), δ (ppm, DMSO-$d_6$): (mixture of tautomers) 10.41 (bs, 1H), 7.78 (d, J=8.78 Hz, 1H), 7.69 (m, 1H), 7.52 (m, 2H), 7.14 (dd, J1=8.90 Hz, J2=2.56 Hz, 1H), 7.06 (d, J=2.56 Hz, 1H), 4.12 (m, 2H), 4.03-3.98 (m, 4H), 3.53-3.44 (m, 8H), 3.18 (s, 3H), 3.17-3.15 (m, 4H), 2.85 (d, J=4.39 Hz, 3H), 2.74 (t, J=5.88 Hz, 2H).

Step 8

N-[5-(3,5-Difluoro-benzenesulfonyl)-4,5,6,7-tetrahydro-1H-pyrazolo[4,3-c]pyridin-3-yl]-2-((R)-2-methoxy-1-methyl-ethylamino)-4-(4-methyl-piperazin-1-yl)-benzamide [(I), Ra=Rb=H, A=D=E=CH, B=CR2, R=3,5-difluorophenyl, R1=NR5R6, R2=4-methyl-piperazin-1-yl, R5=(R)-2-methoxy-1-methyl-ethyl, R6=H], cpd. 579

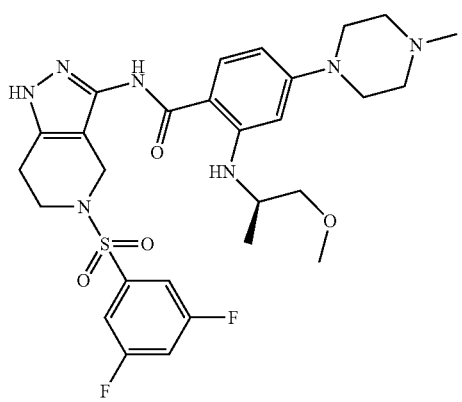

1H-NMR (400 MHz), δ (ppm, DMSO-d$_6$): 12.20 (bs, 1H), 9.86 (bs, 1H), 8.12 (d, J=7.44 Hz, 1H), 7.71-7.63 (m, 2H), 7.54 (m, 2H), 6.20 (d, J=8.17 Hz, 1H), 6.11 (d, J=2.07 Hz, 1H), 4.09 (bs, 2H), 3.78 (m, 1H), 3.49 (t, J=5.61 Hz, 2H), 3.39-3.25 (m, 6H), 3.28 (s, 3H), 2.69 (m, 2H), 2.48 (m, 4H), 2.26 (bs, 3H), 1.15 (d, J=6.34 Hz, 3H).

$[\alpha]^{20}_D = -9.2$ (C=1% in methanol).

N-[5-(3,5-Difluoro-benzenesulfonyl)-4,5,6,7-tetrahydro-1H-pyrazolo[4,3-c]pyridin-3-yl]-2-(2-methoxyethylamino)-4-(4-methyl-piperazin-1-yl)-benzamide [(I), Ra=Rb=H, A=D=E=CH, B=CR2, R=3,5-difluorophenyl, R1=NR5R6, R2=4-methyl-piperazin-1-yl, R5=2-methoxy-ethyl, R6=H], cpd. 580

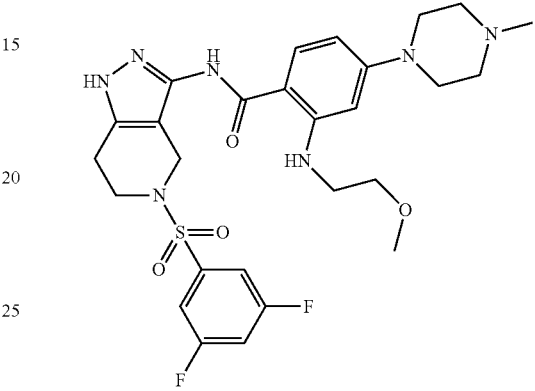

1H-NMR (400 MHz), δ (ppm, DMSO-d$_6$): 12.19 (bs, 1H), 9.86 (bs, 1H), 8.17 (bs, 1H), 7.68 (t, J=2.19 Hz, 1H), 7.65 (t, J=2.19, 1H), 7.56 (m, 2H), 6.20 (d, J=8.41 Hz, 1H), 6.05 (d, J=2.07 Hz, 1H), 4.11 (bs, 2H), 3.54 (t, J=5.37 Hz, 2H), 3.50 (t, J=5.12 Hz, 2H), 3.29 (m, 2H), 3.28 (s, 3H), 3.26 (m, 2H), 2.68 (m, 2H), 2.42 (m, 4H), 2.22 (bs, 3H).

The invention claimed is:

1. A method for treating a disease caused by and/or associated with a dysregulated protein kinase activity selected from the group consisting of breast cancer, colon cancer, colorectal cancer, bladder cancer, cervical cancer, epidermoid cancer, lung cancer, pancreatic cancer, prostate cancer, ovarian cancer, renal cancer, thyroid cancer, astrocytoma, cholangiocarcinoma, Ewing's sarcoma, fibrosarcoma, leukaemia, melanoma, lymphoma, neuroblastoma, osteosarcoma, rhabdomyosarcoma and multiple myeloma which comprises administering to a mammal in need thereof an effective amount of a compound of formula (I)

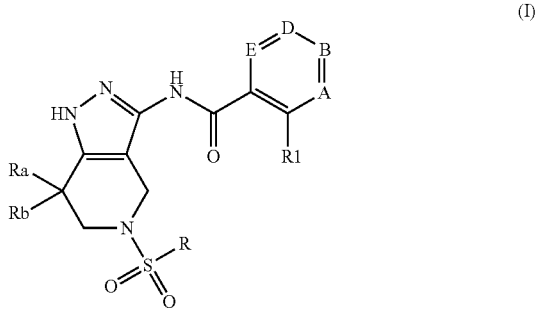

wherein:
R is an optionally further substituted straight or branched $C_1$-$C_6$ alkyl, $C_3$-$C_6$ cycloalkyl, heterocycloalkyl or aryl;
R1 is selected from hydrogen, halogen, nitro, NHCOR4, NHSO$_2$R10, NR5R6, OR7, R8R9N—$C_1$-$C_6$ alkyl, R7O—$C_1$-$C_6$ alkyl and an optionally further substituted straight or branched $C_1$-$C_6$ alkyl, wherein:
R4 is selected from hydrogen, an optionally further substituted straight or branched $C_1$-$C_6$ alkyl, $C_3$-$C_6$ cycloalkyl, heterocycloalkyl, aryl, NR8R9, R8R9N—$C_1$-$C_6$ alkyl and R7O—$C_1$-$C_6$ alkyl;
R5 and R6, being the same or different, are independently selected from hydrogen, an optionally further substituted straight or branched $C_1$-$C_6$ alkyl, $C_3$-$C_6$ cycloalkyl, heterocycloalkyl, aryl, R8R9N—$C_2$-$C_6$ alkyl and R7O—$C_2$-$C_6$ alkyl;
R7 is selected from hydrogen, an optionally further substituted straight or branched $C_1$-$C_6$ alkyl, $C_3$-$C_6$ cycloalkyl, heterocycloalkyl, aryl and R8R9N—$C_2$-$C_6$ alkyl;
R8 and R9, being the same or different, are independently selected from hydrogen, an optionally further substituted straight or branched $C_1$-$C_6$ alkyl, $C_3$-$C_6$ cycloalkyl, heterocycloalkyl and aryl, and R8 and R9, taken together with the nitrogen atom to which they are bonded, form an optionally substituted heterocycloalkyl group;
R10 is an optionally further substituted straight or branched $C_1$-$C_6$ alkyl, $C_3$-$C_6$ cycloalkyl, heterocycloalkyl or aryl;

A, B, D and E represent a nitrogen atom, CH, CR2 or CR3, with a maximum of two of A, B, D and E representing a nitrogen atom, CR2 or CR3, wherein:
R2 and R3 are independently selected from halogen, trifluoromethyl, nitro, OR7, NR8R9, an optionally further substituted straight or branched $C_1$-$C_6$ alkyl, R8R9N—$C_1$-$C_6$ alkyl and R7O—$C_1$-$C_6$ alkyl, wherein R7, R8 and R9 are as defined above;
Ra and Rb are independently hydrogen or methyl, with the proviso that when Ra, Rb, and R1 are hydrogen atoms, then at least one of A, B, D and E is nitrogen;
or optical isomers, tautomers or pharmaceutically acceptable salt thereof.

2. The method according to claim 1 which provides tumor angiogenesis and metastasis inhibition.

3. The method according to claim 1 further comprising subjecting the mammal in need thereof to a radiation therapy or chemotherapy regimen in combination with at least one cytostatic or cytotoxic agent.

4. The method according to claim 1 wherein the mammal in need thereof is a human.

5. A method for inhibition of IGF1-induced IGF1R phosphorylation which comprises administering to a mammal in need thereof an effective amount of a compound of formula (I)

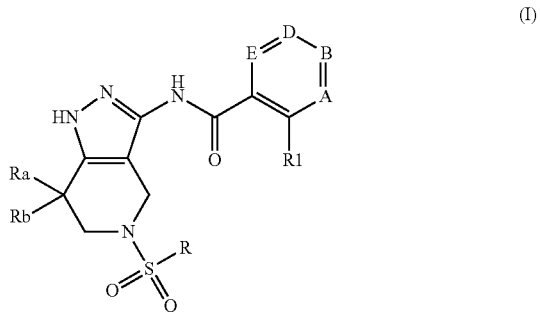

wherein:
R is an optionally further substituted straight or branched $C_1$-$C_6$ alkyl, $C_3$-$C_6$ cycloalkyl, heterocycloalkyl or aryl;
R1 is selected from hydrogen, halogen, nitro, NHCOR4, NHSO$_2$R10, NR5R6, OR7, R8R9N—$C_1$-$C_6$ alkyl, R7O—$C_1$-$C_6$ alkyl and an optionally further substituted straight or branched $C_1$-$C_6$ alkyl, wherein:
R4 is selected from hydrogen, an optionally further substituted straight or branched $C_1$-$C_6$ alkyl, $C_3$-$C_6$ cycloalkyl, heterocycloalkyl, aryl, NR8R9, R8R9N—$C_1$-$C_6$ alkyl and R7O—$C_1$-$C_6$ alkyl;
R5 and R6, being the same or different, are independently selected from hydrogen, an optionally further substituted straight or branched $C_1$-$C_6$ alkyl, $C_3$-$C_6$ cycloalkyl, heterocycloalkyl, aryl, R8R9N—$C_2$-$C_6$ alkyl and R7O—$C_2$-$C_6$ alkyl;

R7 is selected from hydrogen, an optionally further substituted straight or branched $C_1$-$C_6$ alkyl, $C_3$-$C_6$ cycloalkyl, heterocycloalkyl, aryl and R8R9N—$C_2$-$C_6$ alkyl;

R8 and R9, being the same or different, are independently selected from hydrogen, an optionally further substituted straight or branched $C_1$-$C_6$ alkyl, $C_3$-$C_6$ cycloalkyl, heterocycloalkyl and aryl, and R8 and R9, taken together with the nitrogen atom to which they are bonded, form an optionally substituted heterocycloalkyl group;

R10 is an optionally further substituted straight or branched $C_1$-$C_6$ alkyl, $C_3$-$C_6$ cycloalkyl, heterocycloalkyl or aryl;

A, B, D and E represent a nitrogen atom, CH, CR2 or CR3, with a maximum of two of A, B, D and E representing a nitrogen atom, CR2 or CR3, wherein:

R2 and R3 are independently selected from halogen, trifluoromethyl, nitro, OR7, NR8R9, an optionally further substituted straight or branched $C_1$-$C_6$ alkyl, R8R9N—$C_1$-$C_6$ alkyl and R7O—$C_1$-$C_6$ alkyl, wherein R7, R8 and R9 are as defined above;

Ra and Rb are independently hydrogen or methyl, with the proviso that when Ra, Rb, and R1 are hydrogen atoms, then at least one of A, B, D and E is nitrogen;

or optical isomers, tautomers or pharmaceutically acceptable salt thereof.

\* \* \* \* \*

```
                            SEQUENCE LISTING

<160> NUMBER OF SEQ ID NOS: 3

<210> SEQ ID NO 1
<211> LENGTH: 33
<212> TYPE: DNA
<213> ORGANISM: Artificial
<220> FEATURE:
<223> OTHER INFORMATION: forward primer

<400> SEQUENCE: 1
ctcggatcca gaaagagaaa taacagcagg ctg                              33

<210> SEQ ID NO 2
<211> LENGTH: 36
<212> TYPE: DNA
<213> ORGANISM: Artificial
<220> FEATURE:
<223> OTHER INFORMATION: reverse primer

<400> SEQUENCE: 2
ctcggatcct cagcaggtcg aagactgggg cagcgg                           36

<210> SEQ ID NO 3
<211> LENGTH: 19
<212> TYPE: PRT
<213> ORGANISM: Unknown
<220> FEATURE:
<223> OTHER INFORMATION: carboxy-terminally biotinylated peptide enzyme
```

```
substrate

<400> SEQUENCE: 3

Lys Lys Lys Ser Pro Gly Glu Tyr Val Asn Ile Glu Phe Gly Gly Gly
1               5                   10                  15

Gly Gly Lys
```